(12) United States Patent
Tanaka et al.

(10) Patent No.: US 9,988,373 B2
(45) Date of Patent: Jun. 5, 2018

(54) NITROGEN-CONTAINING SIX-MEMBERED CYCLIC DERIVATIVES AND PHARMACEUTICAL COMPOSITION COMPRISING THE SAME

(71) Applicant: SHIONOGI & CO., LTD., Osaka-shi, Osaka (JP)

(72) Inventors: Satoru Tanaka, Toyonaka (JP); Tomoyuki Ogawa, Toyonaka (JP); Yuki Ogata, Toyonaka (JP); Masahide Fujita, Toyonaka (JP)

(73) Assignee: SHIONOGI & CO., LTD., Osaka (JP)

( * ) Notice: Subject to any disclaimer, the term of this patent is extended or adjusted under 35 U.S.C. 154(b) by 0 days. days.

(21) Appl. No.: 15/108,089

(22) PCT Filed: Dec. 26, 2014

(86) PCT No.: PCT/JP2014/084473
§ 371 (c)(1),
(2) Date: Jun. 24, 2016

(87) PCT Pub. No.: WO2015/099107
PCT Pub. Date: Jul. 2, 2015

(65) Prior Publication Data
US 2016/0318916 A1 Nov. 3, 2016

(30) Foreign Application Priority Data
Dec. 26, 2013 (JP) .................................. 2013-268179

(51) Int. Cl.
| | | |
|---|---|---|
| *C07D 417/06* | (2006.01) |
| *C07D 401/04* | (2006.01) |
| *C07D 401/06* | (2006.01) |
| *C07D 405/06* | (2006.01) |
| *C07D 405/12* | (2006.01) |
| *C07D 239/36* | (2006.01) |
| *C07D 239/46* | (2006.01) |
| *C07D 239/47* | (2006.01) |
| *C07D 409/04* | (2006.01) |
| *C07D 409/06* | (2006.01) |
| *C07D 409/10* | (2006.01) |
| *C07D 413/06* | (2006.01) |
| *C07D 213/68* | (2006.01) |
| *C07D 213/69* | (2006.01) |
| *C07D 213/85* | (2006.01) |
| *C07D 237/14* | (2006.01) |
| *C07D 239/54* | (2006.01) |
| *C07D 403/04* | (2006.01) |
| *C07D 405/14* | (2006.01) |

(52) U.S. Cl.
CPC ......... *C07D 417/06* (2013.01); *C07D 213/68* (2013.01); *C07D 213/69* (2013.01); *C07D 213/85* (2013.01); *C07D 237/14* (2013.01); *C07D 239/36* (2013.01); *C07D 239/46* (2013.01); *C07D 239/47* (2013.01); *C07D 239/54* (2013.01); *C07D 401/04* (2013.01); *C07D 401/06* (2013.01); *C07D 403/04* (2013.01); *C07D 405/06* (2013.01); *C07D 405/12* (2013.01); *C07D 405/14* (2013.01); *C07D 409/04* (2013.01); *C07D 409/06* (2013.01); *C07D 409/10* (2013.01); *C07D 413/06* (2013.01)

(58) Field of Classification Search
CPC .. C07D 417/06; C07D 213/68; C07D 213/69; C07D 213/85; C07D 237/14; C07D 239/36; C07D 239/46; C07D 239/47; C07D 239/54; C07D 401/04; C07D 401/06
See application file for complete search history.

(56) References Cited

U.S. PATENT DOCUMENTS

| | | |
|---|---|---|
| 4,278,798 A | 7/1981 | Wick |
| 4,314,063 A | 2/1982 | Wick |

(Continued)

FOREIGN PATENT DOCUMENTS

| | | |
|---|---|---|
| CN | 1465567 | 1/2004 |
| EP | 445 811 A2 | 9/1991 |

(Continued)

OTHER PUBLICATIONS

CAS Abstract of D. Zhou et al., 19 Zhejiang Yike Daxue Xuebao, 211-215 (1991).*

(Continued)

*Primary Examiner* — Alexander R Pagano
(74) *Attorney, Agent, or Firm* — Finnegan, Henderson, Farabow, Garrett & Dunner, LLP

(57) ABSTRACT

A compound represented by formula (I):

[Chemical Formula 1]

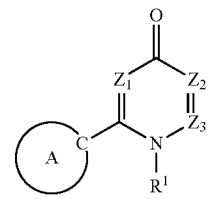

wherein
$Z_1$ is $C(R^2)$ or N; $Z_3$ is CH or N; $Z_2$ is $C(R^3)$ or N;
provided that $Z_1$ is $C(R^2)$ and $Z_3$ is CH when $Z_2$ is N;
Ring A is a substituted or unsubstituted aromatic carbocycle, or the like; $R^1$ is substituted or unsubstituted alkyl, or the like; $R^2$ is a hydrogen atom, halogen, or the like; $R^3$ is a hydrogen atom, halogen, or the like;
or a pharmaceutically acceptable salt thereof.

16 Claims, No Drawings

(56) References Cited

U.S. PATENT DOCUMENTS

| | | | |
|---|---|---|---|
| 4,345,934 | A | 8/1982 | Fujimoto |
| 4,521,535 | A | 6/1985 | Wick |
| 4,549,022 | A * | 10/1985 | Wick .................. C07D 211/90 544/131 |
| 4,661,145 | A | 4/1987 | Fujimoto |
| 5,580,865 | A | 12/1996 | Alpegiani et al. |
| 6,071,913 | A | 6/2000 | Yang et al. |
| 2009/0281107 | A1 | 11/2009 | Congy et al. |
| 2011/0319400 | A1 | 12/2011 | Flores et al. |
| 2011/0319418 | A1 | 12/2011 | Flores et al. |
| 2013/0172317 | A1 | 7/2013 | Kai et al. |
| 2013/0225596 | A1 | 8/2013 | Kai et al. |
| 2016/0024072 | A1 | 1/2016 | Kai et al. |
| 2016/0052892 | A1 | 2/2016 | Kai et al. |
| 2016/0115151 | A1 | 4/2016 | Kai |
| 2017/0158704 | A1 * | 6/2017 | Nagano .............. C07D 491/107 |

FOREIGN PATENT DOCUMENTS

| | | |
|---|---|---|
| EP | 445 811 A3 | 9/1991 |
| EP | 2 399 910 A1 | 12/2011 |
| GB | 2 328 614 | 3/1999 |
| JP | 60-89472 | 5/1985 |
| JP | 61-246163 | 1/1986 |
| JP | 63-225366 | 9/1988 |
| JP | 63-225378 | 9/1988 |
| JP | 6-179683 | 6/1994 |
| JP | 6-263766 | 9/1994 |
| JP | 6-298770 | 10/1994 |
| JP | 8-59670 | 3/1996 |
| KR | 2012/0089074 A | 8/2012 |
| WO | WO 02/060879 A2 | 8/2002 |
| WO | WO 02/060879 A3 | 8/2002 |
| WO | WO 03/042191 | 5/2003 |
| WO | WO 2003/042190 A1 | 5/2003 |
| WO | WO 2004/058270 | 7/2004 |
| WO | WO 2004/058731 A1 | 7/2004 |
| WO | WO 2004/099146 A1 | 11/2004 |
| WO | WO 2005/003513 A1 | 1/2006 |
| WO | WO 2006/003500 A1 | 1/2006 |
| WO | WO 2006/003517 A1 | 1/2006 |
| WO | WO 2006/063812 | 6/2006 |
| WO | WO 2006/086229 | 8/2006 |
| WO | WO 2006/102112 A2 | 9/2006 |
| WO | WO 2006/104713 A1 | 10/2006 |
| WO | WO 2006/104715 A1 | 10/2006 |
| WO | WO 2007/079163 A2 | 7/2007 |
| WO | WO 2007/079214 A2 | 7/2007 |
| WO | WO 2009/058653 A1 | 5/2009 |
| WO | WO 2009/067827 A1 | 5/2009 |
| WO | WO 2010/072597 A1 | 7/2010 |
| WO | WO 2010/072599 | 7/2010 |
| WO | WO-2010/072605 A1 | 7/2010 |
| WO | WO-2010/072607 A1 | 7/2010 |
| WO | WO 2010/072647 A2 | 7/2010 |
| WO | WO 2010/126104 A1 | 11/2010 |
| WO | WO 2010/133973 | 11/2010 |
| WO | WO 2011/012592 A1 | 2/2011 |
| WO | WO 2011/033055 A1 | 3/2011 |
| WO | WO 2011/109254 | 9/2011 |
| WO | WO 2012/036193 | 3/2012 |
| WO | WO 2012/073138 | 6/2012 |
| WO | WO 2013/089212 | 6/2013 |
| WO | WO 2016/084922 A1 | 6/2016 |
| WO | WO 2016/088838 A1 | 6/2016 |

OTHER PUBLICATIONS

X. Wang et al., 10 Nature Medicine, 821-827 (2004).*
D.W. Nelson, 49 Journal of Medicinal Chemistry, 3659-3666 (2006).*
M.A. Letavic et al., 4 Journal of Medicinal Chemistry Letters, 419-422 (2013).*
Notification Concerning Transmittal of International Preliminary Report on Patentability and International Preliminary Report on Patentability (Chapter I of the Patent Cooperation Treaty). International Preliminary Report on Patentability dated Jul. 7, 2016.
Written Opinion of the International Searching Authority for International Application No. PCT/JP2014/084473, dated Mar. 24, 2015.
Friedle et al.; "Recent Patents on Novel P2X$_7$ Receptor Antagonists and Their Potential for Reducing Central Nervous System Inflammation", Recent Patents on CNS Drug Discovery, vol. 5, No. 1, pp. 35-45, (2010).
Bakali et al.; "4-OXO-1,4-Dihydropyridines as Selective CB$_2$ Cannabinoid Receptor Ligands: Structural Insights into the Design of a Novel Inverse Agonist Series", J. Med. Chem., vol. 53, No. 22, pp. 7918-7931, (2010).
Azaroual et al.; "NMR Studies of Interactions of New CB$_2$ Cannabinoid Receptor Ligands with Cyclodextrins Hosts. Correlation with Micellar Electrokinetic Chromatography and Reversed Phase High Performance Liquid Chromatography", J. Incl. Phenom. Macrocycl. Chem., vol. 78, No. 1-4, pp. 265-274, (2014).
Chupakhin et al.; "One-Step Hetarylation of Steroids: Regioselective Synthesis of New Estrone Derivatives", Mendeleev Commun., vol. 16, No. 2, pp. 95-96, (2006), Scheme 2.
Chupakhin et al.; "The First Case of Direct Coupling of Heterocycles With Calixarenes. Reaction of Resorcinarenes With 1,2,4-Triazin-5(2H)-Ones", Heterocyclic Communications, vol. 10, No. 1, pp. 15-18, (2004), Scheme 1.
Brown et al.; "Pyridone-Conjugated Monobactam Antibiotics with Gram-Negative Activity", Journal of Medicinal Chemistry, vol. 56, No. 13, pp. 5541-5552, (2013).
Takahashi et al.; "An Improved Synthesis of 5-Acylamino-6-OXO-2-Phenyl-1(6H)-Pyrimidineacetic Acid from Glycine with Readily Removable Protecting Groups", Heterocycles, vol. 85, No. 9, pp. 2213-2229, (2012).
Mitton-Fry et al.; "Novel Monobactams Utilizing a Siderophore Uptake Mechanism for the Treatment of Gram-Negative Infections", Bioorganic & Medicinal Chemistry Letters, vol. 22, No. 18, pp. 5989-5994. (2012).
Kravtsov et al.; "Synthesis of 3-Arylazo-1H-Pyridazin-4-Ones From Difluoroboron Chelates of 1,3-Diketones", Russian Chemical Bulletin, International Edition, vol. 56, No. 8, pp. 1561-1565, (2007).
Akbas et al.; "Reactions of Substituted Furan-2,3-Diones With C- and N-Nucleophiles" Asian Journal of Chemistry, vol. 19, No. 3, pp. 1913-1918 (2007).
Laursen et al.; "Further Exploration of Antimicrobial Ketodihydronicotinic Acid Derivatives by Multiple Parallel Syntheses", Combinatorial Chemistry & High Throughput Screening, vol. 9, No. 9, pp. 663-681, (2006).
Garg et al.; "Synthesis of Bis(Indole)-1,2,4-Triazinones", Tetrahedron Letters, vol. 46, No. 12, pp. 1997-2000, (2005).
Tice et al; "Syntheses of Heterocyclic Analogs of Herbicidal Aryl Triazolinones", American Chemical Society, vol. 800, (Synthesis and Chemistry of Agrochemicals VI), pp. 41-50, (2002).
Barsy et al.; "Novel Synthesis of Polyfunctionalised Biaryl, Pyridazine, and Phthalazine Derivatives", Synthetic Communications, vol. 31, No. 17, pp. 2569-2581, (2001).
Keiser et al.; "Evaluation of Quinolone Derivatives for Antitrypanosomal Activity", Tropical Medicine and International Health, vol. 6, No. 5, pp. 369-389, (2001).
Elnagdi et al.; "Studies on Polyfunctionalised Heteroaromatics: A Novel Synthesis of Polyfunctionalised Pyridine, Pyridazine and Pyrido[2,3-c]Pyridazine Derivatives", J. Chem. Research, No. 1, pp. 26-27, (1998).
Choi et al.; "Studies on New Catechol Containing Cephalosporins", The Journal of Antibiotics, vol. 50, No. 3, pp. 279-282, (1997).
Elnagdi et al.; "Studies With Polyfunctionally Substituted Heteroaromatics: Arylhydrazononitriles for the Synthesis of Polyfunctionally Substituted Azines", Heterocycles, vol. 38, No. 4, pp. 739-750(1994).
Bassini et al.; "Sinthesis and Antimicrobial Activity of DNA-Gyrase Inhibiting Derivatives of 4-OXO-1,4-Dihydro-3-Pyridinecarboxylic Acid", IL Farmaco, vol. 48, No. 2, pp. 159-189, (1993).

(56) References Cited

OTHER PUBLICATIONS

Dardoize et al.; "High-Performance Liquid Chromatography of Chemical Hybridizing Agent in Wheat", Journal of Liquid Chromatography, vol. 16, No. 7, pp. 1517-1528, (1993).

Torii et al.; "A Novel Approach to 6-Substituted 4-Pyridone-3-Carbooxylic Esters by Palladium-Catalyzed Carbonylative Coupling", Synlett, No. 10. pp. 695-696, (1991).

McCombie et al.; "Generation and In Situ Acylation of Enaminone Anions: A Convenient Synthesis of 3-Carbethoxy-4(1H)-Pyridinones and -4-Pyrones and Related Compounds", J. Org. Chem., vol. 56, No. 16, pp. 4963-4967, (1991).

Neunhoeffer et al.; "The Chemistry of 1,2,4-Triazines. XIV. Synthesis and Reactions of 5-Chloro-1,2,4-Triazines", Liebigs Annalen der Chemie, No. 7, pp. 631-640, (1990).

Seitz et al.; "Cyanamide as Sidechain Dienophile in the Intramolecular [4+2]-Cycloaddition With 1,2,4-Triazines", Archiv. der Pharmazie, vol. 324, No. 1, pp. 65-66, (1991).

Wustrow et al.; "Synthesis of a 3-Acetoxy-6-Phenylpyrone and its conversion to a Pyrido[1,4]Benzodiazepine", Heterocycles, vol. 29, No. 9, pp. 1721-1728, (1989).

Radl et al.; "Preparation of Substituted 1,6-Diphenyl-1,4-Dihydro-4-OXO-3-Pyridazinecarboxylic Acids", Cesko-Slovenska Farmacie, vol. 38, No. 3, pp. 114-117, (1989).

Zvonok et al.; "Synthesis of 1,2,3,4-Tetrahydropyrdin-4-Ones by Heterocyclization of β-Amino-β-Arylacryloyloxiranes", Khimiya Geterotsiklicheskikh Soedinenii, No. 3, pp. 347-350, (1989).

Neunhoeffer et al.; "[1,2,4]TRIAZINO[6,5-e]-1-2,4-Triazine: II", Communication, Synthesis, No. 11, pp. 877-879, (1988).

Zvonok et al.; "Reaction of (β-Arylacryloyl)Oxiranes with Phenyl Azide. Synthesis and Reactions of (β-Anilino-β-Arylacryloyl)Oxiranes", Khimiya Geterotsiklicheskikh Soedinenii, No. 8, pp. 1022-1027, (1988).

Katagiri et al.; "Cycloadditions in Syntheses. XXXVII. Syntheses of 6-Trifluoromethyl-1,2,4-Triazines and -1,2,4-Triazin-5-Ones and their Pericyclic Reactions With OLEFINS", Chem. Pharm. Bull., vol. 36, No. 9, pp. 3354-3372, (1988).

Jacobsen et al.; "New Zwitterionic Methylation Products of Some 1,2,4-Triazin-5(2H)-Ones and Their Identification by Carbon-13 Nuclear Magnetic Resonance Spectroscopy", Aust. J. Chem., vol. 40, No. 5, pp. 967-975, (1987).

Klopman et al.; "Computer Automated Structure Evaluation of Quinolone Antibacterial Agents", Antimicrobial Agents and Chemotherapy, vol. 31, No. 11, pp. 1831-1840, (1987).

Georgopapadakou et al.; "Monocyclic and Tricyclic Analogs of Quinolones: Mechanism of Action", Antimicrobial Agents and Chemotherapy, vol. 31. No. 4, pp. 614-616. (1987).

Narita et al.; "Pyridonecarboxylic Acids as Antibacterial Agents. III. Synthesis and Structure-Activity Relationship of 1-(4-Fluorophenyl)- and 1-(2,4-Difluorophenyl)-6-Substituted-4-Pyridone-3-Carboxylic Acids", Yakugaku Zasshi, vol. 106, No. 9, pp. 788-794, (1986).

Narita et al.; "Pyridonecarboxylic Acids as Antibacterial Agents. II. Synthesis and Structure-Activity Relationship of 1-(4-Hydroxyphenyl)-6-Substituted-4-Pyridone-3-Carboxylic Acids", Yakugaku Zasshi, vol. 106, No. 9, pp. 782-787, (1986).

Narita et al.; "Pyridonecarboxylic Acids as Antibacterial Agents. I. Synthesis and Structure-Activity Relationship of 1-Aryl-6-(4-Dimethylaminophenyl)-4-Pyridone-3-Carboxylic Acids", Yakugaku Zasshi, vol. 106, No. 9, pp. 775-781, (1986).

Neunhoeffer et al.; "Synthesis of 1,2,4-Triazines. XI. Synthesis and Reactions of 6-Amino-1,2,4-Triazin-5-Ones and 6-Amino-1,2,4-Triazine-5-Thiones", Liebigs Annalen der Chemie, No. 2, pp. 283-295, (1984).

Juby et al.; "Antiallergy Agents. 1. 1,6-Dihydro-6-OXO-2-Phenylpyrimidine-5-Carboxylic Acids and Esters", Journal of Medicinal Chemistry, vol. 22, No. 3, pp. 263-269, (1979).

Daunis et al.; "Studies in the AS-Triazine Series. XX. 6-(Ethoxycarbonyl)Triazin-5-Ones as Synthetic Precursors of 6-Triazolyltriazin-5-Ones", Bull. Soc. Chim. (Chim. Mol.), (Issue 11-12, Pt. 2), pp. 1825-1826, (1976).

Daunis et al.; "Etude en Serie AS-Triazine. XIV. Etude de la Synthese et de la Tautomerie de Phenyl-3 et Phenyl-6 Triazinones-5", Tetrahedron, vol. 30, No. 17, pp. 3171-3175, (1974).

Daunis et al.; "AS-Triazine Series. X. Nucleophilic Reactions of 1,2,4-Triazin-5-Ones", Journal of Heterocyclic Chemistry, vol. 10, No. 4, pp. 559-563, (1973).

Johnstone et al.; "Alkaloids of the Australian Rutaceae: Lunasia Quercifolia" Australian Journal of Chemistry, vol. 11, pp. 562-567, (1958).

Shapiro et al.; "The Japp-Klingemann Reaction with γ,δ-Unsaturated β-Ketoesters. Synthesis of Pyridazinones", Journal of the American Chemical Society, vol. 78, pp. 2144-2149, (1956).

Morgan; "A New Synthesis of 4-Pyridazones", Journal of the American Chemical Society, vol. 70, pp. 2253-2254, (1948).

Oostveen et al.; "On the N-Ethylation of 4-Alkoxy- and 4,6-Dialkoxypyrimidines with Triethyloxonium Tetrafluoroborate", Recueil des Travaux Chimiques des Pays-Bas, vol. 96, No. 3, pp. 64-68, (1977).

Oostveen et al.; "Ring Transformations of Heterocyclic Compounds with Nucleophiles. Part XVI. Degenerate Ring Transformations of 1,3-Diethyl-1,4(3,4)-Dihydro-4-Oxopyrimidinium Tetrafluoroborates with Ammonia", Recueil des Travaux Chimiques des Pays-Bas, vol. 96, No. 3, pp. 68-72. (1977).

English-language International Search Report from the Japanese Patent Office for International Application No. PCT/JP2014/084473 dated Mar. 24, 2015.

Chen, X. et al. "Discovery of 2-chloro-N-((4,4-difluoro-1-hydroxycyclohexyl)methyl)-5-(5-flu-oropyrimidin-2-yl)benzamide as a potent and CNS penetrable P2X7 receptor antagonist," Bioorganic & Medicinal Chemistry Letters 20 (2010) 3107-3111.

Baroja-Mazo, A., et al. "The Participation of Plasma Membrane Hemichannels to Purinergic Signaling," Biochimica et Biophysics Acta 1828, 2013, pp. 79-93.

Burnstock, G. "Purinergic Mechanosensory Transduction and Visceral Pain," Molecular Pain, Biomed Central, Nov. 30, 2009, 5:69.

Chessell, I.P. et al. "Disruption of the $P2X_7$ Purinoceptor Gene Abolishes Chronic Inflammatory and Neuropathic Pain," Pain, 2005, 114, pp. 386-396.

Duplantier A.J. et al. "Optimization of the Physicochemical and Pharmacokinetic Attributes in a 6-Azauracil Series of $P2X_7$ Receptor Antagonists Leading to the Discovery of the Clinical Candidate Ce-224.535," Bloorganic & Medicinal Chemistry Letters 21, 2011. pp. 3708-3711.

Lopez-Tapia, F. "Novel Series of Dihydropyridinone P2X7 Receptor Antagonists," Journal of Medicinal Chemistry, 2015, 58, pp. 8413-8426.

Mackenzie, A. et al. "Rapid Secretion of Interleukin-1β by Microvesicle Shedding," Immunity, 2001, 8, pp. 825-835.

Park, J., et al. "P2X7 Receptor Antagonists: A Patent Review (2010-2015)." Expert Opinion on Therapeutic Patents, 2017, 27:3, pp. 257-267.

Skaper, S.D. et al. "The $P2X_7$ Purinergic Receptor: from Physiology to Neurological Disorders," The FASEB Journal, 2010, 24:2, pp. 337-345.

Sorge, R.E. et al. "Genetically Determined P2X7 Receptor Pore Formation Regulates Variability in Chronic Pain Sensitivity," Nature Medicine. 2012, vol. 18:4, pp. 595-560.

Subramanyam, C. et al. "Discovery, Synthesis and SAR of Azinyl- and Azolylbenzaimides Antagonists of the $P2X_7$ Receptor." Bioorganic & Medicinal Chemistry Letters 21, 2011, pp. 5475-5479.

Takenouchi, T. et al. "P2X7 Receptor Signaling Pathway as a Therapeutic Target for Neurodegenerative Diseases," Arch. Immunol. Ther. Exp., 2010, 58, pp. 91-96.

\* cited by examiner

NITROGEN-CONTAINING SIX-MEMBERED CYCLIC DERIVATIVES AND PHARMACEUTICAL COMPOSITION COMPRISING THE SAME

CROSS REFERENCE TO RELATED APPLICATIONS

This application is a United States national stage application, filed under 35 U.S.C. § 371, of International Patent Application No. PCT/JP2014/084473 accorded an international filing date of Dec. 26, 2014, which claims the benefit of priority under 35 U.S.C. § 119(e) to Japanese Patent Application No. 2013-268179, filed Dec. 26, 2013.

TECHNICAL FIELD

The invention relates to a compound useful for the treatment of diseases or conditions associated with the P2X7 receptor and a pharmaceutical composition containing thereof.

BACKGROUND ART

Adenosine triphosphate (ATP) is known to serve as a source of energy in cells and a substrate of phosphorylation, as well as an extracellular messenger. It is known that ATP is released from a cell by various stimulation such as cellular injury, inflammation, nociceptive stimulus, reduced blood oxygen level, and also known to be released together with another messenger from a primary sensory nerve terminal. (Non-Patent Document 1) ATP thus released mediates various extracellular signal transductions through an ATP receptor.

ATP receptor is categorized into ionotropic P2X family and G protein-coupled P2Y family. For P2X family, seven subtypes have been reported, and a member of this family forms a homo-trimeric structure or a hetero-trimeric structure together with another member of this subtype and functions as a non-specific cation channel.

The P2X7 receptor, a non-selective cation channel, belongs to the P2X family, and forms a homo-trimeric structure. Activation of P2X7 by extracellular ATP allows for the passage of cations across the plasma membrane. Prolonged or repeated ATP stimulation leads to the pore formation of pannexin hemichannel, and induces the cellular activation following the release of small molecule such as ATP. (Non-Patent Document 2) It is reported that the activation of P2X7 is involved in inflammation, immune and pain by the maturation and secretion of proinflammatory cytokines such as interleukin-1 beta and interleukin-18. (Non-Patent Document 3) Thus, it is known that the P2X7 receptor is involved in pain, central nervous system disease, immune disease and inflammatory disease. (Non-Patent Document 7-8, and Patent Document 1)

P2X7 is distributed in macrophages, mast cells, microglia, and astrocytes. It is known that disruption of the P2X7 receptor gene abolishes chronic inflammatory and neuropathic pain. (Non-Patent Document 4) It is reported that the P451L mutation of the mouse P2X7 gene has impaired pore formation and shows less mechanical sensitivity of neuropathic pain model mice. (Non-Patent Document 5) Additionally, an association between lower pain intensity in chronic pain patients and the hypofunctional allele of P2X7 has been reported, suggesting that P2X7 antagonist is useful in the treatment of chronic pain such as rheumatoid arthritis, osteoarthritis and neuropathic pain.

Additionally, it has been reported that P2X7 may be involved in multiple sclerosis, spinal cord injury, stroke, Alzheimer's disease, and depression (Non-Patent Document 6), suggesting that P2X7 antagonist is useful in the treatment of these central nervous system disease.

The compounds having an antagonistic activity for the P2X7 receptor are described in Patent Document 2. However, the compounds have different chemical structures from the compounds of the present invention.

The compounds having similar chemical structures to the compound of the invention are described in Patent Documents 3-6, Non-Patent Documents 7 and 8. However, there is neither disclosure nor suggestion about an antagonistic activity for the P2X7 receptor.

PRIOR ART REFERENCES

Patent Document

[Patent Document 1] International Publication WO 2012/036193A
[Patent Document 2] International Publication WO 2006/086229A
[Patent Document 3] International Publication WO 2010/133973A
[Patent Document 4] International Publication WO 2011/109254A
[Patent Document 5] International Publication WO 2012/020742A
[Patent Document 6] International Publication WO 2013/118855A

Non-Patent Document

[Non-patent Document 1] Burnstock G., Mol Pain. 2009. 5. 69
[Non-patent Document 2] Baroja-Mazo A et al., Biochim Biophys Acta. 2013. 1828. 79-93
[Non-patent Document 3] MacKenzie A et al., Immunity. 2001. 15. 825-835
[Non-patent Document 4] Chessell I P et al., Pain. 2005. 114. 386-396
[Non-patent Document 5] Sorge R E et al., Nature Med. 2012. 18. 595-599
[Non-patent Document 6] Skaper S D et al., FASEB J. 2010. 24. 337-345
[Non-patent Document 7] Takenouchi T et al., Arch Immunol Ther Exp (Warsz). 2010 April; 58(2): 91-6
[Non-patent Document 8] Friedle S A et al., Recent Pat CNS Drug Discov. 2010 January; 5(1): 35-45
[Non-patent Document 9] Journal of Medicinal Chemistry 2010, 53(22), 7918-7931
[Non-patent Document 10] Journal of Inclusion Phenomena and Macrocyclic Chemistry (2014), 78(1-4), 265-274

SUMMARY OF THE INVENTION

Problems to be Solved by the Invention

The objective of the present invention is to provide novel compounds having an antagonistic activity for the P2X7 receptor and a pharmaceutical composition having an antagonistic activity for the P2X7 receptor.

Means for Solving the Problem

The present invention relates to the following (1), (1'), (2) to (18) and (101) to (107):

(1)

A compound represented by formula (I):

[Chemical Formula 1]

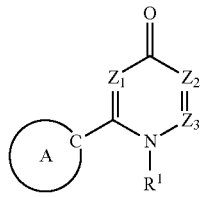

(I)

wherein
$Z_1$ is $C(R^2)$ or N;
$Z_3$ is CH or N;
$Z_2$ is $C(R^3)$ or N;
provided that $Z_1$ is $C(R^2)$, and $Z_3$ is CH when $Z_2$ is N;

Ring A is a substituted or unsubstituted aromatic carbocycle, a substituted or unsubstituted non-aromatic carbocycle, a substituted or unsubstituted aromatic heterocycle, or a substituted or unsubstituted non-aromatic heterocycle;

$R^1$ is substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

$R^2$ is a hydrogen atom, halogen, amino, carbamoyl, sulfamoyl, cyano, ureido, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted monoalkylamino, substituted or unsubstituted dialkylamino, substituted or unsubstituted alkylsulfonyl, substituted or unsubstituted monoalkylcarbonylamino, substituted or unsubstituted monoalkylsulfonylamino, substituted or unsubstituted alkylsulfanyl, substituted or unsubstituted monoalkylcarbamoyl, substituted or unsubstituted dialkylcarbamoyl, substituted or unsubstituted monoalkylsulfamoyl, substituted or unsubstituted dialkylsulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfanyl, substituted or unsubstituted non-aromatic carbocyclylsulfanyl, substituted or unsubstituted aromatic heterocyclylsulfanyl, or substituted or unsubstituted non-aromatic heterocyclylsulfanyl;

provided that $R^2$ is a hydrogen atom when $Z_2$ is $C(R^3)$ and $Z_3$ is CH;

$R^3$ is a hydrogen atom, halogen, amino, carbamoyl, sulfamoyl, cyano, ureido, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted monoalkylamino, substituted or unsubstituted dialkylamino, substituted or unsubstituted monoalkylcarbonylamino, substituted or unsubstituted monoalkylsulfonylamino, substituted or unsubstituted alkylsulfanyl, substituted or unsubstituted alkenylsulfanyl, substituted or unsubstituted alkynylsulfanyl, substituted or unsubstituted monoalkylcarbamoyl, substituted or unsubstituted dialkylcarbamoyl, substituted or unsubstituted monoalkylsulfamoyl, substituted or unsubstituted dialkylsulfamoyl, substituted or unsubstituted alkyloxycarbonylamino, substituted or unsubstituted alkenyloxycarbonylamino, substituted or unsubstituted alkynyloxycarbonylamino, substituted or unsubstituted alkylureido, substituted or unsubstituted alkenylureido, substituted or unsubstituted alkynylureido, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylcarbonylamino, substituted or unsubstituted non-aromatic carbocyclylcarbonylamino, substituted or unsubstituted aromatic heterocyclylcarbonylamino, substituted or unsubstituted non-aromatic heterocyclylcarbonylamino, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylureido, substituted or unsubstituted non-aromatic carbocyclylureido, substituted or unsubstituted aromatic heterocyclylureido, substituted or unsubstituted non-aromatic heterocyclylureido, substituted or unsubstituted aromatic carbocyclyloxycarbonylamino, substituted or unsubstituted non-aromatic carbocyclyloxycarbonylamino, substituted or unsubstituted aromatic heterocyclyloxycarbonylamino, or substituted or unsubstituted non-aromatic heterocyclyloxycarbonylamino;

provided that i) Ring A is not substituted or unsubstituted cyclopropane, unsubstituted dithiane, unsubstituted benzene, or benzene substituted with three methyloxy groups and optionally substituted with one or more and same or different substituent(s), and ii) $R^1$ is not unsubstituted methyl, unsubstituted n-pentyl, substituted or unsubstituted phenyl, or tetrahydrofuranyl substituted with two hydroxy groups and optionally substituted with one or more and same or different substituent(s), provided that the following compounds are excluded:

[Chemical Formula 2]

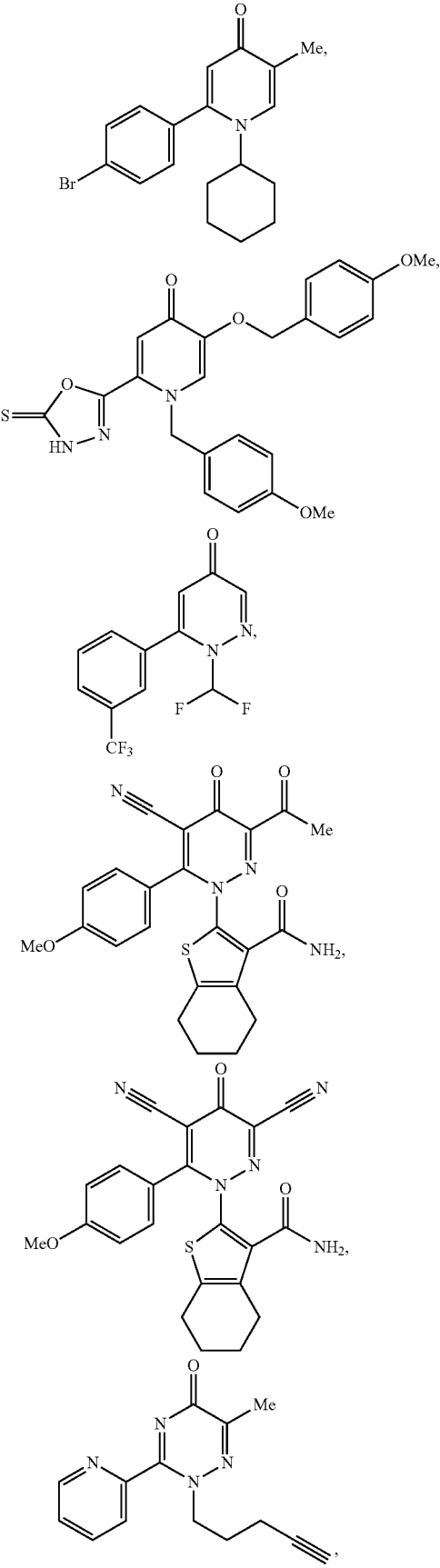

-continued

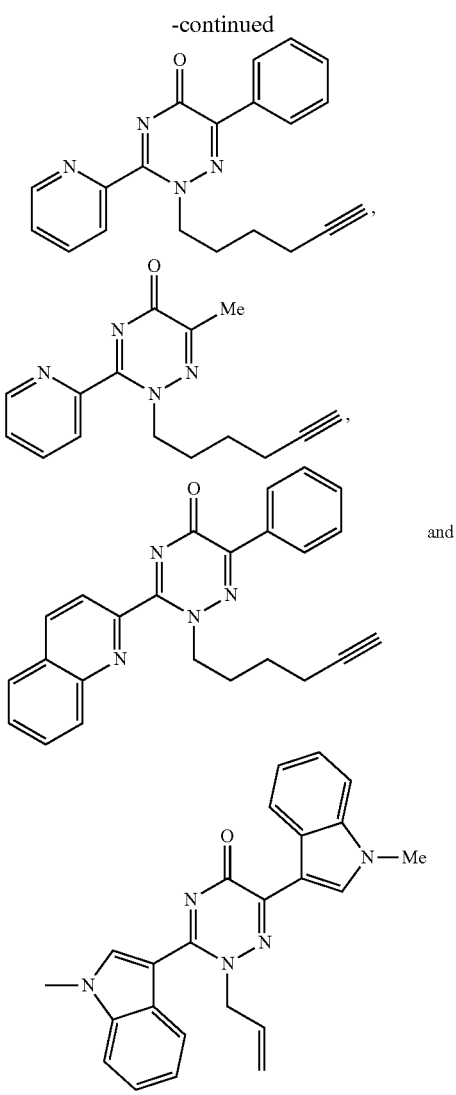

or a pharmaceutically acceptable salt thereof.

(1') A compound represented by formula (I):

[Chemical Formula 3]

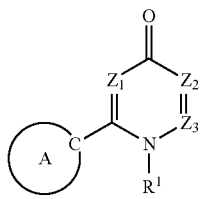
(I)

wherein
$Z_1$ is $C(R^2)$ or N;
$Z_3$ is CH or N;
$Z_2$ is $C(R^3)$ or N:
provided that $Z_1$ is $C(R^2)$ and $Z_3$ is CH when $Z_2$ is N;
Ring A is a substituted or unsubstituted aromatic carbocycle, a substituted or unsubstituted non-aromatic carbocycle, a substituted or unsubstituted aromatic heterocycle, or a substituted or unsubstituted non-aromatic heterocycle;

$R^1$ is, substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

$R^2$ is a hydrogen atom, halogen, amino, carbamoyl, sulfamoyl, cyano, ureido, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted monoalkylamino, substituted or unsubstituted dialkylamino, substituted or unsubstituted alkylsulfonyl, substituted or unsubstituted monoalkylcarbonylamino, substituted or unsubstituted monoalkylsulfonylamino, substituted or unsubstituted alkylsulfanyl, substituted or unsubstituted monoalkylcarbamoyl, substituted or unsubstituted dialkylcarbamoyl, substituted or unsubstituted monoalkylsulfamoyl, substituted or unsubstituted dialkylsulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfanyl, substituted or unsubstituted non-aromatic carbocyclylsulfanyl, substituted or unsubstituted aromatic heterocyclylsulfanyl, or substituted or unsubstituted non-aromatic heterocyclylsulfanyl;

provided that $R^2$ is a hydrogen atom when $Z_2$ is $C(R^3)$ and $Z_3$ is CH;

$R^3$ is a hydrogen atom, halogen, amino, carbamoyl, sulfamoyl, cyano, ureido, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted monoalkylamino, substituted or unsubstituted dialkylamino, substituted or unsubstituted monoalkylcarbonylamino, substituted or unsubstituted monoalkylsulfonylamino, substituted or unsubstituted alkylsulfanyl, substituted or unsubstituted alkenylsulfanyl, substituted or unsubstituted alkynylsulfanyl, substituted or unsubstituted monoalkylcarbamoyl, substituted or unsubstituted dialkylcarbamoyl, substituted or unsubstituted monoalkylsulfamoyl, substituted or unsubstituted dialkylsulfamoyl, substituted or unsubstituted alkyloxycarbonylamino, substituted or unsubstituted alkenyloxycarbonylamino, substituted or unsubstituted alkynyloxycarbonylamino, substituted or unsubstituted alkylureido, substituted or unsubstituted alkenylureido, substituted or unsubstituted alkynylureido, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylcarbonylamino, substituted or unsubstituted non-aromatic carbocyclylcarbonylamino, substituted or unsubstituted aromatic heterocyclylcarbonylamino, substituted or unsubstituted non-aromatic heterocyclylcarbonylamino, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylureido, substituted or unsubstituted non-aromatic carbocyclylureido, substituted or unsubstituted aromatic heterocyclylureido, substituted or unsubstituted non-aromatic heterocyclylureido, substituted or unsubstituted aromatic carbocyclyloxycarbonylamino, substituted or unsubstituted non-aromatic carbocyclyloxycarbonylamino, substituted or unsubstituted aromatic heterocyclyloxycarbonylamino, or substituted or unsubstituted non-aromatic heterocyclyloxycarbonylamino;

provided that
i) Ring A is not unsubstituted benzene;
ii) $R^1$ is not unsubstituted methyl, unsubstituted n-pentyl, substituted or unsubstituted phenyl, or tetrahydrofuranyl substituted with two hydroxy groups and optionally substituted with one or more and same or different substituent(s), provided that the following compounds are excluded:

[Chemical Formula 4]

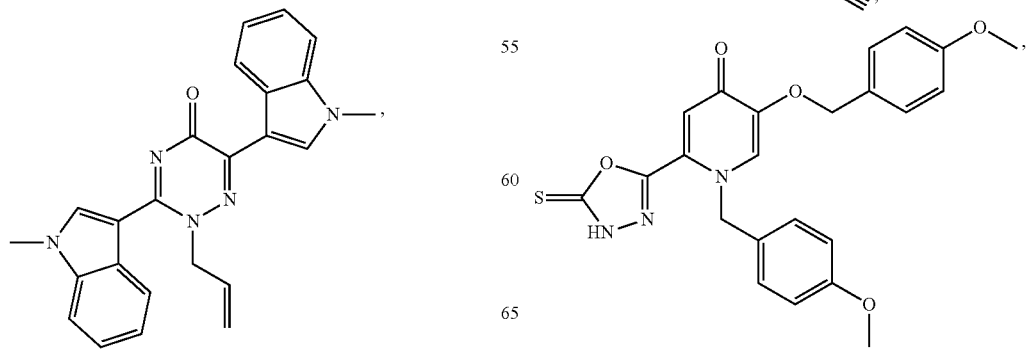

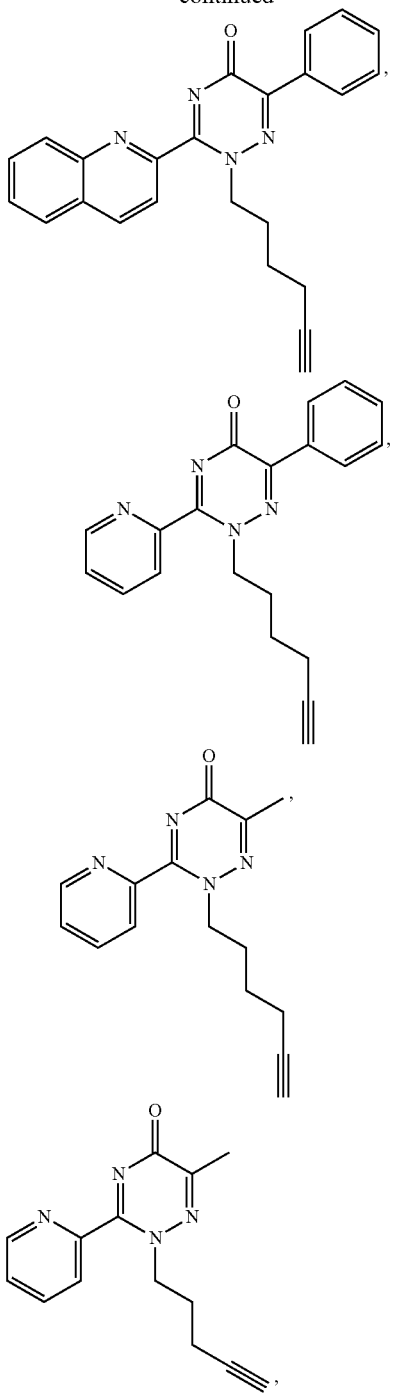

-continued
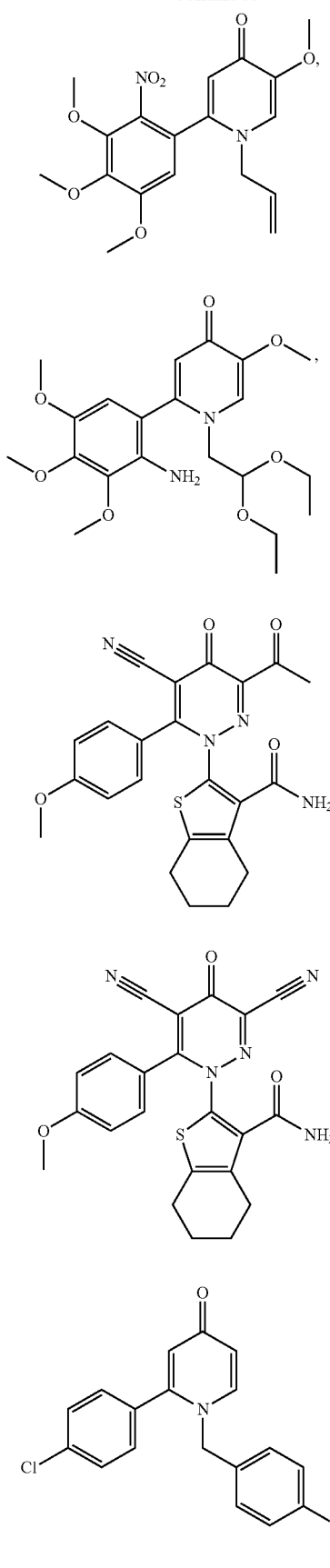
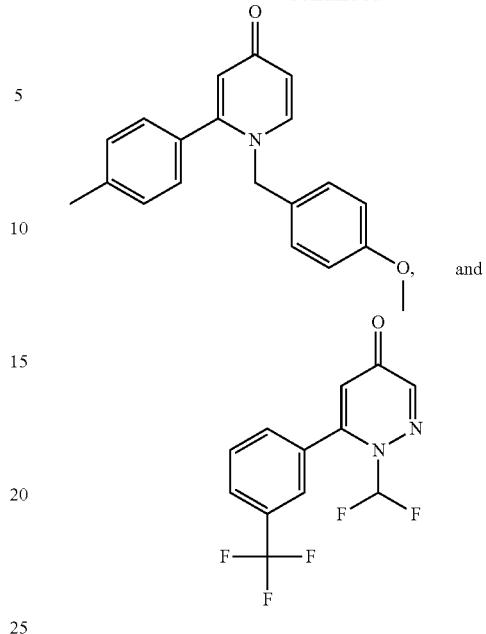
or a pharmaceutically acceptable salt thereof.
(2) The compound according to the above (1) or (1'), wherein
[Chemical Formula 5]
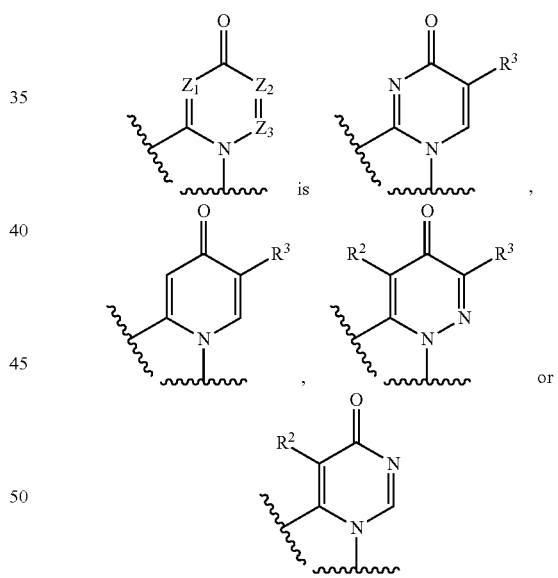
or a pharmaceutically acceptable salt thereof.
(3) The compound according to the above (1), (1') or (2), wherein
[Chemical Formula 6]
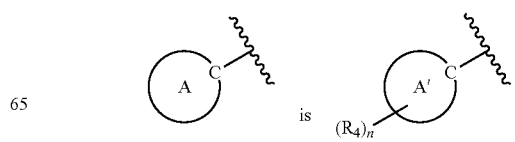

Ring A' is an aromatic carbocycle, a non-aromatic carbocycle, an aromatic heterocycle, or a non-aromatic heterocycle;

$R^4$ is each independently halogen, amino, carbamoyl, sulfamoyl, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkenylcarbonyl, substituted or unsubstituted monoalkylamino, substituted or unsubstituted dialkylamino, substituted or unsubstituted monoalkylcarbonylamino, substituted or unsubstituted monoalkylsulfonylamino, substituted or unsubstituted alkylsulfanyl, substituted or unsubstituted alkenylsulfanyl, substituted or unsubstituted alkynylsulfanyl, substituted or unsubstituted monoalkylcarbamoyl, substituted or unsubstituted dialkylcarbamoyl, substituted or unsubstituted monoalkylsulfamoyl, substituted or unsubstituted dialkylsulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylcarbonylamino, substituted or unsubstituted non-aromatic carbocyclylcarbonylamino, substituted or unsubstituted aromatic heterocyclylcarbonylamino, substituted or unsubstituted non-aromatic heterocyclylcarbonylamino, substituted or unsubstituted aromatic carbocyclylcarbamoyl, substituted or unsubstituted non-aromatic carbocyclylcarbamoyl, substituted or unsubstituted aromatic heterocyclylcarbamoyl, or substituted or unsubstituted non-aromatic heterocyclylcarbamoyl; and n is an integer from 0 to 4 or a pharmaceutically acceptable salt thereof.

(4)

The compound according to the above (3), wherein $R^4$ is each independently halogen, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or a pharmaceutically acceptable salt thereof.

(5)

The compound according to the above (3) or (4), wherein Ring A' is an aromatic carbocycle, or a pharmaceutically acceptable salt thereof.

(6)

The compound according to the above (1), (1'), or (2), wherein

[Chemical Formula 7]

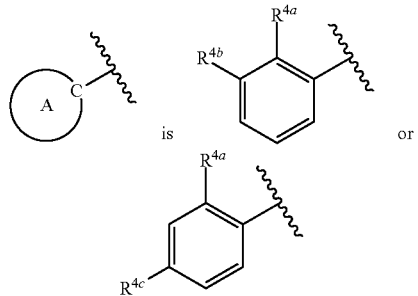

$R^{4a}$, $R^{4b}$ and $R^{4c}$ are each independently halogen, amino, carbamoyl, sulfamoyl, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkenylcarbonyl, substituted or unsubstituted monoalkylamino, substituted or unsubstituted dialkylamino, substituted or unsubstituted monoalkylcarbonylamino, substituted or unsubstituted monoalkylsulfonylamino, substituted or unsubstituted alkylsulfanyl, substituted or unsubstituted alkenylsulfanyl, substituted or unsubstituted alkynylsulfanyl, substituted or unsubstituted monoalkylcarbamoyl, substituted or unsubstituted dialkylcarbamoyl, substituted or unsubstituted monoalkylsulfamoyl, substituted or unsubstituted dialkylsulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylcarbonylamino, substituted or unsubstituted non-aromatic carbocyclylcarbonylamino, substituted or unsubstituted aromatic heterocyclylcarbonylamino, substituted or unsubstituted non-aromatic heterocyclylcarbonylamino, substituted or unsubstituted aromatic carbocyclylcarbamoyl, substituted or unsubstituted non-aromatic carbocyclylcarbamoyl, substituted or unsubstituted aromatic heterocyclylcarbamoyl, or substituted or unsubstituted non-aromatic heterocyclylcarbamoyl; or $R^{4a}$ and $R^{4b}$ is taken together with the adjacent carbon atoms to form a substituted or unsubstituted aromatic carbocycle, a substituted or unsubstituted non-aromatic carbocycle, a substituted or unsubstituted aromatic heterocycle, or a substituted or unsubstituted non-aromatic heterocycle, or a pharmaceutically acceptable salt thereof.

(7)
The compound according to the above (6),
wherein $R^{4a}$, $R^{4b}$ and $R^{4c}$ are each independently halogen, substituted or unsubstituted alkyl, substituted or unsubstituted alkenyl, substituted or unsubstituted alkynyl, substituted or unsubstituted alkyloxy, substituted or unsubstituted alkenyloxy, or substituted or unsubstituted alkynyloxy.
or a pharmaceutically acceptable salt thereof.

(8)
The compound according to any one of the above (1), (1') and (2) to (7), wherein $R^1$ is substituted or unsubstituted alkyl, substituted or unsubstituted alkenyl, or substituted or unsubstituted alkynyl,
or a pharmaceutically acceptable salt thereof.

(9)
The compound according to any one of the above (1), (1') and (2) to (7), wherein $R^1$ is substituted alkyl,
or a pharmaceutically acceptable salt thereof.

(10)
The compound according to any one of the above (1), (1') and (2) to (7), wherein $R^1$ is a group represented by the formula: —$(C(R^{5a})(R^{5b}))$m-$R^{1a}$;
$R^1$ is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;
$R^{5a}$ is each independently a hydrogen atom, halogen, or substituted or unsubstituted alkyl;
$R^{5b}$ is each independently a hydrogen atom, halogen, or substituted or unsubstituted alkyl;
$R^{5a}$ and $R^{5b}$ which are attached to the same carbon atom may be taken together with the carbon atom to which they are attached to form a substituted or unsubstituted non-aromatic carbocycle, or a substituted or unsubstituted non-aromatic heterocycle; and
m is an integer from 0 to 4,
or a pharmaceutically acceptable salt thereof.

(11)
The compound according to the above (10),
wherein $R^{1a}$ is substituted or unsubstituted aromatic carbocyclyl, or substituted or unsubstituted aromatic heterocyclyl,
or a pharmaceutically acceptable salt thereof.

(12)
The compound according to the above (10),
wherein in is an integer from 1 to 4,
or a pharmaceutically acceptable salt thereof.

(13)
The compound according to the above (10) or (11).
wherein m is 1.
or a pharmaceutically acceptable salt thereof.

(14)
The compound according to any one of the above (10) to (13),
wherein $R^{5a}$ and $R^{5b}$ are each independently a hydrogen atom, halogen, or substituted or unsubstituted alkyl.
or a pharmaceutically acceptable salt thereof.

(15)
The compound according to any one of the above (1), (1') and (2) to (14), wherein $R^3$ is a hydrogen atom, halogen, amino, carbamoyl, sulfamoyl, cyano, ureido, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted monoalkylamino, substituted or unsubstituted dialkylamino, substituted or unsubstituted monoalkylcarbonylamino, substituted or unsubstituted monoalkylsulfonylamino, substituted or unsubstituted alkylsulfanyl, substituted or unsubstituted alkenylsulfanyl, substituted or unsubstituted alkynylsulfanyl, substituted or unsubstituted alkyloxycarbonylamino, substituted or unsubstituted alkenyloxycarbonylamino, substituted or unsubstituted alkynyloxycarbonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, or substituted or unsubstituted non-aromatic heterocyclylamino,
or a pharmaceutically acceptable salt thereof.

(16)
The compound according to any one of the above (1), (1') and (2) to (15),
wherein $R^2$ is a hydrogen atom,
or a pharmaceutically acceptable salt thereof.

(17)
A pharmaceutical composition comprising the compound according to any one of the above (1), (1') and (2) to (16), or a pharmaceutically acceptable salt thereof.

(18)
The pharmaceutical composition according to the above (17) having an antagonistic activity for the P2X7 receptor.

(19)
The compound according to any one of the above (1), (1') and (2) to (16), or a pharmaceutically acceptable salt thereof for use in treating and/or preventing a disease associated with the P2X7 receptor.

(20)
A method for treating and/or preventing a disease associated with the P2X7 receptor characterized by administering the compound according to any one of the above (1), (1') and (2) to (16), or a pharmaceutically acceptable salt thereof.

(21)
Use of the compound according to any one of the above (1), (1') and (2) to (16), or a pharmaceutically acceptable salt thereof for manufacture of a medicament for treating and/or preventing a disease associated with the P2X7 receptor.

(101) A pharmaceutical composition comprising the compound according to any one of the above (1), (1') and (2) to (16), or a pharmaceutically acceptable salt thereof, for oral administration.

(102) The pharmaceutical composition according to (101), which is a tablet, powder, granule, capsule, pill, film, suspension, emulsion, elixir, syrup, lemonade, spirit, aromatic water, extract, decoction or tincture.

(103) The pharmaceutical composition according to (102), which is a sugar-coated tablet, film-coated tablet, enteric-coated tablet, sustained-release tablet, troche tablet, sublingual tablet, buccal tablet, chewable tablet, orally dispersing tablet, dry syrup, soft capsule, micro capsule or sustained-release capsule.

(104) A pharmaceutical composition comprising the compound according to any one of the above (1), (1') and (2) to (16), or a pharmaceutically acceptable salt thereof, for parenteral administration.

(105) The pharmaceutical composition according to (104), for dermal, subcutaneous, intravenous, intraarterial, intramuscular, intraperitoneal, transmucosal, inhalation, transnasal, ophthalmic, inner ear or vaginal administration.
(106) The pharmaceutical composition according to (104) or (105), which is injection, infusion, eye drop, nose drop, ear drop, aerosol, inhalation, lotion, impregnation, liniment, mouthwash, enema, ointment, plaster, jelly, cream, patch, cataplasm, external powder or suppository.
(107) A pharmaceutical composition comprising the compound according to any one of the above (1), (1') and (2) to (16), or a pharmaceutically acceptable salt thereof, for a pediatric or geriatric patient.

Effect of the Invention

The compounds of the present invention have an antagonistic activity for the P2X7 receptor, and are useful as a therapeutic and/or preventive agent for diseases or conditions associated with the P2X7 receptor.

MODE FOR CARRYING OUT THE INVENTION

Terms used in this description are explained below. Each term, unless otherwise indicated, has the same meaning when it is used alone or together with other terms.

"Halogen" includes a fluorine atom, a chlorine atom, a bromine atom and an iodine atom. A fluorine atom and a chlorine atom are especially preferable.

"Alkyl" includes a C1 to C15, preferably C1 to C10, more preferably C1 to C6 and further preferably C1 to C4 linear or branched hydrocarbon group. For example, it includes methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl, n-decyl and the like.

A preferred embodiment of "alkyl" is methyl, ethyl, n-propyl, isopropyl, n-butyl, isobutyl, sec-butyl, tert-butyl or n-pentyl. A more preferred embodiment is methyl, ethyl, n-propyl, isopropyl or tert-butyl.

"Alkenyl" includes a C2 to C15, preferably C2 to C10, more preferably C2 to C6 and further preferably C2 to C4 linear or branched hydrocarbon group having one or more double bond(s) at any position(s). For example, it includes vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, pentadecenyl and the like.

A preferred embodiment of "alkenyl" is vinyl, allyl, propenyl, isopropenyl or butenyl.

"Alkynyl" includes a C2 to C10, preferably C2 to C8, more preferably C2 to C6 and further preferably C2 to C4 linear or branched hydrocarbon group having one or more triple bond(s) at any position(s). Furthermore, it may have double bond(s) at any position(s). For example, it includes ethynyl, propynyl, butynyl, pentynyl, hexynyl, heptynyl, octynyl, nonynyl, decynyl and the like.

A preferred embodiment of "alkynyl" is ethynyl, propynyl, butynyl or pentynyl.

"Alkylene" includes a C1 to C15, preferably C1 to C10, more preferably C1 to C6 and further preferably C1 to C4 liner or branched bivalent hydrocarbon group. For example, it includes methylene, ethylene, trimethylene, propylene, tetramethylene, pentamethylene, hexamethylene and the like.

"Alkenylene" includes a C2 to C15, preferably C2 to C10, more preferably C2 to C6 and further preferably C2 to C4 liner or branched bivalent hydrocarbon group having one or more double bond(s) at any position(s). For example, it includes vinylene, prenylene, butenylene, pentenylene and the like.

"Alkynylene" includes a C2 to C15, preferably C2 to C10, more preferably C2 to C6 and further preferably C2 to C4 liner or branched bivalent hydrocarbon group having one or more triple bond(s) at any position(s). Furthermore, it may have double bond(s) at any position(s). For example, it includes ethynylene, propynylene, butynylene, pentynylene, hexynylene and the like.

"Aromatic carbocycle" means a cyclic aromatic hydrocarbon ring which is monocyclic or polycyclic having two or more rings. For example, it includes benzene, naphthalene, anthracene, phenanthrene and the like.

A preferred embodiment of "aromatic carbocycle" is benzene.

"Aromatic carbocyclyl" means a cyclic aromatic hydrocarbon group which is monocyclic or polycyclic having two or more rings. For example, it includes phenyl, naphthyl, anthryl, phenanthryl and the like.

A preferred embodiment of "aromatic carbocyclyl" is phenyl.

"Non-aromatic carbocycle" means a cyclic saturated hydrocarbon ring or a cyclic unsaturated non-aromatic hydrocarbon ring, which is monocyclic or polycyclic having two or more rings, "Non-aromatic carbocycle", which is polycyclic having two or more rings, includes a fused ring wherein a non-aromatic carbocycle, which is monocyclic or polycyclic having two or more rings, is fused with a ring of the above "aromatic carbocycle".

In addition, the "non-aromatic carbocycle" also includes a ring having a bridge or a ring to form a spiro ring.

A non-aromatic carbocycle which is monocyclic is preferably C3 to C16, more preferably C3 to C12 and further preferably C4 to C8 carbocycle. For example, it includes cyclopropane, cyclobutane, cyclopentane, cyclohexane, cycloheptane, cyclooctane, cyclononane, cyclodecane, cyclopropene, cyclobutene, cyclopentene, cyclohexene, cycloheptene, cyclohexadiene and the like.

A non-aromatic carbocycle which is polycyclic having two or more rings includes, for example, indane, indene, acenaphthalene, tetrahydronaphthalene, fluorene and the like.

"Non-aromatic carbocyclyl" means a cyclic saturated hydrocarbon group or a cyclic unsaturated non-aromatic hydrocarbon group, which is monocyclic or polycyclic having two or more rings, "Non-aromatic carbocyclyl", which is polycyclic having two or more rings, includes a fused ring group wherein a non-aromatic carbocyclyl, which is monocyclic or polycyclic having two or more rings, is fused with a ring of the above "aromatic carbocyclyl".

In addition, the "non-aromatic carbocyclyl" also includes a group having a bridge or a group to form a spiro ring as follows:

[Chemical Formula 8]

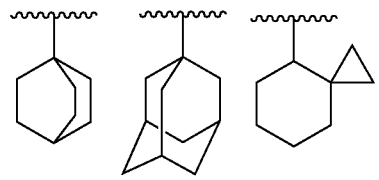

A non-aromatic carbocyclyl which is monocyclic is preferably C3 to C16, more preferably C3 to C12 and further preferably C4 to C8 carbocyclyl. For example, it includes cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptenyl, cyclohexadienyl and the like.

A non-aromatic carbocyclyl which is polycyclic having two or more rings includes, for example, indanyl, indenyl, acenaphthyl, tetrahydronaphthyl, fluorenyl and the like.

"Aromatic heterocycle" means an aromatic ring, which is monocyclic or polycyclic having two or more rings, containing one or more and same or different of heteroatom(s) selected independently from O, S and N.

"Aromatic heterocycle", which is polycyclic having two or more rings, includes a fused ring wherein an aromatic heterocycle, which is monocyclic or polycyclic having two or more rings, is fused with a ring of the above "aromatic carbocycle".

An aromatic heterocycle which is monocyclic is preferably a 5- to 8-membered and more preferably 5- to 6-membered ring. For example, it includes pyrrole, imidazole, pyrazole, pyridine, pyridazine, pyrimidine, pyrazine, triazole, triazine, tetrazole, furan, thiophene, isoxazole, oxazole, oxadiazole, isothiazole, thiazole, thiadiazole and the like.

An aromatic heterocycle which is bicyclic includes, for example, indole, isoindole, indazole, indolizine, quinoline, isoquinoline, cinnoline, phthalazine, quinazoline, naphthyridine, quinoxaline, purine, pteridine, benzimidazole, benzisoxazole, benzoxazole, benzoxadiazole, benzisothiazole, benzothiazole, benzothiadiazole, benzofuran, isobenzofuran, benzothiophene, benzotriazole, imidazopyridine, triazolopyridine, imidazothiazole, pyrazinopyridazine, oxazolopyridine, thiazolopyridine and the like.

An aromatic heterocycle which is polycyclic having three or more rings includes, for example, carbazole, acridine, xanthene, phenothiazine, phenoxathiine, phenoxazine, dibenzofuran and the like.

"Aromatic heterocyclyl" means an aromatic cyclyl, which is monocyclic or polycyclic having two or more rings, containing one or more and same or different of heteroatom(s) selected independently from O, S and N.

"Aromatic heterocyclyl", which is polycyclic having two or more rings, includes a fused ring group wherein an aromatic heterocyclyl, which is monocyclic or polycyclic having two or more rings, is fused with a ring of the above "aromatic carbocyclyl".

An aromatic heterocyclyl which is monocyclic is preferably a 5- to 8-membered and more preferably 5- to 6-membered ring. For example, it includes pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl, thiadiazolyl and the like.

An aromatic heterocyclyl which is bicyclic includes, for example, indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl, thiazolopyridyl and the like.

An aromatic heterocyclyl which is polycyclic having three or more rings includes, for example, carbazolyl, acridinyl, xanthenyl, phenothiazinyl, phenoxathiinyl, phenoxazinyl, dibenzofuryl and the like.

"Non-aromatic heterocycle" means a non-aromatic ring, which is monocyclic or polycyclic having two or more rings, containing one or more and same or different of heteroatom(s) selected independently from O, S and N.

"Non-aromatic heterocycle", which is polycyclic having two or more rings, includes a fused ring wherein a non-aromatic heterocycle, which is monocyclic or polycyclic having two or more ring(s), is fused with a ring of the above "aromatic carbocycle", "non-aromatic carbocycle" and/or "aromatic heterocycle".

In addition, the "non-aromatic heterocycle" also includes a ring having a bridge or a ring to form a spiro ring.

A non-aromatic heterocycle which is monocyclic is preferably a 3- to 8-membered and more preferably 5- to 6-membered ring. For example, it includes dioxane, thiirane, oxirane, oxetane, oxathiolane, azetidine, thiane, thiazolidine, pyrrolidine, pyrroline, imidazolidine, imidazoline, pyrazolidine, pyrazoline, piperidine, piperazine, morpholine, thiomorpholine, dihydropyridine, tetrahydropyridine, tetrahydrofuran, tetrahydropyrane, dihydrothiazole, tetrahydrothiazole, tetrahydroisothiazole, dihydrooxazine, hexahydroazepine, tetrahydrodiazepine, tetrahydropyridazine, hexahydropyrimidine, dioxolane, dioxazine, aziridine, dioxoline, oxepane, thiolane, thiine, thiazine and the like.

A non-aromatic heterocycle which is polycyclic having two or more rings includes, for example, indoline, isoindoline, chromane, isochromane and the like.

"Non-aromatic heterocyclyl" means a non-aromatic cyclyl, which is monocyclic or polycyclic having two or more rings, containing one or more and same or different of heteroatom(s) selected independently from O, S and N.

"Non-aromatic heterocyclyl", which is polycyclic having two or more rings, includes a fused ring group wherein a non-aromatic heterocycle, which is monocyclic or polycyclic having two or more ring(s), is fused with a ring of the above "aromatic carbocyclyl", "non-aromatic carbocyclyl" and/or "aromatic heterocyclyl".

In addition, the "non-aromatic heterocyclyl" also includes a group having a bridge or a group to form a spiro ring as follows:

[Chemical Formula 9]

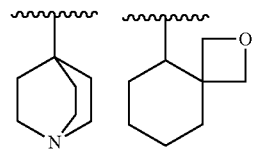

A non-aromatic heterocyclyl which is monocyclic is preferably a 3- to 8-membered and more preferably 5- to 6-membered ring. For example, it includes dioxanyl, thiiranyl, oxiranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidinyl, piperazinyl, morpholinyl, morpholino, thiomorpholinyl, thiomorpholino, dihydropyridinyl, tetrahydropyridinyl, tetrahydrofuryl, tetrahydropyranyl, dihydrothiazolinyl, tetrahydrothiazolinyl, tetrahydroisothiazolinyl, dihydrooxazinyl, hexahydroazepinyl, tetrahydrodiazepinyl, tetrahydropyridazinyl, hexahydropyrimidinyl, dioxolanyl, dioxazinyl, aziridinyl, dioxolinyl, oxepanyl, thiolanyl, thiinyl, thiazinyl and the like.

A non-aromatic heterocyclyl which is polycyclic having two or more rings includes, for example, indolinyl, isoindolinyl, chromanyl, isochromanyl and the like.

"Hydroxyalkyl" means a group wherein hydrogen atom(s) attached to a carbon atom(s) of the above "alkyl" is replaced with one or more hydroxyl group(s). For example, it includes hydroxymethyl, 1-hydroxyethyl, 2-hydroxyethyl, 1-hydroxypropyl, 2-hydroxypropyl, 1,2-hydroxyethyl and the like.

A preferred embodiment of "hydroxyalkyl" is hydroxymethyl.

"Alkyloxy" means a group wherein the above "alkyl" is bonded to an oxygen atom. For example, it includes methyloxy, ethyloxy, n-propyloxy, isopropyloxy, n-butyloxy, tert-butyloxy, isobutyloxy, sec-butyloxy, pentyloxy, isopentyloxy, hexyloxy and the like.

A preferred embodiment of "alkyloxy" is methyloxy, ethyloxy, n-propyloxy, isopropyloxy or tert-butyloxy.

"Alkenyloxy" means a group wherein the above "alkenyl" is bonded to an oxygen atom. For example, it includes vinyloxy, allyloxy, 1-propenyloxy, 2-butenyloxy, 2-pentenyloxy, 2-hexenyloxy, 2-heptenyloxy, 2-octenyloxy and the like.

"Alkynyloxy" means a group wherein the above "alkynyl" is bonded to an oxygen atom. For example, it includes ethynyloxy, 1-propynyloxy, 2-propynyloxy, 2-butynyloxy, 2-pentynyloxy, 2-hexynyloxy, 2-heptynyloxy, 2-octynyloxy and the like.

"Haloalkyl" means a group wherein one or more "halogen" described above is bonded to the above "alkyl". For example, it includes monofluoromethyl, monofluoroethyl, monofluoropropyl, 2,2,3,3,3-pentafluoropropyl, monochloromethyl, trifluoromethyl, trichloromethyl, 2,2,2-trifluoroethyl, 2,2,2-trichloroethyl, 1,2-dibromoethyl, 1,1,1-trifluoropropane-2-yl and the like.

A preferred embodiment of "haloalkyl" is trifluoromethyl or trichloromethyl.

"Haloalkyloxy" means a group wherein the above "haloalkyl" is bonded to an oxygen atom. For example, it includes monofluoromethoxy, monofluoroethoxy, trifluoromethoxy, trichloromethoxy, trifluoroethoxy, trichloroethoxy and the like.

A preferred embodiment of "haloalkyloxy" is trifluoromethoxy or trichloromethoxy.

"Alkylcarbonyl" means a group wherein the above "alkyl" is bonded to a carbonyl group. For example, it includes methylcarbonyl, ethylcarbonyl, propylcarbonyl, isopropylcarbonyl, tert-butylcarbonyl, isobutylcarbonyl, sec-butylcarbonyl, penthylcarbonyl, isopenthylcarbonyl, hexylcarbonyl and the like.

A preferred embodiment of "alkylcarbonyl" is methylcarbonyl, ethylcarbonyl or n-propylcarbonyl.

"Alkenylcarbonyl" means a group wherein the above "alkenyl" is bonded to a carbonyl group. For example, it includes ethylenylcarbonyl, propenylcarbonyl and the like.

"Alkynylcarbonyl" means a group wherein the above "alkynyl" is bonded to a carbonyl group. For example, it includes ethynylcarbonyl, propynylcarbonyl and the like.

"Monoalkylamino" means a group wherein a hydrogen atom attached to a nitrogen atom of an amino group is replaced with the above "alkyl". For example, it includes methylamino, ethylamino, isopropylamino and the like.

A preferred embodiment of "monoalkylamino" is methylamino or ethylamino.

"Dialkylamino" means a group wherein two hydrogen atoms attached to a nitrogen atom of an amino group are replaced with two "alkyl" described above. These two alkyl groups may be the same or different. For example, it includes dimethylamino, diethylamino, N,N-diisopropylamino, N-methyl-N-ethylamino, N-isopropyl-N-ethylamino and the like.

A preferred embodiment of "dialkylamino" is dimethylamino or diethylamino.

"Alkylsulfonyl" means a group wherein the above "alkyl" is bonded to a sulfonyl group. For example, it includes methylsulfonyl, ethylsulfonyl, propylsulfonyl, isopropylsulfonyl, tert-butylsulfonyl, isobutylsulfonyl, sec-butylsulfonyl and the like.

A preferred embodiment of "alkylsulfonyl" is methylsulfonyl or ethylsulfonyl.

"Monoalkylcarbonylamino" means a group wherein a hydrogen atom bonded to a nitrogen atom of an amino group is replaced with the above "alkylcarbonyl". For example, it includes methylcarbonylamino, ethylcarbonylamino, propylcarbonylamino, isopropylcarbonylamino, tert-butylcarbonylamino, isobutylcarbonylamino, sec-butylcarbonylamino and the like.

Furthermore, the amino part of "monoalkylcarbonylamino" may be substituted with unsubstituted alkyl or alkyl substituted with one or more substituent(s) selected from halogen, hydroxy, or alkyloxy.

A preferred embodiment of "monoalkylcarbonylamino" is methylcarbonylamino or ethylcarbonylamino.

"Monoalkylsulfonylamino" means a group wherein a hydrogen atom bonded to a nitrogen atom of an amino group is replaced with the above "alkylsulfonyl". For example, it includes methylsulfonylamino, ethylsulfonylamino, propylsulfonylamino, isopropylsulfonylamino, tert-butylsulfonylamino, isobutylsulfonylamino, sec-butylsulfonylamino and the like.

Furthermore, the amino part of "monoalkylsulfonylamino" may be substituted with unsubstituted alkyl or alkyl substituted with one or more substituent(s) selected from halogen, hydroxy, or alkyloxy.

A preferred embodiment of "monoalkylsulfonylamino" is methylsulfonylamino or ethylsulfonylamino.

"Alkyloxycarbonyl" means a group wherein the above "alkyloxy" is bonded to a carbonyl group. For example, it includes methyloxycarbonyl, ethyloxycarbonyl, propyloxycarbonyl, isopropyloxycarbonyl, tert-butyloxycarbonyl, isobutyloxycarbonyl, sec-butyloxycarbonyl, penthyloxycarbonyl, isopenthyloxycarbonyl, hexyloxycarbonyl and the like.

A preferred embodiment of "alkyloxycarbonyl" is methyloxycarbonyl, ethyloxycarbonyl or propyloxycarbonyl.

"Alkenyloxycarbonyl" means a group wherein the above "alkenyloxy" is bonded to a carbonyl group. For example, it includes ethylenyloxycarbonyl, propenyloxycarbonyl and the like.

"Alkynyloxycarbonyl" means a group wherein the above "alkynyloxy" is bonded to a carbonyl group. For example, it includes ethynyloxycarbonyl, propynyloxycarbonyl and the like.

"Alkylsulfanyl" means a group wherein a hydrogen atom bonded to a sulfur atom of a sulfanyl group is replaced with the above "alkyl". For example, it includes methylsulfanyl, ethylsulfanyl, n-propylsulfanyl, isopropylsulfanyl and the like.

"Alkenylsulfanyl" means a group wherein a hydrogen atom bonded to a sulfur atom of a sulfanyl group is replaced with the above "alkenyl". For example, it includes ethylenylsulfanyl, propenylsulfanyl and the like.

"Alkynylsulfanyl" means a group wherein a hydrogen atom bonded to a sulfur atom of a sulfanyl group is replaced with the above "alkynyl". For example, it includes ethynylsulfanyl, propynylsulfanyl and the like.

"Monoalkylcarbamoyl" means a group wherein a hydrogen atom bonded to a nitrogen atom of a carbamoyl group is replaced with the above "alkyl". For example, it includes methylcarbamoyl, ethylcarbamoyl and the like.

"Dialkylcarbamoyl" means a group wherein two hydrogen atoms bonded to a nitrogen atom of a carbamoyl group are replaced with two "alkyl" described above. Two alkyl groups may be the same or different. For example, it includes dimethylcarbamoyl, diethylcarbamoyl and the like.

"Monoalkylsulfamoyl" means a group wherein a hydrogen atom bonded to a nitrogen atom of a sulfamoyl group is replaced with the above "alkyl". For example, it includes methylsulfamoyl, dimethylsulfamoyl and the like.

"Dialkylsulfamoyl" means a group wherein two hydrogen atoms bonded to a nitrogen atom of a sulfamoyl group are replaced with two "alkyl" described above. Two alkyl groups may be the same or different. For example, it includes dimethylcarbamoyl, diethylcarbamoyl and the like.

"Alkyloxycarbonylamino" means a group wherein a hydrogen atom bonded to a nitrogen atom of an amino group is replaced with the above "alkyloxycarbonyl". For example, it includes methyloxycarbonylamino, ethyloxycarbonylamino, propyloxycarbonylamino and the like.

Furthermore, the amino part of "alkyloxycarbonylamino" may be substituted with unsubstituted alkyl or alkyl substituted with one or more substituent(s) selected from halogen, hydroxy, or alkyloxy.

"Alkenyloxycarbonylamino" means a group wherein a hydrogen atom bonded to a nitrogen atom of an amino group is replaced with the above "alkenyloxycarbonyl". For example, it includes ethylenyloxycarbonylamino, propenyloxycarbonylamino and the like.

Furthermore, the amino part of "alkenyloxycarbonylamino" may be substituted with unsubstituted alkyl or alkyl substituted with one or more substituent(s) selected from halogen, hydroxy, or alkyloxy.

"Alkynyloxycarbonylamino" means a group wherein a hydrogen atom bonded to a nitrogen atom of an amino group is replaced with the above "alkynyloxycarbonyl". For example, it includes ethynyloxycarbonylamino, propynyloxycarbonylamino and the like.

Furthermore, the amino part of "alkynyloxycarbonylamino" may be substituted with unsubstituted alkyl or alkyl substituted with one or more substituent(s) selected from halogen, hydroxy, or alkyloxy.

"Alkylureido" means a group wherein one or two hydrogen atom(s) bonded to a nitrogen atom of an ureido group is replaced with the above "alkyl".
For example, it includes groups of the formula of.

[Chemical Formula 10]

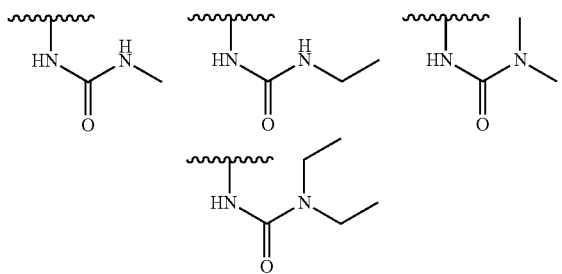

and the like.

"Alkenylureido" means a group wherein a hydrogen atom bonded to a nitrogen atom of an ureido group is replaced with the above "alkenyl".

"Alkynylureido" means a group wherein a hydrogen atom bonded to a nitrogen atom of an ureido group is replaced with the above "alkynyl".

The alkyl part of "aromatic carbocyclylalkyl", "non-aromatic carbocyclylalkyl", "aromatic heterocyclylalkyl", "non-aromatic heterocyclylalkyl", "aromatic carbocyclylalkyloxy", "non-aromatic carbocyclylalkyloxy", "aromatic heterocyclylalkyloxy", "non-aromatic heterocyclylalkyloxy", "aromatic carbocyclylalkyloxycarbonyl", "non-aromatic carbocyclylalkyloxycarbonyl", "aromatic heterocyclylalkyloxycarbonyl", "non-aromatic heterocyclylalkyloxycarbonyl", "aromatic carbocyclylalkyloxyalkyl", "non-aromatic carbocyclylalkyloxyalkyl", "aromatic heterocyclylalkyloxyalkyl", "non-aromatic heterocyclylalkyloxyalkyl", "aromatic carbocyclylalkylamino", "non-aromatic carbocyclylalkylamino", "aromatic heterocyclylalkylamino" or "non-aromatic heterocyclylalkylamino" is also same as the above "alkyl".

"Aromatic carbocyclylalkyl" means an alkyl substituted with one or more "aromatic carbocyclyl" described above. For example, it includes benzyl, phenethyl, phenylpropynyl, benzhydryl, trityl, naphthylmethyl, a group of the formula of

[Chemical Formula 11]

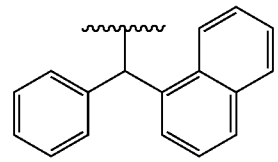

and the like.

A preferred embodiment of "aromatic carbocyclylalkyl" is benzyl, phenethyl or benzhydryl.

"Non-aromatic carbocyclylalkyl" means an alkyl substituted with one or more "non-aromatic carbocyclyl" described above, "Non-aromatic carbocyclylalkyl" also includes "non-aromatic carbocyclylalkyl" wherein the alkyl part is substituted with the above "aromatic carbocyclyl". For example, it includes cyclopropylmethyl, cyclobutylmethyl, cyclopenthylmethyl, cyclohexylmethyl, a group of the formula of

[Chemical Formula 12]

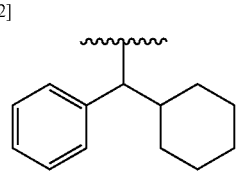

and the like.

"Aromatic heterocyclylalkyl" means an alkyl substituted with one or more "aromatic heterocyclyl" described above, "Aromatic heterocyclylalkyl" also includes "aromatic heterocyclylalkyl" wherein the alkyl part is substituted with the above "aromatic carbocyclyl" and/or "non-aromatic carbocyclyl". For example, it includes pyridylmethyl, furanylmethyl, imidazolylmethyl, indolylmethyl, benzothiophenylmethyl, oxazolylmethyl, isoxazolylmethyl, thiazolylmethyl, isothiazolylmethyl, pyrazolylmethyl, isopyrazolylmethyl, pyrrolidinylmethyl, benzoxazolylmethyl, groups of the formula of

[Chemical Formula 13]

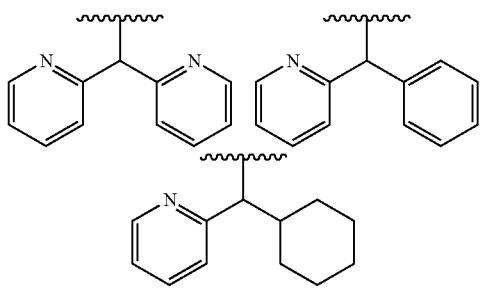

and the like.

"Non-aromatic heterocyclylalkyl" means an alkyl substituted with one or more "non-aromatic heterocyclyl" described above, "Non-aromatic heterocyclylalkyl" also includes "non-aromatic heterocyclylalkyl" wherein the alkyl part is substituted with the above "aromatic carbocyclyl", "non-aromatic carbocyclyl" and/or "aromatic heterocyclyl". For example, it includes tetrahydropyranylmethyl, morpholinylethyl, piperidinylmethyl, piperazinylmethyl, groups of the formula of

[Chemical Formula 14]

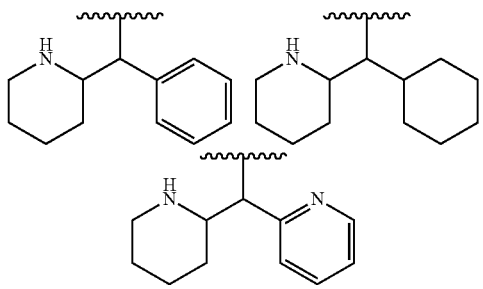

and the like.

"Aromatic carbocyclylalkyloxy" means an alkyloxy substituted with one or more "aromatic carbocyclyl" described above. For example, it includes benzyloxy, phenethyloxy, phenylpropynyloxy, benzhydryloxy, trityloxy, naphthylmethyloxy, a group of the formula of

[Chemical Formula 15]

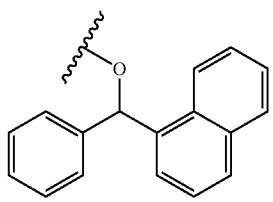

and the like.

"Non-aromatic carbocyclylalkyloxy" means an alkyloxy substituted with one or more "non-aromatic carbocyclyl" described above, "Non-aromatic carbocyclylalkyloxy" also includes "non-aromatic carbocyclylalkyloxy" wherein the alkyl part is substituted with the above "aromatic carbocyclyl". For example, it includes cyclopropylmethyloxy, cyclobutylmethyloxy, cyclopenthylmethyloxy, cyclohexylmethyloxy, a group of the formula of

[Chemical Formula 16]

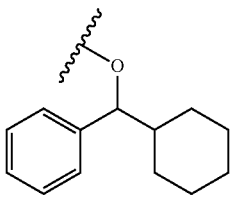

and the like.

"Aromatic heterocyclylalkyloxy" means an alkyloxy substituted with one or more "aromatic heterocyclyl" described above, "Aromatic heterocyclylalkyloxy" also includes "aromatic heterocyclylalkyloxy" wherein the alkyl part is substituted with the above "aromatic carbocyclyl" and/or "non-aromatic carbocyclyl". For example, it includes pyridylmethyloxy, furanylmethyloxy, imidazolylmethyloxy, indolylmethyloxy, benzothiophenylmethyloxy, oxazolylmethyloxy, isoxazolylmethyloxy, thiazolylmethyloxy, isothiazolylmethyloxy, pyrazolylmethyloxy, isopyrazolylmethyloxy, pyrrolidinylmethyloxy, benzoxazolylmethyloxy, groups of the formula of

[Chemical Formula 17]

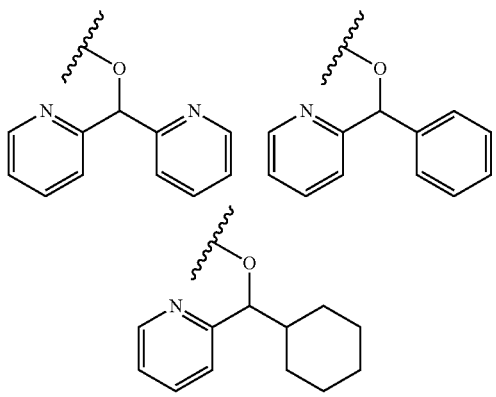

and the like.

"Non-aromatic heterocyclylalkyloxy" means an alkyloxy substituted with one or more "non-aromatic heterocyclyl" described above, "Non-aromatic heterocyclylalkyloxy" also includes "non-aromatic heterocyclylalkyloxy" wherein the alkyl part is substituted with the above "aromatic carbocyclyl", "non-aromatic carbocyclyl" and/or "aromatic heterocyclyl". For example, it includes tetrahydropyranylmethyloxy, morpholinylethyloxy, piperidinylmethyloxy, piperazinylmethyloxy, groups of the formula of

[Chemical Formula 18]

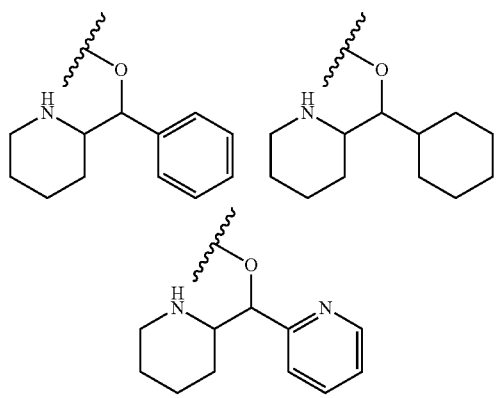

and the like.

"Aromatic carbocyclylalkyloxycarbonyl" means an alkyloxycarbonyl substituted with one or more "aromatic carbocyclyl" described above. For example, it includes benzyloxycarbonyl, phenethyloxycarbonyl, phenylpropynyloxycarbonyl, benzhydryloxycarbonyl, trityloxycarbonyl, naphthylmethyloxycarbonyl, a group of the formula of

[Chemical Formula 19]

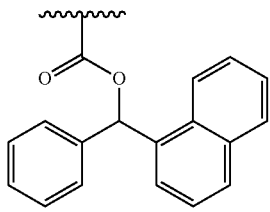

and the like.

"Non-aromatic carbocyclylalkyloxycarbonyl" means an alkyloxycarbonyl substituted with one or more "non-aromatic carbocyclyl" described above, "Non-aromatic carbocyclylalkyloxycarbonyl" also includes "non-aromatic carbocyclylalkyloxycarbonyl" wherein the alkyl part is substituted with the above "aromatic carbocyclyl". For example, it includes cyclopropylmethyloxycarbonyl, cyclobutylmethyloxycarbonyl, cyclopenthylmethyloxycarbonyl, cyclohexylmethyloxycarbonyl, a group of the formula of

[Chemical Formula 20]

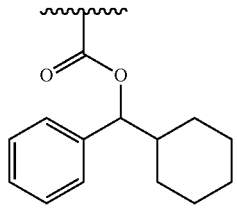

and the like.

"Aromatic heterocyclylalkyloxycarbonyl" means an alkyloxycarbonyl substituted with one or more "aromatic heterocyclyl" described above, "Aromatic heterocyclylalkyloxycarbonyl" also include "aromatic heterocyclylalkyloxycarbonyl" wherein the alkyl part is substituted with the above "aromatic carbocyclyl" and/or "non-aromatic carbocyclyl". For example, it includes pyridylmethyloxycarbonyl, furanylmethyloxycarbonyl, imidazolylmethyloxycarbonyl, indolylmethyloxycarbonyl, benzothiophenylmethyloxycarbonyl, oxazolylmethyloxycarbonyl, isoxazolylmethyloxycarbonyl, thiazolylmethyloxycarbonyl, isothiazolylmethyloxycarbonyl, pyrazolylmethyloxycarbonyl, isopyrazolylmethyloxycarbonyl, pyrrolidinylmethyloxycarbonyl, benzoxazolylmethyloxycarbonyl, groups of the formula of

[Chemical Formula 21]

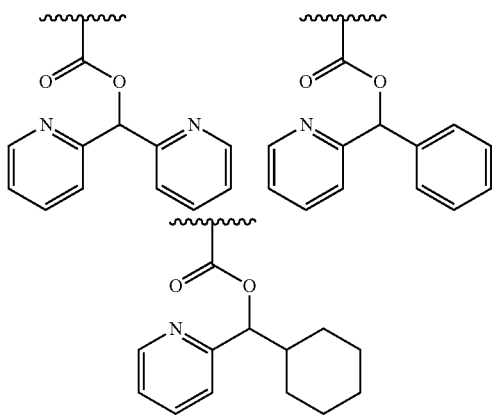

and the like.

"Non-aromatic heterocyclylalkyloxycarbonyl" means an alkyloxycarbonyl substituted with one or more "non-aromatic heterocyclyl" described above, "Non-aromatic heterocyclylalkyloxycarbonyl" also includes "non-aromatic heterocyclylalkyloxycarbonyl" wherein the alkyl part is substituted with the above "aromatic carbocyclyl", "non-aromatic carbocyclyl" and/or "aromatic heterocyclyl". For example, it includes tetrahydropyranylmethyloxy, morpholinylethyloxy, piperidinylmethyloxy, piporazinylmethyloxy, groups of the formula of

[Chemical Formula 22]

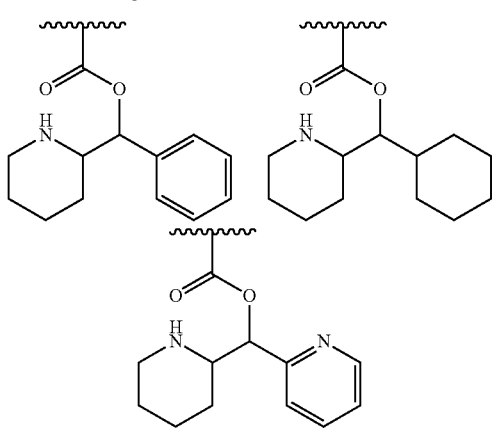

and the like.

"Aromatic carbocyclylalkyloxyalkyl" means an alkyloxyalkyl substituted with one or more "aromatic carbocyclyl"

described above. For example, it includes benzyloxymethyl, phenethyloxymethyl, phenylpropynyloxymethyl, benzhydryloxymethyl, trityloxymethyl, naphthylmethyloxymethyl, a group of the formula of

[Chemical Formula 23]

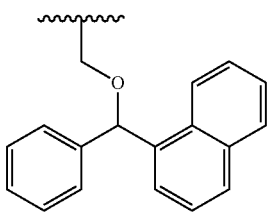

and the like.

"Non-aromatic carbocyclylalkyloxyalkyl" means an alkyloxyalkyl substituted with one or more "non-aromatic carbocyclyl" described above, "Non-aromatic carbocyclylalkyloxyalkyl" also includes "non-aromatic carbocyclylalkyloxyalkyl" wherein the alkyl part bonded to the non-aromatic carbocycle is substituted with the above "aromatic carbocyclyl". For example, it includes cyclopropylmethyloxymethyl, cyclobutylmethyloxymethyl, cyclopenthylmethyloxymethyl, cyclohexylmethyloxymethyl, a group of the formula of

[Chemical Formula 24]

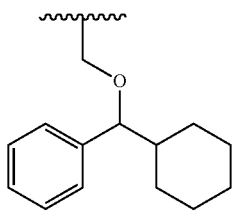

and the like.

"Aromatic heterocyclylalkyloxyalkyl" means an alkyloxyalkyl substituted with one or more "aromatic heterocyclyl" described above, "Aromatic heterocyclylalkyloxyalkyl" also includes "aromatic heterocyclylalkyloxyalkyl" wherein the alkyl part bonded to the aromatic heterocycle is substituted with the above "aromatic carbocyclyl" and/or "non-aromatic carbocyclyl". For example, it includes pyridylmethyloxymethyl, furanylmethyloxymethyl, imidazolylmethyloxymethyl, indolylmethyloxymethyl, benzothiophenylmethyloxymethyl, oxazolylcmethyloxymethyl, isoxazolylmethyloxymethyl, thiazolylmethyloxymethyl, isothiazolylmethyloxymethyl, pyrazolylmethyloxymethyl, isopyrazolylmethyloxymethyl, pyrrolidinylmethyloxymethyl, benzoxazolylmethyloxymethyl, groups of the formula of

[Chemical Formula 25]

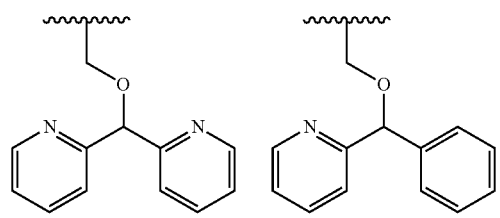

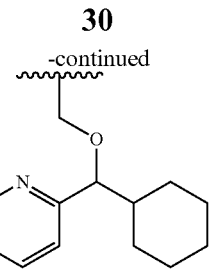

and the like.

"Non-aromatic heterocyclylalkyloxyalkyl" means an alkyloxyalkyl substituted with one or more "non-aromatic heterocyclyl" described above, "Non-aromatic heterocyclylalkyloxyalkyl" also includes "non-aromatic heterocyclylalkyloxyalkyl" wherein the alkyl part bonded to the non-aromatic heterocycle is substituted with the above "aromatic carbocyclyl", "non-aromatic carbocyclyl" and/or "aromatic heterocyclyl". For example, it includes tetrahydropyranylmethyloxymethyl, morpholinylethyloxymethyl, piperidinylmethyloxymethyl, piperazinylmethyloxymethyl, groups of the formula of

[Chemical Formula 26]

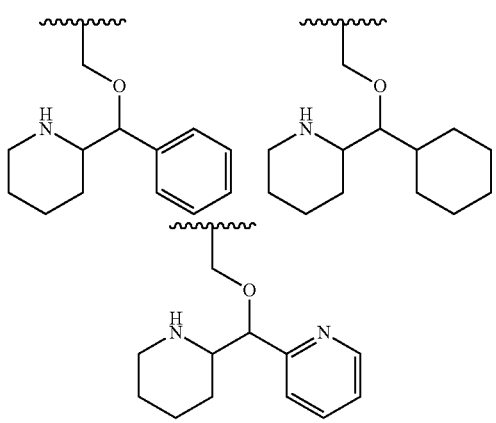

and the like.

"Aromatic carbocyclylalkylamino" means a group wherein one or two hydrogen atom(s) bonded to a nitrogen atom of an amino group is replaced with the above "aromatic carbocyclylalkyl". For example, it includes benzylamino, phenethylamino, phenylpropynylamino, benzhydrylamino, tritylamino, naphthylmethylamino, dibenzylamino and the like.

"Non-aromatic carbocyclylalkylamino" means a group wherein one or two hydrogen atom(s) bonded to a nitrogen atom of an amino group is replaced with the above "non-aromatic carbocyclylalkyl". For example, it includes cyclopropylmethylamino, cyclobutylmethylamino, cyclopenthylmethylamino, cyclohexylmethylamino and the like.

"Aromatic heterocyclylalkylamino" means a group wherein one or two hydrogen atom(s) bonded to a nitrogen atom of an amino group is replaced with the above "aromatic heterocyclylalkyl". For example, it includes pyridylmethylamino, furanylmethylamino, imidazolylmethylamino, indolylmethylamino, benzothiophenylmethylamino, oxazolylmethylamino, isoxazolylmethylamino, thiazolylmethylamino, isothiazolylmethylamino, pyrazolylmethylamino, isopyrazolylmethylamino, pyrrolidinylmethylamino, benzoxazolylmethylamino and the like.

"Non-aromatic heterocyclylalkylamino" means a group wherein one or two hydrogen atom(s) bonded to a nitrogen atom of an amino group is replaced with the above "non-aromatic heterocyclylalkyl". For example, it includes tetrahydropyranylmethylamino, morpholinylethylamino, piperidinylmethylamino, piperazinylmethylamino and the like.

The "carbocycle" part of "aromatic carbocyclyloxy", "aromatic carbocyclylamino", "aromatic carbocyclylcarbonyl", "aromatic carbocyclyloxycarbonyl", "aromatic carbocyclylsulfanyl", "aromatic carbocyclylsulfonyl", "aromatic carbocyclylcarbonylamino", "aromatic carbocyclylcarbamoyl", "aromatic carbocyclylureido", or "aromatic carbocyclyloxycarbonylamino" is same as the above "aromatic carbocyclyl".

"Aromatic carbocyclyloxy" means a group wherein "aromatic carbocycle" is bonded to an oxygen atom. For example, it includes phenyloxy, naphthyloxy and the like.

"Aromatic carbocyclylamino" means a group wherein a hydrogen atom attached to a nitrogen atom of an amino group is replaced with the "aromatic carbocycle". For example, it includes phenylamino, naphthylamino and the like.

Furthermore, the amino part of "aromatic carbocyclylamino" may be substituted with unsubstituted alkyl or alkyl substituted with one or more substituent(s) selected from halogen, hydroxy, or alkyloxy.

"Aromatic carbocyclylcarbonyl" means a group wherein "aromatic carbocycle" is bonded to a carbonyl group. For example, it includes phenylcarbonyl, naphthylcarbonyl and the like.

"Aromatic carbocyclyloxycarbonyl" means a group wherein the above "aromatic carbocyclyloxy" is bonded to a carbonyl group. For example, it includes phenyloxycarbonyl, naphthyloxycarbonyl and the like.

"Aromatic carbocyclylsulfanyl" means a group wherein a hydrogen atom bonded to a sulfur atom of a sulfanyl group is replaced with "aromatic carbocycle". For example, it includes phenylsulfanyl, naphthylsulfanyl and the like.

"Aromatic carbocyclylsulfonyl" means a group wherein "aromatic carbocycle" is bonded to a sulfonyl group. For example, it includes phenylsulfonyl, naphthylsulfonyl and the like.

"Aromatic carbocyclylcarbonylamino" means a group wherein a hydrogen atom attached to a nitrogen atom of an amino group is replaced with the above "aromatic carbocyclylcarbonyl". For example, it includes phenylcarbonylamino, naphthylcarbonylamino and the like.

Furthermore, the amino part of "aromatic carbocyclylcarbonylamino" may be substituted with unsubstituted alkyl or alkyl substituted with one or more substituent(s) selected from halogen, hydroxy, or alkyloxy.

"Aromatic carbocyclylcarbamoyl" means a group wherein a hydrogen atom attached to a nitrogen atom of a carbamoyl group is replaced with the above "aromatic carbocycle". For example, it includes phenylcarbamoyl, naphthylcarbamoyl and the like.

Furthermore, the other hydrogen atom attached to a nitrogen atom of the carbamoyl group in "aromatic carbocyclylcarbamoyl" may be replaced with unsubstituted alkyl or alkyl substituted with one or more substituent(s) selected from halogen, hydroxy, or alkyloxy.

"Aromatic carbocyclylureido" means a group wherein a hydrogen atom attached to a nitrogen atom of an ureido group is replaced with the above "aromatic carbocycle". For example, it includes phenylureido, naphthylureido and the like.

Furthermore, the other hydrogen atom attached to a nitrogen atom of the ureido group in "aromatic carbocyclylureido" may be replaced with unsubstituted alkyl or alkyl substituted with one or more substituent(s) selected from halogen, hydroxy, or alkyloxy.

"Aromatic carbocyclyloxycarbonylamino" means a group wherein a hydrogen atom attached to a nitrogen atom of an amino group is replaced with the above "aromatic carbocyclyloxycarbonyl". For example, it includes phenyloxycarbonylamino, naphthyloxycarbonylamino and the like.

Furthermore, the amino part of "aromatic carbocyclyloxycarbonylamino" may be substituted with unsubstituted alkyl or alkyl substituted with one or more substituent(s) selected from halogen, hydroxy, or alkyloxy.

The "non-aromatic carbocycle" part of "non-aromatic carbocyclyloxy", "non-aromatic carbocyclylcarbonyl", "non-aromatic carbocyclyloxycarbonyl", "non-aromatic carbocyclylsulfanyl", "non-aromatic carbocyclylsulfonyl", "non-aromatic carbocyclylcarbonylamino", "non-aromatic carbocyclylcarbamoyl", "non-aromatic carbocyclylureido", or "non-aromatic carbocyclyloxycarbonylamino", is same as the above "non-aromatic carbocyclyl".

"Non-aromatic carbocyclyloxy" means a group wherein "non-aromatic carbocycle" is bonded to an oxygen atom. For example, it includes cyclopropyloxy, cyclohexyloxy, cyclohexenyloxy and the like.

"Non-aromatic carbocyclylamino" means a group wherein a hydrogen atom attached to a nitrogen atom of an amino group is replaced with the "non-aromatic carbocycle". For example, it includes cyclopropylamino, cyclohexylamino, cyclohexenylamino and the like.

Furthermore, the amino part of "non-aromatic carbocyclylamino" may be substituted with unsubstituted alkyl or alkyl substituted with one or more substituent(s) selected from halogen, hydroxy, or alkyloxy.

"Non-aromatic carbocyclylcarbonyl" means a group wherein "non-aromatic carbocycle" is bonded to a carbonyl group. For example, it includes cyclopropylcarbonyl, cyclohexylcarbonyl, cyclohexenylcarbonyl and the like.

"Non-aromatic carbocyclyloxycarbonyl" means a group wherein the above "non-aromatic carbocyclyloxy" is bonded to a carbonyl group. For example, it includes cyclopropyloxycarbonyl, cyclohexyloxycarbonyl, cyclohexenyloxycarbonyl and the like.

"Non-aromatic carbocyclylsulfanyl" means a group wherein a hydrogen atom bonded to a sulfur atom of a sulfanyl group is replaced with "non-aromatic carbocycle". For example, it includes cyclopropylsulfanyl, cyclohexylsulfanyl, cyclohexenylsulfanyl and the like.

"Non-aromatic carbocyclylsulfonyl" means a group wherein "non-aromatic carbocycle" is bonded to a sulfonyl group. For example, it includes cyclopropylsulfonyl, cyclohexylsulfonyl, cyclohexenylsulfonyl and the like.

"Non-aromatic carbocyclylcarbonylamino" means a group wherein a hydrogen atom attached to a nitrogen atom of an amino group is replaced with the above "non-aromatic carbocyclylcarbonyl". For example, it includes cyclopropylcarbonylamino, cyclohexylcarbonylamino, cyclohexenylcarbonylamino and the like.

Furthermore, the amino part of "non-aromatic carbocyclylcarbonylamino" may be substituted with unsubstituted alkyl or alkyl substituted with one or more substituent(s) selected from halogen, hydroxy, or alkyloxy.

"Non-aromatic carbocyclylcarbamoyl" means a group wherein a hydrogen atom attached to a nitrogen atom of a carbamoyl group is replaced with the above "non-aromatic carbocycle". For example, it includes cyclopropylcarbamoyl, cyclohexylcarbamoyl, cyclohexenylcarbamoyl and the like.

Furthermore, the other hydrogen atom attached to a nitrogen atom of the carbamoyl group in "non-aromatic carbocyclylcarbamoyl" may be replaced with unsubstituted alkyl or alkyl substituted with one or more substituent(s) selected from halogen, hydroxy, or alkyloxy.

"Non-aromatic carbocyclylureido" means a group wherein a hydrogen atom attached to a nitrogen atom of an ureido group is replaced with the above "non-aromatic carbocycle". For example, it includes cyclopropylureido, cyclohexylureido, cyclohexenylureido and the like.

Furthermore, the other hydrogen atom attached to a nitrogen atom of the ureido group in "non-aromatic carbocyclylureido" may be replaced with unsubstituted alkyl or alkyl substituted with one or more substituent(s) selected from halogen, hydroxy, or alkyloxy.

"Non-aromatic carbocyclyloxycarbonylamino" means a group wherein a hydrogen atom attached to a nitrogen atom of an amino group is replaced with the above "non-aromatic carbocyclyloxycarbonyl". For example, it includes cyclopropyloxycarbonylamino, cyclohexyloxycarbonylamino, cyclohexenyloxycarbonylamino and the like.

Furthermore, the amino part of "non-aromatic carbocyclyloxycarbonylamino" may be substituted with unsubstituted alkyl or alkyl substituted with one or more substituent(s) selected from halogen, hydroxy, or alkyloxy.

The "aromatic heterocycle" part of "aromatic heterocyclyloxy", "aromatic heterocyclylcarbonyl", "aromatic heterocyclyloxycarbonyl", "aromatic heterocyclyloxycarbonyl", "aromatic heterocyclylsulfanyl", "aromatic heterocyclylsulfonyl", "aromatic heterocyclylcarbonylamino", "aromatic heterocyclylcarbamoyl", "aromatic heterocyclylureido", or "aromatic heterocyclyloxycarbonylamino" is also same as the above "aromatic heterocyclyl".

"Aromatic heterocyclyloxy" means a group wherein "aromatic heterocycle" is bonded to an oxygen atom. For example, it includes pyridyloxy, oxazolyloxy and the like.

"Aromatic heterocyclylamino" means a group wherein a hydrogen atom attached to a nitrogen atom of an amino group is replaced with the "aromatic heterocycle". For example, it includes pyridylamino, oxazolylamino and the like.

Furthermore, the amino part of "aromatic heterocyclylamino" may be substituted with unsubstituted alkyl or alkyl substituted with one or more substituent(s) selected from halogen, hydroxy, or alkyloxy.

"Aromatic heterocyclylcarbonyl" means a group wherein "aromatic heterocycle" is bonded to a carbonyl group. For example, it includes pyridylcarbonyl, oxazolylcarbonyl and the like.

"Aromatic heterocyclyloxycarbonyl" means a group wherein the above "aromatic heterocyclyloxy" is bonded to a carbonyl group. For example, it includes pyridyloxycarbonyl, oxazolyloxycarbonyl and the like.

"Aromatic heterocyclylsulfanyl" means a group wherein a hydrogen atom bonded to a sulfur atom of a sulfanyl group is replaced with "aromatic heterocycle". For example, it includes pyridylsulfanyl, oxazolylsulfanyl and the like.

"Aromatic heterocyclylsulfonyl" means a group wherein "aromatic heterocycle" is bonded to a sulfonyl group. For example, it includes pyridylsulfonyl, oxazolylsulfonyl and the like.

"Aromatic heterocyclylcarbonylamino" means a group wherein a hydrogen atom attached to a nitrogen atom of an amino group is replaced with the above "aromatic heterocyclylcarbonyl". For example, it includes pyridylcarbonylamino, oxazolylcarbonylamino and the like.

Furthermore, the amino part of "aromatic heterocyclylcarbonylamino" may be substituted with unsubstituted alkyl or alkyl substituted with one or more substituent(s) selected from halogen, hydroxy, or alkyloxy.

"Aromatic heterocyclylcarbamoyl" means a group wherein a hydrogen atom attached to a nitrogen atom of a carbamoyl group is replaced with the above "aromatic heterocycle". For example, it includes pyridylcarbamoyl, oxazolylcarbamoyl and the like.

Furthermore, the other hydrogen atom attached to a nitrogen atom of the carbamoyl group in "aromatic heterocyclylcarbamoyl" may be replaced with unsubstituted alkyl or alkyl substituted with one or more substituent(s) selected from halogen, hydroxy, or alkyloxy.

"Aromatic heterocyclylureido" means a group wherein a hydrogen atom attached to a nitrogen atom of an ureido group is replaced with the above "aromatic heterocycle". For example, it includes pyridylureido, oxazolylureido and the like.

Furthermore, the other hydrogen atom attached to a nitrogen atom of the ureido group in "aromatic heterocyclylureido" may be replaced with unsubstituted alkyl or alkyl substituted with one or more substituent(s) selected from halogen, hydroxy, or alkyloxy.

"Aromatic heterocyclyloxycarbonylamino" means a group wherein a hydrogen atom attached to a nitrogen atom of an amino group is replaced with the above "aromatic heterocyclyloxycarbonyl". For example, it includes pyridyloxycarbonylamino, oxazolyloxycarbonylamino and the like.

Furthermore, the amino part of "aromatic heterocyclyloxycarbonylamino" may be substituted with unsubstituted alkyl or alkyl substituted with one or more substituent(s) selected from halogen, hydroxy, or alkyloxy.

The "non-aromatic heterocycle" part of "non-aromatic heterocyclyloxy", "non-aromatic heterocyclylcarbonyl", "non-aromatic heterocyclyloxycarbonyl", "non-aromatic heterocyclylsulfanyl", "non-aromatic heterocyclylsulfonyl", "non-aromatic heterocyclylcarbonylamino", "non-aromatic heterocyclylcarbamoyl", "non-aromatic heterocyclylureido", or "non-aromatic heterocyclyloxycarbonylamino" is also same as the above "non-aromatic heterocyclyl".

"Non-aromatic heterocyclyloxy" means a group wherein "non-aromatic heterocycle" is bonded to an oxygen atom. For example, it includes piperidinyloxy, tetrahydrofuryloxy and the like.

"Non-aromatic heterocyclylcarbonyl" means a group wherein "non-aromatic heterocycle" is bonded to a carbonyl group. For example, it includes piperidinylcarbonyl, tetrahydrofurylcarbonyl and the like.

"Non-aromatic heterocyclylamino" means a group wherein a hydrogen atom attached to a nitrogen atom of an amino group is replaced with the "non-aromatic heterocycle". For example, it includes piperidinylamino, tetrahydrofurylamino and the like.

Furthermore, the amino part of "non-aromatic heterocyclylamino" may be substituted with unsubstituted alkyl or alkyl substituted with one or more substituent(s) selected from halogen, hydroxy, or alkyloxy.

"Non-aromatic heterocyclyloxycarbonyl" means a group wherein the above "non-aromatic heterocyclyloxy" is bonded to a carbonyl group. For example, it includes piperidinyloxycarbonyl, tetrahydrofuryloxycarbonyl and the like.

"Non-aromatic heterocyclylsulfanyl" means a group wherein a hydrogen atom bonded to a sulfur atom of a sulfanyl group is replaced with "non-aromatic heterocycle". For example, it includes piperidinylsulfanyl, tetrahydrofurylsulfanyl and the like.

"Non-aromatic heterocyclylsulfonyl" means a group wherein "non-aromatic heterocycle" is bonded to a sulfonyl group. For example, it includes piperidinylsulfonyl, tetrahydrofurylsulfonyl and the like.

"Non-aromatic heterocyclylcarbonylamino" means a group wherein a hydrogen atom attached to a nitrogen atom of an amino group is replaced with the above "non-aromatic heterocyclylcarbonyl". For example, it includes piperidinylcarbonylamino, tetrahydrofurylcarbonylamino and the like.

Furthermore, the amino part of "non-aromatic heterocyclylcarbonylamino" may be substituted with unsubstituted alkyl or alkyl substituted with one or more substituent(s) selected from halogen, hydroxy, or alkyloxy.

"Non-aromatic heterocyclylcarbamoyl" means a group wherein a hydrogen atom attached to a nitrogen atom of a carbamoyl group is replaced with the above "non-aromatic heterocycle". For example, it includes piperidinylcarbamoyl, tetrahydrofurylcarbamoyl and the like.

Furthermore, the other hydrogen atom attached to a nitrogen atom of the carbamoyl group in "non-aromatic heterocyclylcarbamoyl" may be replaced with unsubstituted alkyl or alkyl substituted with one or more substituent(s) selected from halogen, hydroxy, or alkyloxy.

"Non-aromatic heterocyclylureido" means a group wherein a hydrogen atom attached to a nitrogen atom of an ureido group is replaced with the above "non-aromatic heterocycle". For example, it includes piperidinylureido, tetrahydrofurylureido and the like.

Furthermore, the other hydrogen atom attached to a nitrogen atom of the ureido group in "non-aromatic heterocyclylureido" may be replaced with alkyl or alkyl substituted with one or more substituent(s) selected from halogen, hydroxy, or alkyloxy.

"Non-aromatic heterocyclyloxycarbonylamino" means a group wherein a hydrogen atom attached to a nitrogen atom of an amino group is replaced with the above "non-aromatic heterocyclyloxycarbonyl". For example, it includes piperidinyloxycarbonylamino, tetrahydrofuryloxycarbonylamino and the like.

Furthermore, the amino part of "non-aromatic heterocyclyloxycarbonylamino" may be substituted with unsubstituted alkyl or alkyl substituted with one or more substituent(s) selected from halogen, hydroxy, or alkyloxy.

The substituents on the ring of "substituted or unsubstituted aromatic carbocycle", "substituted or unsubstituted non-aromatic carbocycle", "substituted or unsubstituted aromatic heterocycle", and "substituted or unsubstituted non-aromatic heterocycle" in Ring A;

"substituted or unsubstituted aromatic carbocyclyl", "substituted or unsubstituted non-aromatic carbocyclyl", "substituted or unsubstituted aromatic heterocyclyl", and "substituted or unsubstituted non-aromatic heterocyclyl" in $R^1$;

and "substituted or unsubstituted aromatic carbocyclyl", "substituted or unsubstituted non-aromatic carbocyclyl", "substituted or unsubstituted aromatic heterocyclyl", "substituted or unsubstituted non-aromatic heterocyclyl", "substituted or unsubstituted aromatic carbocyclyloxy", "substituted or unsubstituted non-aromatic carbocyclyloxy", "substituted or unsubstituted aromatic heterocyclyloxy", "substituted or unsubstituted non-aromatic heterocyclyloxy", "substituted or unsubstituted aromatic carbocyclylamino", "substituted or unsubstituted non-aromatic carbocyclylamino", "substituted or unsubstituted aromatic heterocyclylamino", "substituted or unsubstituted non-aromatic heterocyclylamino", "substituted or unsubstituted aromatic carbocyclylcarbonyl", "substituted or unsubstituted non-aromatic carbocyclylcarbonyl", "substituted or unsubstituted aromatic heterocyclylcarbonyl", "substituted or unsubstituted non-aromatic heterocyclylcarbonyl", "substituted or unsubstituted aromatic carbocyclylsulfanyl", "substituted or unsubstituted non-aromatic carbocyclylsulfanyl", "substituted or unsubstituted aromatic heterocyclylsulfanyl", "substituted or unsubstituted non-aromatic heterocyclylsulfanyl", "substituted or unsubstituted aromatic carbocyclylcarbonylamino", "substituted or unsubstituted non-aromatic carbocyclylcarbonylamino", "substituted or unsubstituted aromatic heterocyclylcarbonylamino", "substituted or unsubstituted non-aromatic heterocyclylcarbonylamino", "substituted or unsubstituted aromatic carbocyclylcarbamoyl", "substituted or unsubstituted non-aromatic carbocyclylcarbamoyl", "substituted or unsubstituted aromatic heterocyclylcarbamoyl", "substituted or unsubstituted non-aromatic heterocyclylcarbamoyl", "substituted or unsubstituted aromatic carbocyclylureido", "substituted or unsubstituted non-aromatic carbocyclylureido", "substituted or unsubstituted aromatic heterocyclylureido", "substituted or unsubstituted non-aromatic heterocyclylureido", "substituted or unsubstituted aromatic carbocyclyloxycarbonylamino", "substituted or unsubstituted non-aromatic carbocyclyloxycarbonylamino", "substituted or unsubstituted aromatic heterocyclyloxycarbonylamino", and "substituted or unsubstituted non-aromatic heterocyclyloxycarbonylamino" in $R^2$ and $R^3$; include the substituent group A. An atom at any position(s) on the ring may be bonded to one or more group(s) selected from the substituent group A.

The substituent group A; halogen, hydroxy, amino, carbamoyl, sulfamoyl, cyano, nitro, ureido, alkyl, alkenyl, alkynyl, alkyloxy, alkenyloxy, alkynyloxy, alkylcarbonyl, alkenylcarbonyl, alkenylcarbonyl, monoalkylamino, dialkylamino, alkylsulfonyl, monoalkylcarbonylamino, monoalkylsulfonylamino, alkylsulfanyl, alkenylsulfanyl, alkynylsulfanyl, monoalkylcarbamoyl, dialkylcarbamoyl, monoalkylsulfamoyl, dialkylsulfamoyl, aromatic carbocyclyl, non-aromatic carbocyclyl, aromatic heterocyclyl, non-aromatic heterocyclyl, aromatic carbocyclyloxy, non-aromatic carbocyclyloxy, aromatic heterocyclyloxy, non-aromatic heterocyclyloxy, aromatic carbocyclylamino, non-aromatic carbocyclylamino, aromatic heterocyclylamino, non-aromatic heterocyclylamino, aromatic carbocyclylsulfanyl, non-aromatic carbocyclylsulfanyl, aromatic heterocyclylsulfanyl, non-aromatic heterocyclylsulfanyl, aromatic carbocyclylsulfonyl, non-aromatic carbocyclylsulfonyl, aromatic heterocyclylsulfonyl, non-aromatic heterocyclylsulfonyl, aromatic carbocyclylcarbonylamino, non-aromatic carbocyclylcarbonylamino, aromatic heterocyclylcarbonylamino, non-aromatic heterocyclylcarbonylamino, aromatic carbocyclylcarbamoyl, non-aromatic carbocyclylcarbamoyl, aromatic heterocyclylcarbamoyl, and non-aromatic heterocyclylcarbamoyl.

In the substituent group A, a carbon atom at any position(s) of alkyl, alkenyl, alkynyl, alkyloxy, alkenyloxy, alkynyloxy, alkylcarbonyl, alkenylcarbonyl, alkenylcarbonyl, monoalkylamino, dialkylamino, alkylsulfonyl, monoalkylcarbonylamino, monoalkylsulfonylamino, alkylsulfanyl, alkenylsulfanyl, alkynylsulfanyl, monoalkylcarbamoyl, dialkylcarbamoyl, monoalkylsulfamoyl, and dialkylsulfamoyl may be optionally substituted with one or more group(s) selected from the substituent group a1.

The substituent group a1; halogen, hydroxy, amino, carbamoyl, sulfamoyl, cyano, nitro, ureido, alkyloxy, alkenyloxy, alkynyloxy, haloalkyloxy, alkylcarbonyl, alkenylcarbonyl, alkenylcarbonyl, monoalkylamino, dialkylamino, alkylsulfonyl, monoalkylcarbonylamino, monoalkylsulfonylamino, alkylsulfanyl, alkenylsulfanyl, alkynylsulfanyl, monoalkylcarbamoyl, dialkylcarbamoyl, monoalkylsulfamoyl, dialkylsulfamoyl, aromatic carbocyclyl, non-aromatic carbocyclyl, aromatic heterocyclyl, and non-aromatic heterocyclyl.

For example, as the substituent group a1, halogen, hydroxy, amino, carbamoyl, cyano, ureido, alkyloxy, haloalkyloxy, alkylcarbonyl, monoalkylamino, dialkylamino, alkylsulfonyl, monoalkylcarbonylamino, monoalkylsulfonylamino, alkylsulfanyl, alkenylsulfanyl, alkynylsulfanyl, alkylsulfinyl, alkenylsulfinyl, alkynylsulfinyl, monoalkylcarbamoyl, dialkylcarbamoyl, monoalkylsulfamoyl, dialkylsulfamoyl, aromatic carbocyclyl, non-aromatic carbocyclyl, aromatic heterocyclyl, and non-aromatic heterocyclyl are exemplified.

For example, as the substituent group a1, halogen, hydroxy, amino, carbamoyl, cyano, ureido, alkyloxy, haloalkyloxy, alkylcarbonyl, monoalkylamino, dialkylamino, alkylsulfonyl, monoalkylcarbonylamino, monoalkylsulfonylamino, alkylsulfanyl, alkenylsulfanyl, alkynylsulfanyl, alkylsulfinyl, alkenylsulfinyl, alkynylsulfinyl, monoalkylcarbamoyl, dialkylcarbamoyl, monoalkylsulfamoyl, dialkylsulfamoyl, aromatic carbocyclyl, non-aromatic carbocyclyl, aromatic heterocyclyl, and non-aromatic heterocyclyl are exemplified.

For example, as the substituent group a1, halogen, hydroxy, amino, carbamoyl, cyano, ureido, aromatic carbocyclyl, non-aromatic carbocyclyl, aromatic heterocyclyl, and non-aromatic heterocyclyl are exemplified.

For example, as the substituent group a1, halogen, hydroxy, amino, carbamoyl, cyano, and ureido are exemplified.

In the substituent group A and the substituent group a1, an atom at any position(s) on the ring of aromatic carbocyclyl, non-aromatic carbocyclyl, aromatic heterocyclyl, non-aromatic heterocyclyl, aromatic carbocyclyloxy, non-aromatic carbocyclyloxy, aromatic heterocyclyloxy, non-aromatic heterocyclyloxy, aromatic carbocyclylamino, non-aromatic carbocyclylamino, aromatic heterocyclylamino, non-aromatic heterocyclylamino, aromatic carbocyclylsulfanyl, non-aromatic carbocyclylsulfanyl, aromatic heterocyclylsulfanyl, non-aromatic heterocyclylsulfanyl, aromatic carbocyclylsulfonyl, non-aromatic carbocyclylsulfonyl, aromatic heterocyclylsulfonyl, non-aromatic heterocyclylsulfonyl, aromatic carbocyclylcarbonylamino, non-aromatic carbocyclylcarbonylamino, aromatic heterocyclylcarbonylamino, non-aromatic heterocyclylcarbonylamino, aromatic carbocyclylcarbamoyl, non-aromatic carbocyclylcarbamoyl, aromatic heterocyclylcarbamoyl, and non-aromatic heterocyclylcarbamoyl may be optionally substituted with one or more group(s) selected from the substituent group a2.

The substituent group a2; halogen, hydroxy, amino, carbamoyl, sulfamoyl, cyano, nitro, ureido, alkyl, alkenyl, alkynyl, haloalkyl, hydroxyalkyl, alkyloxy, alkenyloxy, alkynyloxy, haloalkyloxy, and alkyloxyalkyl.

For example, as the substituent group a2, halogen, hydroxy, amino, carbamoyl, cyano, ureido, alkyl, haloalkyl, hydroxyalkyl, alkyloxy, and haloalkyloxy are exemplified.

For example, as the substituent group a2, halogen, hydroxy, amino, alkyl, haloalkyl, hydroxyalkyl, alkyloxy, and haloalkyloxy are exemplified.

In $R^4$, $R^{4a}$, $R^{4b}$, $R^{4c}$ and the substituent group $\alpha 3$ to $\alpha 6$, the substituents of "substituted or unsubstituted alkyl", "substituted or unsubstituted alkenyl", "substituted or unsubstituted alkynyl", "substituted or unsubstituted alkyloxy", "substituted or unsubstituted alkenyloxy", "substituted or unsubstituted alkynyloxy", "substituted or unsubstituted alkylcarbonyl", "substituted or unsubstituted alkenylcarbonyl", "substituted or unsubstituted alkenylcarbonyl", "substituted or unsubstituted monoalkylamino", "substituted or unsubstituted dialkylamino", "substituted or unsubstituted monoalkylcarbonylamino", "substituted or unsubstituted monoalkylsulfonylamino", "substituted or unsubstituted alkylsulfanyl", "substituted or unsubstituted alkenylsulfanyl", "substituted or unsubstituted alkynylsulfanyl", "substituted or unsubstituted monoalkylcarbamoyl", "substituted or unsubstituted dialkylcarbamoyl", "substituted or unsubstituted monoalkylsulfamoyl", and "substituted or unsubstituted dialkylsulfamoyl" include the substituent group a1. A carbon atom at any position(s) may be bonded to one or more group(s) selected from the substituent group a1.

In $R^4$, $R^{4a}$, $R^{4b}$, $R^{4c}$ and the substituent group $\alpha 3$ to $\alpha 6$, the substituents on the ring of "substituted or unsubstituted aromatic carbocycle", "substituted or unsubstituted non-aromatic carbocycle", "substituted or unsubstituted aromatic heterocycle", "substituted or unsubstituted non-aromatic heterocycle", "substituted or unsubstituted aromatic carbocyclyl", "substituted or unsubstituted non-aromatic carbocyclyl", "substituted or unsubstituted aromatic heterocyclyl", "substituted or unsubstituted non-aromatic heterocyclyl", "substituted or unsubstituted aromatic carbocyclyloxy", "substituted or unsubstituted non-aromatic carbocyclyloxy", "substituted or unsubstituted aromatic heterocyclyloxy", "substituted or unsubstituted non-aromatic heterocyclyloxy", "substituted or unsubstituted aromatic carbocyclylamino", "substituted or unsubstituted non-aromatic carbocyclylamino", "substituted or unsubstituted aromatic heterocyclylamino", "substituted or unsubstituted non-aromatic heterocyclylamino", "substituted or unsubstituted aromatic carbocyclylsulfanyl", "substituted or unsubstituted non-aromatic carbocyclylsulfanyl", "substituted or unsubstituted aromatic heterocyclylsulfanyl", "substituted or unsubstituted non-aromatic heterocyclylsulfanyl", "substituted or unsubstituted aromatic carbocyclylcarbonylamino", "substituted or unsubstituted non-aromatic carbocyclylcarbonylamino", "substituted or unsubstituted aromatic heterocyclylcarbonylamino", "substituted or unsubstituted non-aromatic heterocyclylcarbonylamino", "substituted or unsubstituted aromatic carbocyclylcarbamoyl", "substituted or unsubstituted non-aromatic carbocyclylcarbamoyl", "substituted or unsubstituted aromatic heterocyclylcarbamoyl", and "substituted or unsubstituted non-aromatic heterocyclylcarbamoyl" include the substituent group a2. An atom at any position(s) on the ring may be bonded to one or more group(s) selected from the substituent group A.

For example, as the substituent group a1 in Ring A, $R^4$, $R^{4a}$, $R^{4b}$, $R^{4c}$ and the substituent group $\alpha 3$ to $\alpha 6$, halogen, hydroxy, aromatic carbocyclyl, non-aromatic carbocyclyl, aromatic heterocyclyl, and non-aromatic heterocyclyl are exemplified.

For example, as the substituent group a1 in Ring A, $R^4$, $R^{4a}$, $R^{4b}$, $R^{4c}$, and the substituent group $\alpha 3$ to $\alpha 6$, halogen is exemplified.

For example, as the substituent group a2 in Ring A, $R^4$, $R^{4a}$, $R^{4b}$, $R^{4c}$ and the substituent group $\alpha 3$ to $\alpha 6$, halogen, hydroxy, amino, alkyl, haloalkyl, hydroxyalkyl, alkyloxy, and haloalkyloxy are exemplified.

The substituents of "substituted or unsubstituted alkyl", "substituted or unsubstituted alkenyl", and "substituted or unsubstituted alkynyl" in $R^1$ include the substituent group B. A carbon atom at any position(s) may be bonded to one or more group(s) selected from the substituent group B.

The substituent group B; halogen, hydroxy, amino, carbamoyl, sulfamoyl, cyano, nitro, ureido, alkyloxy, alkenyloxy, alkynyloxy, alkylcarbonyl, alkenylcarbonyl, alkenylcarbonyl, monoalkylamino, dialkylamino, alkylsulfonyl, monoalkylcarbonylamino, monoalkylsulfonylamino, alkylsulfanyl, alkenylsulfanyl, alkynylsulfanyl, monoalkylcarbamoyl, dialkylcarbamoyl, monoalkylsulfamoyl, dialkylsulfamoyl, aromatic carbocyclyl, non-aromatic carbocyclyl, aromatic heterocyclyl, non-aromatic heterocyclyl, aromatic carbocyclyloxy, non-aromatic carbocyclyloxy, aromatic heterocyclyloxy, non-aromatic heterocyclyloxy, aromatic carbocyclylamino, non-aromatic carbocyclylamino, aromatic heterocyclylamino, non-aromatic heterocyclylamino, aromatic carbocyclylsulfanyl, non-aromatic carbocyclylsulfanyl, aromatic heterocyclylsulfanyl, non-aromatic heterocyclylsulfanyl, aromatic carbocyclylsulfonyl, non-aromatic carbocyclylsulfonyl, aromatic heterocyclylsulfonyl, aromatic carbocyclylcarbonylamino, non-aromatic carbocyclylcarbonylamino, aromatic heterocyclylcarbonylamino, non-aromatic heterocyclylcarbonylamino, aromatic carbocyclylcarbamoyl, non-aromatic carbocyclylcarbamoyl, aromatic heterocyclylcarbamoyl, and non-aromatic heterocyclylcarbamoyl.

In the substituent group B, a carbon atom at any position(s) of alkyloxy, alkenyloxy, alkynyloxy, alkylcarbonyl, alkenylcarbonyl, alkenylcarbonyl, monoalkylamino, dialkylamino, alkylsulfonyl, monoalkylcarbonylamino, monoalkylsulfonylamino, alkylsulfanyl, alkenylsulfanyl, alkynylsulfanyl, monoalkylcarbamoyl, dialkylcarbamoyl, monoalkylsulfamoyl, and dialkylsulfamoyl may be optionally substituted with one or more group(s) selected from the substituent group b1.

The substituent group b1; halogen, hydroxy, amino, carbamoyl, sulfamoyl, cyano, nitro, ureido, aromatic carbocyclyl, non-aromatic carbocyclyl, aromatic heterocyclyl, and non-aromatic heterocyclyl are exemplified.

For example, as the substituent group b1, halogen, hydroxy, amino, carbamoyl, cyano, and ureido are exemplified.

In the substituent group b1, an atom at any position(s) on the ring of aromatic carbocyclyl, non-aromatic carbocyclyl, aromatic heterocyclyl, and non-aromatic heterocyclyl may be optionally substituted with one or more group(s) selected from the substituent group a2.

In the substituent group B, an atom at any position(s) on the ring of aromatic carbocyclyl, non-aromatic carbocyclyl, aromatic heterocyclyl, non-aromatic heterocyclyl, aromatic carbocyclyloxy, non-aromatic carbocyclyloxy, aromatic heterocyclyloxy, non-aromatic heterocyclyloxy, aromatic carbocyclylamino, non-aromatic carbocyclylamino, aromatic heterocyclylamino, non-aromatic heterocyclylamino, aromatic carbocyclylsulfanyl, non-aromatic carbocyclylsulfanyl, aromatic heterocyclylsulfanyl, non-aromatic heterocyclylsulfanyl, aromatic carbocyclylsulfonyl, non-aromatic carbocyclylsulfonyl, aromatic heterocyclylsulfonyl, non-aromatic heterocyclylsulfonyl, aromatic carbocyclylcarbonylamino, non-aromatic carbocyclylcarbonylamino, aromatic heterocyclylcarbonylamino, non-aromatic heterocyclylcarbonylamino, aromatic carbocyclylcarbamoyl, non-aromatic carbocyclylcarbamoyl, aromatic heterocyclylcarbamoyl, and non-aromatic heterocyclylcarbamoyl may be optionally substituted with one or more group(s) selected from the substituent group b2.

The substituent group b2; halogen, hydroxy, amino, carbamoyl, sulfamoyl, cyano, nitro, ureido, alkyl, alkenyl, alkynyl, haloalkyl, hydroxyalkyl, alkyloxy, alkenyloxy, alkynyloxy, haloalkyloxy, alkylcarbonyl, alkenylcarbonyl, alkenylcarbonyl, monoalkylamino, dialkylamino, alkylsulfonyl, monoalkylcarbonylamino, monoalkylsulfonylamino, alkylsulfanyl, alkenylsulfanyl, alkynylsulfanyl, monoalkylcarbamoyl, dialkylcarbamoyl, monoalkylsulfamoyl, dialkylsulfamoyl, alkylureido, aromatic carbocyclyl, non-aromatic carbocyclyl, aromatic heterocyclyl, non-aromatic heterocyclyl, aromatic carbocyclylalkyl, non-aromatic carbocyclylalkyl, aromatic heterocyclylalkyl, non-aromatic heterocyclylalkyl, aromatic carbocyclyloxy, non-aromatic carbocyclyloxy, aromatic heterocyclyloxy, non-aromatic heterocyclyloxy, aromatic carbocyclylalkyloxy, non-aromatic carbocyclylalkyloxy, aromatic heterocyclylalkyloxy, non-aromatic heterocyclylalkyloxy, aromatic carbocyclylamino, non-aromatic carbocyclylamino, aromatic heterocyclylamino, non-aromatic heterocyclylamino, aromatic carbocyclylcarbonyl, non-aromatic carbocyclylcarbonyl, aromatic heterocyclylcarbonyl, non-aromatic heterocyclylcarbonyl, aromatic carbocyclylsulfanyl, non-aromatic carbocyclylsulfanyl, aromatic heterocyclylsulfanyl, non-aromatic heterocyclylsulfanyl, aromatic carbocyclylsulfonyl, non-aromatic carbocyclylsulfonyl, aromatic heterocyclylsulfonyl, non-aromatic heterocyclylsulfonyl, aromatic carbocyclylcarbonylamino, non-aromatic carbocyclylcarbonylamino, aromatic heterocyclylcarbonylamino, non-aromatic heterocyclylcarbonylamino, aromatic carbocyclylcarbamoyl, non-aromatic carbocyclylcarbamoyl, aromatic heterocyclylcarbamoyl, non-aromatic heterocyclylcarbamoyl, aromatic carbocyclylsulfonyl alkyl, non-aromatic carbocyclylsulfonyl alkyl, aromatic heterocyclylsulfonyl alkyl, and non-aromatic heterocyclylsulfonyl alkyl.

For example, as the substituent group b2, halogen, hydroxy, amino, carbamoyl, cyano, ureido, alkyl, haloalkyl, hydroxyalkyl, alkyloxy, haloalkyloxy, alkylcarbonyl, monoalkylamino, dialkylamino, alkylsulfonyl, monoalkylcarbonylamino, monoalkylcarbamoyl, dialkylcarbamoyl, alkylureido, aromatic carbocyclyl, non-aromatic carbocyclyl, aromatic heterocyclyl, non-aromatic heterocyclyl, aromatic carbocyclylalkyl, non-aromatic carbocyclylalkyl, aromatic heterocyclylalkyl, non-aromatic heterocyclylalkyl, aromatic carbocyclyloxy, non-aromatic carbocyclyloxy, aromatic heterocyclyloxy, non-aromatic heterocyclyloxy, aromatic carbocyclylalkyloxy, non-aromatic carbocyclylalkyloxy, aromatic heterocyclylalkyloxy, non-aromatic heterocyclylalkyloxy, aromatic carbocyclylcarbonyl, non-aromatic carbocyclylcarbonyl, aromatic heterocyclylcarbonyl, non-aromatic heterocyclylcarbonyl, aromatic carbocyclylsulfonyl, non-aromatic carbocyclylsulfonyl, aromatic heterocyclylsulfonyl, non-aromatic heterocyclylsulfonyl, aromatic carbocyclylsulfonyl alkyl, non-aromatic carbocyclylsulfonyl alkyl, aromatic heterocyclylsulfonyl alkyl, and non-aromatic heterocyclylsulfonyl alkyl are exemplified.

For example, as the substituent group b2, halogen, carbamoyl, cyano, alkyl, haloalkyl, hydroxyalkyl, alkyloxy, haloalkyloxy, alkylsulfonyl, alkylureido, aromatic carbocyclyl, non-aromatic carbocyclyl, aromatic heterocyclyl, non-aromatic heterocyclyl, aromatic carbocyclylalkyl, non-aromatic carbocyclylalkyl, aromatic heterocyclylalkyl, non-aromatic heterocyclylalkyl, aromatic carbocyclyloxy, non-aromatic carbocyclyloxy, aromatic heterocyclyloxy, non-aromatic heterocyclyloxy, aromatic carbocyclylalkyloxy, non-aromatic carbocyclylalkyloxy, aromatic heterocyclylalkyloxy, non-aromatic heterocyclylalkyloxy, aromatic carbocyclylcarbonyl, non-aromatic carbocyclylcarbonyl, aromatic heterocyclylcarbonyl, non-aromatic heterocyclylcarbonyl, aromatic carbocyclylsulfonyl, non-aromatic carbocyclylsulfonyl, aromatic heterocyclylsulfonyl, non-aromatic heterocyclylsulfonyl, aromatic carbocyclylsulfonyl alkyl, non-aromatic carbocyclylsulfonyl alkyl, aromatic heterocyclylsulfonyl alkyl, and non-aromatic heterocyclylsulfonyl alkyl are exemplified.

For example, as the substituent group b2, halogen, carbamoyl, cyano, alkyl, haloalkyl, hydroxyalkyl, alkyloxy, haloalkyloxy, alkylsulfonyl, alkylureido, aromatic carbocyclyl, aromatic heterocyclyl, aromatic carbocyclyloxy, aromatic carbocyclylalkyloxy, aromatic carbocyclylcarbonyl, non-aromatic heterocyclylsulfonyl, and aromatic carbocyclylsulfonyl alkyl are exemplified.

For example, as the substituent group b2, halogen, carbamoyl, cyano, alkyl, haloalkyl, hydroxyalkyl, alkyloxy, haloalkyloxy, alkylsulfonyl, and alkylureido are exemplified.

For example, as the substituent group b2, halogen, cyano, alkyl, haloalkyl, hydroxyalkyl, alkyloxy, and haloalkyloxy are exemplified.

In the substituent group b2, an atom at any position(s) on the ring of aromatic carbocyclyl, non-aromatic carbocyclyl, aromatic heterocyclyl, non-aromatic heterocyclyl, aromatic carbocyclylalkyl, non-aromatic carbocyclylalkyl, aromatic heterocyclylalkyl, non-aromatic heterocyclylalkyl, aromatic carbocyclyloxy, non-aromatic carbocyclyloxy, aromatic heterocyclyloxy, non-aromatic heterocyclyloxy, aromatic carbocyclylalkyloxy, non-aromatic carbocyclylalkyloxy, aromatic heterocyclylalkyloxy, non-aromatic heterocyclylalkyloxy, aromatic carbocyclylamino, non-aromatic carbocyclylamino, aromatic heterocyclylamino, non-aromatic heterocyclylamino, aromatic carbocyclylsulfanyl, non-aromatic carbocyclylsulfanyl, aromatic heterocyclylsulfanyl, non-aromatic heterocyclylsulfanyl, aromatic carbocyclylsulfonyl, non-aromatic carbocyclylsulfonyl, aromatic heterocyclylsulfonyl, non-aromatic heterocyclylsulfonyl, aromatic carbocyclylcarbonylamino, non-aromatic carbocyclylcarbonylamino, aromatic heterocyclylcarbonylamino, non-aromatic heterocyclylcarbonylamino, aromatic carbocyclylcarbamoyl, non-aromatic carbocyclylcarbamoyl, aromatic heterocyclylcarbamoyl, non-aromatic heterocyclylcarbamoyl, aromatic carbocyclylsulfonyl alkyl, non-aromatic carbocyclylsulfonyl alkyl, aromatic heterocyclylsulfonyl alkyl, and non-aromatic heterocyclylsulfonyl alkyl may be optionally substituted with one or more group(s) selected from the substituent group b3.

The substituent group b3; halogen, hydroxy, amino, carbamoyl, cyano, ureido, alkyl, haloalkyl, hydroxyalkyl, alkyloxy, and haloalkyloxy are exemplified.

For example, as the substituent group b3, halogen, hydroxy, amino, alkyl, haloalkyl, hydroxyalkyl, alkyloxy, and haloalkyloxy are exemplified.

For example, as the substituent group b3, halogen, alkyl, and alkyloxy are exemplified.

The substituents of "substituted or unsubstituted alkyloxy", "substituted or unsubstituted alkenyloxy", and "substituted or unsubstituted alkynyloxy" in the substituent group α1 include the substituent group b1. A carbon atom at any position(s) may be bonded to one or more group(s) selected from the substituent group b1.

The substituents of "substituted or unsubstituted aromatic carbocyclyl", "substituted or unsubstituted non-aromatic carbocyclyl", "substituted or unsubstituted aromatic heterocyclyl", "substituted or unsubstituted non-aromatic heterocyclyl", "substituted or unsubstituted aromatic carbocyclyloxy", "substituted or unsubstituted non-aromatic carbocyclyloxy", "substituted or unsubstituted aromatic heterocyclyloxy", and "substituted or unsubstituted non-aromatic heterocyclyloxy" in the substituent group α1 and α2 include the substituent group b2. A carbon atom at any position(s) may be bonded to one or more group(s) selected from the substituent group b2.

The substituents of "substituted or unsubstituted aromatic carbocyclyl", "substituted or unsubstituted non-aromatic carbocyclyl", "substituted or unsubstituted aromatic heterocyclyl", or "substituted or unsubstituted non-aromatic heterocyclyl" in $R^{1a}$ include the substituent group b2. A carbon atom at any position(s) may be bonded to one or more group(s) selected from the substituent group a1.

The substituents of "substituted or unsubstituted alkyl", "substituted or unsubstituted alkenyl", "substituted or unsubstituted alkynyl", "substituted or unsubstituted alkyloxy", "substituted or unsubstituted alkenyloxy", "substituted or unsubstituted alkynyloxy", "substituted or unsubstituted alkylcarbonyl", "substituted or unsubstituted monoalkylamino", "substituted or unsubstituted dialkylamino", "substituted or unsubstituted monoalkylcarbonylamino", "substituted or unsubstituted monoalkylsulfonylamino", "substituted or unsubstituted alkylsulfanyl", "substituted or unsubstituted alkenylsulfanyl", "substituted or unsubstituted alkynylsulfanyl", "substituted or unsubstituted monoalkylcarbamoyl", "substituted or unsubstituted dialkylcarbamoyl", "substituted or unsubstituted monoalkylsulfamoyl", "substituted or unsubstituted dialkylsulfamoyl", "substituted or unsubstituted alkyloxycarbonylamino", "substituted or unsubstituted alkenyloxycarbonylamino", "substituted or unsubstituted alkynyloxycarbonylamino", "substituted or unsubstituted alkylureido", "substituted or unsubstituted alkenylureido", "substituted or unsubstituted alkynylureido", and "substituted or unsubstituted alkylsulfonyl" in $R^2$ and $R^3$ include the substituent group C. A carbon atom at any position(s) may be bonded to one or more group(s) selected from the substituent group C.

The substituent group C; halogen, hydroxy, amino, carbamoyl, sulfamoyl, cyano, nitro, ureido, alkyloxy, alkenyloxy, alkynyloxy, haloalkyloxy, alkylcarbonyl, alkenylcarbonyl, alkenylcarbonyl, monoalkylamino, dialkylamino, alkylsulfonyl, monoalkylcarbonylamino, monoalkylsulfonylamino, alkylsulfanyl, alkenylsulfanyl, alkynylsulfanyl, monoalkylcarbamoyl, dialkylcarbamoyl, monoalkylsulfamoyl, dialkylsulfamoyl, aromatic carbocyclyl, non-aromatic carbocyclyl, aromatic heterocyclyl, non-aromatic heterocyclyl, aromatic carbocyclyloxy, non-aromatic carbocyclyloxy, aromatic heterocyclyloxy, non-aromatic heterocyclyloxy, aromatic carbocyclylcarbonyl, non-aromatic carbocyclylcarbonyl, aromatic heterocyclylcarbonyl, non-aromatic heterocyclylcarbonyl, aromatic carbocyclylalkyloxy, non-aromatic carbocyclylalkyloxy, aromatic heterocyclylalkyloxy, non-aromatic heterocyclylalkyloxy, aromatic carbocyclylalkylamino, non-aromatic carbocyclylalkylamino, aromatic heterocyclylalkylamino, non-aromatic heterocyclylalkylamino, aromatic carbocyclylsulfanyl, non-aromatic carbocyclylsulfanyl, aromatic heterocyclylsulfanyl, non-aromatic heterocyclylsulfanyl, non-aromatic carbocyclylsulfonyl, aromatic carbocyclylsulfonyl, aromatic heterocyclylsulfonyl, and non-aromatic heterocyclylsulfonyl.

For example, as the substituent group C, halogen, hydroxy, amino, cyano, alkyloxy, alkenyloxy, alkynyloxy, haloalkyloxy, alkylcarbonyl, alkenylcarbonyl, alkenylcarbonyl, monoalkylamino, dialkylamino, alkylsulfonyl, monoalkylcarbonylamino, monoalkylsulfonylamino, alkylsulfanyl, alkenylsulfanyl, alkynylsulfanyl, monoalkylcarbamoyl, dialkylcarbamoyl, monoalkylsulfamoyl, dialkylsulfamoyl, aromatic carbocyclyl, non-aromatic carbocyclyl, aromatic heterocyclyl, and non-aromatic heterocyclyl are exemplified.

For example, as the substituent group C, halogen, hydroxy, amino, cyano, alkyloxy, haloalkyloxy, alkylcarbonyl, monoalkylamino, dialkylamino, aromatic carbocyclyl, non-aromatic carbocyclyl, aromatic heterocyclyl, and non-aromatic heterocyclyl are exemplified.

For example, as the substituent group C, halogen, hydroxy, amino, cyano, alkylcarbonyl, monoalkylamino, dialkylamino, and aromatic carbocyclyl are exemplified.

The substituents of "substituted or unsubstituted alkyl" in $R^{5a}$ and $R^{5b}$ include the substituent group D. A carbon atom at any position(s) may be bonded to one or more group(s) selected from the substituent group H.

The substituent group D; halogen, hydroxy, amino, carbamoyl, and alkyloxy are exemplified.

For example, as the substituent group D, halogen, hydroxy, or alkyloxy is exemplified.

For example, as the substituent group D, hydroxy, or alkyloxy is exemplified.

The substituents on the ring of "substituted or unsubstituted non-aromatic carbocycle", and "substituted or unsubstituted non-aromatic heterocycle" in $R^{5a}$ and $R^{5b}$ include the substituent group I. An atom at any position(s) on the ring may be bonded to one or more group(s) selected from the substituent group I.

The substituent group E; halogen, hydroxy, amino, carbamoyl, alkyl, haloalkyl, alkyloxy, and haloalkyloxy are exemplified.

For example, as the substituent group E, halogen, alkyl, and alkyloxy are exemplified.

For example, as the substituent group E, halogen is exemplified.

"Substituted or unsubstituted non-aromatic carbocycle", "substituted or unsubstituted non-aromatic heterocycle", "substituted or unsubstituted non-aromatic carbocyclyl" and "substituted or unsubstituted non-aromatic heterocyclyl" may be optionally substituted with "oxo". In this case, "oxo" means a group wherein two hydrogen atoms on a carbon atom are replaced with oxygen atom as below.

[Chemical Formula 27]

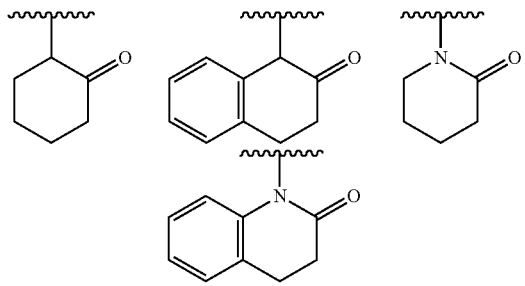

The non-aromatic carbocycle or non-aromatic heterocycle part of the above "substituted or unsubstituted non-aromatic carbocyclyloxy", "substituted or unsubstituted non-aromatic heterocyclyloxy", "substituted or unsubstituted non-aromatic carbocyclylamino", "substituted or unsubstituted non-aromatic heterocyclylamino", "substituted or unsubstituted non-aromatic carbocyclylcarbonyl", "substituted or unsubstituted non-aromatic heterocyclylcarbonyl", "substituted or unsubstituted non-aromatic carbocyclylsulfanyl", "substituted or unsubstituted non-aromatic heterocyclylsulfanyl", "substituted or unsubstituted non-aromatic carbocyclylcarbonylamino", "substituted or unsubstituted non-aromatic heterocyclylcarbonylamino", "substituted or unsubstituted non-aromatic carbocyclylcarbamoyl", "substituted or unsubstituted non-aromatic heterocyclylcarbamoyl", "substituted or unsubstituted non-aromatic carbocylylureido", "substituted or unsubstituted non-aromatic heterocyclylureido", "substituted or unsubstituted non-aromatic carbocyclyloxycarbonylamino", and "substituted or unsubstituted non-aromatic heterocyclyloxycarbonylamino", "substituted or unsubstituted non-aromatic carbocyclylsulfonyl", and "substituted or unsubstituted non-aromatic heterocyclylsulfonyl" の non-aromatic carbocycle, and non-aromatic heterocycle may be optionally substituted with "oxo" as above.

In the compound represented by formula (I) or pharmaceutically acceptable salt thereof,

[Chemical Formula 28]

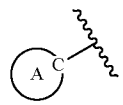

means the atom on Ring A bonded to the ring which includes $Z_1$, $Z_2$ and $Z_3$ is a carbon atom. In also Ring A', Ring A' bonded to the ring which includes $Z_1$, $Z_2$ and $Z_3$ is a carbon atom. In also Ring A", Ring A" bonded to the ring which includes $Z_1$, $Z_2$ and $Z_3$ is a carbon atom.

Specific embodiments of the present invention are illustrated below.

The embodiments for the compound represented by formula (I) or pharmaceutically acceptable salt thereof are described as the following (IA) to the following (IE).

(IA)
(IA-1)

The compound according to the above (1) or (1'), represented by formula (Ia), formula (Ib), formula (Ic), formula (Id) or formula (Ie):

[Chemical Formula 29]

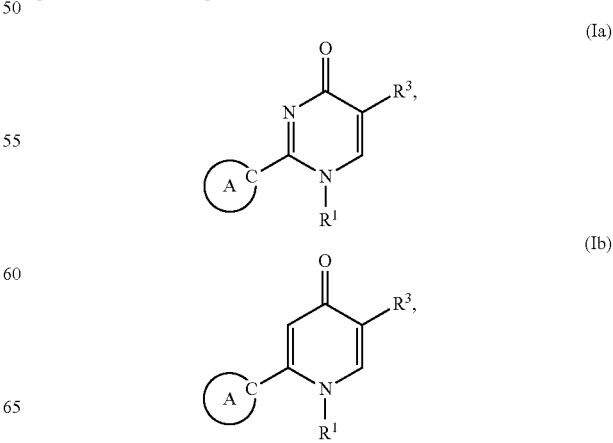

-continued

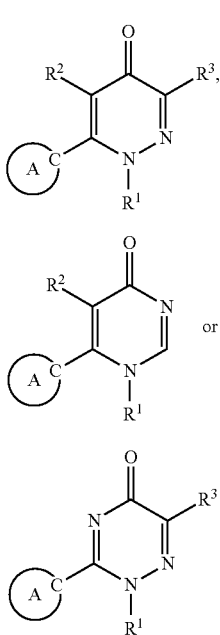

wherein each symbol is the same as the above (1), or a pharmaceutically acceptable salt thereof.

(IA-2)
The compound according to the above (1) or (1'), represented by formula (Ia), formula (Ib), formula (Ic) or formula (Id), or pharmaceutically acceptable salt thereof.

(IA-3)
The compound according to the above (1) or (1'), represented by formula (Ia), formula (Ib), formula (Ic) or formula (Ie), or pharmaceutically acceptable salt thereof.

(IA-4)
The compound according to the above (1) or (1'), represented by formula (Ia), formula (Ic), formula (Id) or formula (Ie), or pharmaceutically acceptable salt thereof.

(IA-5)
The compound according to the above (1) or (1'), represented by formula (Ia), formula (Ib) or formula (Ic), or pharmaceutically acceptable salt thereof.

(IA-6)
The compound according to the above (1) or (1'), represented by formula (Ia), formula (Ic) or formula (Id), or pharmaceutically acceptable salt thereof.

(IA-7)
The compound according to the above (1) or (1'), represented by formula (Ia), formula (Ic) or formula (Ie), or pharmaceutically acceptable salt thereof.

(IA-8)
The compound according to the above (1) or (1'), represented by formula (Ia) or formula (Ib), or pharmaceutically acceptable salt thereof.

(IA-9)
The compound according to the above (1) or (1'), represented by formula (Ia) or formula (Ic), or pharmaceutically acceptable salt thereof.

(IA-10)
The compound according to the above (1) or (1'), represented by formula (Ia), or pharmaceutically acceptable salt thereof.

(IA-11)
The compound according to the above (1) or (1'), represented by formula (Ib), or pharmaceutically acceptable salt thereof.

(IA-12)
The compound according to the above (1) or (1'), represented by formula (Ic), or pharmaceutically acceptable salt thereof.

(IA-13)
The compound according to the above (1) or (1'), represented by formula (Id), or pharmaceutically acceptable salt thereof.

(IA-14)
The compound according to the above (1) or (1'), represented by formula (Ie), or pharmaceutically acceptable salt thereof.

(IB)
(IB-1)
In the compound of formula (I) or the above (IA),
the compound wherein $R^1$ is substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl,
or pharmaceutically acceptable salt thereof.

(IB-2)
In the compound of formula (I) or the above (IA),
the compound wherein $R^1$ is substituted or unsubstituted non-aromatic carbocyclyl, or substituted or unsubstituted non-aromatic heterocyclyl, or pharmaceutically acceptable salt thereof.

(IB-3)
In the compound of formula (I) or the above (IA),
the compound wherein $R^1$ is substituted or unsubstituted alkyl, substituted or unsubstituted alkenyl, or substituted or unsubstituted alkynyl,
or pharmaceutically acceptable salt thereof.

(IB-4)
In the compound of formula (I) or the above (IA),
the compound wherein $R^1$ is substituted alkyl,
or pharmaceutically acceptable salt thereof.

(IB-5)
In the compound of formula (I) or the above (IA),
the compound wherein $R^1$ is unsubstituted alkyl, alkyl substituted with one or more substituent(s) selected from the substituent group α1 (the substituent group α1: cyano, substituted or unsubstituted alkyloxy, substituted or unsubstituted alkenyloxy, substituted or unsubstituted alkynyloxy, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, or substituted or unsubstituted non-aromatic heterocyclyloxy),
unsubstituted alkenyl, alkenyl substituted with one or more substituent(s) selected from the substituent group α1,
unsubstituted alkynyl, or alkynyl substituted with one or more substituent(s) selected from the substituent group α1,
or pharmaceutically acceptable salt thereof.

(IB-6)
In the compound of formula (I) or the above (IA),
the compound wherein $R^1$ is alkyl substituted with one or more substituent(s) selected from the substituent group α1,
or pharmaceutically acceptable salt thereof.

(IB-7)
In the compound of formula (I) or the above (IA),
the compound wherein $R^1$ is unsubstituted alkyl, alkyl substituted with one or more substituent(s) selected from the substituent group α2 (the substituent group α2: cyano, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl), unsubstituted alkenyl, alkenyl substituted with one or more substituent(s) selected from the substituent group α2,
unsubstituted alkynyl, alkynyl substituted with one or more substituent(s) selected from the substituent group α2,
or pharmaceutically acceptable salt thereof.
(IB-8)
In the compound of formula (I) or the above (IA),
the compound wherein $R^1$ is alkyl substituted with one or more substituent(s) selected from the substituent group α2,
or pharmaceutically acceptable salt thereof.
(IB-9)
In the compound of formula (I) or the above (IA),
the compound wherein $R^1$ is the group represented by —$(C(R^{5a})(R^{5b}))$m-$R^{1a}$; $R^{1a}$, $R^{5a}$ and $R^{5b}$ are the same as the above (10),
or pharmaceutically acceptable salt thereof.
(IB-10)
In the compound of the above (IB-9),
the compound wherein $R^{5a}$ is each independently a hydrogen atom, halogen, or substituted or unsubstituted alkyl, and
$R^{5b}$ is each independently a hydrogen atom, halogen, or substituted or unsubstituted alkyl,
or pharmaceutically acceptable salt thereof.
(IB-11)
In the compound of the above (IB-9),
the compound wherein $R^{5a}$ is each independently a hydrogen atom, unsubstituted alkyl, or alkyl substituted with one or more substituent(s) selected from halogen, hydroxy, or alkyloxy,
$R^{5b}$ is each independently a hydrogen atom, unsubstituted alkyl, or alkyl substituted with one or more substituent(s) selected from halogen, hydroxy, or alkyloxy,
or pharmaceutically acceptable salt thereof.
(IB-12)
In the compound of the above (IB-9),
the compound wherein $R^{5a}$ and $R^{5b}$ are a hydrogen atom.
or pharmaceutically acceptable salt thereof.
(IB-13)
In the compound of any one of the above (IB-9) to the above (IB-12),
the compound wherein m is an integer from 1 to 4,
or pharmaceutically acceptable salt thereof.
(IB-14)
In the compound of any one of the above (IB-9) to the above (IB-12),
the compound wherein m is 1 or 2,
or pharmaceutically acceptable salt thereof.
(IB-15)
In the compound of any one of the above (IB-9) to the above (IB-12),
the compound wherein m is 1,
or pharmaceutically acceptable salt thereof.
(IB-16)
In the compound of any one of the above (IB-9) to the above (IB-15),
the compound wherein $R^{1a}$ is substituted or unsubstituted aromatic carbocyclyl, or substituted or unsubstituted aromatic heterocyclyl,
or pharmaceutically acceptable salt thereof.
(IB-17)
In the compound of any one of the above (IB-8) to the above (IB-15),
the compound wherein $R^{1a}$ is substituted or unsubstituted aromatic carbocyclyl,
or pharmaceutically acceptable salt thereof.
(IC)
(IC-1)
In the compound of formula (I), the above (IA) or the above (IB),
the compound wherein Ring A is a substituted or unsubstituted aromatic carbocycle, a substituted or unsubstituted non-aromatic carbocycle, a substituted or unsubstituted aromatic heterocycle, or a substituted or unsubstituted non-aromatic heterocycle,
or pharmaceutically acceptable salt thereof.
(IC-2)
In the compound of formula (I), the above (IA) or the above (IB),
the compound wherein Ring A is a substituted or unsubstituted six-membered aromatic carbocycle, a substituted or unsubstituted six-membered non-aromatic carbocycle, a substituted or unsubstituted six-membered aromatic heterocycle, or a substituted or unsubstituted six-membered non-aromatic heterocycle,
or pharmaceutically acceptable salt thereof.
(IC-3)
In the compound of formula (I), the above (IA) or the above (IB),
the compound wherein Ring A is a substituted aromatic carbocycle, or pharmaceutically acceptable salt thereof.
(IC-4)
In the compound of formula (I), the above (IA) or the above (IB),
the compound wherein Ring A is substituted benzene ring,
or pharmaceutically acceptable salt thereof.
(IC-5)
In the compound of formula (I), the above (IA) or the above (IB),
the compound wherein Ring A is an unsubstituted aromatic carbocycle, an aromatic carbocycle substituted with one or more substituent(s) selected from the substituent group α3 (the substituent group α3: halogen, amino, carbamoyl, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted monoalkylamino, substituted or unsubstituted dialkylamino, substituted or unsubstituted monoalkylcarbonylamino, substituted or unsubstituted monoalkylcarbamoyl, substituted or unsubstituted dialkylcarbamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino), an unsubstituted non-aromatic carbocycle, a non-aromatic carbocycle substituted with one or more substituent(s) selected from the substituent group α3, an unsubstituted aromatic heterocycle, an aromatic heterocycle substituted with one or more substituent(s) selected from the substituent group α3,
an unsubstituted non-aromatic heterocycle, or a non-aromatic heterocycle substituted with one or more substituent(s) selected from the substituent group α3,
or pharmaceutically acceptable salt thereof.
(IC-6)
In the compound of formula (I), the above (IA) or the above (IB),
the compound wherein Ring A is an aromatic carbocycle substituted with one or more substituent(s) selected from the substituent group α3,
or pharmaceutically acceptable salt thereof.
(IC-7)
In the compound of formula (I), the above (IA) or the above (IB),
the compound wherein Ring A is an unsubstituted aromatic carbocycle, an aromatic carbocycle substituted with one or more substituent(s) selected from the substituent group α4 (the substituent group α4: halogen, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl),
an unsubstituted non-aromatic carbocycle, a non-aromatic carbocycle substituted with one or more substituent(s) selected from the substituent group α4,
an unsubstituted aromatic heterocycle, an aromatic heterocycle substituted with one or more substituent(s) selected from the substituent group α4,
an unsubstituted non-aromatic heterocycle, or a non-aromatic heterocycle substituted with one or more substituent(s) selected from the substituent group α4,
or pharmaceutically acceptable salt thereof.
(IC-8)
In the compound of formula (I), the above (IA) or the above (IB),
the compound wherein Ring A is an aromatic carbocycle substituted with one or more substituent(s) selected from the substituent group α4,
or pharmaceutically acceptable salt thereof.
(IC-9)
In the compound of formula (I), the above (IA) or the above (IB),
the compound wherein Ring A is an unsubstituted aromatic carbocycle, an aromatic carbocycle substituted with one or more substituent(s) selected from the substituent group α5 (the substituent group α5: halogen, substituted or unsubstituted alkyl, substituted or unsubstituted alkyloxy, or substituted or unsubstituted aromatic carbocyclyl).
an unsubstituted non-aromatic carbocycle, a non-aromatic carbocycle substituted with one or more substituent(s) selected from the substituent group α5,
an unsubstituted aromatic heterocycle, an aromatic heterocycle substituted with one or more substituent(s) selected from the substituent group α5.
an unsubstituted non-aromatic heterocycle, or a non-aromatic heterocycle substituted with one or more substituent(s) selected from the substituent group α5,
or pharmaceutically acceptable salt thereof.

(IC-10)
In the compound of formula (I), the above (IA) or the above (IB),
the compound wherein Ring A is an aromatic carbocycle substituted with one or more substituent(s) selected from the substituent group α5,
or pharmaceutically acceptable salt thereof.
(IC-11)
In the compound of formula (I), the above (IA) or the above (IB),
the compound wherein Ring A is an unsubstituted aromatic carbocycle,
an aromatic carbocycle substituted with one or more substituent(s) selected from the substituent group α6 (the substituent group α6: halogen or substituted or unsubstituted alkyl),
an unsubstituted non-aromatic carbocycle, a non-aromatic carbocycle substituted with one or more substituent(s) selected from the substituent group α6,
an unsubstituted aromatic heterocycle, an aromatic heterocycle substituted with one or more substituent(s) selected from the substituent group α6,
an unsubstituted non-aromatic heterocycle, or a non-aromatic heterocycle substituted with one or more substituent(s) selected from the substituent group α6,
or pharmaceutically acceptable salt thereof.
(IC-12)
In the compound of formula (I), the above (IA) or the above (IB),
the compound wherein Ring A is an aromatic carbocycle substituted with one or more substituent(s) selected from the substituent group α6,
or pharmaceutically acceptable salt thereof.
(IC-13)
In the compound of formula (I), the above (IA) or the above (IB),
the compound wherein

[Chemical Formula 30]

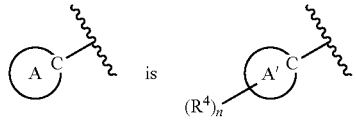

and Ring A', $R^4$ and n are the same as the above (3),
or pharmaceutically acceptable salt thereof.
(IC-14)
In the compound of the above (IC-13),
the compound wherein $R^4$ is each independently a substituent selected from the substituent group α3,
or pharmaceutically acceptable salt thereof.
(IC-15)
In the compound of the above (IC-13),
the compound wherein $R^4$ is each independently a substituent selected from the substituent group α4
or pharmaceutically acceptable salt thereof.
(IC-16)
In the compound of the above (IC-13),
the compound wherein $R^4$ is each independently a substituent selected from the substituent group α5,
or pharmaceutically acceptable salt thereof.

(IC-17)
In the compound of the above (IC-13),
the compound wherein $R^4$ is each independently a substituent selected from the substituent group α6,
or pharmaceutically acceptable salt thereof.
(IC-18)
In the compound of any one of the above (IC-13) to the above (IC-17),
the compound wherein n is an integer from 1 to 4,
or pharmaceutically acceptable salt thereof.
(IC-19)
In the compound of any one of the above (IC-13) to the above (IC-17),
the compound wherein n is an integer from 2 to 4,
or pharmaceutically acceptable salt thereof.
(IC-20)
In the compound of any one of the above (IC-13) to the above (IC-17),
the compound wherein n is an integer from 2 to 3,
or pharmaceutically acceptable salt thereof.
(IC-21)
In the compound of any one of the above (IC-13) to the above (IC-17),
the compound wherein n is an integer from 0 to 2,
or pharmaceutically acceptable salt thereof.
(IC-22)
In the compound of any one of the above (IC-13) to the above (IC-17),
the compound wherein n is 1 or 2,
or pharmaceutically acceptable salt thereof.
(IC-23)
In the compound of any one of the above (IC-13) to the above (IC-17),
the compound wherein n is 2,
or pharmaceutically acceptable salt thereof.
(IC-24)
In the compound of any one of the above (IC-13) to the above (IC-23),
the compound wherein Ring A' is a six-membered aromatic carbocycle, a six-membered non-aromatic carbocycle, a six-membered aromatic heterocycle, or a six-membered non-aromatic heterocycle,
or pharmaceutically acceptable salt thereof.
(IC-25)
In the compound of any one of the above (IC-13) to the above (IC-23),
the compound wherein Ring A' is an aromatic carbocycle,
or pharmaceutically acceptable salt thereof.
(IC-26)
In the compound of any one of the above (IC-13) to the above (IC-23),
the compound wherein Ring A' is a benzene ring,
or pharmaceutically acceptable salt thereof.
(IC-27)
In the compound of formula (I), the above (IA) or the above (IB),
the compound wherein

[Chemical Formula 31]

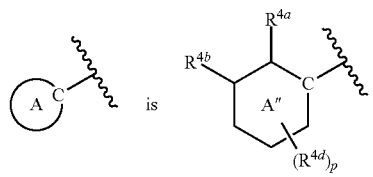

$R^{4a}$ and $R^{4b}$ are the same as the above (6); Ring A" is a six-membered aromatic carbocycle, a six-membered non-aromatic carbocycle, a six-membered aromatic heterocycle, or a six-membered non-aromatic heterocycle; $R^{4d}$ is the same as $R^4$ in the above (3); and p is an integer from 0 to 2,
or pharmaceutically acceptable salt thereof.
(IC-28)
In the compound of formula (I), the above (IA) or the above (IB),
the compound wherein

[Chemical Formula 32]

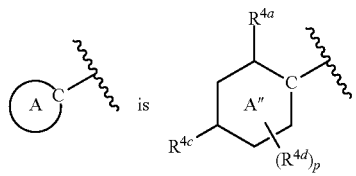

$R^{4a}$ and $R^{4b}$ are the same as the above (6); and Ring A", $R^{4d}$ and p are the same as the above (IC-27),
or pharmaceutically acceptable salt thereof.
(IC-29)
In the compound of formula (I), the above (IA) or the above (IB),
the compound wherein

[Chemical Formula 33]

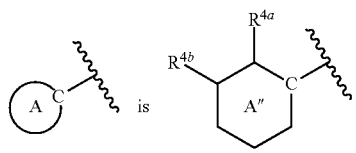

$R^{4a}$ and $R^{4b}$ are the same as the above (6); and Ring A" is the same as the above (IC-27),
or pharmaceutically acceptable salt thereof.
(IC-30)
In the compound of formula (I), the above (IA) or the above (IB),
the compound wherein

[Chemical Formula 34]

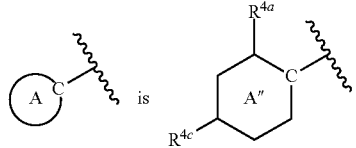

$R^{4a}$ and $R^{4b}$ are the same as the above (6); and Ring A" is the same as the above (IC-27),
or pharmaceutically acceptable salt thereof.)
(IC-31)
In the compound of formula (I), the above (IA) or the above (IB),
the compound wherein

[Chemical Formula 35]

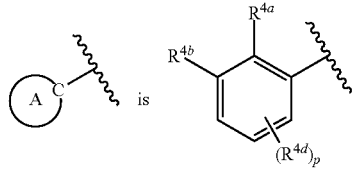

$R^{4a}$ and $R^{4b}$ are the same as the above (6); and $R^{4d}$ and p are the same as the above (IC-27),
or pharmaceutically acceptable salt thereof.

(IC-32)
In the compound of formula (I), the above (IA) or the above (IB),
the compound wherein

[Chemical Formula 36]

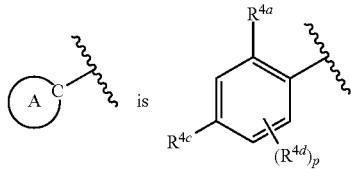

$R^{4b}$ and $R^{4c}$ are the same as the above (6); and $R^{4d}$ and p are the same as the above (IC-27),
or pharmaceutically acceptable salt thereof.
(IC-33)
In the compound of formula (I), the above (IA) or the above (IB),
the compound wherein

[Chemical Formula 37]

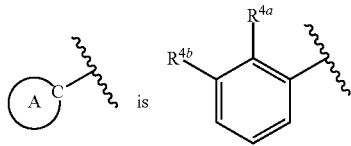

and $R^{4a}$ and $R^{4b}$ are the same as the above (6),
or pharmaceutically acceptable salt thereof.
(IC-34)
In the compound of formula (I), the above (IA) or the above (IB),
the compound wherein

[Chemical Formula 38]

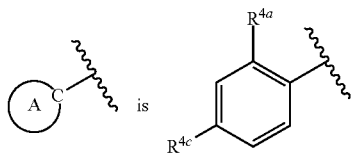

and $R^{4b}$ and $R^{4c}$ are the same as the above (6),
or pharmaceutically acceptable salt thereof.
(IC-35)
In the compound of any one of the above (IC-27) to the above (IC-34),
the compound wherein $R^{4a}$, $R^{4b}$ and $R^{4c}$ are each independently a substituent selected from the substituent group α3,
or pharmaceutically acceptable salt thereof.
(IC-36)
In the compound of any one of the above (IC-27) to the above (IC-34),
the compound wherein $R^{4a}$, $R^{4b}$ and $R^{4c}$ are each independently a substituent selected from the substituent group α4,
or pharmaceutically acceptable salt thereof.

(IC-37)
In the compound of any one of the above (IC-27) to the above (IC-34),
the compound wherein $R^{4a}$, $R^{4b}$ and $R^{4c}$ are each independently a substituent selected from the substituent group α5,
or pharmaceutically acceptable salt thereof.
(IC-38)
In the compound of any one of the above (IC-27) to the above (IC-34),
the compound wherein $R^{4a}$, $R^{4b}$ and $R^{4c}$ are each independently a substituent selected from the substituent group α6,
or pharmaceutically acceptable salt thereof.
(IC-39)
In the compound of any one of the above (IC-27) to the above (IC-34),
the compound wherein $R^{4a}$ is halogen,
$R^{4b}$ and $R^{4c}$ is substituted or unsubstituted alkyl,
or pharmaceutically acceptable salt thereof.
(IC-40)
In the compound of any one of the above (IC-27) to the above (IC-39),
the compound wherein p is 0 or 1,
or pharmaceutically acceptable salt thereof.
(IC-41)
In the compound of any one of the above (IC-27) to the above (IC-39),
the compound wherein p is 2,
or pharmaceutically acceptable salt thereof.
(IC-42)
In the compound of any one of the above (IC-27) to the above (IC-39),
the compound wherein p is 1,
or pharmaceutically acceptable salt thereof.
(IC-43)
In the compound of any one of the above (IC-27) to the above (IC-39),
the compound wherein p is 0,
or pharmaceutically acceptable salt thereof.
(IC-44)
In the compound of any one of the above (IC-27) to the above (IC-43),
the compound wherein $R^{4d}$ is halogen, cyano, substituted or unsubstituted alkyl, or substituted or unsubstituted alkyloxy,
or pharmaceutically acceptable salt thereof.
(IC-45)
In the compound of any one of the above (IC-27) to the above (IC-43),
the compound wherein $R^{4d}$ is halogen or substituted or unsubstituted alkyl,
or pharmaceutically acceptable salt thereof.
(IC-46)
In the compound of any one of the above (IC-27) to the above (IC-43),
the compound wherein $R^{4d}$ is halogen or unsubstituted alkyl,
or pharmaceutically acceptable salt thereof.
(IC-47)
In the compound of any one of the above (IC-27) to the above (IC-43),
the compound wherein $R^{4d}$ is halogen,
or pharmaceutically acceptable salt thereof.

(ID)
(ID-1)
In the compound of formula (I) or any one of the above (IA) to the above (IC),
the compound wherein $R^3$ is halogen, amino, carbamoyl, sulfamoyl, cyano, ureido, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted monoalkylamino, substituted or unsubstituted dialkylamino, substituted or unsubstituted monoalkylcarbonylamino, substituted or unsubstituted monoalkylsulfonylamino, substituted or unsubstituted alkylsulfanyl, substituted or unsubstituted alkenylsulfanyl, substituted or unsubstituted alkynylsulfanyl, substituted or unsubstituted monoalkylcarbamoyl, substituted or unsubstituted dialkylcarbamoyl, substituted or unsubstituted monoalkylsulfamoyl, substituted or unsubstituted dialkylsulfamoyl, substituted or unsubstituted alkyloxycarbonylamino, substituted or unsubstituted alkenyloxycarbonylamino, substituted or unsubstituted alkynyloxycarbonylamino, substituted or unsubstituted alkylureido, substituted or unsubstituted alkenylureido, substituted or unsubstituted alkynylureido, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylcarbonylamino, substituted or unsubstituted non-aromatic carbocyclylcarbonylamino, substituted or unsubstituted aromatic heterocyclylcarbonylamino, substituted or unsubstituted non-aromatic heterocyclylcarbonylamino, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylureido, substituted or unsubstituted non-aromatic carbocyclylureido, substituted or unsubstituted aromatic heterocyclylureido, substituted or unsubstituted non-aromatic heterocyclylureido, substituted or unsubstituted aromatic carbocyclyloxycarbonylamino, substituted or unsubstituted non-aromatic carbocyclyloxycarbonylamino, substituted or unsubstituted aromatic heterocyclyloxycarbonylamino, or substituted or unsubstituted non-aromatic heterocyclyloxycarbonylamino,
or pharmaceutically acceptable salt thereof.

(ID-2)
In the compound of formula (I) or any one of the above (IA) to the above (IC),
the compound wherein $R^3$ is halogen, amino, carbamoyl, sulfamoyl, cyano, ureido, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted monoalkylamino, substituted or unsubstituted dialkylamino, substituted or unsubstituted monoalkylcarbonylamino, substituted or unsubstituted monoalkylsulfonylamino, substituted or unsubstituted alkylsulfanyl, substituted or unsubstituted alkenylsulfanyl, substituted or unsubstituted alkynylsulfanyl, substituted or unsubstituted alkyloxycarbonylamino, substituted or unsubstituted alkenyloxycarbonylamino, substituted or unsubstituted alkynyloxycarbonylamino, substituted or unsubstituted alkylureido, substituted or unsubstituted alkenylureido, substituted or unsubstituted alkynylureido, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylcarbonylamino, substituted or unsubstituted non-aromatic carbocyclylcarbonylamino, substituted or unsubstituted aromatic heterocyclylcarbonylamino, or substituted or unsubstituted non-aromatic heterocyclylcarbonylamino,
or pharmaceutically acceptable salt thereof.

(ID-3)
In the compound of formula (I) or any one of the above (IA) to the above (IC),
the compound wherein $R^3$ is halogen, amino, carbamoyl, sulfamoyl, cyano, ureido, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted monoalkylamino, substituted or unsubstituted dialkylamino, substituted or unsubstituted monoalkylcarbonylamino, substituted or unsubstituted monoalkylsulfonylamino, substituted or unsubstituted alkylsulfanyl, substituted or unsubstituted alkenylsulfanyl, substituted or unsubstituted alkynylsulfanyl, substituted or unsubstituted alkyloxycarbonylamino, substituted or unsubstituted alkenyloxycarbonylamino, substituted or unsubstituted alkynyloxycarbonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, or substituted or unsubstituted non-aromatic heterocyclylamino,
or pharmaceutically acceptable salt thereof.
(ID-4)
In the compound of formula (I) or any one of the above (IA) to the above (IC),
the compound wherein $R^3$ is halogen, amino, carbamoyl, sulfamoyl, cyano, ureido, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted monoalkylamino, substituted or unsubstituted dialkylamino, substituted or unsubstituted monoalkylcarbonylamino, substituted or unsubstituted monoalkylsulfonylamino, substituted or unsubstituted alkyloxycarbonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, or substituted or unsubstituted non-aromatic heterocyclylamino,
or pharmaceutically acceptable salt thereof.
(ID-5)
In the compound of formula (I) or any one of the above (IA) to the above (IC),
the compound wherein $R^3$ is halogen, amino, carbamoyl, sulfamoyl, cyano, ureido, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted monoalkylamino, substituted or unsubstituted dialkylamino, substituted or unsubstituted monoalkylcarbonylamino, substituted or unsubstituted monoalkylsulfonylamino, substituted or unsubstituted alkyloxycarbonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, or substituted or unsubstituted non-aromatic heterocyclyloxy,
or pharmaceutically acceptable salt thereof.
(ID-6)
In the compound of formula (I) or any one of the above (IA) to the above (IC),
the compound wherein $R^3$ is halogen, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted monoalkylcarbonylamino, substituted or unsubstituted dialkylcarbonylamino, substituted or unsubstituted alkyloxycarbonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, or substituted or unsubstituted non-aromatic heterocyclyloxy,
or pharmaceutically acceptable salt thereof.
(ID-7)
In the compound of formula (I) or any one of the above (IA) to the above (IC),
the compound wherein $R^3$ is halogen, cyano, substituted or unsubstituted alkyl, substituted or unsubstituted alkenyl, substituted or unsubstituted alkynyl, substituted or unsubstituted alkyloxy, substituted or unsubstituted monoalkylcarbonylamino, substituted or unsubstituted alkyloxycarbonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, or substituted or unsubstituted non-aromatic heterocyclyloxy,
or pharmaceutically acceptable salt thereof.
(ID-8)
In the compound of formula (I) or any one of the above (IA) to the above (IC),
the compound wherein $R^3$ is a hydrogen atom,
or pharmaceutically acceptable salt thereof.
(IE)
(IE-1)
In the compound of formula (I) or any one of the above (IA) to the above (ID),
the compound wherein $R^2$ is a hydrogen atom, halogen, hydroxy, amino, carbamoyl, sulfamoyl, cyano, ureido, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted monoalkylamino, substituted or unsubstituted dialkylamino, substituted or unsubstituted alkylsulfonyl, substituted or unsubstituted monoalkylcarbonylamino, substituted or unsubstituted monoalkylsulfonylamino, substituted or unsubstituted alkylsulfanyl, substituted or unsubstituted monoalkylcarbamoyl, substituted or unsubstituted dialkylcarbamoyl, substituted or unsubstituted monoalkylsulfamoyl, substituted or unsubstituted dialkylsulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted aromatic carbocyclylsulfanyl, substituted or unsubstituted non-aromatic carbocyclylsulfanyl, substituted or unsubstituted aromatic heterocyclylsulfanyl, or substituted or unsubstituted non-aromatic heterocyclylsulfanyl,
or pharmaceutically acceptable salt thereof.
(IE-2)

In the compound of formula (I) or any one of the above (IA) to the above (ID),
the compound wherein $R^2$ is a hydrogen atom, halogen, amino, carbamoyl, sulfamoyl, cyano, ureido, substituted or unsubstituted alkyl, substituted or unsubstituted alkenyl, substituted or unsubstituted alkynyl, substituted or unsubstituted alkyloxy, substituted or unsubstituted alkenyloxy, or substituted or unsubstituted alkynyloxy,
or pharmaceutically acceptable salt thereof.
(IE-3)

In the compound of formula (I) or any one of the above (IA) to the above (ID),
the compound wherein $R^2$ is a hydrogen atom, halogen, cyano, substituted or unsubstituted alkyl, or substituted or unsubstituted alkyloxy,
or pharmaceutically acceptable salt thereof.
(IE-4)

In the compound of formula (I) or any one of the above (IA) to the above (ID),
the compound wherein $R^2$ is a hydrogen atom, or halogen, or pharmaceutically acceptable salt thereof.
(IE-5)

In the compound of formula (I) or any one of the above (IA) to the above (ID),
the compound wherein $R^2$ is a hydrogen atom,
or pharmaceutically acceptable salt thereof.

The compounds represented by formula (I) are not limited to specific isomers but include all possible isomers (e.g., keto-enol isomers, imine-enamine isomers, diastereoisomers, enantiomers, rotamers or the like), racemates or mixtures thereof. For example, a compound represented by formula (I) includes the following tautomer.

[Chemical Formula 39]

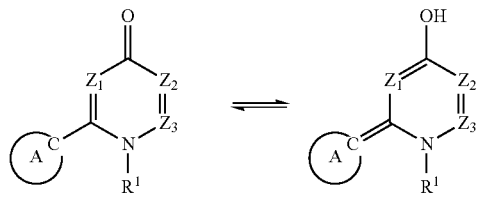

One or more hydrogen, carbon and/or other atoms in the compounds represented by formula (I) may be replaced with isotopes of hydrogen, carbon and/or other atoms respectively. Example a of isotopes include hydrogen, carbon, nitrogen, oxygen, phosphorus, sulfur, fluorine, iodine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$ and $^{36}Cl$ respectively. The compounds represented by formula (I) include the compounds replaced with these isotopes. The compounds replaced with the above isotopes are useful as medicines and include all of radiolabeled compounds of the compound of formula (I). A "method of radiolabeling" in the manufacture of the "radiolabeled compounds" is encompassed by the present invention, and is useful for studies on metabolized drug pharmacokinetics, studies on binding assay and/or diagnostic tools.

A radiolabeled compound of the compounds represented by formula (I) can be prepared using well-known methods in the art. For example, a tritium-labeled compound represented by formula (I) can be prepared by introducing a tritium to a certain compound represented by formula (I), through a catalytic dehalogenation reaction using a tritium. This method comprises reacting with an appropriately-halogenated precursor of the compound represented by formula (I) with tritium gas in the presence of an appropriate catalyst, such as Pd/C, and in the presence or absent of a base. The other appropriate method of preparing a tritium-labeled compound can be referred to "Isotopes in the Physical and Biomedical Sciences, Vol. 1, Labeled Compounds (Part A), Chapter 6 (1987)". A $^{14}C$-labeled compound can be prepared by using a raw material having $^{14}C$.

The pharmaceutically acceptable salts of the compounds represented by formula (I) include, for example, salts with alkaline metal (e.g., lithium, sodium, potassium or the like), alkaline earth metal (e.g., calcium, barium or the like), magnesium, transition metal (e.g., zinc, iron or the like), ammonia, organic bases (e.g., trimethylamine, triethylamine, dicyclohexylamine, ethanolamine, diethanolamine, triethanolamine, meglumine, ethylenediamine, pyridine, picoline, quinoline or the like) or amino acids, or salts with inorganic acids (e.g., hydrochloric acid, sulfuric acid, nitric acid, carbonic acid, hydrobromic acid, phosphoric acid, hydroiodic acid or the like) or organic acids (e.g., formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, ethanesulfonic acid or the like). Especially, salts with hydrochloric acid, sulfuric acid, phosphoric acid, tartaric acid, methanesulfonic acid and the like are included. These salts can be formed by the usual methods.

The compounds represented by formula (T) of the present invention or pharmaceutically acceptable salts thereof may form solvates (e.g., hydrates or the like) and/or crystal polymorphs. The present invention encompasses those various solvates and crystal polymorphs. "Solvates" may be those wherein any numbers of solvent molecules (e.g., water molecules or the like) are coordinated with the compounds represented by formula (I). When the compounds represented by formula (I) or pharmaceutically acceptable salts thereof are allowed to stand in the atmosphere, the compounds may absorb water, resulting in attachment of adsorbed water or formation of hydrates. Recrystallization of the compounds represented by formula (I) or pharmaceutically acceptable salts thereof may produce crystal polymorphs.

The compounds represented by formula (I) of the present invention or pharmaceutically acceptable salts thereof may form prodrugs. The present invention also encompasses such various prodrugs. Prodrugs are derivatives of the compounds of the present invention that have chemically or metabolically degradable groups, and compounds that are converted to the pharmaceutically active compounds of the present invention through solvolysis or under physiological conditions in vivo. Prodrugs include compounds that are converted to the compounds represented by formula (I) through enzymatic oxidation, reduction, hydrolysis or the like under physiological conditions in vivo, compounds that are converted to the compounds represented by formula (I) through hydrolysis by gastric acid etc., and the like. Methods for selecting and preparing suitable prodrug derivatives are described in, for example, "Design of Prodrugs, Elsevier, Amsrdam, 1985". Prodrugs themselves may have some activity.

When the compounds represented by formula (I) or pharmaceutically acceptable salts thereof have hydroxyl group(s), prodrugs include acyloxy derivatives and sulfonyloxy derivatives that are prepared by, for example, reacting compounds having hydroxyl group(s) with suitable acyl halide, suitable acid anhydride, suitable sulfonyl chloride, suitable sulfonyl anhydride and mixed anhydride, or with a condensing agent. For example, they include $CH_3COO-$, $C_2H_5COO-$, tert-BuCOO—, $C_{15}H_{31}COO-$, PhCOO—, (m-NaOOCPh)COO—, $NaOOCCH_2CH_2COO-$, $CH_3CH(NH_2)COO-$, $CH_2N(CH_3)_2COO-$, $CH_3SO_3-$, $CH_3CH_2SO_3-$, $CF_3SO_3-$, $CH_2FSO_3-$, $CF_3CH_2SO_3-$, p-$CH_3O$-$PhSO_3-$, $PhSO_3-$ and p-$CH_3PhSO_3$.

(Synthetic Procedures for the Compound of the Present Invention)

For example, the compounds represented by formula (I) of the present invention can be prepared by the general procedures described below. The methods for extraction, purification and the like may be carried out by using the usual method for the experiments of organic chemistry.

The compounds of the present invention can be synthesized by referring to the known methods in the art.

The general procedures for the synthesis of the compounds of the present invention are described below. The starting materials and reaction reagents used in such synthesis are commercially available or can be synthesized according to methods well known in the art using the compounds commercially available. The methods for extraction, purification and the like may be carried out by using the usual method for the experiments of organic chemistry.

The compounds of the present invention can be synthesized by referring to the known methods in the art.

In all the following steps, when a substituent which interferes with the reaction, e.g. hydroxy, mercapto, amino, formyl, carbonyl, carboxy, is possessed, the substituent is protected by the method such as those described in Protective Groups in Organic Synthesis, Theodora W Greene (John Wiley & Sons) in advance, and the protective group may be removed at a desirable step.

During all the following steps, the order of the steps to be performed may be appropriately changed. In each step, an intermediate may be isolated and then used in the next step.

In this description, meanings of each abbreviation are as follows:
DIEA: N,N-diisopropylethylamine
DMA: N,N-dimethyl acetamide
DME: Dimethoxyethane
DMF: N,N-dimethylformamide
DMSO: Dimethyl sulfoxide
mCPBA: m-chloroperoxybenzoic acid
NMP: N-methylpyrrolidone
$PdCl_2$(dppf): [1,1'-bis(diphenylphosphino)ferrocene]palladium (II) dichloride dichloromethane adduct
Xantphos: 4,5'-bis(diphenylphosphino)-9,9'-dimethylxanthene For example, the compounds represented by formula (I) of the present invention can be prepared by the general synthetic methods described below.

[Method A]

[Chemical Formula 40]

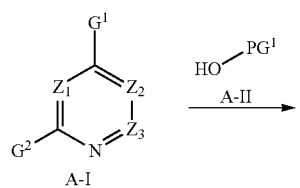

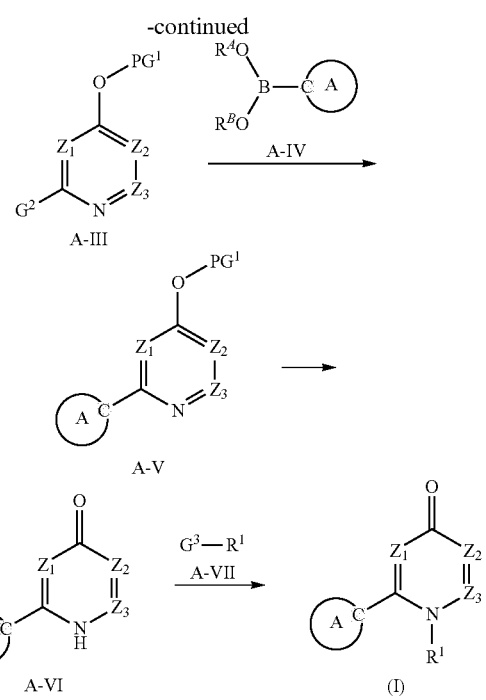

wherein $G^1$, $G^2$ and $G^3$ are each independently a leaving group such as halogen, substituted or unsubstituted alkylthio, substituted or unsubstituted alkylsulfinyl, substituted or unsubstituted alkylsulfonyl or the like, $PG^1$ is an appropriate protecting group of a hydroxy group, $R^A$ and $R^B$ are each independently a hydrogen atom, or substituted or unsubstituted alkyl, or is taken together to form substituted or unsubstituted non-aromatic heterocycle; and the other symbols are the same as the above (1).

(Step 1)

A compound (A-III) can be synthesized by the reaction of a compound (A-I) with a compound (A-II) in the presence of a base in the appropriate solvent.

In this reaction, 1.0 or more mole equivalent(s) of the compound (A-II), preferably 1.0 to 5.0 mole equivalent(s) can be used per an equivalent of the compound (A-I).

As the base which can be used, for example, metal hydride (e.g., sodium hydride, lithium hydride etc.), metal carboxylate (e.g., sodium carbonate, potassium bicarbonate, cesium carbonate etc.), metal alkoxide (e.g., sodium methoxide, sodium ethoxide, potassium tert-butoxide etc.), metal alkyl (e.g., butyllithium etc.) are exemplified, 1.0 or more mole equivalent(s), preferably 1.0 to 1.5 mole equivalent(s) can be used per an equivalent of the compound (A-I).

As the reaction solvent, alcohols (e.g., tert-butanol, isopropanol etc.), aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), DMF, DMSO, NMP, a mixed solvent thereof and the like are exemplified.

As the reaction temperature, −20° C. to 200° C., preferably 0° C. to 30° C. are exemplified.

As the reaction time, 0.1 to 80 hours, preferably 1 to 16 hours are exemplified.

The obtained desired compound (A-III) can be purified as necessary by the methods which are usually used (e.g., column chromatography, recrystallization etc.).

(Step 2)

A compound (A-V) can be synthesized by the reaction of the compound (A-III) with boronic acid or boronate ester (A-IV) in the presence of a metal catalyst and a base in the appropriate solvent.

In this reaction, 1.0 or more mole equivalent(s) of boronic acid or boronate ester (A-IV), preferably 1.0 to 5.0 mole equivalent(s) can be used per an equivalent of the compound (A-III).

As the metal catalyst, palladium (II) acetate, bis(dibenzylideneacetone)palladium, Tetrakis(triphenylphosphine)palladium, bis(triphenylphosphine)palladium (II) dichloride, bis(tri-tert-butylphosphine)palladium, [1,1'-bis(diphenylphosphino)ferrocene]palladium (II) dichloride dichloromethane adduct and the like are exemplified. 0.001 to 0.5 mole equivalent(s) can be used per an equivalent of the compound (A-III).

As the base, lithium hydroxide, sodium hydroxide, potassium hydroxide, potassium tert-butoxide, sodium tert-butoxide, sodium carbonate, cesium carbonate, potassium bicarbonate, sodium hydrogen carbonate, sodium phosphate, sodium hydrogen phosphate, potassium phosphate, potassium hydrogen phosphate and the like are exemplified. 1.0 to 10.0 mole equivalent(s) can be used per an equivalent of the compound (A-III).

As the reaction solvent, aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), DMF, DMA, NMP, DMSO, water and a mixed solvent thereof and the like are exemplified.

The reaction temperature is 20 to 250° C., under microwave irradiation as necessary, preferably 0 to 200° C.

The reaction time is 0.1 to 48 hours, preferably 0.5 to 12 hours.

The obtained desired compound (A-V) can be purified as necessary by the methods which are usually used (e.g., column chromatography, recrystallization etc.).

(Step 3)

A compound (A-VI) can be synthesized by the deprotection of the compound (A-V) in the presence of an acid, a Lewis acid or a base in the appropriate solvent.

As the acid, hydrochloric acid-ethyl acetate, hydrochloric acid-methanol, hydrochloric acid-dioxane, hydrobromic acid-acetic acid, hydrobromic acid, sulfuric acid, formic acid, trifluoroacetic acid and the like are exemplified. As the Lewis acid, trimethylsilyl iodide, $BBr_3$, $AlCl_3$, $BF_3 \cdot (Et_2O)$ and the like are exemplified. As the base, lithium hydroxide, sodium hydroxide, potassium hydroxide, potassium tert-butoxide, sodium tert-butoxide, sodium carbonate, cesium carbonate, potassium bicarbonate, sodium hydrogen carbonate, sodium phosphate, sodium hydrogen phosphate, potassium phosphate, potassium hydrogen phosphate, tetrabutyl ammonium fluoride, hydrogen fluoride-pyridine and the like are exemplified. 0.01 or more mole equivalent(s), preferably 0.5 to 10.0 mole equivalent(s) can be used per an equivalent of the compound (A-V).

As the reaction solvent, alcohols (e.g., methanol, ethanol, isopropanol etc.), aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), halogenated hydrocarbons (e.g., chloroform, dichloromethane etc.), DMF, DMSO, NMP, acetonitrile, DMA, pyridine, water and the like are exemplified. The reaction solvent may be used alone or in combination.

The reaction temperature is 0 to 200° C., under microwave irradiation as necessary, preferably 0 to 150° C.

The reaction time is 0.1 to 72 hours, preferably 0.5 to 18 hours.

The obtained desired compound (A-VI) can be purified as necessary by the methods which are usually used (e.g., column chromatography, recrystallization etc.).

(Step 4)

The compound (I) can be synthesized by the reaction of the compound (A-VI) and a compound (A-VII) in the presence of a base in the appropriate solvent.

In this reaction, 1.0 or more mole equivalent(s) of the compound (A-VII), preferably 1.0 to 5.0 mole equivalent(s) can be used per an equivalent of the compound (A-VI).

As the base, for example, metal hydroxide (e.g., sodium hydroxide, potassium hydroxide, tripotassium phosphate etc.), metal hydride (e.g., sodium hydride, lithium hydride etc.), metal carboxylate (e.g., sodium carbonate, potassium bicarbonate, cesium carbonate etc.), metal alkoxide (e.g., sodium methoxide, sodium ethoxide, potassium tert-butoxide etc.), metal alkyl (e.g., butyllithium etc.), pyridine, triethylamine, DIEA and the like are exemplified. 1.0 or more mole equivalent(s), preferably 1.0 to 5.0 mole equivalent(s) can be used per an equivalent of the compound (A-VI).

As the reaction solvent, aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), halogenated hydrocarbons (e.g., chloroform, dichloromethane etc.), DMF, DMSO, NMP, acetonitrile, pyridine, water and the like are exemplified. The reaction solvent may be used alone or in combination.

The reaction temperature is 0 to 200° C., under microwave irradiation as necessary, preferably 0 to 150° C.

The reaction time is 0.1 to 72 hours, preferably 0.5 to 18 hours.

The obtained desired compound (I) can be purified as necessary by the methods which are usually used (e.g., column chromatography, recrystallization etc.).

[Method B]

[Chemical Formula 41]

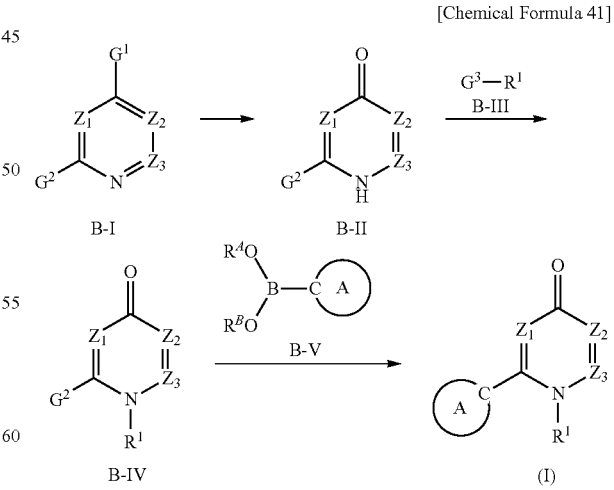

wherein each symbol is the same as the method A.

(Step 1)

A compound (B-II) can be synthesized by the reaction of a compound (B-I) with a basic aqueous solution.

As the base, for example, metal hydroxide (e.g., sodium hydroxide, potassium hydroxide, lithium hydroxide etc.), metal carboxylate (e.g., sodium carbonate, potassium bicarbonate, cesium carbonate etc.) and the like are exemplified. 1.0 or more mole equivalent(s), preferably 1.0 to 5.0 mole equivalent(s) can be used per an equivalent of the compound (B-I).

As the reaction solvent, ethers (e.g., tetrahydrofuran, diethyl ether, dioxane, dimethoxyethane etc.), DMF, DMSO, NMP, water and a mixed solvent thereof and the like are exemplified.

The reaction temperature is, 0° C. to 40° C., preferably 0° C. to 20° C.

The reaction time is 0.5 to 48 hours, preferably 1 to 16 hours.

The obtained desired compound (B-II) can be purified as necessary by the methods which are usually used (e.g., column chromatography, recrystallization etc.).
(Step 2)

A compound (B-IV) can be synthesized by the reaction of the compound (B-II) and a compound (B-III) according to the synthetic procedures described in the step 4 of method A.

The obtained desired compound (B-IV) can be purified as necessary by the methods which are usually used (e.g., column chromatography, recrystallization etc.).
(Step 3)

A compound (I) can be synthesized by the reaction of the compound (B-IV) with boronic acid or boronate ester (B-V) according to the synthetic procedures described in the step 2 of method A.

The obtained desired compound (I) can be purified as necessary by the methods which are usually used (e.g., column chromatography, recrystallization etc.).

[Method C]

[Chemical Formula 42]

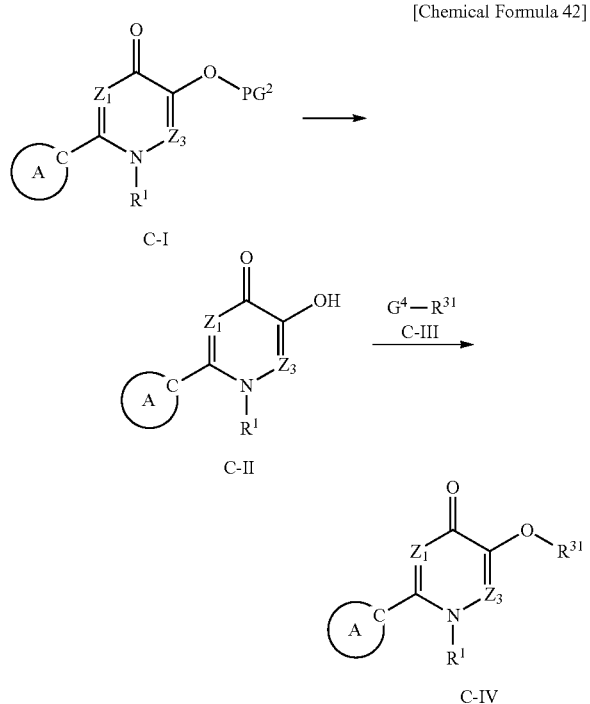

wherein PG$^2$ is an appropriate protecting group of a hydroxy group,

G$^4$ is each independently a leaving group, such as halogen, substituted or unsubstituted alkylthio, substituted or unsubstituted alkylsulfinyl, or substituted or unsubstituted alkylsulfonyl and the like, R$^{31}$ is substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, and the other symbols are the same as the method A.
(Step 1)

A compound (C-II) can be synthesized using the compound (C-I) obtained by the method A and the method B instead of the compound (A-V) according to the synthetic procedures described in the step 3 of the method A.
(Step 2)

A compound (C-IV) can be synthesized by the reaction of the compound (C-II) and a compound (C-III) according to the synthetic procedures described in the step 4 of the method A.

The obtained desired compound (C-IV) can be purified as necessary by the methods which are usually used (e.g., column chromatography, recrystallization etc.).

[Method D]

[Chemical Formula 43]

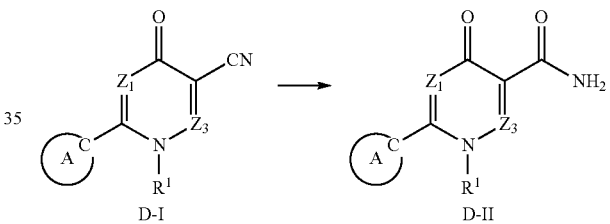

wherein each symbol is the same as the method A.

A compound (D-II) can be synthesized by the reaction of a compound (D-I) obtained by the method A and the method B with a basic aqueous solution.

As the base, for example, metal hydroxide (e.g., sodium hydroxide, potassium hydroxide, lithium hydroxide etc.), metal carboxylate (e.g., sodium carbonate, potassium bicarbonate, cesium carbonate etc.) and the like are exemplified. 1.0 or more mole equivalent(s), preferably 1.0 to 5.0 mole equivalent(s) can be used per an equivalent of the compound (D-I).

As the reaction solvent, alcohols (e.g., methanol, ethanol, isopropanol etc.), aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.). DMF, DMSO, NMP, water and the like are exemplified. The reaction solvent may be used alone or in combination.

The reaction temperature is −10 to 200° C., preferably 0 to 120° C.

The reaction time is 0.1 to 72 hours, preferably 0.5 to 18 hours.

The obtained desired compound (D-II) can be purified as necessary by the methods which are usually used (e.g., column chromatography, recrystallization etc.).

[Method E]

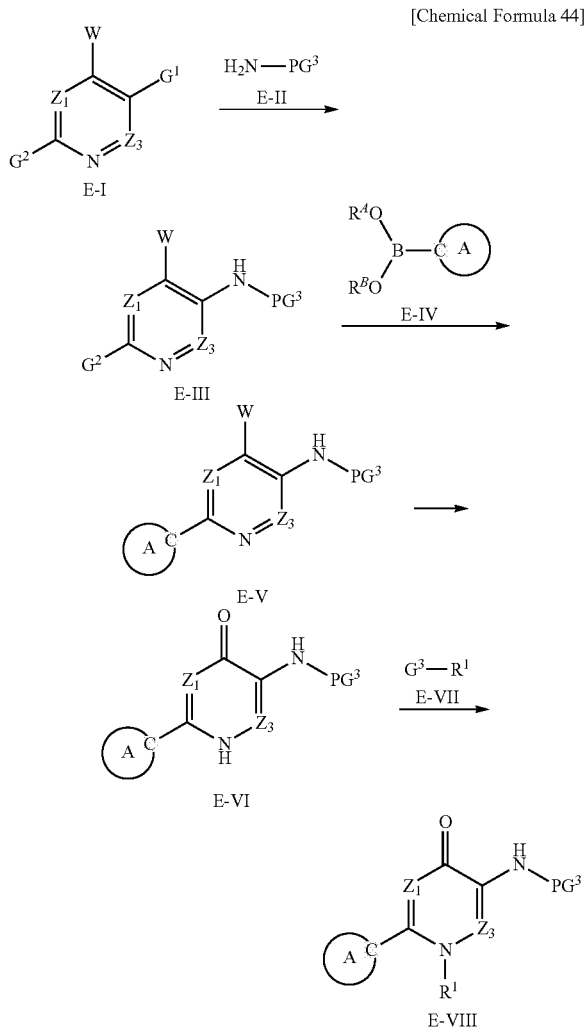

wherein W is a leaving group such as halogen, substituted or unsubstituted alkylthio, substituted or unsubstituted alkylsulfinyl, or substituted or unsubstituted alkylsulfonyl and the like, or a protected hydroxy group,
$PG^3$ is an appropriate protecting group of an amino group, and
the other symbols are the same as the method A.
(Step 1)

A compound (E-III) can be synthesized by the reaction a compound (E-I) and a compound (E-II) in the presence of a metal catalyst and a base in the appropriate solvent.

In this reaction, 1.0 or more mole equivalent(s) of the compound (E-II), preferably 1.0 to 3.0 mole equivalent(s) can be used per an equivalent of the compound (E-I).

As the metal catalyst, palladium (II) acetate, bis(dibenzylideneacetone)palladium, Tetrakis (triphenylphosphine) palladium, bis(triphenylphosphine)palladium (II) dichloride, bis(tri-tert-butylphosphine)palladium, [1,1'-bis (diphenylphosphino)ferrocene]palladium (II) dichloride dichloromethane adduct and the like are exemplified. 0.01 or more mole equivalent(s), preferably 0.001 to 0.5 mole equivalent(s) can be used per an equivalent of the compound (E-I).

A phosphine ligand which can chelate with the palladium atom, the central element in the above palladium catalyst, can be used with the catalyst as necessary. As the phosphine ligand, for example, triphenylphosphine, tri-o-tolylphosphine, tri-m-tolylphosphine, tri-p-tolylphosphine, tris(2,6-di methoxyphenyl)phosphine, tris[2-(diphenylphosphino) ethyl]phosphine, bis(2-methoxyphenyl)phenyl phosphine, 2-(di-tert-butyl phosphino)biphenyl, 2-(dicyclohexyl phosphino)biphenyl, 2-(diphenylphosphino)-2'-(N,N-dimethyl amino)biphenyl, tri-tert-butylphosphine, bis(diphenylphosphino)methane, 1,2-bis(diphenylphosphino)ethane, 1,2-bis (dimethyl phosphino)ethane, 1,3-bis(diphenylphosphino) propane, 1,4-bis(diphenylphosphino)butane, 1,5-bis (diphenylphosphino)pentane, 1,6-bis(diphenylphosphino) hexane, 1,2-bis(dimethyl phosphino)ethane, 1,1'-bis (diphenylphosphino)ferrocene, bis(2-diphenylphosphino ethyl)phenyl phosphine, 2-(dicyclohexyl phosphino)-2',6'-dimethyloxy-1,1'-biphenyl, 2-(dicyclohexyl phosphino)-2', 4',6'-tri-isopropyl-1,1'-biphenyl, bis(2-diphenylphosphino phenyl)ether, 4,5'-bis(diphenylphosphino)-9,9'-dimethylxanthene and the like are exemplified. In this step, 4,5'-bis (diphenylphosphino)-9,9'-dimethylxanthene and the like are preferable. Amount of use of a phosphine ligand can be 0.5 to 2.5 mole equivalent(s), preferably 1.0 to 1.5 mole equivalent(s) per an equivalent of the palladium a compound.

As the base, lithium hydroxide, sodium hydroxide, potassium hydroxide, potassium tert-butoxide, sodium tert-butoxide, sodium carbonate, cesium carbonate, potassium bicarbonate, sodium hydrogen carbonate, sodium phosphate, sodium hydrogen phosphate, potassium phosphate, potassium hydrogen phosphate and the like are exemplified. 1.0 to 3.0 mole equivalent(s) can be used per an equivalent of the compound (E-I).

As the reaction solvent, aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), DMF, DMA, DMSO, NMP, water and a mixed solvent thereof and the like are exemplified.

The reaction temperature is 20 to 250° C., under microwave irradiation as necessary, preferably 20 to 200° C.

The reaction time is 0.1 to 48 hours, preferably 0.5 to 12 hours.

The obtained desired compound (E-III) can be purified as necessary by the methods which are usually used (e.g., column chromatography, recrystallization etc.).

(Step 2)

A compound (E-V) can be synthesized by the reaction of the compound (E-III) with boronic acid or boronate ester (E-IV) according to the synthetic procedures described in the step 2 of the method A.

The obtained desired compound (E-V) can be purified as necessary by the methods which are usually used (e.g., column chromatography, recrystallization etc.).

(Step 3)

A compound (E-VI) can be synthesized by the deprotection of the compound (E-V) in the presence of an acid, a Lewis acid or a base in the appropriate solvent or by the reaction of the compound (E-V) with a basic aqueous solution.

As the acid, hydrochloric acid-ethyl acetate, hydrochloric acid-methanol, hydrochloric acid-dioxane, hydrobromic acid-acetic acid, hydrobromic acid, sulfuric acid, formic acid, trifluoroacetic acid and the like are exemplified. As the Lewis acid, trimethylsilyl iodide, $BBr_3$, $AlCl_3$, $BF_3.(Et_2O)$ and the like are exemplified.

As the base, for example, metal hydroxide (e.g., sodium hydroxide, potassium hydroxide, lithium hydroxide etc.), metal carboxylate (e.g., sodium carbonate, potassium bicarbonate, cesium carbonate etc.), tetrabutyl ammonium fluoride, hydrogen fluoride-pyridine and the like are exemplified. 0.01 or more mole equivalent(s), preferably 0.5 to 10.0 mole equivalent(s) can be used per an equivalent of the compound (E-V).

As the reaction solvent, alcohols (e.g., methanol, ethanol, isopropanol etc.), aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), halogenated hydrocarbons (e.g., chloroform, dichloromethane etc.), DMF, DMSO, NMP, DMA, acetonitrile, pyridine, water and the like are exemplified. The reaction solvent may be used alone or in combination.

The reaction temperature is −10 to 200° C., under microwave irradiation as necessary, preferably 0 to 150° C.

The reaction time is 0.1 to 72 hours, preferably 0.5 to 18 hours.

The obtained desired compound (E-VI) can be purified as necessary by the methods which are usually used (e.g., column chromatography, recrystallization etc.).

(Step 4)

A compound (E-VIII) can be synthesized by the reaction of the compound (E-VI) and a compound (E-VII) according to the synthetic procedures described in the step 4 of the method A.

The obtained desired compound (E-VIII) can be purified as necessary by the methods which are usually used (e.g., column chromatography, recrystallization etc.).

[Method F]

[Chemical Formula 45]

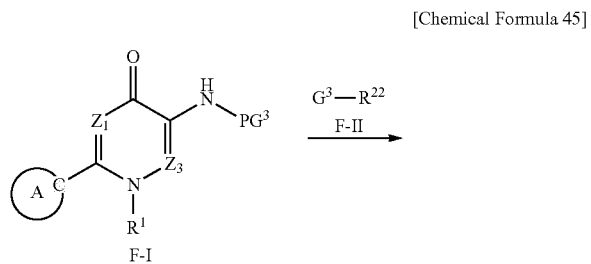

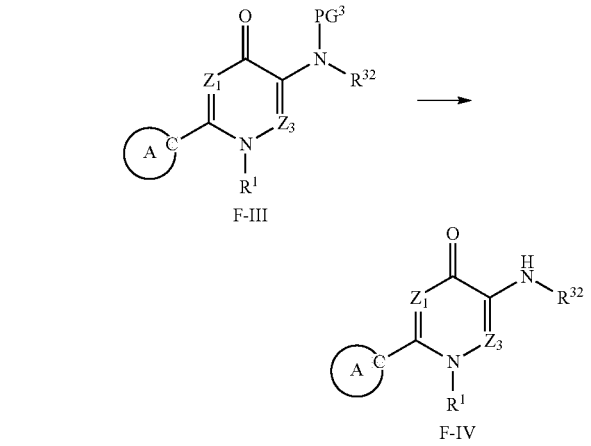

wherein $R^{32}$ is substituted or unsubstituted alkyl, substituted or unsubstituted aromatic carbocyclyl, substituted or unsubstituted non-aromatic carbocyclyl, or substituted or unsubstituted aromatic heterocyclyl, substituted or unsubstituted non-aromatic heterocyclyl, and the other symbols are the same as the method A and the method E.

(Step 1)

A compound (F-III) can be synthesized by the reaction of a compound (F-I) and a compound (F-II) obtained by the method E according to the synthetic procedures described in the step 4 of the method A.

The obtained desired compound (F-III) can be purified as necessary by the methods which are usually used (e.g., column chromatography, recrystallization etc.).

(Step 2)

A compound (F-IV) can be synthesized by the reaction of the compound (F-III) with an acid or a Lewis acid in the appropriate solvent.

As the acid which can be used, hydrochloric acid-ethyl acetate, hydrochloric acid-methanol, hydrochloric acid-dioxane, sulfuric acid, formic acid, trifluoroacetic acid and the like are exemplified. As the Lewis acid, trimethylsilyl iodide, $BBr_3$, $AlCl_3$, $BF_3.(Et_2O)$ and the like are exemplified. 1.0 or more mole equivalent(s), preferably 1.0 to 10.0 mole equivalent(s) can be used per an equivalent of the compound (F-III).

As the reaction solvent, alcohols (e.g., methanol, ethanol, isopropanol etc.), aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), halogenated hydrocarbons (e.g., chloroform, dichloromethane etc.), DMF, DMSO, NMP, DMA, acetonitrile, water and a mixed solvent thereof and the like are exemplified.

The reaction temperature is −10 to 60° C., preferably 0 to 20° C.

The reaction time is 0.5 to 12 hours, preferably 1 to 6 hours.

The obtained desired compound (F-IV) can be purified as necessary by the methods which are usually used (e.g., column chromatography, recrystallization etc.) or salt formation.

[Method G]

[Chemical Formula 46]

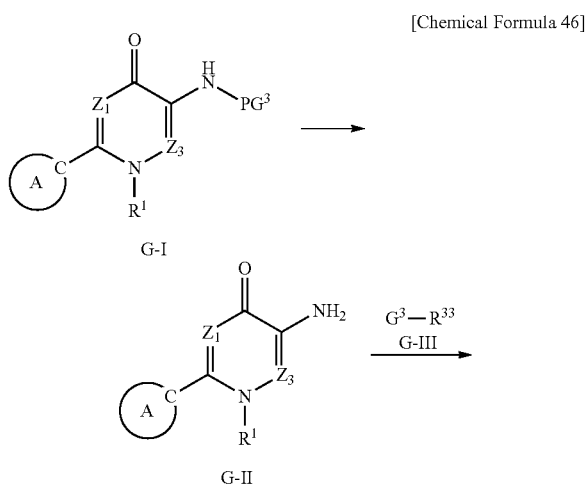

-continued

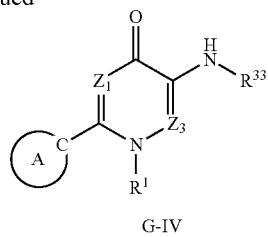

G-IV wherein R[33] is substituted or unsubstituted alkylcarbonyl, substituted or unsubstituted alkylsulfonyl, substituted or unsubstituted alkyloxy carbonyl, substituted or unsubstituted alkenyloxycarbonyl, substituted or unsubstituted alkynyloxycarbonyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylamino carbonyl, substituted or unsubstituted non-aromatic carbocyclylamino carbonyl, substituted or unsubstituted aromatic heterocyclylamino carbonyl, or substituted or unsubstituted non-aromatic heterocyclylamino carbonyl, and the other symbols are the same as the method A and the method E.

(Step 1)

A compound (G-II) can be synthesized by the reaction of the compound (G-I) obtained by the method E with an acid or a Lewis acid in the appropriate solvent.

As the acid which can be used, hydrochloric acid-ethyl acetate, hydrochloric acid-methanol, hydrochloric acid-dioxane, sulfuric acid, formic acid, trifluoroacetic acid and the like are exemplified. As the Lewis acid, trimethylsilyl iodide, BBr$_3$, AlCl$_3$, BF$_3$.(Et$_2$O) and the like are exemplified. 1.0 or more mole equivalent(s), preferably 1.0 to 10.0 mole equivalent(s) can be used per an equivalent of the compound (G-I).

As the reaction solvent, alcohols (e.g., methanol, ethanol, isopropanol etc.), aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), halogenated hydrocarbons (e.g., chloroform, dichloromethane etc.), DMF, DMSO, NMP, DMA, acetonitrile, water and a mixed solvent thereof and the like are exemplified.

The reaction temperature is −10 to 60° C., preferably 0 to 20° C.

The reaction time is 0.5 to 12 hours, preferably 1 to 6 hours.

The obtained desired compound (G-II) can be purified as necessary by the methods which are usually used (e.g., column chromatography, recrystallization etc.) or salt formation.

(Step 2)

The compound (G-IV) can be synthesized by the reaction of the compound (G-II) and a compound (G-III) according to the synthetic procedures described in the step 4 of the method A.

The reaction time is 0.1 to 72 hours, preferably 0.5 to 18 hours.

The obtained desired compound (G-IV) can be purified as necessary by the methods which are usually used (e.g., column chromatography, recrystallization etc.).

[Method H]

[Chemical Formula 47]

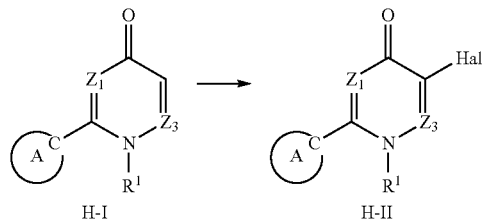

wherein Hal is halogen, and the other symbols are the same as the method A.

A compound (H-II) can be synthesized by the reaction of the compound (H-I) obtained by the method A and the method B with a halogenating agent, in the presence of a base as necessary, in the appropriate inert solvent.

As the halogenating agent, N-chlorosuccinimide, N-bromosuccinimide, N-iodosuccinimide and bromine and the like are exemplified. 1.0 or more mole equivalent(s), preferably 1.0 to 2.0 mole equivalent(s) can be used.

As the base, sodium acetate and the like are exemplified. 1.0 or more mole equivalent(s), preferably 1.0 to 2.0 mole equivalent(s) can be used.

As the reaction solvent, halogenated hydrocarbons (e.g., chloroform, dichloromethane), aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), alcohols (e.g., methanol, ethanol, isopropanol etc.), DMF, DMSO, NMP, DMA, acetonitrile, acetic acid and the like are exemplified. The reaction solvent may be used alone or in combination.

The reaction temperature is −10 to 150° C., preferably 0 to 60° C.

The reaction time is 0.1 to 72 hours, preferably 0.5 to 18 hours.

The obtained desired compound (H-I) can be purified as necessary by the methods which are usually used (e.g., column chromatography, recrystallization etc.).

[Method I]

[Chemical Formula 48]

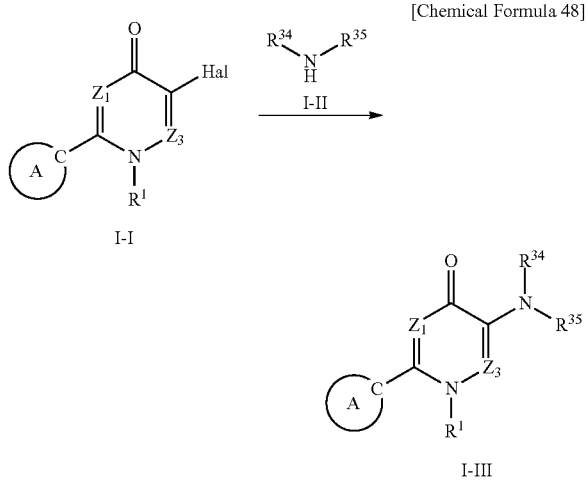

wherein R[34] is substituted or unsubstituted alkyl, substituted or unsubstituted alkylcarbonyl, substituted or unsubstituted alkylsulfonyl, substituted or unsubstituted alkyloxy carbonyl, substituted or unsubstituted alkenyloxycarbonyl, substituted or unsubstituted alkynyloxycarbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylamino carbonyl, substituted or unsubstituted non-aromatic carbocyclylamino carbonyl, substituted or unsubstituted aromatic heterocyclylamino carbonyl, or substituted or unsubstituted non-aromatic heterocyclylamino carbonyl.

$R^{35}$ is hydrogen, unsubstituted alkyl, or, alkyl substituted with one or more substituent(s) selected from halogen, hydroxy, or alkyloxy, and the other symbols are the same as the method A and the method H.

(Step 1)

A compound (I-III) can be synthesized by the reaction of the compound (I-I) and the compound (I-II) obtained by the method A, the method B and the method H in the presence of a metal catalyst and a base in the appropriate solvent.

In this reaction, 1.0 or more mole equivalent(s) of the compound (I-II), preferably 1.0 to 3.0 mole equivalent(s) can be used per an equivalent of the compound (I-I).

As the metal catalyst, palladium (II) acetate, bis(dibenzylideneacetone)palladium, Tetrakis (triphenylphosphine) palladium, bis(triphenylphosphine)palladium (II) dichloride, bis(tri-tert-butylphosphine)palladium, [1,1'-bis(diphenylphosphino)ferrocene]palladium (II) dichloride dichloromethane adduct and the like are exemplified. 0.01 or more mole equivalent(s), preferably 0.001 to 0.5 mole equivalent(s) can be used per an equivalent of the compound (I-I).

A phosphine ligand which can chelate with the palladium atom, the central element in the above palladium catalyst, can be used with the catalyst as necessary. As the phosphine ligand, for example, triphenylphosphine, tri-o-tolylphosphine, tri-m-tolylphosphine, tri-p-tolylphosphine, tris(2,6-dimethoxyphenyl)phosphine, tris[2-(diphenylphosphino) ethyl]phosphine, bis(2-methoxyphenyl)phenylphosphine, 2-(di-tert-butylphosphino)biphenyl, 2-(dicyclohexyl phosphino)biphenyl, 2-(diphenylphosphino)-2'-(N,N-dimethylamino)biphenyl, tri-tert-butylphosphine, bis(diphenylphosphino)methane, 1,2-bis(diphenylphosphino)ethane, 1,2-bis (dimethyl phosphino)ethane, 1,3-bis(diphenylphosphino) propane, 1,4-bis(diphenylphosphino)butane, 1,5-bis (diphenylphosphino)pentane, 1,6-bis(diphenylphosphino) hexane, 1,2-bis(dimethyl phosphino)ethane, 1,1'-bis (diphenylphosphino)ferrocene, bis(2-diphenylphosphino ethyl)phenyl phosphine, 2-(dicyclohexyl phosphino)-2',6'-dimethyloxy-1,1'-biphenyl (S-Phos), 2-(dicyclohexyl phosphino)-2',4',6'-tri-isopropyl-1,1'-biphenyl (X-Phos), bis(2-diphenylphosphino phenyl)ether (DPEPhos), 4,5'-bis (diphenylphosphino)-9,9'-dimethylxanthene and the like are exemplified. Amount of use of a phosphine ligand can be 0.5 to 2.5 mole equivalent(s), preferably 1.0 to 1.5 mole equivalent(s) per an equivalent of the palladium a compound.

As the base, lithium hydroxide, sodium hydroxide, potassium hydroxide, potassium tert-butoxide, sodium tert-butoxide, sodium carbonate, cesium carbonate, potassium bicarbonate, sodium hydrogen carbonate, sodium phosphate, sodium hydrogen phosphate, potassium phosphate, potassium hydrogen phosphate and the like are exemplified. 1.0 to 3.0 mole equivalent(s) can be used per an equivalent of the compound (I-I).

As the reaction solvent, aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), DMF, DMA, NMP and a mixed solvent thereof and the like are exemplified.

The reaction temperature is 20 to 250° C., under microwave irradiation as necessary, preferably 20 to 200° C.

The reaction time is 0.1 to 48 hours, preferably 0.5 to 12 hours.

The obtained desired compound (I-III) can be purified as necessary by the methods which are usually used (e.g., column chromatography, recrystallization etc.).

[Method J]

[Chemical Formula 49]

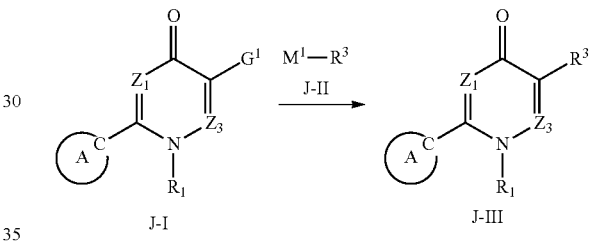

wherein $R^3$ is the same as the above (1), $M^1$ is a metallic substituent such as boronic acid, boronate ester, organotin, zinc, zinc halide, magnesium halide, organosilicon, lithium and the like, and the other symbols are the same as the method A.

A compound (J-III) can be synthesized by the coupling reaction of the compound (J-I) and the compound (J-II) obtained by the method A, the method B and the method H in the presence of a metal catalyst and a base according to the methods which are usually used.

In this reaction, amount of use of the compound (J-II) is 1.0 to 4.0 mole equivalent(s), preferably 1.0 to 2.0 mole equivalent(s) per an equivalent of the compound (J-I).

As the metal catalyst, a palladium catalyst such as tris (dibenzylideneacetone)dipalladium complex, bis[tri(tert-butyl)phosphine]palladium complex, Tetrakis (triphenylphosphine)palladium complex and bis(trifluoroacetoxy) palladium complex; a copper catalyst such as copper iodide; a nickel catalyst such as nickel chloride-1,2-bis(diphenylphosphino)ethane complex; a zinc reagent and an iron chelating reagent and the like are exemplified. 0.01 or more mole equivalent(s), preferably 0.001 to 0.5 mole equivalent(s) can be used per an equivalent of the compound (J-I).

In some cases, it is achieved by the cross-coupling reactions in the presence of a phosphine ligand such as triphenylphosphine, tri(tert-butyl)phosphine, tri-o-tolylphosphine, diphenylphosphino ferrocene, diphenylphosphino butane and the like.

Amount of use of a phosphine ligand can be 0.5 to 2.5 mole equivalent(s), preferably 1.0 to 1.5 mole equivalent(s) per an equivalent of the metal catalyst.

As the base, alkali metal carbonate (e.g., sodium carbonate, potassium, bicarbonate, cesium carbonate etc.), alkali metal phosphate (potassium phosphate etc.), organic base (triethylamine, diisopropylethylamine etc.), halogenated alkali metal (lithium chloride, cesium fluoride etc.), alkali metal hydroxide (sodium hydroxide etc.), metal alkoxide (potassium tert-butoxide etc.) and the like are exemplified. 1.0 to 3.0 mole equivalent(s) can be used per an equivalent of the compound (J-I).

As the reaction solvent, alcohols (e.g., tert-butanol, isopropanol etc.), aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), halogenated hydrocarbons (e.g., chloroform, dichloromethane etc.), DMF, DMA, NMP, DMSO, water and a mixed solvent thereof and the like are exemplified.

The reaction temperature is 20 to 200° C., under microwave irradiation as necessary, preferably 60 to 130° C.

The reaction time is 0.5 to 72 hours, preferably 1 to 16 hours.

The obtained desired compound (J-III) can be purified as necessary by the methods which are usually used (e.g., column chromatography, recrystallization etc.).

The compound (C-II) can be synthesized by using the method K as another method for the synthesis of the compound (C-II) described in the method C.

[Method K]

[Chemical Formula 50]

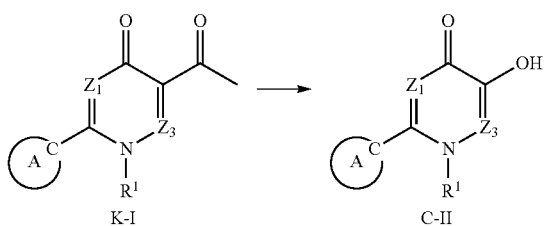

K-I     C-II wherein each symbol is the same as the method A.

A compound (C-II) can be synthesized by adding m-chloroperoxybenzoic acid to the compound (K-I) obtained by the method A, the method B and the method J to react therewith in the appropriate solvent.

In this reaction, 1.0 or more mole equivalent(s) of m-chloroperoxybenzoic acid, preferably 1.0 to 5.0 mole equivalent(s) can be used per an equivalent of the compound (K-I).

As the reaction solvent, aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), halogenated hydrocarbons (e.g., chloroform, dichloromethane) and the like are exemplified. The reaction solvent may be used alone or in combination.

The reaction temperature is 0 to 60° C., preferably 0 to 30° C.

The reaction time is 0.5 to 72 hours, preferably 1.0 to 6 hours.

The obtained desired compound (C-II) can be purified as necessary by the methods which are usually used (e.g., column chromatography, recrystallization etc.).

[Method L]

[Chemical Formula 51]

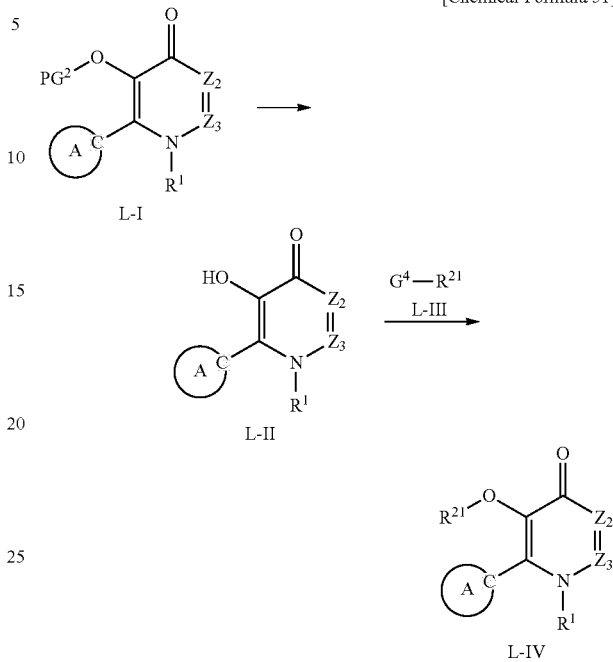

wherein $PG^2$, and $G^4$ are the same as the method C:

$R^{21}$ is substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, and the other symbols are the same as the method A.

(Step 1)

A compound (L-II) can be synthesized using the compound (L-I) obtained by the method A and the method B instead of the compound (A-V) according to the synthetic procedures described in the step 3 of the method A.

The obtained desired compound (L-II) can be purified as necessary by the methods which are usually used (e.g., column chromatography, recrystallization etc.).

(Step 2)

A compound (L-IV) can be synthesized by the reaction of the compound (L-I) and a compound (L-III) according to the synthetic procedures described in the step 2 of the method C.

The obtained desired compound (L-IV) can be purified as necessary by the methods which are usually used (e.g., column chromatography, recrystallization etc.).

[Method M]

[Chemical Formula 52]

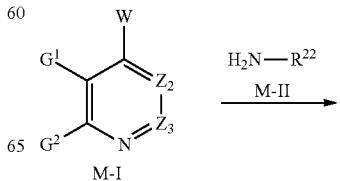

-continued

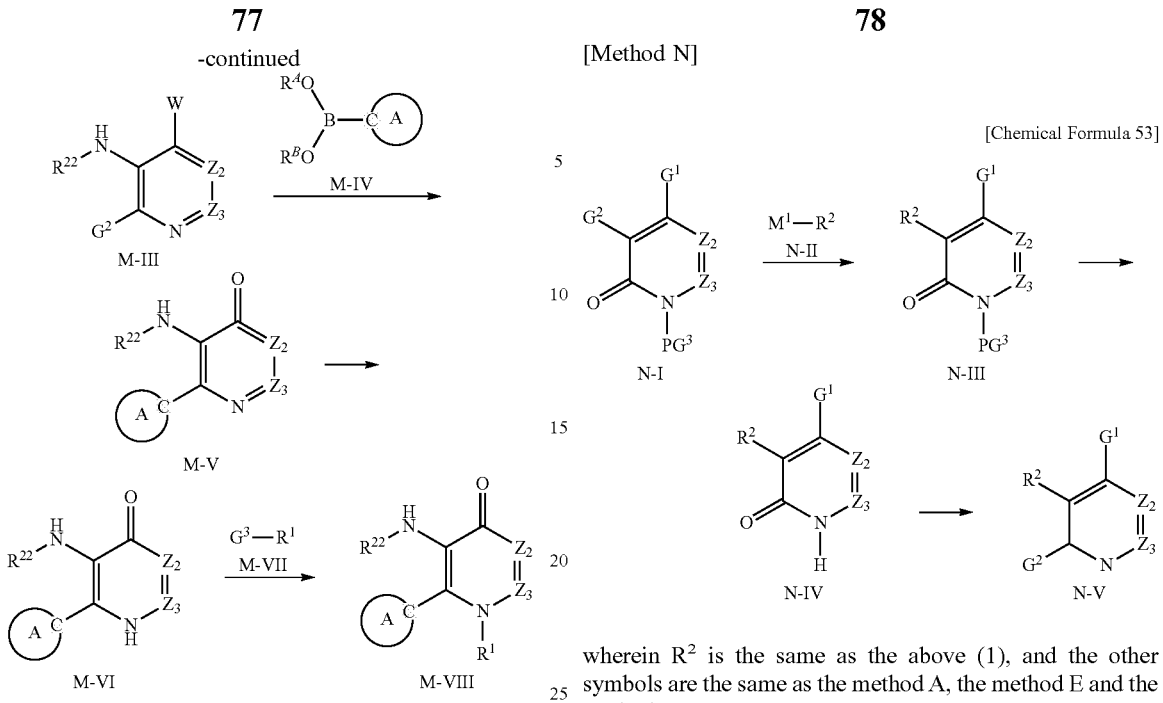

[Method N]

[Chemical Formula 53]

wherein $R^2$ is the same as the above (1), and the other symbols are the same as the method A, the method E and the method J.

(Step 1)

A compound (N-III) can be synthesized by the reaction of a compound (N-I) and a compound (N-II) according to the synthetic procedures described in the step 1 of the method J.

The obtained desired compound (N-III) can be purified as necessary by the methods which are usually used (e.g., column chromatography, recrystallization etc.).

(Step 2)

A compound (N-IV) can be synthesized using a compound (N-III) instead of the compound (E-V) according to the synthetic procedures described in the **c procedures described in the step 3 of the method E.

The obtained desired compound (N-IV) can be purified as necessary by the methods which are usually used (e.g., column chromatography, recrystallization etc.).

(Step 3)

A compound (N-IV) can be synthesized by the reaction the compound (N-IV) and a halogenating agent in the presence or the absence of an inert solvent.

As the halogenating agent to be used, for example, phosphorus oxychloride, phosphorus oxybromide, thionyl chloride, thionyl bromide, oxalyl chloride, phosphorus pentachloride, phosphorus pentabromide and the like are exemplified. 1.0 or more mole equivalent(s), preferably 1.0 to 10.0 mole equivalent(s) can be used per an equivalent of the compound (N-IV).

An organic amine such as triethylamine, tributylamine, diisopropylethylamine, N-ethylmorpholine, pyridine, picoline, 4-(N,N-dimethylamino)pyridine can be added in order to carry out this reaction effectively. 0.1 or more mole equivalent(s), preferably 0.1 to 10.0 mole equivalent(s) can be used per an equivalent of the compound (N-IV).

As the reaction solvent, aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), halogenated hydrocarbons (e.g., chloroform, dichloromethane etc.), DMF, DMSO, NMP, DMA and the like are exemplified. The reaction solvent may be used alone or in combination.

The reaction temperature is −10 to 150° C., under microwave irradiation as necessary, preferably 0 to 120° C.

wherein W is the same as the method E,
$R^{22}$ is substituted or unsubstituted alkyl, substituted or unsubstituted alkylcarbonyl, substituted or unsubstituted alkylsulfonyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, and the other symbols are the same as the method A.

(Step 1)

A compound (L-IV) can be synthesized by the reaction of a compound (M-I) and a compound (M-II) according to the synthetic procedures described in the step 4 of the method A.

The obtained desired compound (M-III) can be purified as necessary by the methods which are usually used (e.g., column chromatography, recrystallization etc.).

(Step 2)

A compound (M-V) can be synthesized by the reaction of a compound (M-Ill) with boronic acid or boronate ester (M-IV) according to the synthetic procedures described in the step 2 of the method A.

The obtained desired compound (M-V) can be purified as necessary by the methods which are usually used (e.g., column chromatography, recrystallization etc.).

(Step 3)

A compound (M-VI) can be synthesized by using a compound (M-V) instead of the compound (E-V) according to the synthetic procedures described in the step 3 of the method E.

The obtained desired compound (M-VI) can be purified as necessary by the methods which are usually used (e.g., column chromatography, recrystallization etc.).

(Step 4)

The compound (M-VIII) can be synthesized by the reaction of the compound (M-VI) and a compound (M-VII) according to the synthetic procedures described in the step 4 of the method E.

The obtained desired compound (M-VIII) can be purified as necessary by the methods which are usually used (e.g., column chromatography, recrystallization etc.).

The compound (A-I) described in the method A can be also synthesized according to the procedures described in the method N.

The reaction time is 0.5 to 24 hours, preferably 1.0 to 6 hours.

The obtained desired compound (N-IV) can be purified as necessary by the methods which are usually used (e.g., column chromatography, recrystallization etc.).

[Method P]

[Chemical Formula 54]

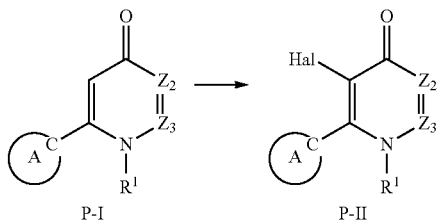

wherein Hal is halogen, and the other symbols are the same as the method A.

A compound (P-II) can be synthesized by using a compound (P-I) instead of the compound (H-I) according to the synthetic procedures described in the method H.

The obtained desired compound (P-II) can be purified as necessary by the methods which are usually used (e.g., column chromatography, recrystallization etc.).

The compounds of the present invention have an antagonistic activity for the P2X7 receptor, and therefore, are useful as a therapeutic and/or preventive agent for diseases associated with the P2X7 receptor.

As the diseases associated with the P2X7 receptor, pain, central nervous system diseases, immune diseases and inflammatory diseases and the like, preferably pain are exemplified (Non-patent Document 7-8 and Patent Document 1 etc.).

As pain, pain associated with zoster, postherpetic neuralgia, trigeminal neuralgia, thalamic pain, cancer pain, postoperative pain, menstrual pain, labor pain, chest pain, abdominal pain, colic pain, lumbar backache, headache, migraine, sciatica, sore muscle, orofacial pain, toothache, glossagra, shoulder pain, nociceptive pain, pain associated with deafferentation, psychogenic pain and the like; pain associated with the disease such as entrapment neuropathy, carpal canal syndrome, diabetes, Guillain-Barre syndrome, myofascial pain syndrome, fibromyalgia syndrome, complex regional pain syndrome, causalgia, Hansen's disease, spinal cord injury, stroke, multiple sclerosis, Parkinson's disease, endometriosis, hernia of intervertebral disk, arthritis, rheumatoid arthritis, osteoarthritis, cervical spondylosis deformans, spinal canal stenosis, thoracic outlet syndrome, traumatic brachial plexus injury syndrome, shoulder-hand syndrome, whiplash injury, cholelithiasis, pancreatitis, cystitis, urethritis, urinary calculosis, prostatitis, ulcerative colitis, Crohn's disease, irritable bowel syndrome, bone fracture, osteoporosis, gout, cauda equina syndrome, ankylosing spondylitis, painful spasm, ABC syndrome, skin disease, arteriosclerosis obliterans, Buerger's disease, Raynaud's phenomenon, gangrene, temporomandibular arthrosis, somatoform disorder, somatization disorder, depression and the like;
pain associated with drug therapy, and pain associated with radiation therapy are exemplified.

Additionally, effects for opioid tolerance can be expected.

As central nervous system diseases, Alzheimer's disease, Cerebral amyloid angiopathy, Parkinson's disease, Creutzfeldt-Jakob disease, Huntington's chorea, depression, schizophrenia, attention deficit hyperactivity disorder, sleep disorder, autism spectrum disorder, epilepsy, stroke, multiple sclerosis, spinal cord injury, amyotrophic lateral sclerosis, opioid dependence, cocaine dependence, nicotine dependence and the like are exemplified.

Preferably, as central nervous system diseases, Alzheimer's disease, Cerebral amyloid angiopathy, Parkinson's disease, depression, schizophrenia, attention deficit hyperactivity disorder, sleep disorder, autism spectrum disorder, epilepsy, stroke, multiple sclerosis, spinal cord injury, amyotrophic lateral sclerosis, opioid dependence, cocaine dependence, nicotine dependence and the like are exemplified.

As immune diseases and inflammatory diseases, rheumatoid arthritis, osteoarthritis, asthma, bronchitis, chronic obstructive pulmonary disease, pulmonary emphysema, septic shock, hepatitis, hepatic fibrosis, hepatic cirrhosis, cholecystitis, glomerulonephritis, nephrotic syndrome, pancreatitis, cystitis, urethritis, prostatitis, ulcerative colitis, Crohn's disease, irritable bowel syndrome, psoriasis, atopic dermatitis, contact dermatitis, eczematous dermatitis, delayed-type hypersensitivity reaction, conjunctivitis, uveitis, growth and metastasis of malignant cell (prostate cancer, breast cancer, lung cancer, uterine cancer, pancreatic cancer, colorectal cancer etc.), leukemia, meningitis, burn injury, glossitis, gingivitis, periodontal disease, esophagitis and the like are exemplified. It is possible that rejection associated with allograft or blood transfusion is involved in the P2X7 receptor. As the other diseases associated with the P2X7 receptor, circulatory diseases such as atherosclerosis, ischemic heart disease, diabetes and the like, bone diseases such as osteoporosis, bone Paget's disease, osteonecrosis, temporomandibular arthrosis and the like, and urologic diseases such as overactive bladder, stress urinary incontinence, prostatomegaly and the like are exemplified.

Preferably, as immune diseases and inflammatory diseases, rheumatoid arthritis, arthritis, osteoarthritis, asthma, bronchitis, chronic obstructive pulmonary disease, cystitis, ulcerative colitis, Crohn's disease and the like are exemplified.

The preferred compound of the present invention not only has an antagonistic activity for the P2X7 receptor but also is useful as a medicine and has any or all of the following superior characteristics:

a) The inhibitory activity for CYP enzymes (e.g., CYP1A2, CYP2C9, CYP2C19, CYP2D6, CYP3A4 and the like) is weak.

b) The compound demonstrates good pharmacokinetics, such as a high bioavailability, moderate clearance and the like.

c) The compound has a high metabolic stability.

d) The compound has no irreversible inhibitory effect against CYP enzymes (e.g., CYP3A4) when the concentration is within the range described in the present description as the measurement conditions.

e) The compound has no mutagenicity.

f) The compound is associated with a low cardiovascular risk.

g) The compound has a high solubility.

h) The compound has a high selectivity for the P2X7 receptor (e.g., high selectivity in the other receptors of the P2X family).

i) The compound has a high distribution for the central nervous system.

A pharmaceutical composition of the present invention can be administered orally or parenterally. Methods for parenteral administration include dermal, subcutaneous, intravenous, intraarterial, intramuscular, intraperitoneal, transmucosal, inhalation, transnasal, ophthalmic, inner ear or vaginal administration and the like.

In case of oral administration, any forms, which are usually used, such as oral solid formulations (e.g., tablets, powders, granules, capsules, pills, films or the like), oral liquid formulations (e.g., suspension, emulsion, elixir, syrup, lemonade, spirit, aromatic water, extract, decoction, tincture or the like) and the like may prepared according to the usual method and administered. The tablets can be sugar-coated tablets, film-coated tablets, enteric-coating tablets, sustained-release tablets, troche tablets, sublingual tablets, buccal tablets, chewable tablets or orally dispersing tablets. Powders and granules can be dry syrups. Capsules can be soft capsules, micro capsules or sustained-release capsules.

In case of parenteral administration, any forms, which are usually used, such as injections, drips, external preparations (e.g., ophthalmic drops, nasal drops, ear drops, aerosols, inhalations, lotion, infusion, liniment, mouthwash, enema, ointment, plaster, jelly, cream, patch, cataplasm, external powder, suppository or the like) and the like can be preferably administered. Injections can be emulsions whose type is O/W, W/O, O/W/O, W/O/W or the like.

The pharmaceutical composition may be manufactured by mixing an effective amount of the compound of the present invention with various pharmaceutical additives suitable for the formulation, such as excipients, binders, moistening agents, disintegrants, lubricants, diluents and the like. Furthermore, the pharmaceutical composition can be for pediatric patients, geriatric patients, serious cases or operations by appropriately changing the effective amount of the compound of the present invention, formulation and/or various pharmaceutical additives. The pediatric pharmaceutical compositions are preferably administered to patients under 12 or 15 years old. In addition, the pediatric pharmaceutical compositions can be administered to patients who are under 27 days old after the birth, 28 days to 23 months old after the birth, 2 to 11 years old, 12 to 16 years old, or 18 years old. The geriatric pharmaceutical compositions are preferably administered to patients who are 65 years old or over.

Although the dosage of a pharmaceutical composition of the present invention should be determined in consideration of the patient's age and body weight, the type and degree of diseases, the administration route and the like, a usual oral dosage is 0.05 to 100 and preferably 0.1 to 10 mg/kg/day. For parenteral administration, although the dosage highly varies with administration routes, a usual dosage is 0.005 to 10 and preferably 0.01 to 1 mg/kg/day. The dosage may be administered in one to several divisions per day.

EXAMPLE

The present invention will be described in more detail with reference to, but not limited to, the following Examples and Test Examples.

NMR analysis of each example was performed by 300 MHz using DMSO-ds or CDCl$_3$.

"RT" in tables means retention time in LC/MS: liquid column chromatography/mass analysis and these are measured under the conditions as below:
Condition[1]
Column: ACQUITY UPLC (registered trademark) BEH C18 (1.7 μm i.d. 2.1×50 mm)(Waters)
Flow rate: 0.8 mL/min
UV detection wavelength: 254 nm
Mobile phases: [A] is 0.1% formic acid solution, and [B] is 0.1% formic acid in acetonitrile solvent.

Gradient: linear gradient of 5% to 100% solvent [B] for 3.5 minutes was performed, and 100% solvent [B] was maintained for 0.5 minute.
Condition[2]
Column: ACQUITY UPLC (registered trademark BEH C18 (1.7 μm i.d. 2.1×50 mm)(Waters)
Flow rate: 0.8 mL/min
UV detection wavelength: 254 nm
Mobile phases: [A] is 10 mmol/L Ammonium Carbonate solution, and [B] is acetonitrile.
Gradient: linear gradient of 5% to 100% solvent [B] for 3.5 minutes was performed, and 100% solvent [B] was maintained for 0.5 minute.
Condition[3]
Column: Shim-pack XR-ODS (2.2 μm, i.d. 50×3.0 mm) (Shimadzu)
Flow rate: 1.6 mL/min
UV detection wavelength: 254 nm
Mobile phases: [A] is 0.1% formic acid solution, and [B] is 0.1% formic acid in acetonitrile solvent.
Gradient: linear gradient of 10% to 100% solvent [B] for 3 minutes was performed, and 100% solvent [B] was maintained for 0.5 minute.

Example A1

[Chemical Formula 55]

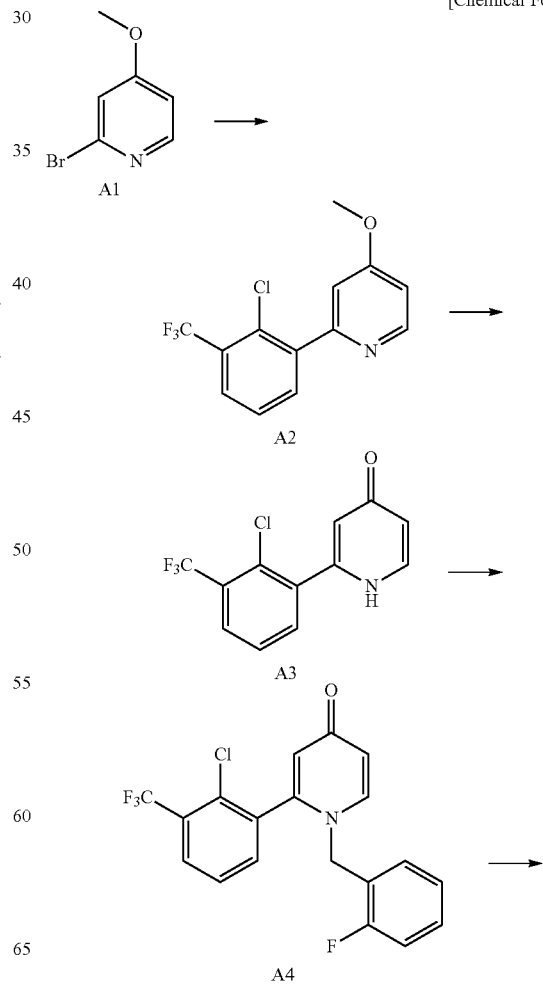

-continued

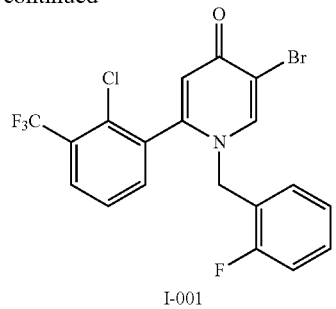

I-001

Step 1

The compound A1 (1 g, 5.32 mmol) was dissolved in tetrahydrofuran (10 mL), 2-chloro-3-trifluoromethoxyphenyl boronic acid (2.387 g, 10.64 mmol), [1,1'-bis(diphenylphosphino)ferrocene]palladium (II)dichloride (0.217 g, 0.266 mol) and 2 mol/L aqueous solution of sodium carbonate (7.98 mL, 15.96 mmol) were added to the solution. The mixture was stirred under microwave irradiation at 130° C. for 10 minutes. The reaction mixture was poured into water. The mixture was extracted with chloroform. The organic layer was washed by water and brine, and dried over anhydrous sodium sulfate. The solvent was evaporated under reduced pressure. The obtained residue was purified by silica-gel column chromatography (hexane-ethyl acetate) to afford the compound A2 (1.03 g, yield 67%).

$^1$H-NMR (DMSO-$d_6$) δ: 8.51 (d, J=5.7 Hz, 1H), 7.95 (d, J=7.7 Hz, 1H), 7.81 (d, J=7.7 Hz, 1H), 7.66 (t, J=7.7 Hz, 1H), 7.21 (s, 1H), 7.07 (d, J=5.7 Hz, 1H), 3.89 (s, 3H).

Step 2

The compound A2 (1 g, 3.48 mmol) was dissolved in acetic acid (10 mL). 25% hydrobromic acid acetic acid solution (3.78 mL, 17.38 mmol) was added to the solution. The mixture was stirred under microwave irradiation at 130° C. for 2 hours. 25% hydrobromic acid acetic acid solution (0.755 mL, 3.48 mmol) was added to the reaction mixture. The mixture was stirred under microwave irradiation at 130° C. for 1 hour. After cooled to room temperature, the precipitates were filtered to afford the crude product of the compound A3 (960 mg).

MS m/z: 274 [(M+H)$^+$]

Step 3

The crude product of the compound A3 (100 mg) was dissolved in DMF (1 mL). DIEA (0.191 mL, 1.096 mmol) and 2-fluorobenzyl bromide (0.053 mL, 0.439 mmol) were added to the solution. The mixture was stirred at 70° C. for 7 hours. The reaction mixture was poured into water. The mixture was extracted with chloroform-methanol (9:1). The organic layer was dried over anhydrous sodium sulfate. The solvent was evaporated under reduced pressure. The obtained residue was purified by the preparative high performance liquid chromatography to afford the compound A4 (77.8 mg, yield 56%).

MS m/z: 382 [(M+H)$^+$]

Step 4

The compound A4 (75 mg, 0.196 mmol) was dissolved in dichloromethane (2 mL). N-bromosuccinimide (38.5 mg, 0.216 mmol) was added to the solution under ice cooling. The mixture was stirred at 0° C. for 1 hour. The reaction mixture was warmed to room temperature, and stirred for 2 hours. The reaction mixture was warmed to 40° C., and stirred at 40° C. for 3 hours. N-bromosuccinimide (38.5 mg, 0.216 mmol) was added to the reaction mixture. The mixture was stirred at 40° C. for 3 hours. After cooled to room temperature. 10% aqueous solution of sodium hydrogen sulfite was added to the reaction mixture. The mixture was extracted with chloroform. The organic layer was washed by the saturated aqueous solution of sodium hydrogen carbonate, water and brine, dried over anhydrous sodium sulfate. The solvent was evaporated under reduced pressure. The obtained residue was washed by diisopropyl ether, and filtered to afford the compound I-001 (57.1 mg, yield 63%).

MS m/z: 460 [(M+H)$^+$]

$^1$H-NMR (DMSO-$d_6$) δ: 8.74 (s, 1H), 7.98 (dd, J=7.7, 1.5 Hz, 1H), 7.64 (dd, J=7.7, 1.5 Hz, 1H), 7.58 (t, J=7.7 Hz, 1H), 7.33-7.30 (m, 1H), 7.06-7.02 (m, 2H), 6.77 (td, J=7.7, 1.5 Hz, 1H), 6.24 (s, 1H), 5.04 (dd, J=46.2, 15.8 Hz, 2H).

Example A2

[Chemical Formula 56]

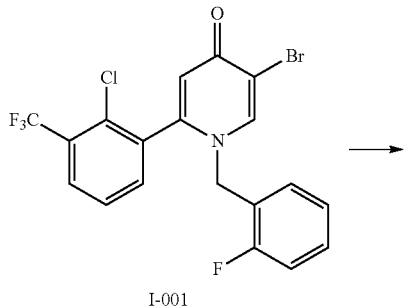

I-001

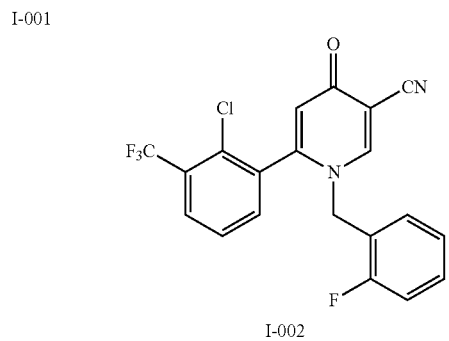

I-002

Step 1

The compound I-001 (45 mg, 0.098 mmol) obtained by Example A1 was dissolved in NMP. Zinc cyanide (12.62 mg, 0.107 mmol), zinc (1.277 mg, 0.020 mmol) and bis(tritertbutylphosphine)palladium (4.99 mg, 0.0097 mmol) were added to the solution. The mixture was stirred under microwave irradiation at 130° C. for 30 minutes. Zinc cyanide (8.03 mg, 0.068 mmol), zinc (1.277 mg, 0.020 mmol) and bis(tritert-butylphosphine)palladium (4.99 mg, 0.0097 mmol) were added to the reaction mixture. The mixture was stirred under microwave irradiation at 135° C. for 30 minutes. Zinc cyanide (5.74 mg, 0.049 mmol), zinc (0.639 mg, 0.0097 mmol) and bis(tritert-butyl phosphine)palladium (2.496 mg, 0.0048 mmol) were added to the reaction mixture. The mixture was stirred under microwave irradiation at 135° C. for 30 minutes. The reaction mixture was filtered. Water was added to the filtrate. The mixture was extracted with ethyl acetate. The organic layer was washed by water and brine, and dried over anhydrous sodium sulfate. The solvent was evaporated under reduced pressure. The obtained residue was purified by the preparative high performance liquid chromatography to afford the compound I-002 (12.8 mg, yield 32%).

MS m/z: 407 [(M+H)+]

$^1$H-NMR (DMSO-$d_6$) δ: 9.05 (s, 1H), 7.99 (d, J=7.8 Hz, 1H), 7.67 (d, J=7.8 Hz, 1H), 7.60 (t, J=7.8 Hz, 1H), 7.32 (dd, J=13.2, 6.9 Hz, 1H), 7.03 (dd, J=13.2, 6.9 Hz, 2H), 6.80 (t, J=7.6 Hz, 1H), 6.39 (s, 1H), 5.06 (dd, J=27.2, 15.9 Hz, 2H).

Example A3

[Chemical Formula 57]

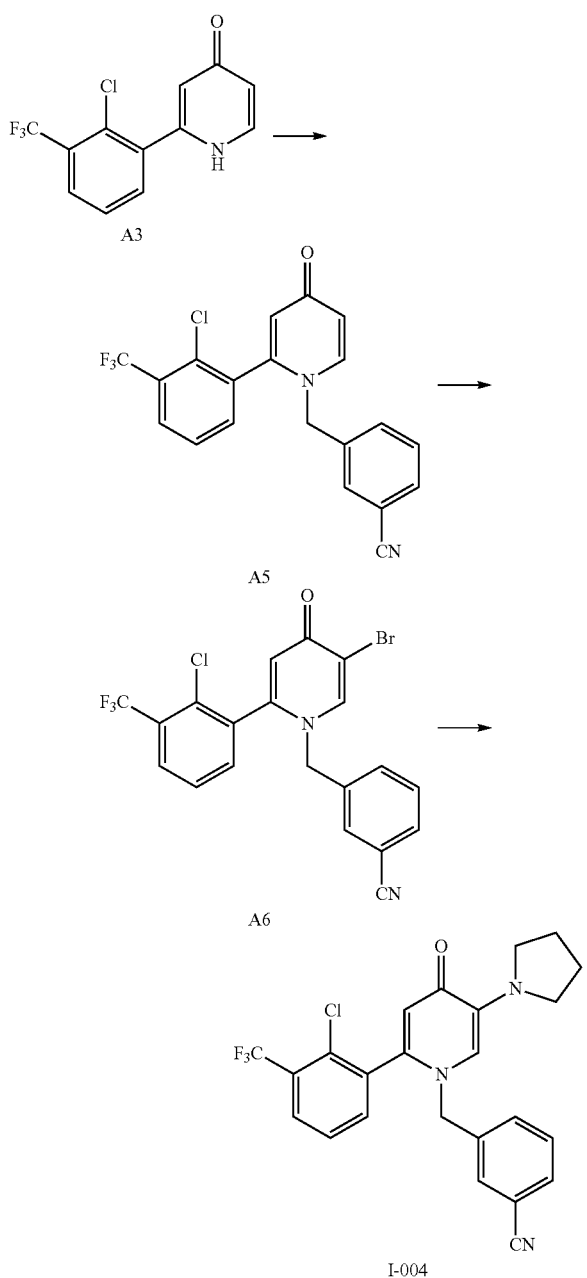

Step 1

The compound A3 (1 g, 3.65 mmol) obtained by the similar synthesis of Example A1 was dissolved in DMF (10 mL). DIEA (1.915 mL, 10.96 mmol) and 3-cyano benzyl bromide (860 mg, 4.39 mmol) were added to the solution. The mixture was stirred at 70° C. for 14 hours. After cooled to room temperature, water was added to the reaction mixture. The mixture was extracted with ethyl acetate, the organic layer was washed by the saturated aqueous solution of sodium hydrogen carbonate, water and brine, and dried over anhydrous sodium sulfate. The solvent was evaporated under reduced pressure. The obtained residue was purified by silica-gel column chromatography (chloroform-methanol) to afford the compound A5 (662.8 mg, yield 47%).

MS m/z: 389 [(M+H)+]

Step 2

The compound A5 (660 mg, 1.698 mmol) was dissolved in dichloromethane (7 mL). N-bromo succinimide (453 mg, 2.55 mmol) was added to the solution under ice cooling. The mixture was stirred at room temperature for 15 minutes. After warmed to 40° C., the mixture was stirred for 3 hours. After cooled to room temperature, 10% aqueous solution of sodium hydrogen sulfite was added to the reaction mixture. The mixture was extracted with chloroform. The organic layer was washed by water and brine, and dried over anhydrous sodium sulfate. The solvent was evaporated under reduced pressure to afford the crude product of compound A6 (802 mg).

MS m/z: 467 [(M+H)+]

Step 3

Under nitrogen atmosphere, the crude product of the compound A6 (50 mg) was dissolved in 1,4-dioxane (1 mL). Palladium (II) acetate (2.40 mg, 0.011 mmol), Xantphos (9.28 mg, 0.016 mmol), cesium carbonate (69.7 mg, 0.214 mmol) and pyrrolidine (0.013 mL, 0.160 mmol) were added to the solution. The mixture was stirred at 90° C. for 3 hours was stirred. After cooled to room temperature, water was added to the reaction mixture. The mixture was extracted with dichloromethane-methanol (9:1). The solvent in the organic layer was evaporated under reduced pressure. The obtained residue was purified by the preparative high performance liquid chromatography to afford the compound I-004 (12.6 mg, yield 26%).

MS m/z: 458 [(M+H)+]

$^1$H-NMR (DMSO-$d_6$) δ: 8.30 (s, 1H), 7.95 (d, J=7.8 Hz, 1H), 7.70 (d, J=7.8 Hz, 1H), 7.63 (d, J=7.8 Hz, 1H), 7.57 (t, J=7.8 Hz, 1H), 7.45 (t, J=7.8 Hz, 1H), 7.28 (s, 1H), 7.20 (d, J=7.8 Hz, 1H), 7.16 (s, 1H), 5.89 (s, 1H), 4.95 (dd, J=74.8, 16.1 Hz, 2H), 3.34-3.30 (m, 4H), 1.84-1.81 (brm, 4H).

Example A4

[Chemical Formula 58]

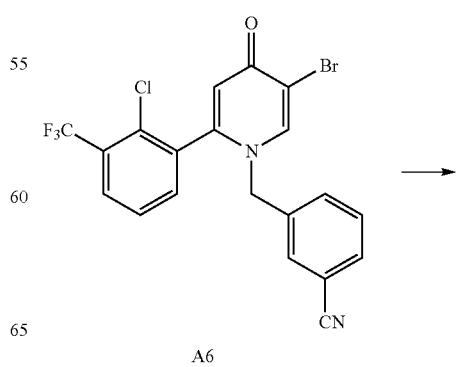

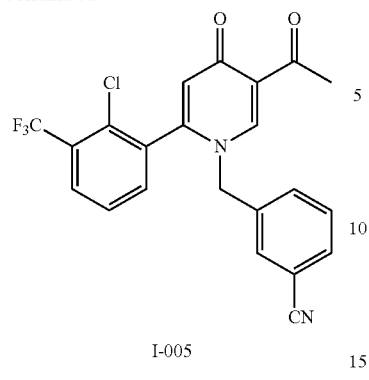

I-005

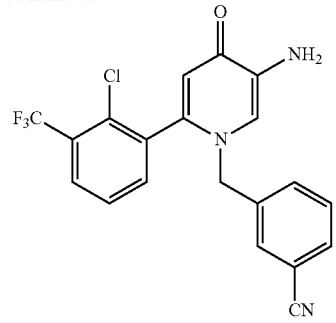

I-006

Step 1

Under nitrogen atmosphere, the crude product of the compound A6 (100 mg) obtained by the similar synthesis of Example A3 was dissolved in 1,4-dioxane (2 mL). Bis(triphenylphosphine)palladium (II)dichloride (15.01 mg, 0.021 mmol) and tributyl (1-ethyloxyvinyl) tin (0.087 mL, 0.257 mmol) were added to the solution. The mixture was stirred at 100° C. for 4.5 hours. After cooled to room temperature, 2 mol/L aqueous solution of hydrochloric acid was added to the reaction mixture. The mixture was stirred at room temperature for 30 minutes. Ethyl acetate and the saturated aqueous solution of saturated potassium fluoride were added to the reaction mixture. The mixture was stirred at room temperature for 1 hour. The reaction mixture was filtered. Water was added to the filtrate. The mixture was extracted with ethyl acetate. The organic layer was washed by brine, and was dried over anhydrous sodium sulfate. The solvent was evaporated under reduced pressure. The obtained residue was purified by silica-gel column chromatography (chloroform-methanol). Diisopropyl ether was added to the obtained crude product. The precipitates was filtered to afford the compound I-005 (51.7 mg, 56%).

MS m/z: 431 [(M+H)$^+$]

$^1$H-NMR (DMSO-d$_6$) δ: 8.69 (s, 1H), 7.99 (d, J=7.7 Hz, 1H), 7.72 (d, J=7.7 Hz, 2H), 7.61 (t, J=7.7 Hz, 1H), 7.43 (t, J=7.7 Hz, 1H), 7.18-7.15 (m, 2H), 6.37 (s, 1H), 5.13 (dd, J=28.5, 15.9 Hz, 2H), 2.61 (s, 3H)

Step 1

Under nitrogen atmosphere, the crude product of the compound A6 (100 mg) obtained by the similar synthesis of Example A3 was dissolved in 1,4-dioxane (2 mL). Palladium (II) acetate (4.80 mg, 0.021 mmol), Xantphos (18.56 mg, 0.032 mmol), cesium carbonate (139 mg, 0.428 mmol) and benzophenone imine (0.054 mL, 0.321 mmol) were added to the solution. The mixture was stirred at 95° C. for 6 hours. After cooled to room temperature, water was added to the reaction mixture. The mixture was extracted with ethyl acetate, and dried over anhydrous sodium sulfate. The solvent was evaporated under reduced pressure. The obtained residue was dissolved in ethyl acetate (2 mL). 4 mol/L hydrochloric acid-ethyl acetate solution (1 mL) was added to the mixture. The mixture was stirred at room temperature for 4 hours. The reaction mixture was added to diisopropyl ether. The precipitates were filtered to afford the crude product. The obtained crude product was purified by the preparative high performance liquid chromatography to afford the compound I-006 (14 mg, yield 16%).

MS m/z: 404 [(M+H)$^+$]

$^1$H-NMR (DMSO-d$_6$) δ: 7.97 (d, J=7.6 Hz, 1H), 7.74 (d, J=7.8 Hz, 2H), 7.60 (t, J=7.8 Hz, 1H), 7.50 (t, J=7.8 Hz, 1H), 7.32-7.30 (m, 2H), 7.25 (d, J=7.8 Hz, 1H), 5.93 (s, 1H), 5.02 (d, J=15.9 Hz, 1H), 4.88 (s, 2H), 4.78 (d, J=15.9 Hz, 1H).

Example A5

[Chemical Formula 59]

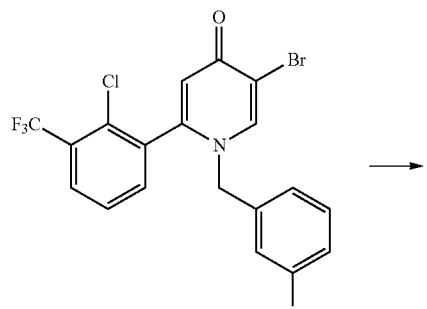

A6

Example A6

[Chemical Formula 60]

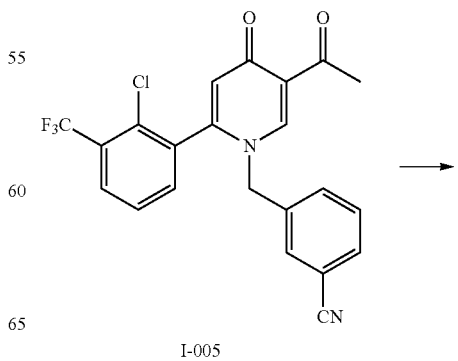

I-005

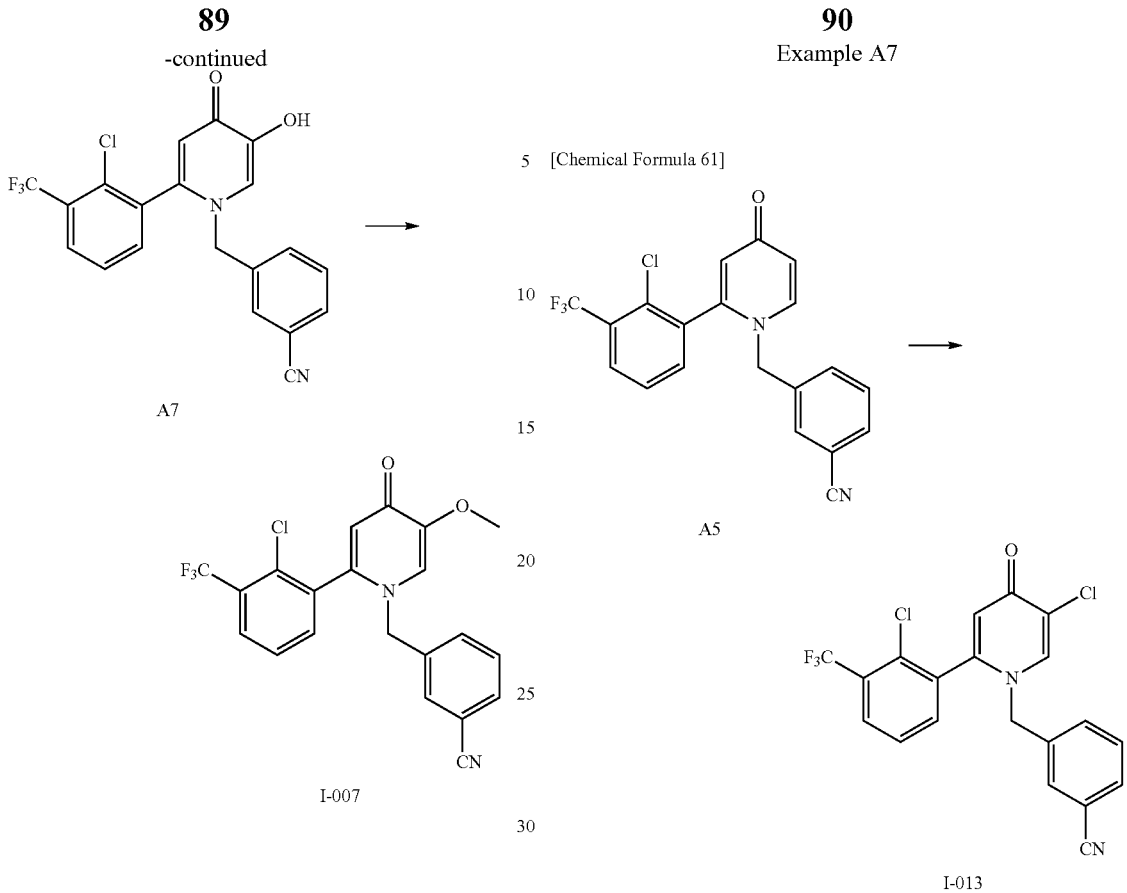

Example A7

[Chemical Formula 61]

Step 1

Under nitrogen atmosphere, the compound I-005 (40 mg, 0.093 mmol) obtained by Example A4 was dissolved in dichloromethane (1 mL). Under ice cooling, mCPBA (32 mg, 0.139 mmol) was added to the solution. The mixture was stirred at room temperature for 2 hours. After warmed to 40° C., the reaction mixture was stirred for 8 hours. After cooled to room temperature, water was added to the reaction mixture. The mixture was extracted with dichloromethane. The organic layer was washed by water and brine, and dried over anhydrous sodium sulfate. The solvent was evaporated under reduced pressure. The obtained residue was purified by the preparative high performance liquid chromatography to afford the crude product of the compound A7 (17 mg).

MS m/z: 405 [(M+H)$^+$]

Step 2

The crude product of the compound A7 (17 mg) was dissolved in DMF (0.3 mL). Potassium bicarbonate (6.28 mg, 0.045 mmol) and methyl iodide (0.002 μL, 0.030 mmol) were added to the solution. The mixture was stirred at 60° C. for 3 hours. After cooled to room temperature, water was added to the reaction mixture. The mixture was extracted with dichloromethane. The organic layer was washed by water. The solvent was evaporated under reduced pressure. The obtained residue was purified by the preparative high performance liquid chromatography the compound I-007 (5.7 mg, yield 60%) to afford the compound I-007 (5.7 mg, yield 60%).

MS m/z: 419 [(M+H)$^+$]

$^1$H-NMR (DMSO-d6) δ: 7.98 (d, J=7.5 Hz, 1H), 7.90 (s, 1H), 7.72 (d J=7.8 Hz, 1H), 7.66 (d J=7.5 Hz, 1H), 7.59 (t J=7.8 Hz, 1H), 7.45 (t, J=7.5 Hz, 1H), 7.22-7.20 (m, 2H), 6.07 (s, 1H), 4.98 (dd, J=64.5, 16.2 Hz, 2H), 3.76 (s, 3H).

Step 1

The compound A5 (50 mg, 0.129 mmol) obtained by the similar synthesis of Example A3 was dissolved in dichloromethane (1 mL). N-chloro succinimide (18.03 mg, 0.135 mmol) was added to the solution. The mixture was stirred in sealed flask at 60° C. for 1 hour. After cooled to room temperature, 10% aqueous solution of sodium hydrogen sulfite was added to the reaction mixture. The mixture was extracted with dichloromethane. The solvent was evaporated under reduced pressure. The obtained residue was purified by silica-gel chromatography (chloroform-methanol) to afford the compound I-013 (17.4 mg, yield 32%).

MS m/z: 423 [(M+H)$^+$]

$^1$H-NMR (DMSO-d$_6$) δ: 8.65 (s, 1H), 7.98 (d, J=7.7 Hz, 1H), 7.72-7.71 (m, 2H), 7.61 (t, J=7.7 Hz, 1H), 7.44 (t, J=7.7 Hz, 1H), 7.21-7.18 (m, 2H), 6.28 (s, 1H), 5.00 (dd, J=40.2, 16.2 Hz, 2H).

Example B1

[Chemical Formula 62]

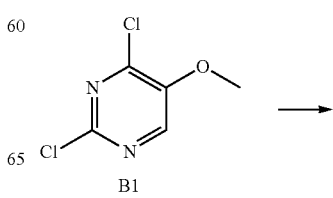

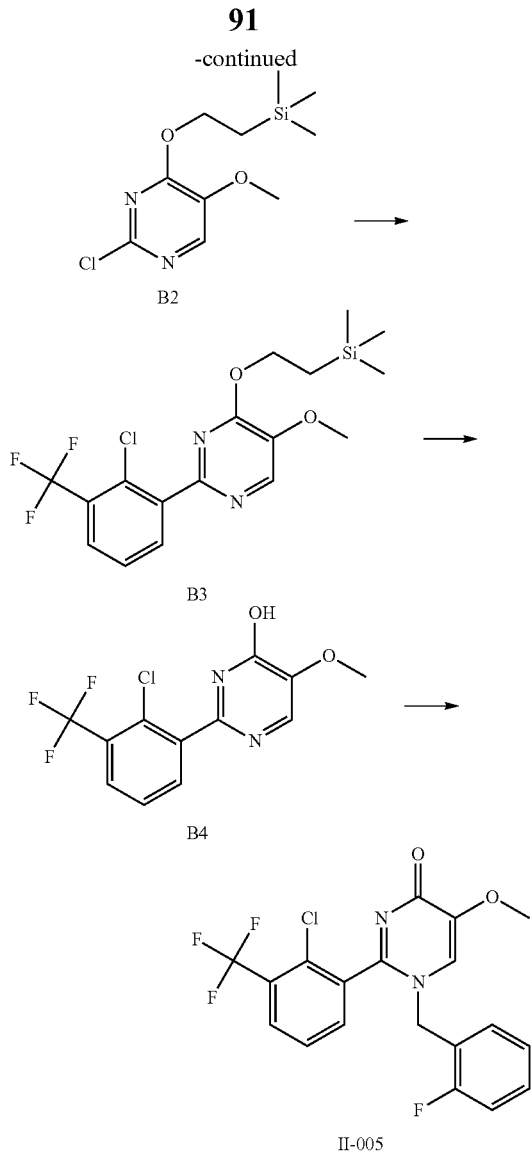

3-(trifluoromethyl)phenyl boronic acid (6.9 g, 30.8 mmol), PdCl$_2$ (dppf)(1.7 g, 2.1 mmol) and 2 mol/L aqueous solution of sodium carbonate (31 mL, 62 mmol) were added to the solution. The mixture was stirred under reflux for 4 hours. After cooled to room temperature, water was added to the mixture. The mixture was extracted with ethyl acetate. The organic layer was washed by brine, and dried over anhydrous sodium sulfate. The solvent was evaporated under reduced pressure. The obtained residue was purified by silica-gel column chromatography (hexane-ethyl acetate) to afford the compound B3 (2.86 g, yield 34.4%).

$^1$H-NMR (CDCl$_3$) δ: 0.07 (s, 9H), 1.24 (t, J=8.0 Hz, 2H), 3.99 (s, 3H), 4.60 (t, J=8.0 Hz, 2H), 7.44 (t, J=8.0 Hz, 1H), 7.76 (d, J=8.0 Hz, 1H), 7.84 (d, J=8.0 Hz, 1H), 8.15 (s, 1H).

Step 3

The compound B3 (3.13 g, 7.73 mmol) was dissolved in tetrahydrofuran (30 mL). Tetrabutyl ammonium fluoride (1 mol/L tetrahydrofuran solution, 11.6 mL, 11.6 mmol) was added to the solution. The mixture was stirred at room temperature for 3 days. The solvent was evaporated under reduced pressure. The obtained residue was purified by silica-gel column chromatography (chloroform-methanol) to afford the compound B4 (2.01 g, yield 85.3%).

$^1$H-NMR (DMSO-d$_6$) δ: 3.81 (s, 3H), 7.64-7.71 (m, 2H), 7.86 (d, J=8.0 Hz, 1H), 8.01 (d, J=8.0 Hz, 1H), 12.96 (br s, 1H).

Step 4

The compound B4 (50 mg, 0.164 mmol) was dissolved in dichloromethane (2 mL). DIEA (0.043 mL, 0.246 mmol), ortho-fluorobenzyl bromide (0.024 mL, 0.197 mmol) was added to the solution. The mixture was stirred at room temperature for 24 hours. 2 mol/L aqueous solution of hydrochloric acid was added to the mixture. The mixture was extracted with ethyl acetate. The organic layer was washed by brine, and dried over anhydrous sodium sulfate. The solvent was evaporated under reduced pressure. The obtained residue was purified by silica-gel column chromatography (chloroform-methanol) to afford the compound II-005 (21 mg, yield 31.0%).

$^1$H-NMR (CDCl$_3$) δ: 3.79 (s, 3H), 4.87 (d, J=16.0 Hz, 1H), 4.91 (d, J=16.0 Hz, 1H), 6.87-6.95 (m, 2H), 7.03-7.16 (m, 2H), 7.33-7.41 (m, 1H), 7.48 (t, J=8.0 Hz, 1H), 7.56 (d, J=8.0 Hz, 1H), 7.85 (d, J=8.0 Hz, 1H).

Step 1

Under nitrogen atmosphere, 2-(trimethylsilyl)ethanol (6.04 mL, 41.9 mmol) was dissolved in tetrahydrofuran (100 mL). Under ice cooling, sodium hydride (60% oil dispersion, 1.23 g, 30.7 mmol) was added to the solution. The mixture was stirred at room temperature for 30 minutes. Under ice cooling, the tetrahydrofuran solution of the compound B1 (5.0 g, 27.9 mmol, 50 mL) was added dropwise to the mixture. The mixture was stirred at room temperature for 3 hours. 1 mol/L aqueous solution of hydrochloric acid was added to the mixture. The mixture was extracted with ethyl acetate. The organic layer was washed by the saturated aqueous solution of sodium hydrogen carbonate and brine, and dried over anhydrous sodium sulfate. The solvent was evaporated under reduced pressure. The obtained residue was purified by silica-gel column chromatography (hexane-ethyl acetate) to afford the compound B2 (6.24 g, yield 85.7%).

$^1$H-NMR (CDCl$_3$) δ: 0.09 (s, 9H), 1.20 (t, J=8.0 Hz, 2H), 3.91 (s, 3H), 4.54 (t, J=8.0 Hz, 2H), 7.86 (s, 1H).

Step 2

Under nitrogen atmosphere, the compound B2 (5.35 g, 20.5 mmol) was dissolved in dioxane (100 mL). 2-chloro- Example B2

[Chemical Formula 63]

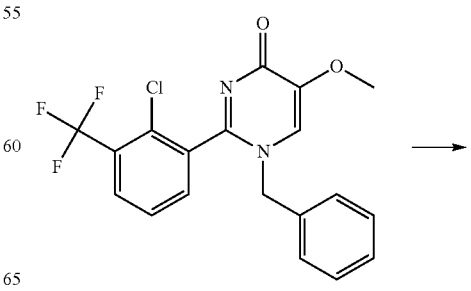

II-008

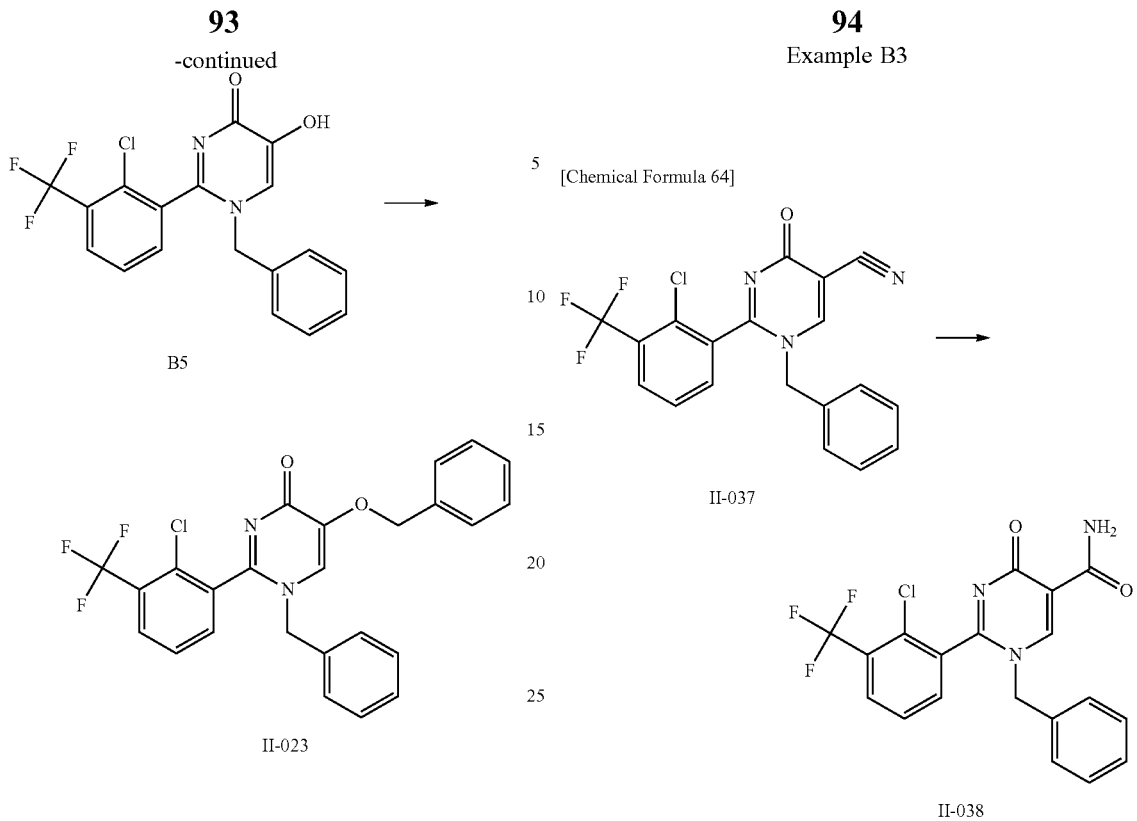

Step 1

The compound II-008 (764 mg, 1.935 mmol) obtained by the similar synthesis of Example B1 was dissolved in dichloromethane (15 mL). Boron tribromide (1 mol/L dichloromethane solution, 4.64 mL, 4.64 mmol) was added to the solution under ice cooling. The mixture was stirred at room temperature for 0.5 hour. The saturated aqueous solution of sodium hydrogen carbonate was added to the mixture. The mixture was extracted with chloroform. The organic layer was washed by brine, and dried over anhydrous sodium sulfate. The solvent was evaporated under reduced pressure. The obtained precipitates was washed by diethyl ether to afford the compound B5 (665 mg, yield 90.2%).

$^1$H-NMR (DMSO-$d_6$) δ: 4.81 (d, J=15.6 Hz, 1H), 4.97 (d, J=15.6 Hz, 1H), 6.93-7.02 (m, 2H), 7.23-7.33 (m, 3H), 7.59-7.69 (m, 2H), 7.80 (d, J=7.0 Hz, 1H), 8.00 (d, J=7.0 Hz, 1H), 9.13-9.81 (br, 1H).

Step 2

Under nitrogen atmosphere, the compound B5 (30 mg, 0.079 mmol) was dissolved in N,N-dimethyl acetamide (1 mL). Potassium bicarbonate (16.33 mg, 0.118 mmol) and (bromomethyl)benzene (0.028 mL, 0.236 mmol) were added to the solution. The mixture was stirred at 60° C. for 2.5 hours. After cooled to room temperature, 2 mol/L aqueous solution of hydrochloric acid was added to the mixture. The mixture was extracted with ethyl acetate. The organic layer was washed by brine, and dried over anhydrous sodium sulfate. The solvent was evaporated under reduced pressure. The obtained residue was purified by silica-gel column chromatography (chloroform-methanol) to afford the compound II-023 (30 mg, yield 80.9%).

$^1$H-NMR (DMSO-$d_6$) δ: 4.85 (d, J=15.8 Hz, 1H), 4.94-5.14 (m, 3H), 6.88 (d, J=6.5 Hz, 2H), 7.22-7.30 (m, 3H), 7.36-7.47 (m, 5H), 7.59-7.68 (m, 1H), 7.74 (d, J=7.0 Hz, 1H), 7.93 (s, 1H), 8.00 (d, J=7.0 Hz, 1H).

Example B3

[Chemical Formula 64]

The compound II-037 (390 mg, 0.100 mmol obtained by the similar synthesis of Example B1 was suspended in methanol (2 mL). 2 mol/L aqueous solution of sodium hydroxide (0.09 mL, 0.180 mmol) was added to the suspension. The mixture was stirred at 60° C. for 4 hours. 2 mol/L aqueous solution of hydrochloric acid was added to the mixture. The mixture was extracted with chloroform. The organic layer was washed by brine, and dried over anhydrous sodium sulfate. The solvent was evaporated under reduced pressure. The obtained residue was purified by silica-gel column chromatography (chloroform-methanol) to afford the compound II-038 (7.0 mg, yield 17.2%).

$^1$H-NMR (DMSO-$d_6$) δ: 4.88 (d, J=16.0 Hz, 1H), 5.10 (d, J=16.0 Hz, 1H), 6.94-6.99 (m, 2H), 7.25-7.32 (m, 3H), 7.59 (t, J=8.0 Hz, 1H), 7.76 (d, J=8.0 Hz, 1H), 7.97 (d, J=8.0 Hz, 1H), 8.30-8.90 (br, 1H), 9.60-10.20 (br, 1H), 9.97 (s, 1H).

Example B4

[Chemical Formula 65]

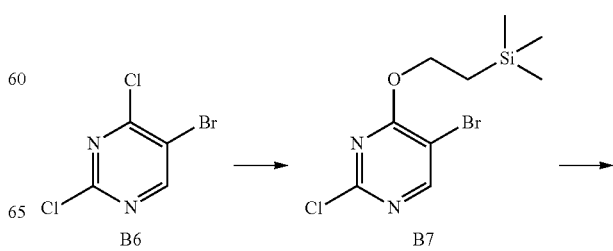

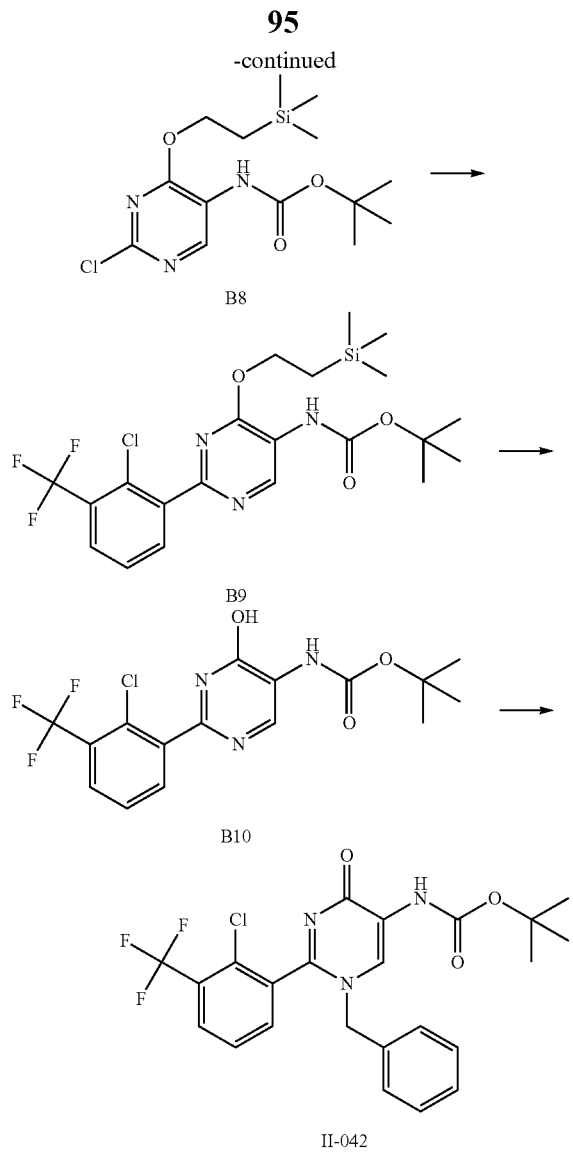

Step 1

Under nitrogen atmosphere, 2-(trimethylsilyl)ethanol (2.85 mL, 19.8 mmol) was dissolved in tetrahydrofuran (30 mL). Sodium hydride (60% oil dispersion, 632 mg, 15.8 mmol) was added to the solution under ice cooling. The mixture was stirred at room temperature for 1 hour. The tetrahydrofuran solution of the compound B6 (3.0 g, 13.2 mmol, 15 mL) was added dropwise to the mixture under ice cooling. The mixture was stirred at room temperature for 2.5 hours. 2 mol/L aqueous solution of hydrochloric acid was added to the mixture. The mixture was extracted with ethyl acetate. The organic layer was washed by brine, and dried over anhydrous sodium sulfate. The solvent was evaporated under reduced pressure. The obtained residue was purified by silica-gel column chromatography (hexane-ethyl acetate) to afford the compound B7 (3.81 g, yield 93.5%).

$^1$H-NMR (CDCl$_3$) δ: 0.10 (s, 9H), 1.12 (t, J=8.0 Hz, 2H), 4.57 (t, J=8.0 Hz, 2H), 8.41 (s, 1H).

Step 2

Under nitrogen atmosphere, the compound B7 (3.24 g, 10.46 mmol) was dissolved in dioxane (30 mL). Tert-butyl carbamate (1.72 g, 14.7 mmol), Xantphos (908 mg, 1.57 mmol), bis(dibenzylideneacetone)palladium(0) (602 mg, 1.04 mmol) and cesium carbonate (4.77 g, 14.7 mmol) were added to the mixture. The mixture was stirred under reflux for 6 hours. After cooled to room temperature, water was added to the mixture. The mixture was filtered through Celite. The aqueous layer was extracted with ethyl acetate. The organic layer was washed by brine, and dried over anhydrous sodium sulfate. The solvent was evaporated under reduced pressure. The obtained residue was purified by silica-gel column chromatography (hexane-ethyl acetate) to afford the compound B8 (1.76 g, yield 48.6%).

$^1$H-NMR (CDCl$_3$) δ: 0.10 (s, 9H), 1.16-1.22 (m, 2H), 1.53 (s, 9H), 4.51-4.57 (m, 2H), 6.64 (br s, 1H), 9.00 (br s, 1H).

Step 3

Under nitrogen atmosphere, the compound B8 (1.76 g, 5.09 mmol) was dissolved in dioxane (30 mL). 2-chloro-3-(trifluoromethyl)phenyl boronic acid (2.3 g, 10.25 mmol), PdCl$_2$(dppf)(416 mg, 0.509 mmol) and 2 mol/L aqueous solution of sodium carbonate (7.6 mL, 15.2 mmol) were added to the solution. The mixture was stirred under reflux for 4 hours. After cooled to room temperature, water was added to the mixture. The mixture was extracted with ethyl acetate. The organic layer was washed by brine, and dried over anhydrous sodium sulfate. The solvent was evaporated under reduced pressure. The obtained residue was purified by silica-gel column chromatography (hexane-ethyl acetate) to afford the compound B9 (1.14 g, yield 45.7%).

$^1$H-NMR (CDCl$_3$) δ: 0.08 (s, 9H), 1.19-1.25 (m, 2H), 1.55 (s, 9H), 4.56-4.62 (m, 2H), 6.80 (br s, 1H), 7.44 (t, J=8.0 Hz, 1H), 7.75 (d, J=8.0 Hz, 1H), 7.86 (d, J=8.0 Hz, 1H), 9.26 (br s, 1H).

Step 4

The compound B9 (1.14 g, 2.33 mmol) was dissolved in tetrahydrofuran (5 mL). Tetrabutyl ammonium fluoride (1 mol/L tetrahydrofuran solution, 3.5 mL, 3.5 mmol) was added to the solution. The mixture was stirred at room temperature for 1 day. The solvent was evaporated under reduced pressure. The obtained residue was purified by silica-gel column chromatography (chloroform-methanol) to afford the compound B10 (840 mg, yield 92.6%).

$^1$H-NMR (DMSO-d$_6$) δ: 1.50 (s, 9H), 7.72 (t, J=8.0 Hz, 1H), 7.92 (d, J=8.0 Hz, 1H), 8.04-8.09 (m, 2H), 8.45 (s, 1H).

Step 5

The compound B10 (838 mg, 2.15 mmol) was dissolved in dichloromethane (10 mL). DIEA (751 μl, 4.30 mmol) and benzyl bromide (435 μl, 3.66 mmol) were added to the solution. The mixture was stirred at room temperature for 3 days. 2 mol/L aqueous solution of hydrochloric acid was added to the mixture. The mixture was extracted with ethyl acetate. The organic layer was washed by brine, and dried over anhydrous sodium sulfate. The solvent was evaporated under reduced pressure. The obtained residue was purified by silica-gel column chromatography (hexane-ethyl acetate) to afford the compound II-042 (815 mg, yield 79.0%).

$^1$H-NMR (CDCl$_3$) δ: 1.50 (s, 9H), 4.86 (s, 2H), 6.88-6.94 (m, 2H), 7.28-7.40 (m, 5H), 7.60 (br s, 1H), 7.79-7.83 (m, 1H), 8.39 (br s, 1H).

Example B5

[Chemical Formula 66]

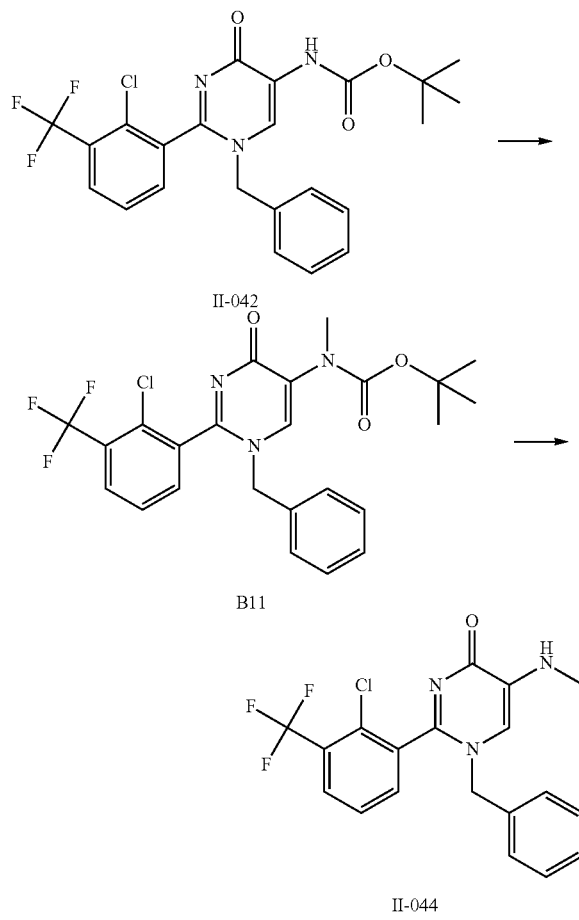

Step 1

Under nitrogen atmosphere, the compound II-042 (50 mg, 0.104 mmol) obtained by Example B4 was dissolved in DMF (1 mL). Under ice cooling, sodium hydride (60% oil dispersion, 12 mg, 0.30 mmol) and methyl iodide (0.026 mL, 0.416 mmol) were added to the solution. The mixture was stirred at the same temperature for 1.5 hours. 2 mol/L aqueous solution of hydrochloric acid was added to the mixture. The mixture was extracted with ethyl acetate. The organic layer was washed by water, and dried over anhydrous sodium sulfate. The solvent was evaporated under reduced pressure. The obtained residue was purified by silica-gel column chromatography (chloroform-methanol) to afford the compound B11 (45 mg, yield 87.4%).

MS (m/z): 494 [(M+H)$^+$]

Step 2

The compound B11 (45 mg, 0.091 mmol) was dissolved in dichloromethane (0.4 mL). Trifluoroacetic acid (0.4 mL, 5.21 mmol) was added to the solution. The mixture was stirred at room temperature for 1 hour. 2 mol/L aqueous solution of sodium carbonate was added to the mixture. The mixture was extracted with ethyl acetate. The organic layer was washed by brine, and dried over anhydrous sodium sulfate. The solvent was evaporated under reduced pressure. The obtained residue was purified by silica-gel column chromatography (chloroform-methanol) to afford the compound II-044 (26 mg, yield 72.5%).

$^1$H-NMR (DMSO-d$_6$) δ: 2.66 (d, J=8.0 Hz, 3H), 4.83 (d, J=16.0 Hz, 1H), 5.02 (d, J=16.0 Hz, 1H), 5.56 (q, J=8.0 Hz, 1H), 6.94-6.98 (m, 2H), 7.02 (s, 1H), 7.25-7.29 (m, 3H), 7.61 (t, J=8.0 Hz, 1H), 7.71 (d, J=8.0 Hz, 1H), 7.98 (d, J=8.0 Hz, 1H).

Example B6

[Chemical Formula 67]

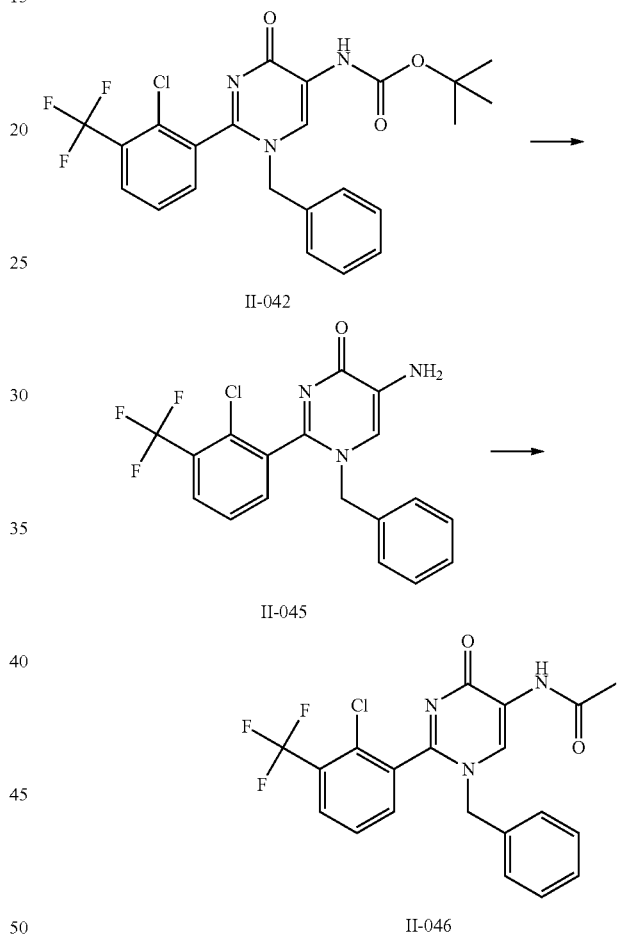

Step 1

The compound II-042 (200 mg, 0.417 mmol) obtained by Example B4 was dissolved in dichloromethane (0.8 mL). Trifluoroacetic acid (0.8 mL, 10.42 mmol) was added to the solution. The mixture was stirred at room temperature for 1 hour. 2 mol/L aqueous solution of sodium carbonate was added to the mixture. The mixture was extracted with ethyl acetate. The organic layer was washed by brine, and dried over anhydrous sodium sulfate. The solvent was evaporated under reduced pressure. The obtained solid was washed by diethyl ether to afford the compound II-045 (149 mg, yield 94.1%).

$^1$H-NMR (DMSO-d$_6$) δ: 4.83 (s, 2H), 6.99-7.03 (m, 1H), 7.17-7.35 (m, 5H), 7.44-7.55 (m, 2H), 7.84-7.88 (m, 1H).

Step 2

The compound II-045 (50 mg, 0.132 mmol) was dissolved in dichloromethane (1 mL). Under ice cooling, DIEA (0.105 mL, 0.601 mmol) and acetyl chloride (0.033 mL, 0.462 mmol) were added to the solution. The mixture was stirred at room temperature for 3 hours. 2 mol/L aqueous solution of hydrochloric acid was added to the mixture. The mixture was extracted with chloroform. The organic layer was washed by the saturated aqueous solution of sodium hydrogen carbonate and brine, and dried over anhydrous sodium sulfate. The solvent was evaporated under reduced pressure. The obtained residue was purified by silica-gel column chromatography (chloroform-methanol) to afford the compound II-046 (43 mg, yield 77.4%).

$^1$H-NMR (DMSO-$d_6$) δ: 2.14 (s, 3H), 4.91 (d, J=12.0 Hz, 1H), 5.07 (d, J=12.0 Hz, 1H), 6.98-7.04 (m, 2H), 7.27-7.32 (m, 3H), 7.68 (t, J=8.0 Hz, 1H), 7.89 (d, J=8.0 Hz, 1H), 8.03 (d, J=8.0 Hz, 1H), 8.84 (s, 1H), 9.49 (s, 1H).

Example C1

[Chemical Formula 68]

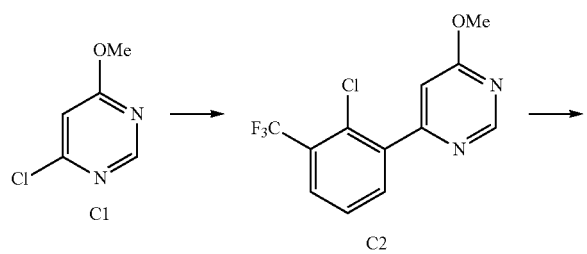

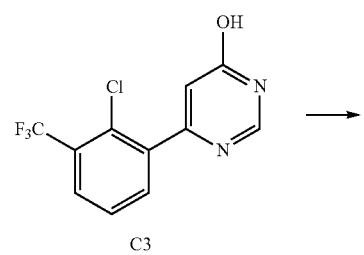

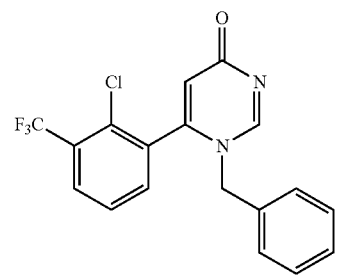

III-001

Step 1

Under nitrogen atmosphere, the compound C1 (500 mg, 3.46 mmol was dissolved in DME (10 mL). 2-chloro-3-(trifluoromethyl)phenyl boronic acid (1.164 g, 5.19 mmol), 2 mol/L aqueous solution of sodium carbonate (5.19 mL, 10.38 mmol) and PdCl$_2$ (dppf)(282 mg, 0.346 mmol) were added to the solution. The mixture was stirred at 90° C. for 1 hour. After cooled to room temperature, water was added to the mixture. The mixture was extracted with ethyl acetate. The organic layer was washed by brine, and dried over anhydrous magnesium sulfate. The solvent was evaporated under reduced pressure. The obtained residue was purified by column chromatography (chloroform-methanol) to afford the compound C2 (600 mg, yield 60%).

MS (m/z): 289 [(M+H)$^+$]

Step 2

48% aqueous solution of hydrobromic acid (2.35 mL, 20.8 mmol) was added to the compound C2 (600 mg, 2.08 mmol). The mixture was stirred at 100° C. for 18 hours. After cooled to room temperature, the solvent was evaporated under reduced pressure to afford the compound C3 as the crude product.

MS (m/z): 275 [(M+H)$^+$]

Step 3

Under nitrogen atmosphere, the crude product of the compound C3 (570 mg, 2.08 mmol) was dissolved in dichloromethane (20 mL). (Bromo methyl)benzene (0.383 mL, 3.22 mmol) and DIEA (0.563 mL, 3.22 mmol) were added to the solution. The mixture was stirred at room temperature for 16 hours. The solvent was evaporated under reduced pressure. Water was added to the obtained residue. The mixture was extracted with ethyl acetate. The organic layer was washed by brine, and dried over anhydrous magnesium sulfate. The solvent was evaporated under reduced pressure. The obtained residue was purified by column chromatography (chloroform-methanol) to afford the compound III-001 (40 mg, yield 5.3%).

$^1$H-NMR (DMSO-d6) δ: 4.84 (d, J=15.8 Hz, 1H), 5.00 (d, J=15.8 Hz, 1H), 6.06 (s, 1H), 6.74-6.79 (m, 2H), 7.17-7.26 (m, 3H), 7.54-7.69 (m, 2H), 7.94-8.00 (m, 1H), 8.75 (a, 1H).

According to the above Examples A1 to A7, the following compounds were synthesized.

TABLE 1

| No. | Chemical Structure | [M + H] | RT (min) | Method |
|---|---|---|---|---|
| I-001 | 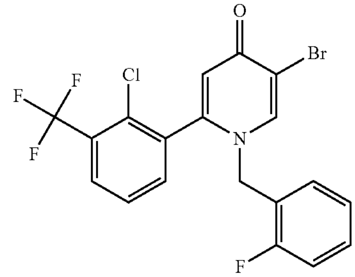 [SMILES: O=c1cc(-c2cccc(C(F)(F)F)c2Cl)n(Cc2ccccc2F)cc1Br] | 460 | 2.07 | [2] |
| I-002 | 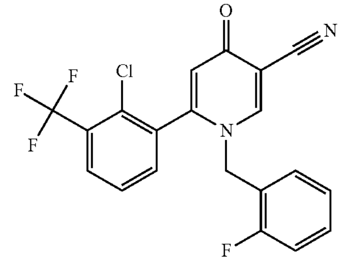 [SMILES: N#Cc1cn(Cc2ccccc2F)c(-c2cccc(C(F)(F)F)c2Cl)cc1=O] | 407 | 2.08 | [2] |

TABLE 1-continued

| No. | Chemical Structure | [M + H] | RT (min) | Method |
|---|---|---|---|---|
| I-003 | 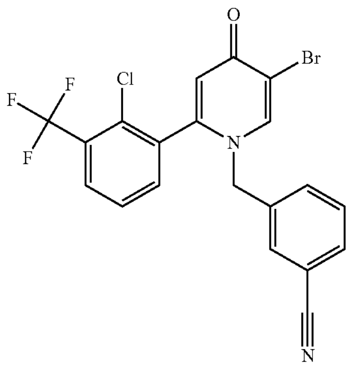 [SMILES: N#Cc1cccc(Cn2cc(Br)c(=O)cc2-c2cccc(C(F)(F)F)c2Cl)c1] | 467 | 1.82 | [2] |
| I-004 | 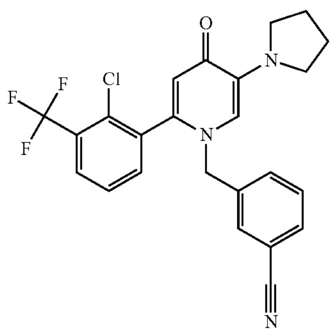 [SMILES: N#Cc1cccc(Cn2cc(N3CCCC3)c(=O)cc2-c2cccc(C(F)(F)F)c2Cl)c1] | 458 | 1.99 | [2] |
| I-005 | 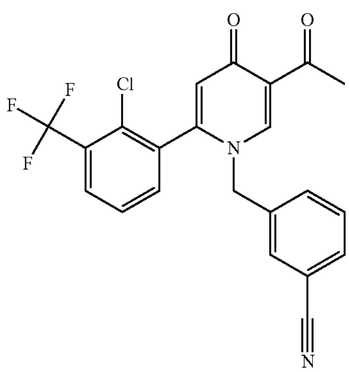 [SMILES: CC(=O)c1cn(Cc2cccc(C#N)c2)c(-c2cccc(C(F)(F)F)c2Cl)cc1=O] | 431 | 1.82 | [2] |

TABLE 2

| I-006 | | 404 | 1.63 | [2] |
|---|---|---|---|---|
| I-007 | | 419 | 1.64 | [2] |
| I-008 | | 442 | 2.01 | [1] |
| I-009 | | 472 | 2.01 | [1] |
| I-010 | | 460 | 2.00 | [1] |

TABLE 3
I-011  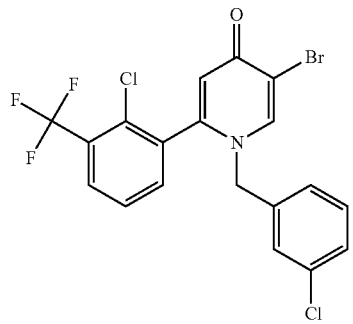 [SMILES: O=c1cc(-c2cccc(C(F)(F)F)c2Cl)n(Cc2cccc(F)c2)cc1Br]  476  2.13  [1]
I-012  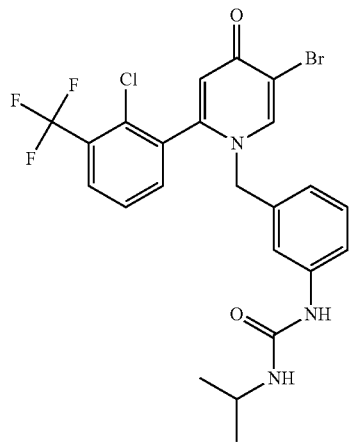 [SMILES: CC(C)NC(=O)Nc1cccc(Cn2cc(Br)c(=O)cc2-c2cccc(C(F)(F)F)c2Cl)c1]  542  1.86  [1]
I-013  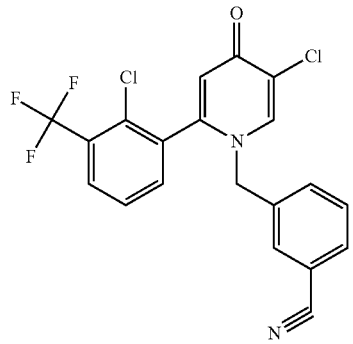 [SMILES: N#Cc1cccc(Cn2cc(Cl)c(=O)cc2-c2cccc(C(F)(F)F)c2Cl)c1]  423  1.83  [1]
I-014  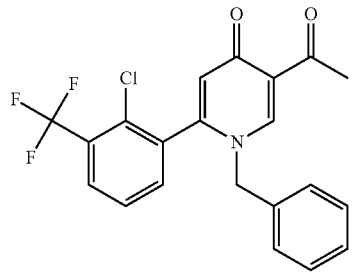 [SMILES: CC(=O)c1cn(Cc2ccccc2)c(-c2cccc(C(F)(F)F)c2Cl)cc1=O]  406  2.50  [1]
TABLE 3-continued
I-015  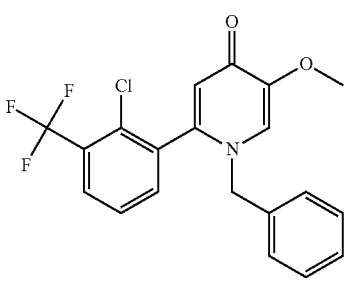 [SMILES: COc1cn(Cc2ccccc2)c(-c2cccc(C(F)(F)F)c2Cl)cc1=O]  394  1.83  [1]
TABLE 4
I-016  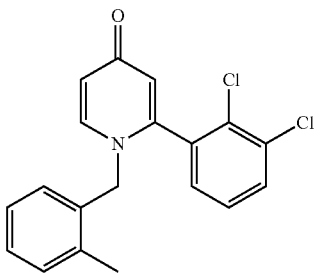 [SMILES: Cc1ccccc1Cn1ccc(=O)cc1-c1cccc(Cl)c1Cl]  344  1.90  [2]
I-017  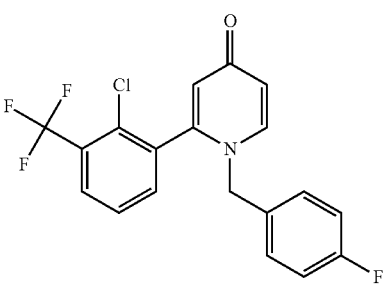 [SMILES: O=c1ccn(Cc2ccc(F)cc2)c(-c2cccc(C(F)(F)F)c2Cl)c1]  382  1.87  [2]
I-018  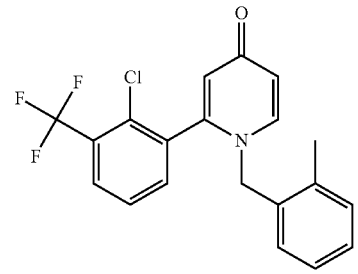 [SMILES: Cc1ccccc1Cn1ccc(=O)cc1-c1cccc(C(F)(F)F)c1Cl]  378  1.93  [2]
I-019  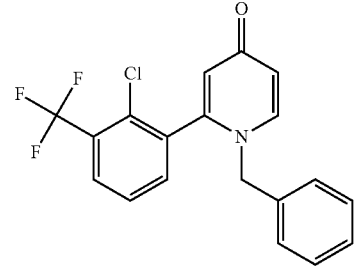 [SMILES: O=c1ccn(Cc2ccccc2)c(-c2cccc(C(F)(F)F)c2Cl)c1]  364  1.81  [2]

TABLE 4-continued
I-020  348  1.76  [2]
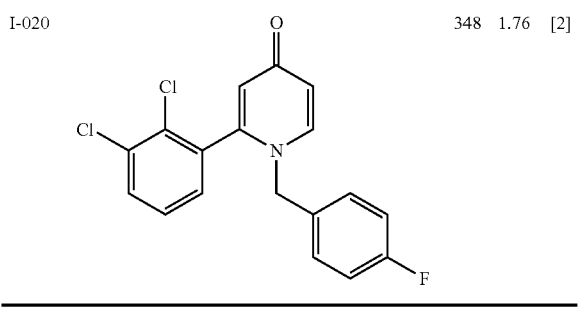
TABLE 5
I-021  330  1.75  [2]
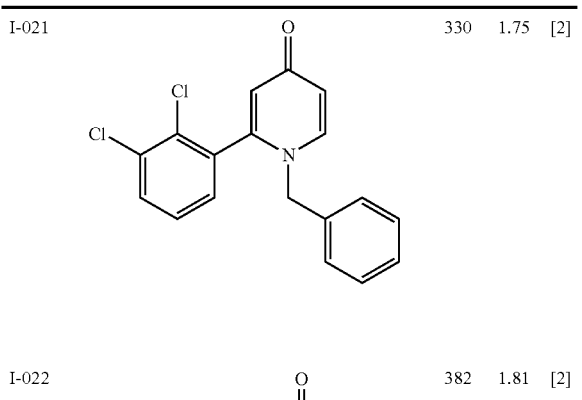
I-022  382  1.81  [2]
I-023  389  1.69  [2]
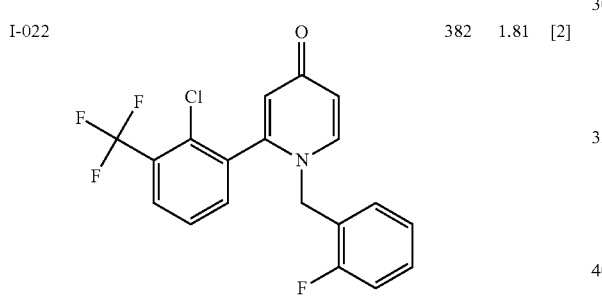
I-024  389  1.69  [2]
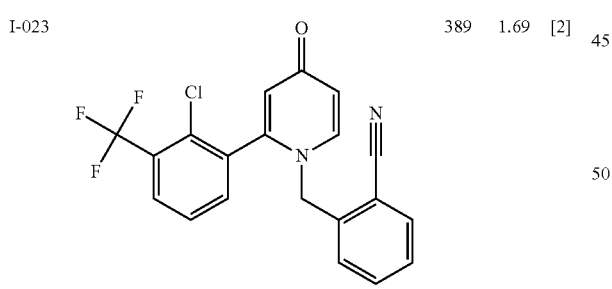
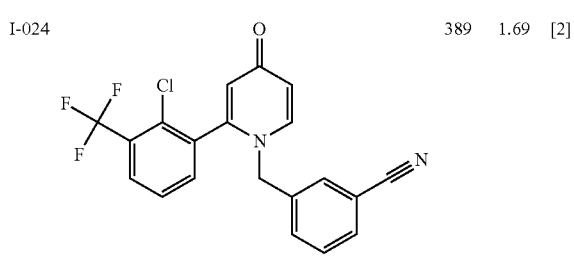
TABLE 5-continued
I-025  389  1.70  [2]
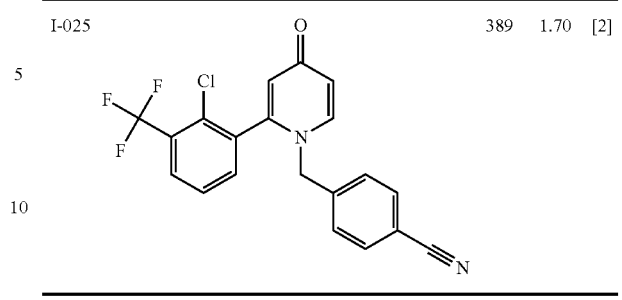
TABLE 6
I-026  513  1.74  [2]
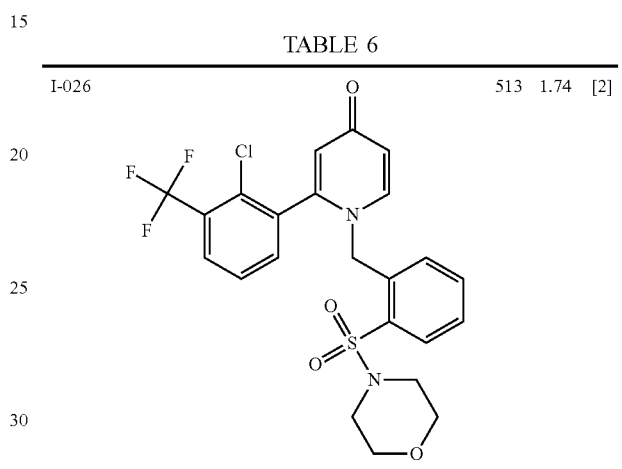
I-027  382  1.86  [2]
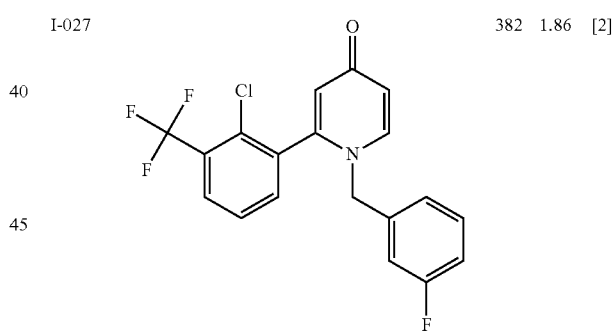
I-028  378  1.99  [2]
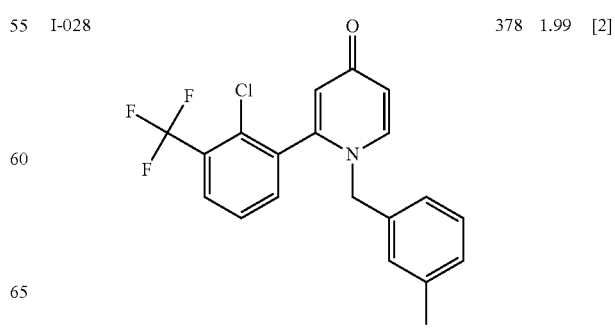

TABLE 6-continued

| ID | Structure | MW | RT | Method |
|---|---|---|---|---|
| I-029 | 2-(2-chloro-3-(trifluoromethyl)phenyl)-1-(4-methylbenzyl)pyridin-4(1H)-one | 378 | 2.01 | [2] |
| I-030 | 2-(2-chloro-3-(trifluoromethyl)phenyl)-1-(2-(trifluoromethoxy)benzyl)pyridin-4(1H)-one | 448 | 2.09 | [2] |

TABLE 7

| ID | Structure | MW | RT | Method |
|---|---|---|---|---|
| I-031 | 2-(2-chloro-3-(trifluoromethyl)phenyl)-1-(3-(trifluoromethoxy)benzyl)pyridin-4(1H)-one | 448 | 2.10 | [2] |
| I-032 | 2-(2-chloro-3-(trifluoromethyl)phenyl)-1-((6-methoxypyridin-2-yl)methyl)pyridin-4(1H)-one | 395 | 1.81 | [2] |
| I-033 | 2-(2-chloro-3-(trifluoromethyl)phenyl)-1-(2-(trifluoromethyl)benzyl)pyridin-4(1H)-one | 432 | 2.07 | [2] |
| I-034 | 2-(2-chloro-3-(trifluoromethyl)phenyl)-1-((6-oxo-1,6-dihydropyridin-2-yl)methyl)pyridin-4(1H)-one | 381 | 1.16 | [2] |
| I-035 | 2-(2-chloro-3-(trifluoromethyl)phenyl)-1-(3-(hydroxymethyl)benzyl)pyridin-4(1H)-one | 394 | 1.49 | [2] |

TABLE 8

| ID | Structure | MW | RT | Method |
|---|---|---|---|---|
| I-036 | 2-(2-chloro-3-(trifluoromethyl)phenyl)-1-(3-phenoxybenzyl)pyridin-4(1H)-one | 456 | 2.20 | [2] |
| I-037 | 1-(3-(3-isopropylureido)benzyl)-2-(2-chloro-3-(trifluoromethyl)phenyl)pyridin-4(1H)-one | 464 | 1.66 | [2] |

TABLE 8-continued
| I-038 | 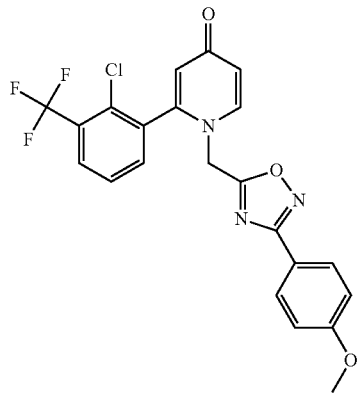 [SMILES: COc1ccc(-c2noc(Cn3ccc(=O)cc3-c3cccc(C(F)(F)F)c3Cl)n2)cc1] | 462 1.91 [2] |
| I-039 | 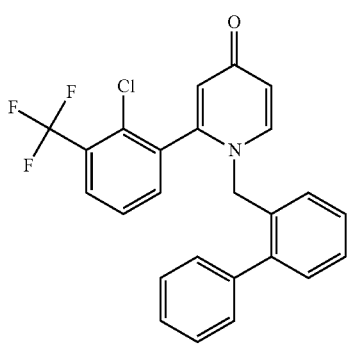 [SMILES: O=c1ccn(Cc2ccccc2-c2ccccc2)c(-c2cccc(C(F)(F)F)c2Cl)c1] | 440 2.17 [2] |
| I-040 | 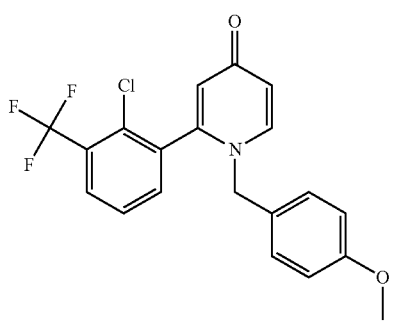 [SMILES: COc1ccc(Cn2ccc(=O)cc2-c2cccc(C(F)(F)F)c2Cl)cc1] | 394 1.81 [2] |
TABLE 9
| I-041 | 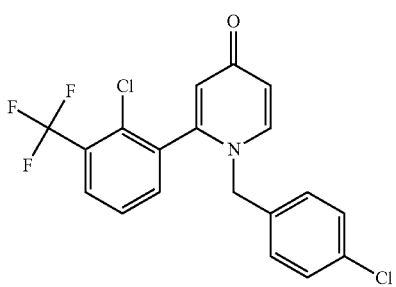 [SMILES: O=c1ccn(Cc2ccc(Cl)cc2)c(-c2cccc(C(F)(F)F)c2Cl)c1] | 398 1.96 [2] |
TABLE 9-continued
| I-042 | 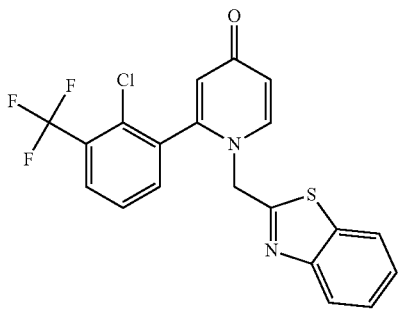 [SMILES: O=c1ccn(Cc2nc3ccccc3s2)c(-c2cccc(C(F)(F)F)c2Cl)c1] | 421 1.80 [2] |
| I-043 | 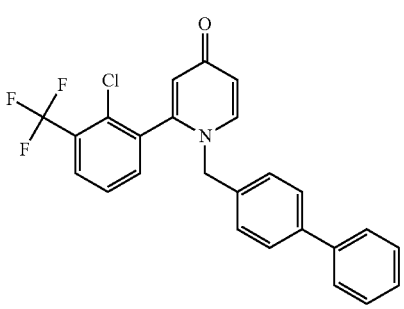 [SMILES: O=c1ccn(Cc2ccc(-c3ccccc3)cc2)c(-c2cccc(C(F)(F)F)c2Cl)c1] | 440 2.23 [2] |
| I-044 | 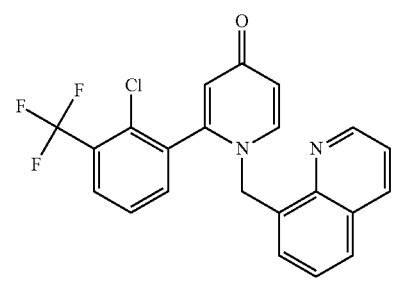 [SMILES: O=c1ccn(Cc2cccc3cccnc23)c(-c2cccc(C(F)(F)F)c2Cl)c1] | 415 1.84 [2] |
| I-045 | 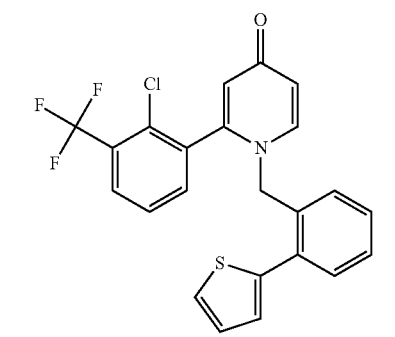 [SMILES: O=c1ccn(Cc2ccccc2-c2cccs2)c(-c2cccc(C(F)(F)F)c2Cl)c1] | 446 2.12 [2] |

TABLE 10
I-046 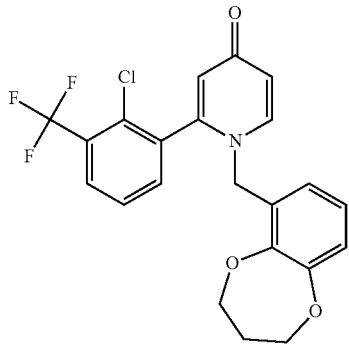 [SMILES: O=c1ccn(Cc2cccc3c2OCCCO3)c(-c2cccc(C(F)(F)F)c2Cl)c1] 436 1.86 [2]
I-047 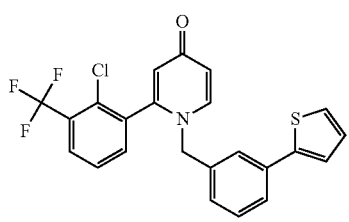 [SMILES: O=c1ccn(Cc2cccc(-c3cccs3)c2)c(-c2cccc(C(F)(F)F)c2Cl)c1] 446 2.13 [2]
I-048 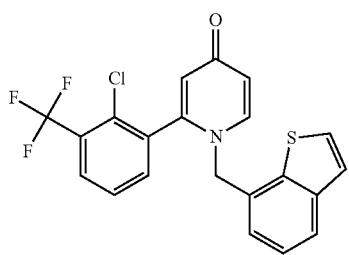 [SMILES: O=c1ccn(Cc2cccc3ccsc23)c(-c2cccc(C(F)(F)F)c2Cl)c1] 420 1.97 [2]
I-049 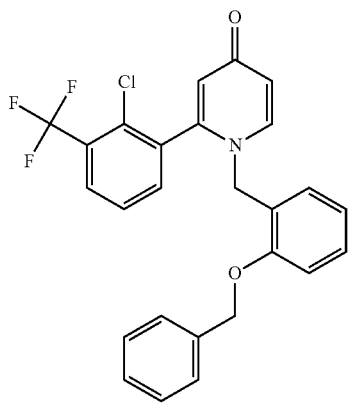 [SMILES: O=c1ccn(Cc2ccccc2OCc2ccccc2)c(-c2cccc(C(F)(F)F)c2Cl)c1] 470 2.23 [2]
I-050 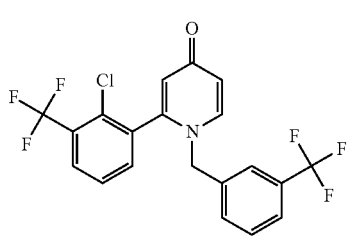 [SMILES: O=c1ccn(Cc2cccc(C(F)(F)F)c2)c(-c2cccc(C(F)(F)F)c2Cl)c1] 432 1.99 [2]
TABLE 11
I-051 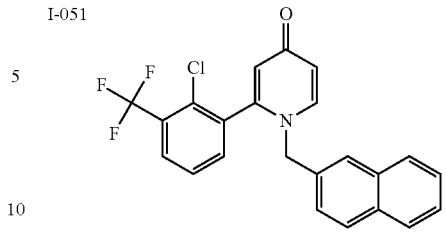 414 2.05 [2]
I-052 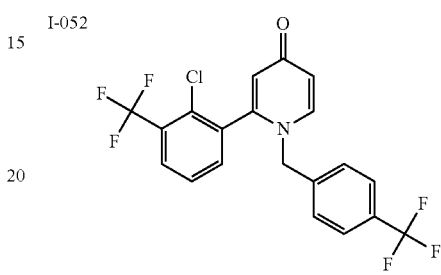 432 2.01 [2]
I-053 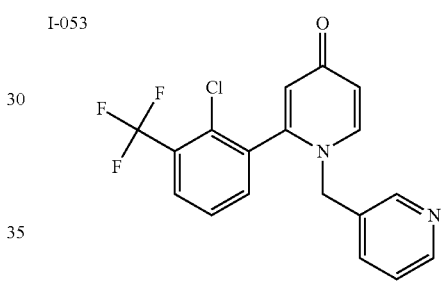 365 1.31 [2]
I-054 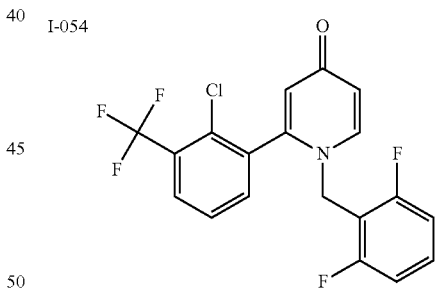 400 1.79 [2]
I-055 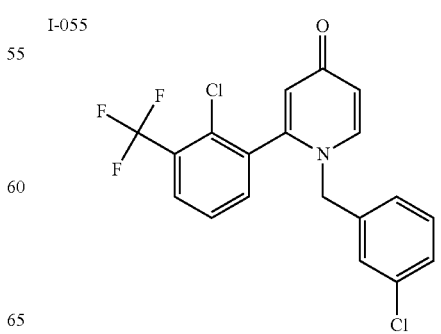 398 1.93 [2]

TABLE 12
| I-056 | 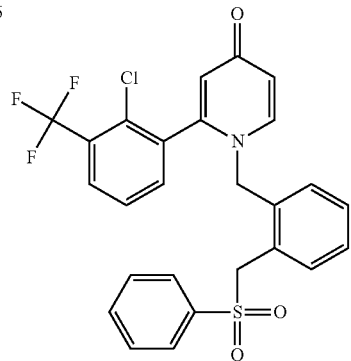 | 518 | 1.90 | [2] |
| I-057 | 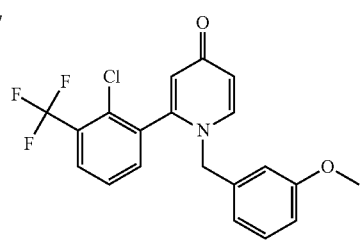 | 394 | 1.81 | [2] |
TABLE 12-continued
| I-058 | 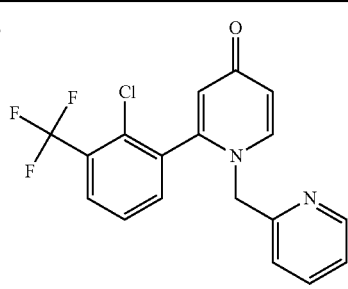 | 365 | 1.45 | [2] |
| I-059 | 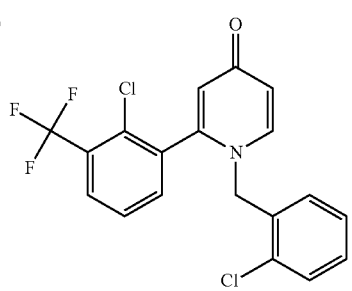 [SMILES: O=c1ccn(Cc2ccccc2Cl)c(-c2cccc(C(F)(F)F)c2Cl)c1] | 398 | 1.94 | [2] |
| I-060 | 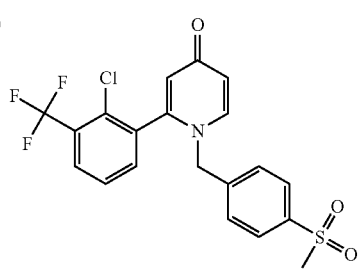 [SMILES: CS(=O)(=O)c1ccc(Cn2ccc(=O)cc2-c2cccc(C(F)(F)F)c2Cl)cc1] | 442 | 1.46 | [2] |
TABLE 13
| I-061 | 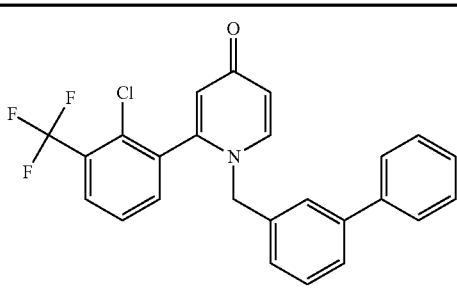 | 440 | 2.19 | [2] |
| I-062 | 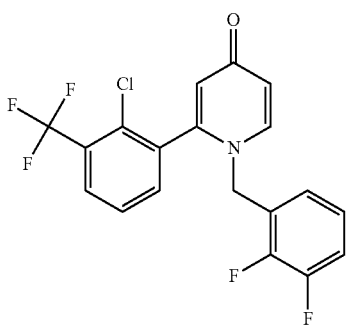 [SMILES: O=c1ccn(Cc2cccc(F)c2F)c(-c2cccc(C(F)(F)F)c2Cl)c1] | 400 | 1.83 | [2] |

TABLE 13-continued
| I-063 | 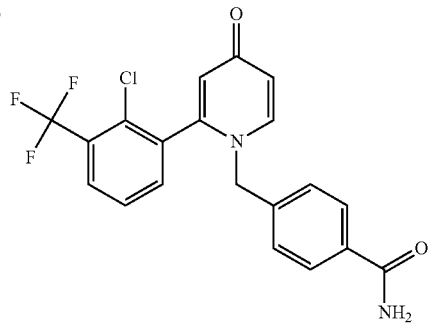 [SMILES: NC(=O)c1ccc(Cn2ccc(=O)cc2-c2cccc(C(F)(F)F)c2Cl)cc1] | 407 | 1.28 | [2] |
| I-064 | 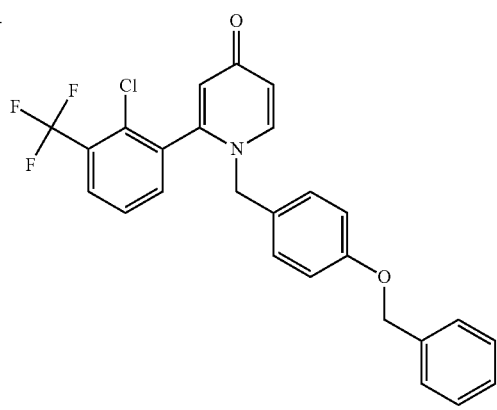 | 470 | 2.25 | [2] |
| I-065 | 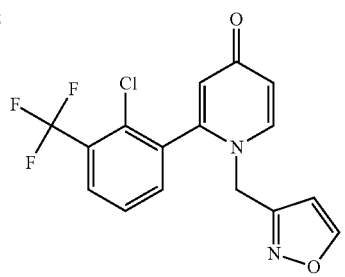 [SMILES: O=c1ccn(Cc2ccon2)c(-c2cccc(C(F)(F)F)c2Cl)c1] | 355 | 1.43 | [2] |
TABLE 14
| I-066 | 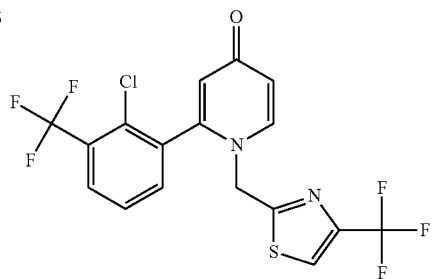 | 439 | 1.78 | [2] |

TABLE 14-continued
| ID | Structure | | | |
|---|---|---|---|---|
| I-067 | 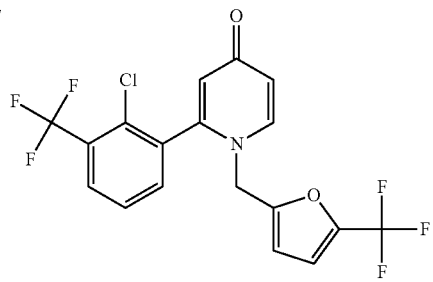 | 422 | 1.91 | [2] |
| I-068 | 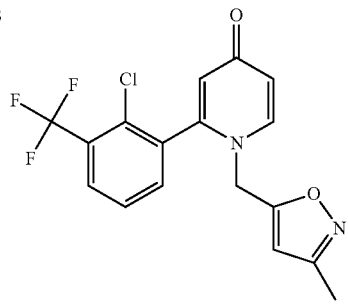 | 369 | 1.48 | [2] |
| I-069 | 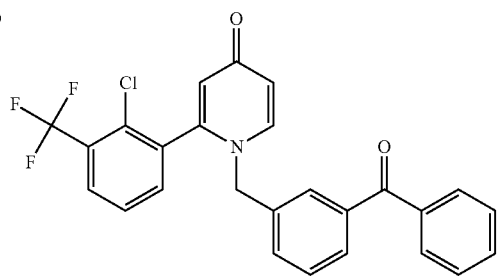 | 468 | 1.99 | [2] |
| I-070 | 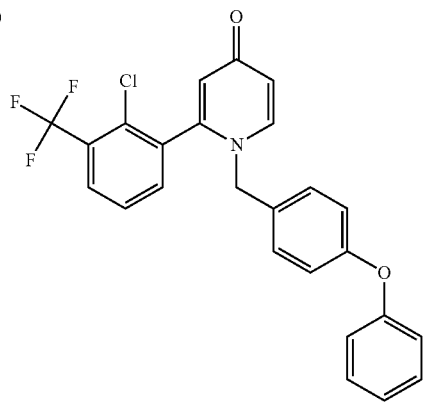 | 456 | 2.22 | [2] |
TABLE 15
| ID | Structure | | | |
|---|---|---|---|---|
| I-071 | 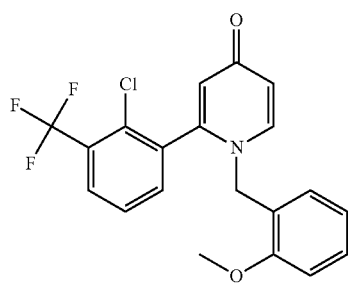 [SMILES: COc1ccccc1Cn1ccc(=O)cc1-c1cccc(C(F)(F)F)c1Cl] | 394 | 1.86 | [1] |
| I-072 | 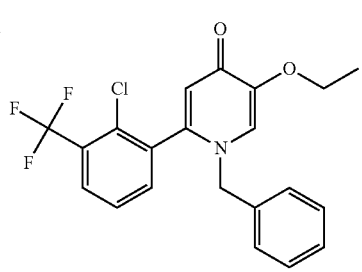 [SMILES: CCOc1cn(Cc2ccccc2)c(-c2cccc(C(F)(F)F)c2Cl)cc1=O] | 408 | 1.92 | [1] |

TABLE 15-continued
| I-073 | 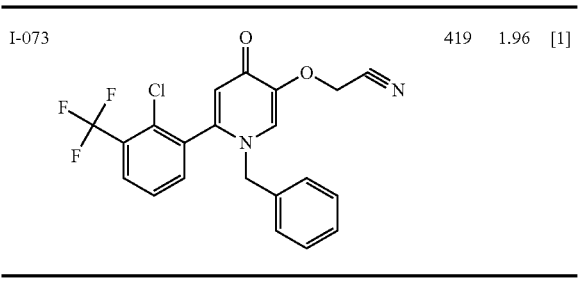 | 419 | 1.96 | [1] |
According to the above Examples B1 to B6 and Example C, the following compounds were synthesized.
TABLE 16
| II-001 | 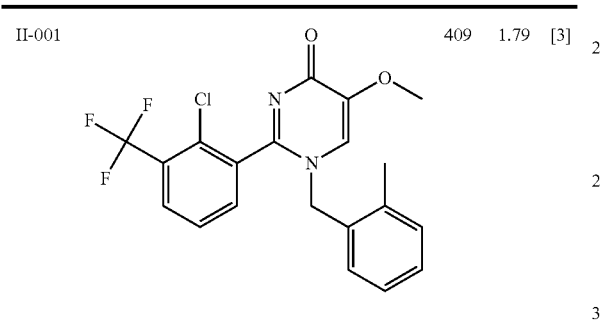 | 409 | 1.79 | [3] |
| II-002 | 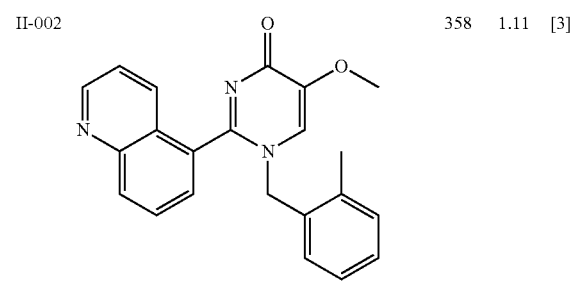 | 358 | 1.11 | [3] |
| II-003 | 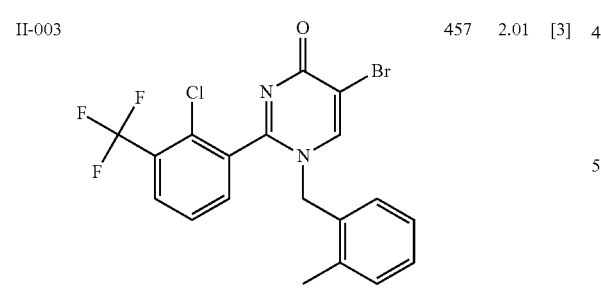 | 457 | 2.01 | [3] |
| II-004 | 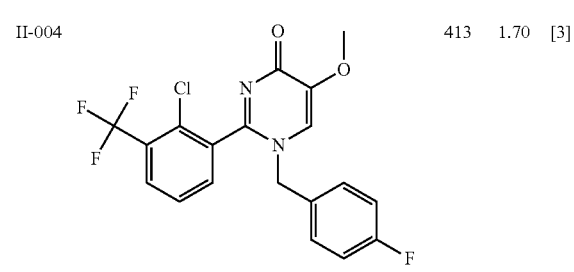 | 413 | 1.70 | [3] |
TABLE 16-continued
| II-005 | 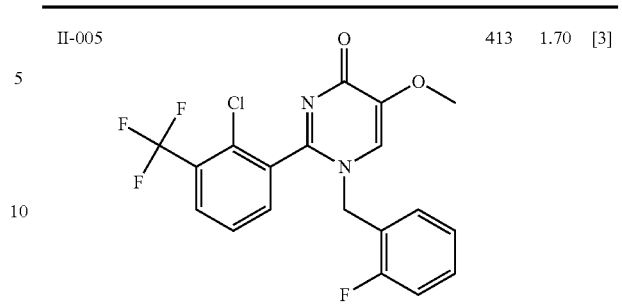 | 413 | 1.70 | [3] |
TABLE 17
| II-006 | 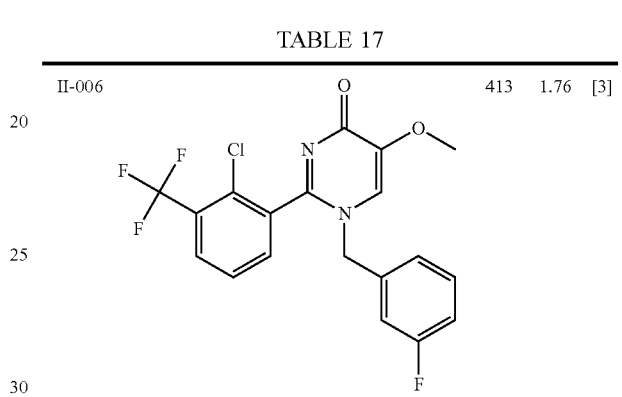 | 413 | 1.76 | [3] |
| II-007 | 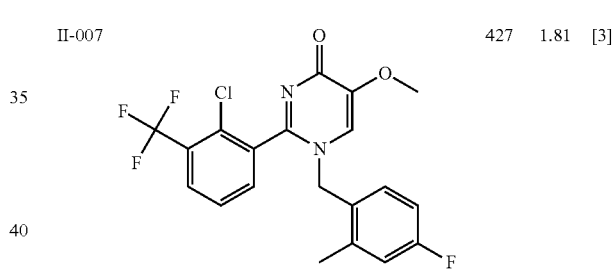 | 427 | 1.81 | [3] |
| II-008 | 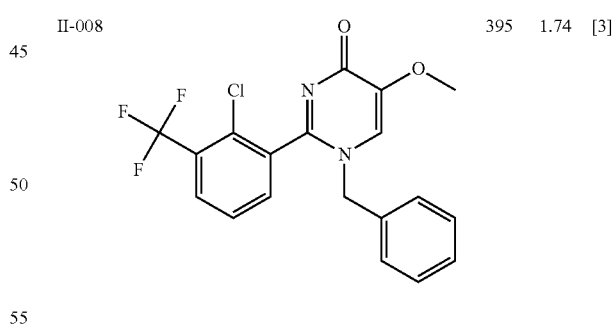 | 395 | 1.74 | [3] |
| II-009 | 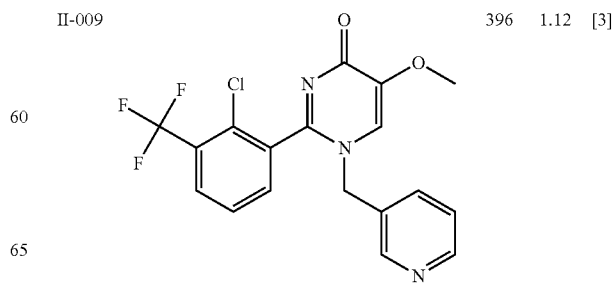 | 396 | 1.12 | [3] |

TABLE 17-continued
| II-010 | 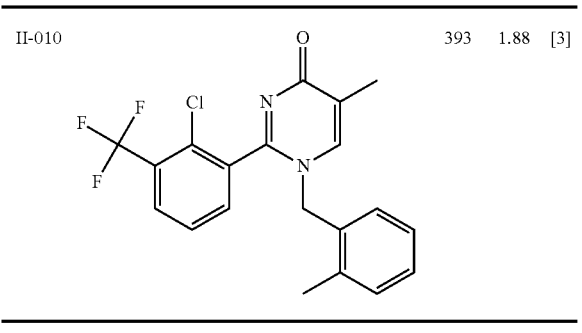 | 393 | 1.88 | [3] |
TABLE 18
| II-011 | 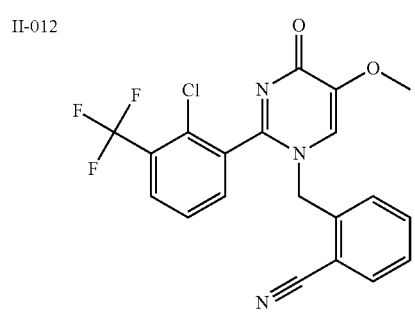 | 397 | 1.91 | [3] |
| II-012 | | 420 | 1.55 | [3] |
| II-013 | 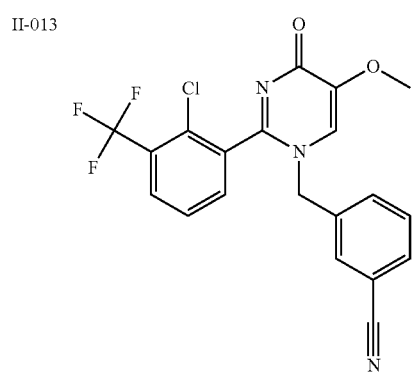 | 420 | 1.54 | [3] |
| II-014 | 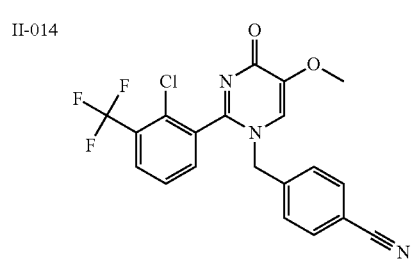 | 420 | 1.55 | [3] |
TABLE 18-continued
| II-015 | 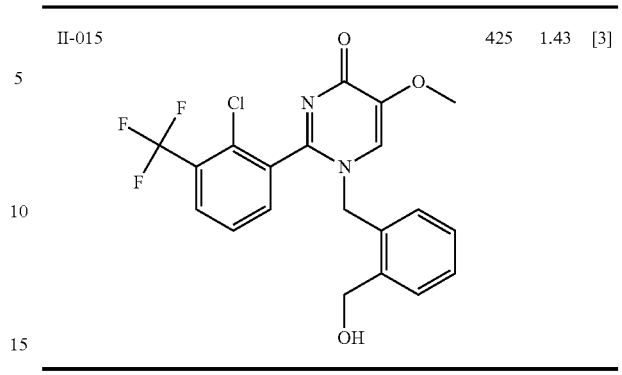 | 425 | 1.43 | [3] |
TABLE 19
| II-016 | 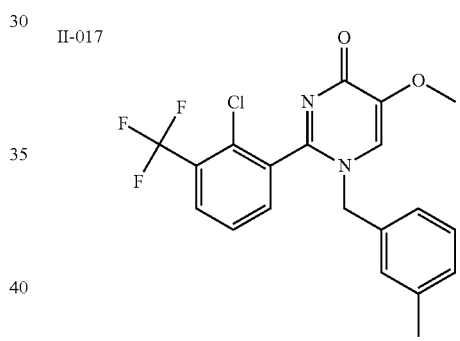 | 409 | 1.85 | [3] |
| II-017 | | 409 | 1.84 | [3] |
| II-018 | 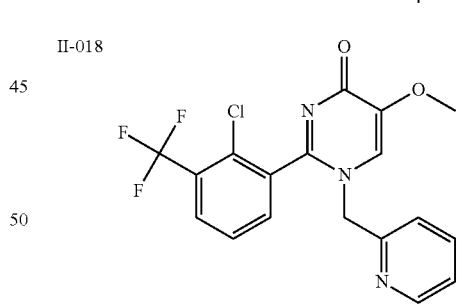 | 396 | 1.39 | [3] |
| II-019 | 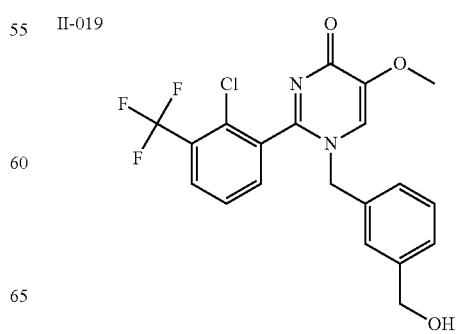 | 425 | 1.40 | [3] |

TABLE 19-continued

| ID | Structure | MW | RT | Ref |
|---|---|---|---|---|
| II-0-20 | 2-(2-chloro-3-(trifluoromethyl)phenyl)-5-methoxy-1-(pyridin-4-ylmethyl)pyrimidin-4(1H)-one | 396 | 0.99 | [3] |

TABLE 20

| ID | Structure | MW | RT | Ref |
|---|---|---|---|---|
| II-021 | 1-benzyl-2-(2-chloro-3-(trifluoromethyl)phenyl)-5-isopropoxypyrimidin-4(1H)-one | 423 | 1.92 | [3] |
| II-022 | 2-((1-benzyl-2-(2-chloro-3-(trifluoromethyl)phenyl)-6-oxo-1,6-dihydropyrimidin-5-yl)oxy)acetonitrile | 420 | 1.82 | [3] |
| II-023 | 1-benzyl-5-(benzyloxy)-2-(2-chloro-3-(trifluoromethyl)phenyl)pyrimidin-4(1H)-one | 471 | 2.08 | [3] |
| II-024 | 1-benzyl-2-(2-chloro-3-(trifluoromethyl)phenyl)-5-ethoxypyrimidin-4(1H)-one | 409 | 1.82 | [3] |

TABLE 20-continued
| II-025 | 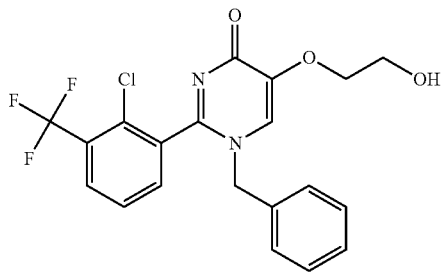 [SMILES: O=c1nc(-c2cccc(C(F)(F)F)c2Cl)n(Cc2ccccc2)cc1OCCO] | 425 | 1.60 | [3] |
TABLE 21
| II-026 | 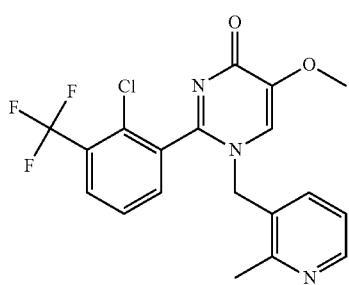 [SMILES: COc1cn(Cc2cccnc2C)c(-c2cccc(C(F)(F)F)c2Cl)nc1=O] | 410 | 0.94 | [3] |
| II-027 | 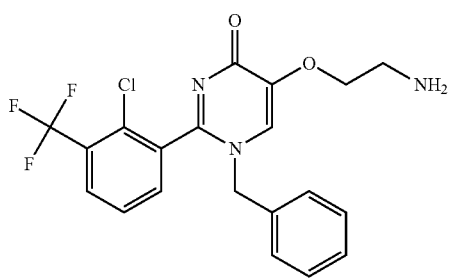 [SMILES: NCCOc1cn(Cc2ccccc2)c(-c2cccc(C(F)(F)F)c2Cl)nc1=O] | 424 | 1.13 | [3] |
| II-028 | 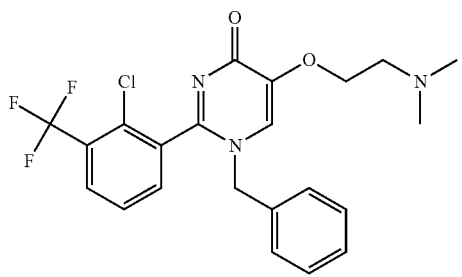 [SMILES: CN(C)CCOc1cn(Cc2ccccc2)c(-c2cccc(C(F)(F)F)c2Cl)nc1=O] | 452 | 1.32 | [3] |
| II-029 | 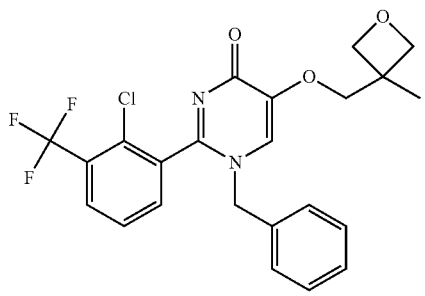 [SMILES: CC1(COc2cn(Cc3ccccc3)c(-c3cccc(C(F)(F)F)c3Cl)nc2=O)COC1] | 465 | 1.81 | [3] |

TABLE 21-continued

| | | | | |
|---|---|---|---|---|
| II-030 | [structure] | 379 | 1.77 | [3] |

TABLE 22

| | | | | |
|---|---|---|---|---|
| II-031 | [structure] | 383 | 1.79 | [3] |
| II-032 | [structure] | 344 | 1.26 | [3] |
| II-033 | [structure] | 463 | 2.05 | [3] |
| II-034 | [structure] | 437 | 1.73 | [3] |
| II-035 | [structure] | 431 | 2.00 | [3] |

TABLE 23

| | | | | |
|---|---|---|---|---|
| II-036 | [structure] | 433 | 2.07 | [3] |
| II-037 | [structure] | 390 | 1.89 | [3] |
| II-038 | [structure] | 408 | 1.65 | [3] |
| II-039 | [structure] | 409 | 1.80 | [3] |

TABLE 23-continued
| | | | | | |
|---|---|---|---|---|---|
| II-0-40 | 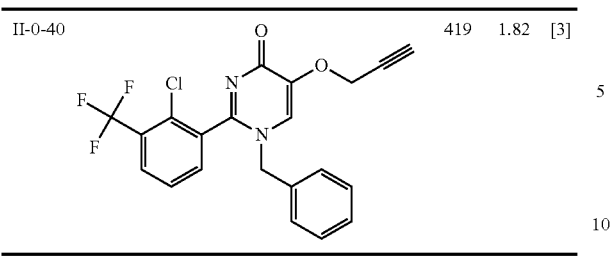 | 419 | 1.82 | [3] | |
TABLE 24
| | | | | | |
|---|---|---|---|---|---|
| II-041 | 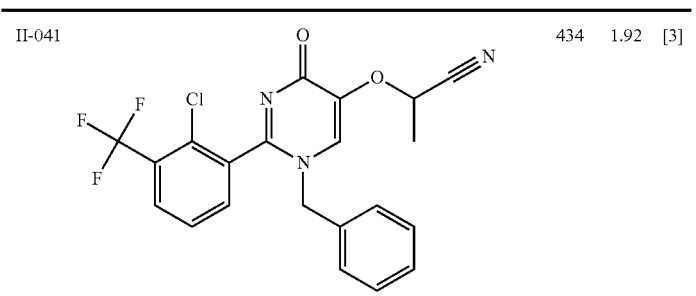 | 434 | 1.92 | [3] | |
| II-042 | 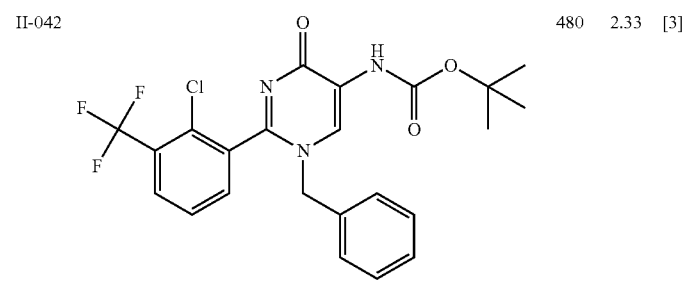 | 480 | 2.33 | [3] | |
| II-043 | 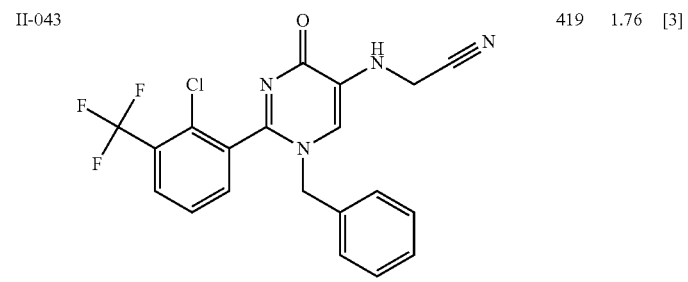 | 419 | 1.76 | [3] | |
| II-044 | 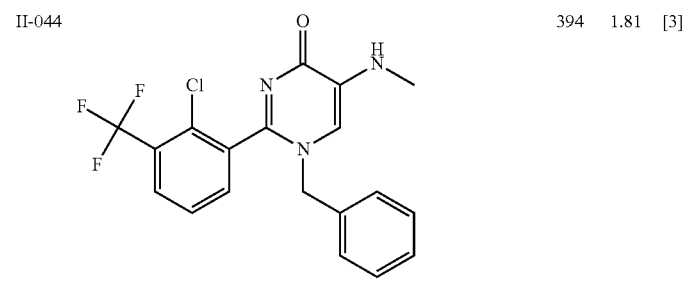 | 394 | 1.81 | [3] | |

TABLE 24-continued
| | | | | |
|---|---|---|---|---|
| II-045 | 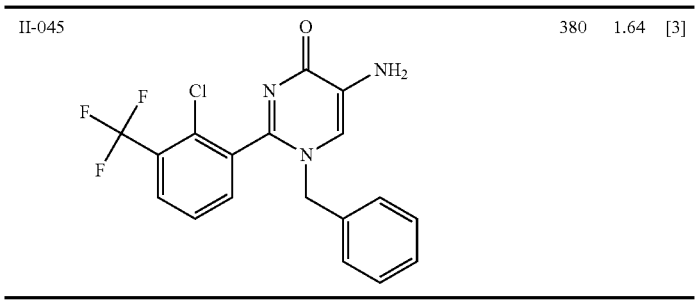 | 380 | 1.64 | [3] |
TABLE 25
| | | | | |
|---|---|---|---|---|
| II-046 | 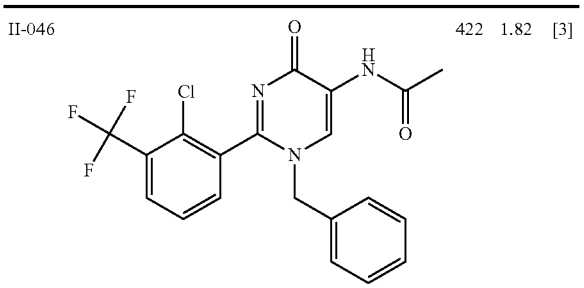 | 422 | 1.82 | [3] |
| II-047 | 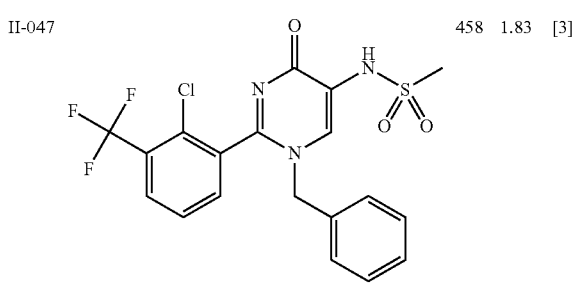 | 458 | 1.83 | [3] |
| II-048 | 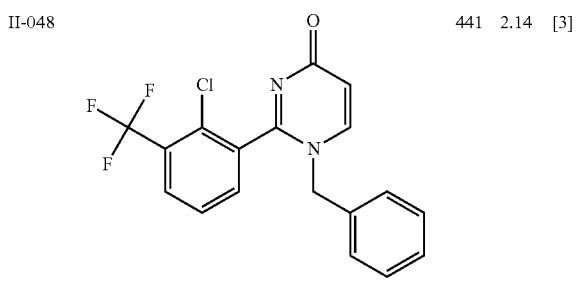 | 441 | 2.14 | [3] |
| II-049 | 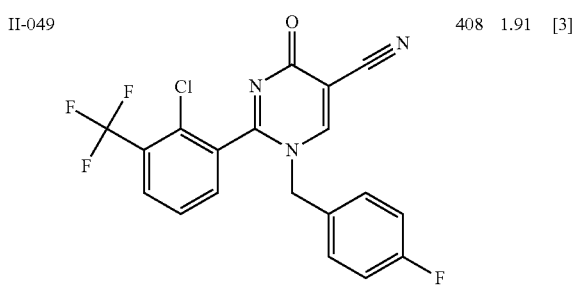 | 408 | 1.91 | [3] |
TABLE 25-continued
| | | | | |
|---|---|---|---|---|
| II-050 | 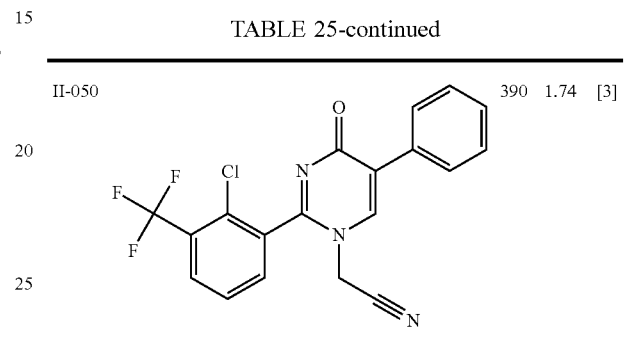 | 390 | 1.74 | [3] |
TABLE 26
| | | | | |
|---|---|---|---|---|
| II-051 | 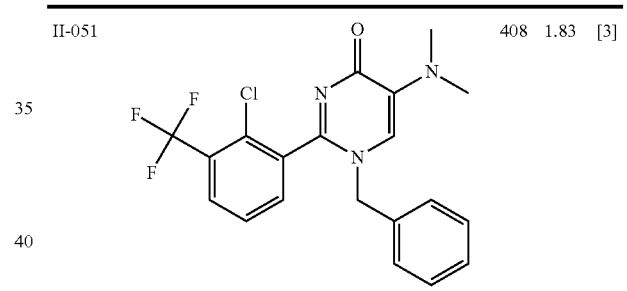 | 408 | 1.83 | [3] |
| II-052 | 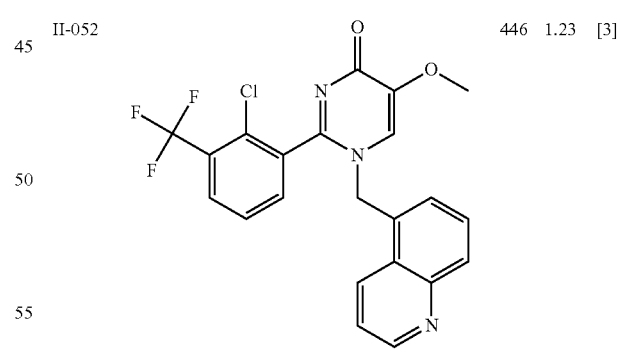 | 446 | 1.23 | [3] |
| II-053 | 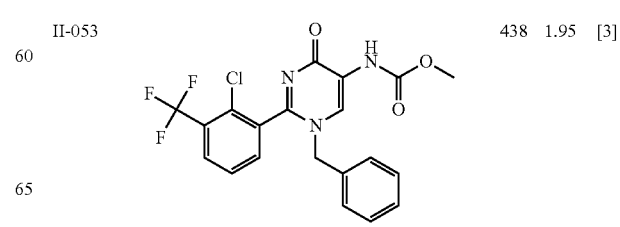 | 438 | 1.95 | [3] |

TABLE 26-continued

| ID | Structure | MW | RT | [M] |
|---|---|---|---|---|
| II-054 | 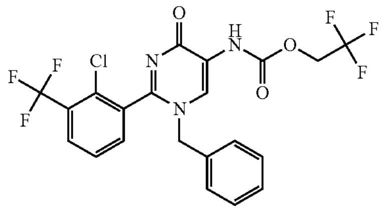 [SMILES: O=C(Nc1cn(Cc2ccccc2)c(-c2cccc(C(F)(F)F)c2Cl)nc1=O)OCC(F)(F)F] | 506 | 2.19 | [3] |
| II-055 | 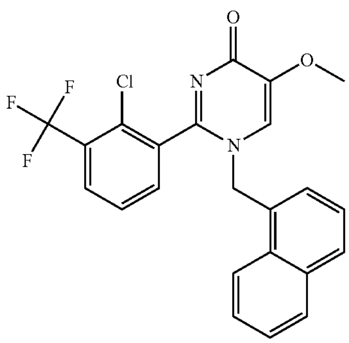 [SMILES: COc1cn(Cc2cccc3ccccc23)c(-c2cccc(C(F)(F)F)c2Cl)nc1=O] | 445 | 1.91 | [3] |

TABLE 27

| ID | Structure | MW | RT | [M] |
|---|---|---|---|---|
| II-056 | 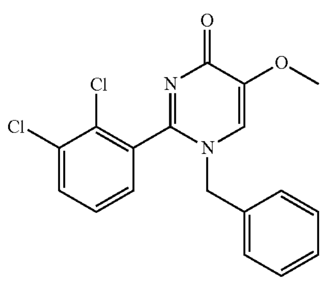 [SMILES: COc1cn(Cc2ccccc2)c(-c2cccc(Cl)c2Cl)nc1=O] | 361 | 1.60 | [3] |
| II-057 | 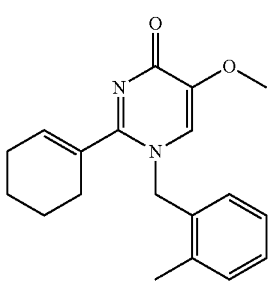 [SMILES: COc1cn(Cc2ccccc2C)c(C2=CCCCC2)nc1=O] | 311 | 1.54 | [1] |
| II-058 | 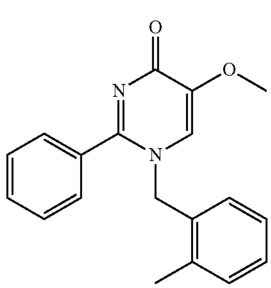 [SMILES: COc1cn(Cc2ccccc2C)c(-c2ccccc2)nc1=O] | 307 | 1.50 | [1] |

TABLE 27-continued

| ID | Structure | MW | RT | [M] |
|---|---|---|---|---|
| II-059 | 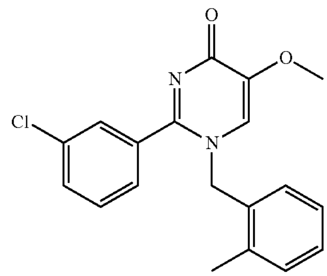 [SMILES: COc1cn(Cc2ccccc2C)c(-c2cccc(Cl)c2)nc1=O] | 341 | 1.69 | [1] |
| II-060 | 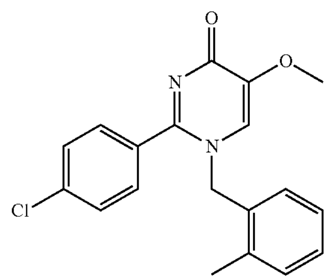 [SMILES: COc1cn(Cc2ccccc2C)c(-c2ccc(Cl)cc2)nc1=O] | 341 | 1.72 | [1] |

TABLE 28

| ID | Structure | MW | RT | [M] |
|---|---|---|---|---|
| II-061 | 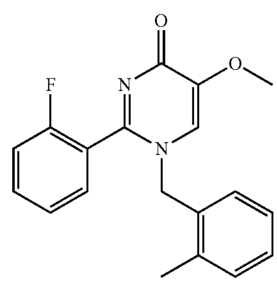 [SMILES: COc1cn(Cc2ccccc2C)c(-c2ccccc2F)nc1=O] | 325 | 1.51 | [1] |
| II-062 | 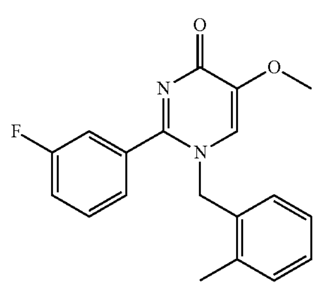 [SMILES: COc1cn(Cc2ccccc2C)c(-c2cccc(F)c2)nc1=O] | 325 | 1.56 | [1] |
| II-063 | 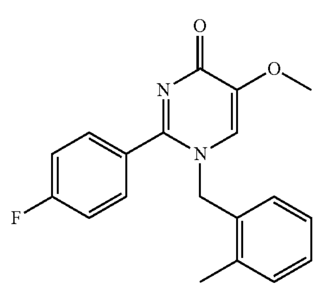 [SMILES: COc1cn(Cc2ccccc2C)c(-c2ccc(F)cc2)nc1=O] | 325 | 1.56 | [1] |

TABLE 28-continued
| | | | | |
|---|---|---|---|---|
| II-064 | 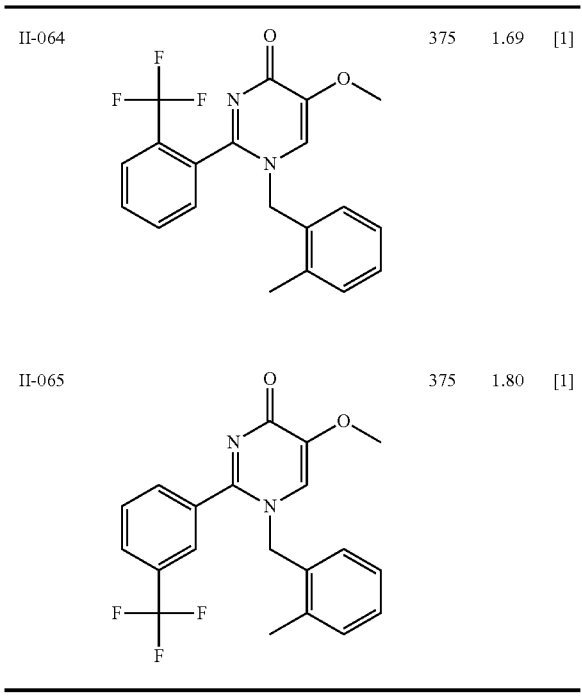 | 375 | 1.69 | [1] |
| II-065 | | 375 | 1.80 | [1] |
TABLE 29
| | | | | |
|---|---|---|---|---|
| II-066 | 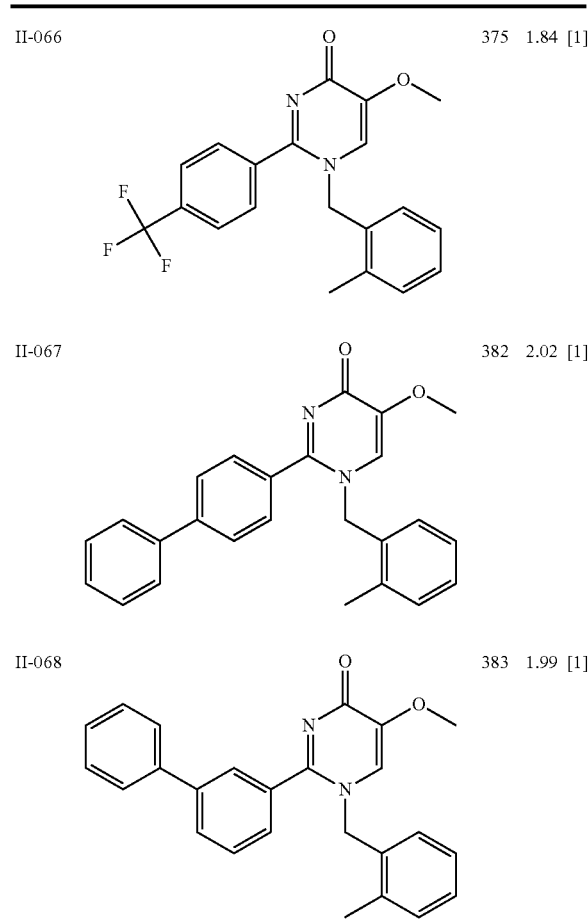 | 375 | 1.84 | [1] |
| II-067 | | 382 | 2.02 | [1] |
| II-068 | | 383 | 1.99 | [1] |
TABLE 29-continued
| | | | | |
|---|---|---|---|---|
| II-069 | 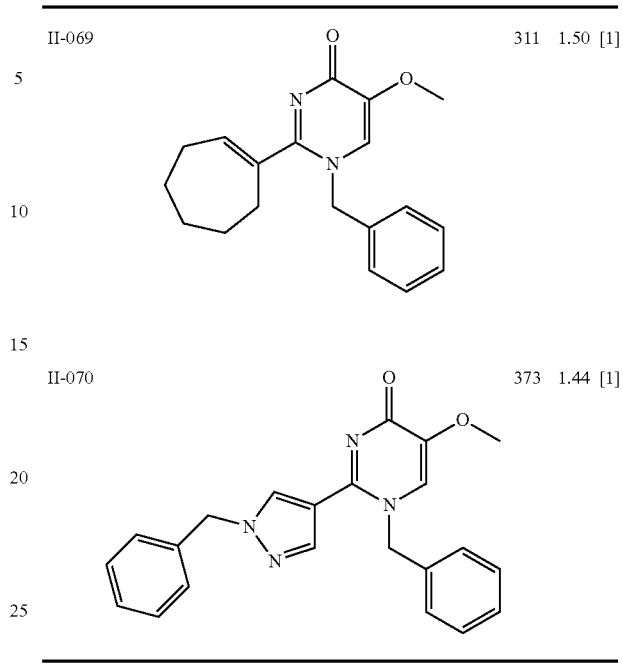 | 311 | 1.50 | [1] |
| II-070 | | 373 | 1.44 | [1] |
TABLE 30
| | | | | |
|---|---|---|---|---|
| II-071 | 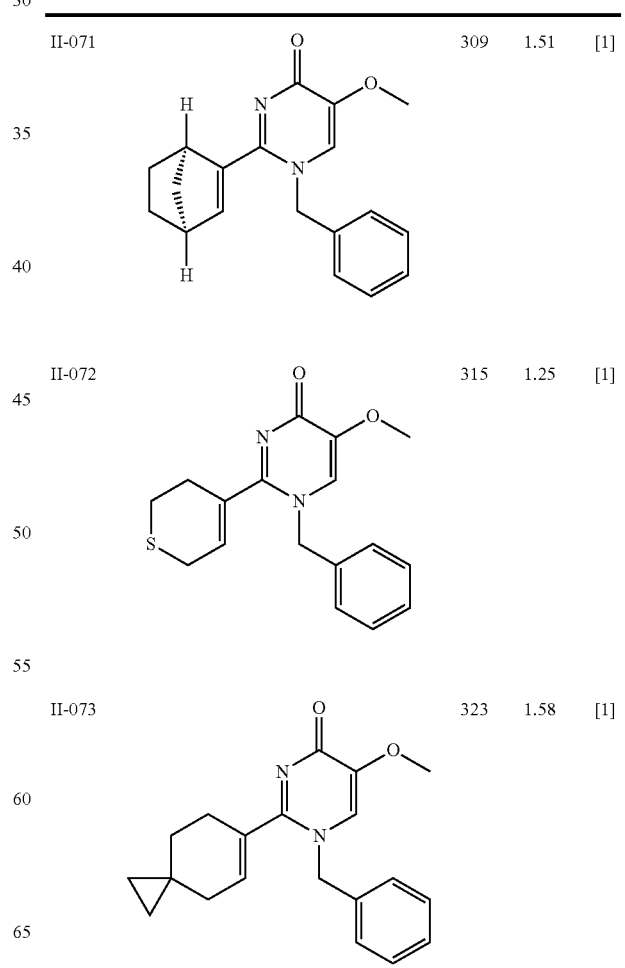 | 309 | 1.51 | [1] |
| II-072 | | 315 | 1.25 | [1] |
| II-073 | | 323 | 1.58 | [1] |

TABLE 30-continued
| II-074 | 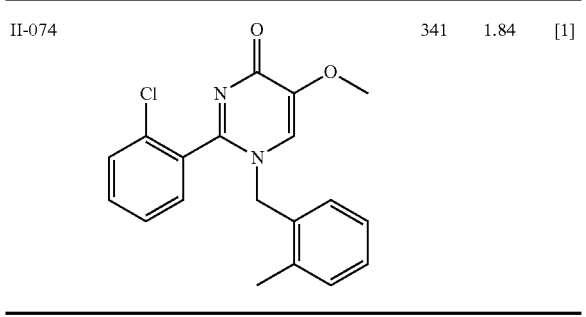 | 341 | 1.84 | [1] |
TABLE 31
| II-075 | 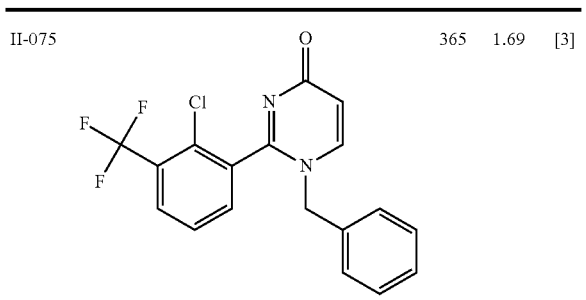 | 365 | 1.69 | [3] |
| II-076 | 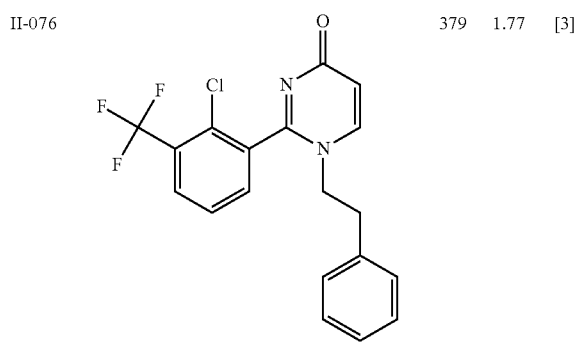 | 379 | 1.77 | [3] |
| II-077 | 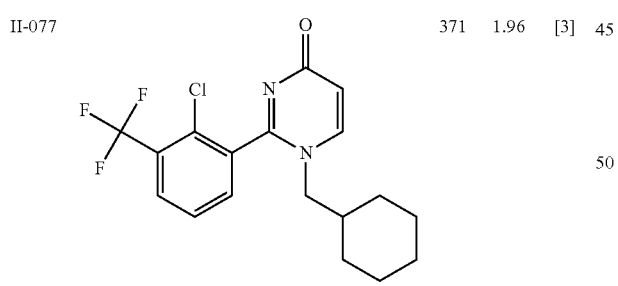 | 371 | 1.96 | [3] |
| II-078 | 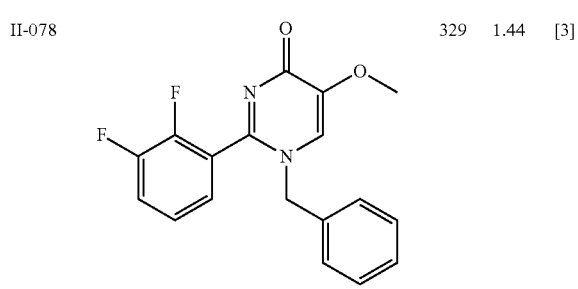 | 329 | 1.44 | [3] |
TABLE 31-continued
| II-079 | 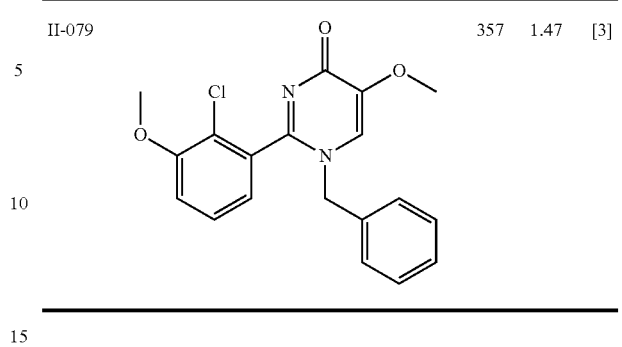 | 357 | 1.47 | [3] |
TABLE 32
| II-080 | 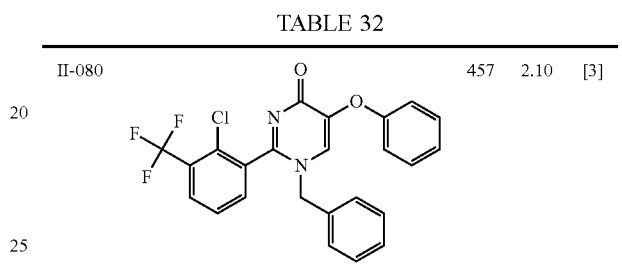 | 457 | 2.10 | [3] |
| II-081 | 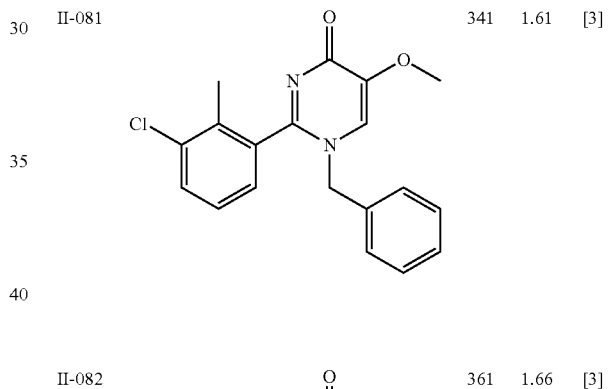 | 341 | 1.61 | [3] |
| II-082 | 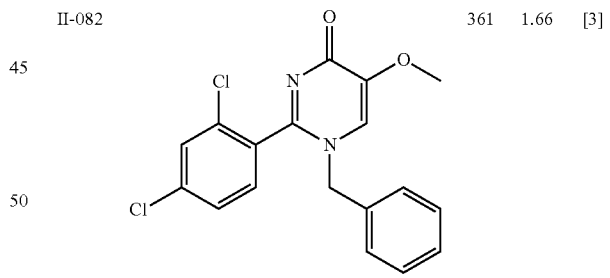 | 361 | 1.66 | [3] |
| II-083 | 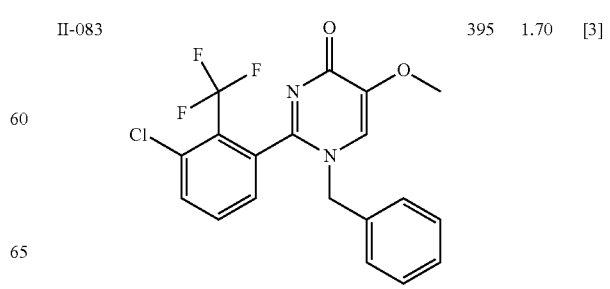 | 395 | 1.70 | [3] |

TABLE 32-continued
| II-084 | 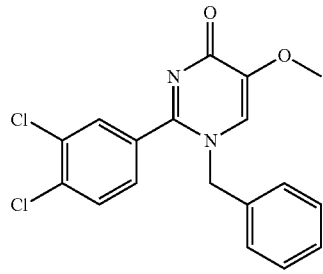 [SMILES: COc1cn(Cc2ccccc2)c(-c2ccc(Cl)c(Cl)c2)nc1=O] | 361 | 1.73 | [3] |
TABLE 33
| II-085 | 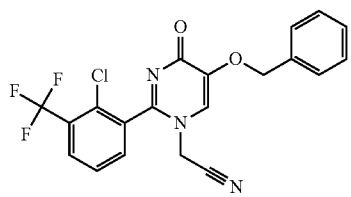 [SMILES: N#CCn1cc(OCc2ccccc2)c(=O)nc1-c1cccc(C(F)(F)F)c1Cl] | 420 | 1.75 | [3] |
TABLE 34
| II-086 | 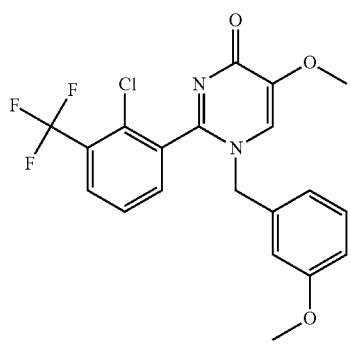 [SMILES: COc1cccc(Cn2cc(OC)c(=O)nc2-c2cccc(C(F)(F)F)c2Cl)c1] | 425 | 1.69 | [3] |
| II-087 | 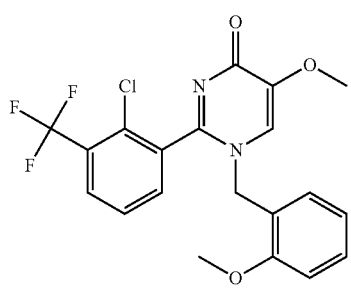 [SMILES: COc1ccccc1Cn1cc(OC)c(=O)nc1-c1cccc(C(F)(F)F)c1Cl] | 425 | 1.74 | [3] |
| II-088 | 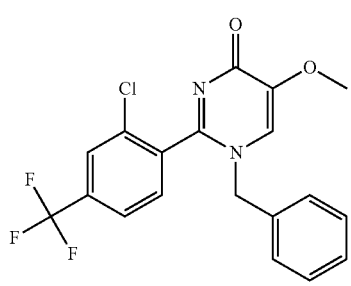 [SMILES: COc1cn(Cc2ccccc2)c(-c2ccc(C(F)(F)F)cc2Cl)nc1=O] | 395 | 1.74 | [3] |
TABLE 34-continued
| II-089 | 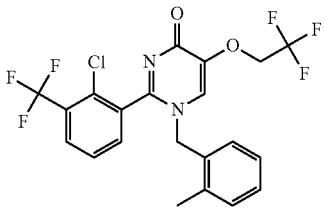 [SMILES: Cc1ccccc1Cn1cc(OCC(F)(F)F)c(=O)nc1-c1cccc(C(F)(F)F)c1Cl] | 477 | 2.14 | [3] |
TABLE 35
| II-090 | 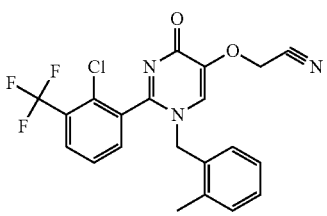 [SMILES: Cc1ccccc1Cn1cc(OCC#N)c(=O)nc1-c1cccc(C(F)(F)F)c1Cl] | 434 | 1.91 | [3] |
| II-091 | 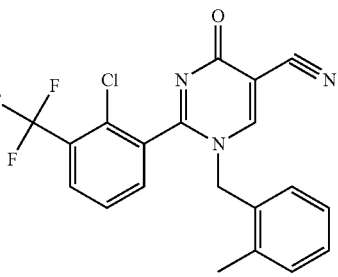 | 404 | 1.99 | [3] |
| II-092 | 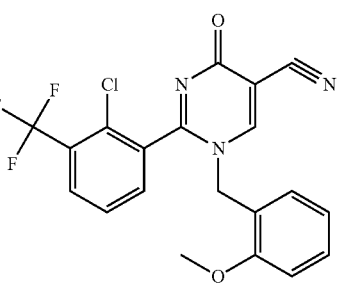 | 420 | 1.94 | [3] |
| II-093 | 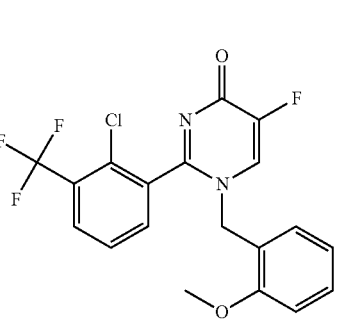 | 413 | 1.87 | [3] |

TABLE 35-continued
| ID | Structure | | | |
|---|---|---|---|---|
| II-094 | 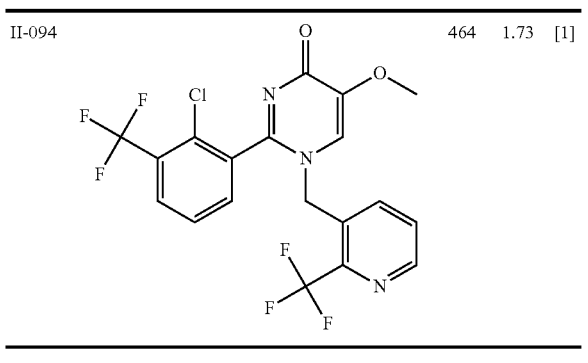 | 464 | 1.73 | [1] |
TABLE 36
| ID | Structure | | | |
|---|---|---|---|---|
| II-095 | 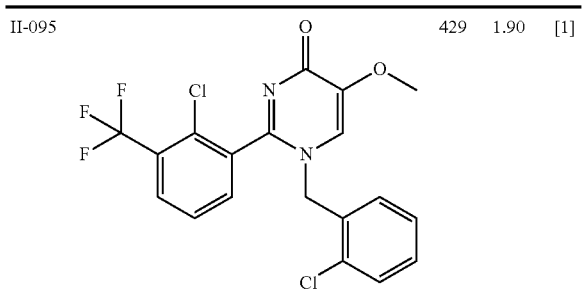 | 429 | 1.90 | [1] |
| II-096 | 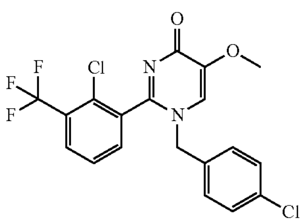 [SMILES: COc1cn(Cc2ccc(Cl)cc2)c(-c2cccc(C(F)(F)F)c2Cl)nc1=O] | 429 | 1.94 | [1] |
| II-097 | 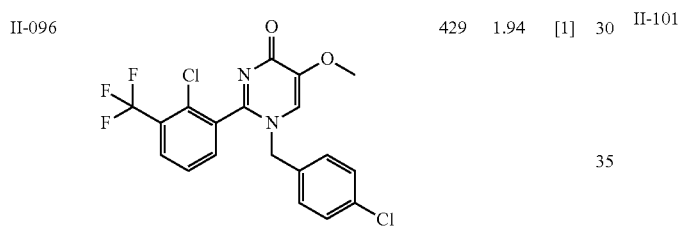 | 479 | 2.02 | [1] |
| II-098 | 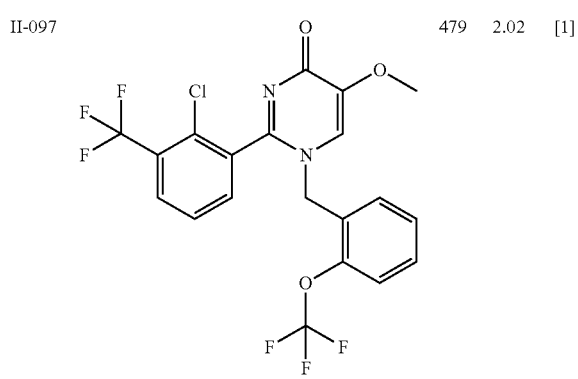 | 495 | 2.14 | [1] |
TABLE 36-continued
| ID | Structure | | | |
|---|---|---|---|---|
| II-099 | 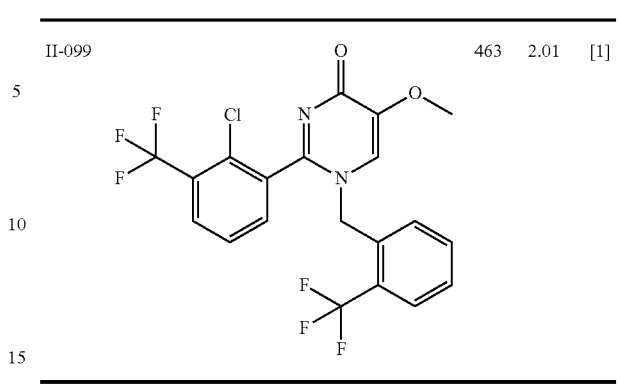 | 463 | 2.01 | [1] |
TABLE 37
| ID | Structure | | | |
|---|---|---|---|---|
| II-100 | 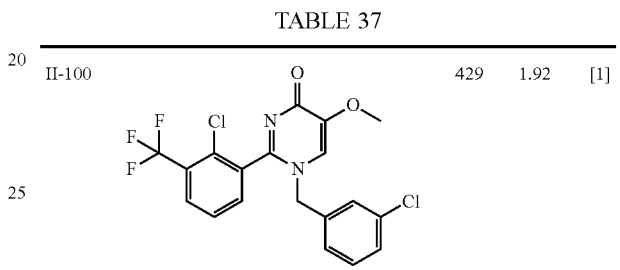 | 429 | 1.92 | [1] |
| II-101 | 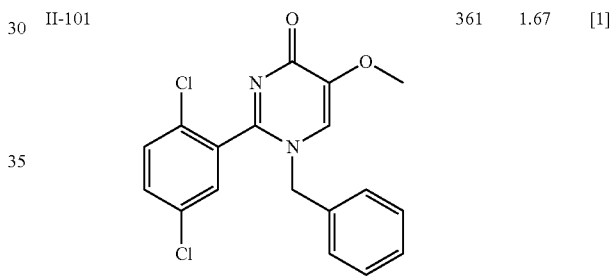 | 361 | 1.67 | [1] |
| II-102 | 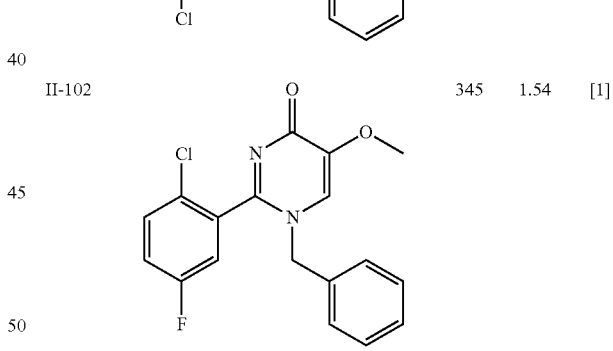 | 345 | 1.54 | [1] |
TABLE 38
| ID | Structure | | | |
|---|---|---|---|---|
| III-001 | 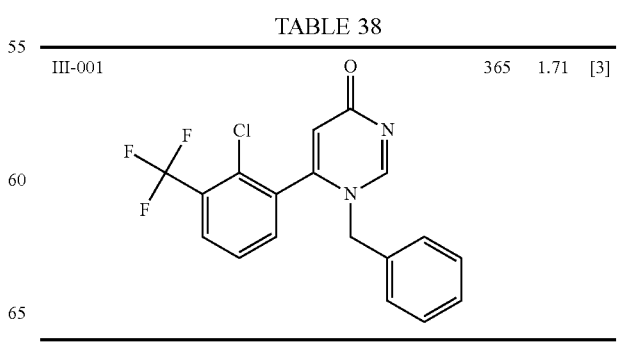 | 365 | 1.71 | [3] |

| III-002 | ![structure] | 365 | 1.97 | [3] |

Biological test examples for the compounds of the present invention are described below.

Test Example 1 Evaluation of a Human P2X7 Receptor Inhibitory Activity

Stably expressing cell line (1321N1 cell transfected with the human P2X7 receptor gene (GenBank accession number NM_002562.5 including T606C and G952A SNP)) was used. The cells were seeded in a 384-well microtiter plate at a concentration of 8000 cells/well and cultured in the medium (10% fetal bovine serum, 25 mM HEPES, 1% penicillin and streptomycin in DMEM) for one day at 37° C. under 5% carbon dioxide atmosphere. After replacing with 20 μL of the HBSS buffer (20 mM HEPES. 55.6 mM D-glucose, 1×HBSS(−), pH 7.4-7.5), 15 μL of 17.3 μM Yo-Pro solution in the HBSS buffer was added. The plate was placed in high-throughput cellular screening system FLIPR TETRA (Molecullar Devices, LLC.) and 15 μL of 130 μM BzATP solution in the HBSS buffer was added. Measurement of fluorescence intensity by FLIPR TETRA was started. After eight minutes, 15 μL of DMSO solutions containing different concentrations of the compound of the present invention as prepared by dilution with the HBSS buffer were dispensed to each well through the built-in automatic dispenser, and the measurement of fluorescence intensity was continued for 20 minutes. The maximum fluorescence intensity without the compound of the present invention is calculated as 0% inhibition and the maximum fluorescence intensity when the reference compound was added is calculated as 100% inhibition. Changing values of fluorescence intensity by the compound of the present invention were calculated by difference between maximum and minimum fluorescence intensity for 20 minutes. Inhibition ratios (%) were calculated from the following equation:

Inhibition ratio:

$$\left[1 - \frac{\text{changing values by a compound of the present invention} - \text{changing values by reference compound}}{\text{changing values without a compound of the present invention} - \text{changing values by reference compound}}\right] \times 100(\%)$$

$IC_{50}$ was calculated using logistic approximation.

The antagonistic activity for the human P2X7 receptor of the compounds of the present invention is shown in the following table.

TABLE 40

| No. | IC50 (uM) |
|---|---|
| I-001 | 0.067 |
| I-015 | 0.044 |
| I-020 | 0.810 |
| I-048 | 0.110 |
| II-008 | 0.041 |
| II-030 | 0.210 |
| II-031 | 0.058 |
| II-032 | 1.000 |
| II-033 | 0.060 |
| II-045 | 0.270 |
| II-046 | 0.180 |
| II-053 | 0.071 |
| II-055 | 0.020 |
| II-056 | 0.130 |
| II-073 | 0.630 |
| II-077 | 0.610 |
| II-082 | 0.190 |
| III-001 | 0.110 |
| III-002 | 0.110 |

The antagonistic activity for the human P2X7 receptor of the other compounds of the present invention is shown in the following table. As for $IC_{50}$ value, value from 0 nmol/L to below 50 nmol/L is represented as "A", value from 50 nmol/L to below 100 nmol/L is represented as "B", value from 100 nmol/L to below 500 nmol/L is represented as "C", value from 500 nmol/L to below 1 μmol/L is represented as "D", and value from 1 μmol/L to below 10 μmol/L is represented as "E".

TABLE 41

| No. | IC50 |
|---|---|
| I-002 | A |
| I-003 | C |
| I-004 | D |
| I-005 | D |
| I-006 | D |
| I-007 | C |
| I-008 | C |
| I-009 | C |
| I-010 | C |
| I-011 | C |
| I-012 | D |
| I-013 | C |
| I-014 | C |
| I-016 | C |
| I-017 | D |
| I-018 | B |
| I-019 | C |
| I-021 | D |
| I-022 | C |
| I-023 | D |
| I-024 | D |
| I-025 | E |
| I-026 | E |
| I-027 | D |
| I-028 | C |
| I-029 | E |
| I-030 | D |
| I-031 | E |
| I-032 | D |
| I-033 | C |
| I-034 | D |
| I-035 | C |
| I-036 | D |
| I-037 | C |
| I-038 | E |
| I-039 | E |
| I-040 | E |
| I-041 | E |
| I-042 | E |
| I-043 | E |
| I-044 | D |

TABLE 41-continued

| No. | IC50 |
|---|---|
| I-045 | E |
| I-046 | C |
| I-047 | E |
| I-049 | C |
| I-050 | E |
| I-051 | D |
| I-052 | E |
| I-053 | D |
| I-054 | C |
| I-055 | C |
| I-056 | E |
| I-057 | C |
| I-058 | D |
| I-059 | C |
| I-060 | E |
| I-061 | E |
| I-062 | D |
| I-063 | E |
| I-064 | E |
| I-065 | E |
| I-066 | E |
| I-067 | D |
| I-068 | E |
| I-069 | D |
| I-070 | E |
| I-071 | C |
| I-072 | A |
| I-073 | A |
| II-001 | A |
| II-002 | E |
| II-003 | A |
| II-004 | C |
| II-005 | B |
| II-006 | B |
| II-007 | B |
| II-009 | C |
| II-010 | A |
| II-011 | A |
| II-012 | C |
| II-013 | C |
| II-014 | E |
| II-015 | A |
| II-016 | D |
| II-017 | C |
| II-018 | C |
| II-019 | B |
| II-020 | E |
| II-021 | B |
| II-022 | A |
| II-023 | A |
| II-024 | B |
| II-025 | B |
| II-026 | B |
| II-027 | D |
| II-028 | D |
| II-029 | C |
| II-034 | B |
| II-035 | C |
| II-036 | C |
| II-037 | A |
| II-038 | D |
| II-039 | B |
| II-040 | A |
| II-041 | A |
| II-042 | B |
| II-043 | B |
| II-044 | C |
| II-047 | C |
| II-048 | C |
| II-049 | B |
| II-050 | C |
| II-051 | C |
| II-052 | A |
| II-054 | C |
| II-057 | E |
| II-058 | E |
| II-059 | E |
| II-060 | E |
| II-061 | E |
| II-062 | E |
| II-063 | E |
| II-064 | D |
| II-065 | C |
| II-066 | E |
| II-067 | E |
| II-068 | E |
| II-069 | E |
| II-070 | E |
| II-071 | E |
| II-072 | E |
| II-074 | D |
| II-075 | C |
| II-076 | E |
| II-078 | D |
| II-079 | E |
| II-080 | B |
| II-081 | D |
| II-083 | B |
| II-084 | C |
| II-085 | A |
| II-086 | A |
| II-087 | A |
| II-088 | D |
| II-089 | A |
| II-090 | A |
| II-091 | A |
| II-092 | A |
| II-093 | A |
| II-094 | C |
| II-095 | A |
| II-096 | C |
| II-097 | A |
| II-098 | C |
| II-099 | A |
| II-100 | B |
| II-101 | E |

Test Example 2 Evaluation of the Rat P2X7 Receptor Inhibitory Activity

Stably expressing cell line (1321N1 cell transfected with the rat P2X7 receptor gene (GenBank accession number NM_019256.1 including C586T and C652A SNP)) is used. The cells are seeded in a 384-well microtiter plate at a concentration of 10000 cells/well and cultured in the medium (10% fetal bovine serum, 2 mM ClutaMax-1, 1% penicillin and streptomycin in DMEM) for one day at 37° C. under 5% carbon dioxide atmosphere. After replacing with 20 µL of the HBSS buffer (20 mM HEPES, 55.6 mM D-glucose, 1×HBSS(+), pH 7.4), 15 µL of 17.3 µM Yo-Pro solution in the HBSS buffer is added. The plate is placed in high-throughput cellular screening system FLIPR TETRA (Molecullar Devices, LLC.) and 15 µL of 1083 µM BzATP solution in the HBSS buffer is added. Measurement of fluorescence intensity by FLIPR TETRA is started. Eight minutes after, 15 µL of DMSO solutions containing different concentrations of the compound of the present invention as prepared by dilution with the HBSS buffer are dispensed to each well through the built-in automatic dispenser, and the measurement of fluorescence intensity is continued for 20 minutes. The maximum fluorescence intensity without the compound of the present invention is calculated as 0% inhibition and the maximum fluorescence intensity when the reference compound is added is calculated as 100% inhibition. Changing values of fluorescence intensity by the compound of the present invention are calculated by difference between maximum and minimum fluorescence intensity for 20 minutes. Inhibition ratios (%) are calculated from the following equation:

Inhibition ratio:

$$\left[1 - \frac{\text{changing values by a compound of the present invention} - \text{changing values by reference compound}}{\text{changing values without a compound of the present invention} - \text{changing values by reference compound}}\right] \times 100(\%)$$

$IC_{50}$ is calculated using logistic approximation.

Test Example 3: Analgesic Effect in a Seltzer Model

Preparation of Partial Sciatic Nerve Ligation Model in Rats

Rats are anaesthetized using isoflurane/O2 inhalation anaesthesia. After induction of anesthesia, the left thigh is shaved. An incision is made in the skin just below the hip bone. The muscle is bluntly dissected to expose the sciatic nerve. About one half (½) of the sciatic nerve thickness is tightly ligated with a nylon thread and the wound is closed. The right thigh is used as a sham-operated control. The right thigh undergoes an identical procedure with the left hind limb, however, the sciatic nerve is not manipulated or ligated.

Evaluation (1)

Two weeks after nerve ligation, the effect on mechanical allodynia is assessed using a series of von Frey filaments. For habituation, the rats are placed into a plastic cage on a wire mesh bottom. The mechanical sensitivity (mechanical threshold) of the hind paws is estimated with a series of von Frey filaments (0.4-26 g). The measurement of mechanical sensitivity of the right and left hind paws is performed to obtain predose mechanical sensitivity. The rats showing the threshold change from 0.6 to 2 g (in nerve ligated side) and 8 to 15 g (in sham operated side) are used in the experiments. On the day before the experiment, the rats are evaluated with a series of von Frey filaments to familiarize them with the test procedure. The adopted animal is administrated with the compounds of the present invention. The compounds of the present invention are homogenized with mortar and pestle and suspended or diluted in 0.5% Methyl Cellulose to prepare 0.03-100 mg/2 mL/kg suspension and orally administered to rat using a syringe attached with a sonde. Post-dose mechanical sensitivities of the right and left hind paws are measured at approximately 1 to 5 hours after drug administration. Percent reversal of mechanical allodynia for each rat is calculated using the following formula. The analgesic effects of the compounds are compared.

$$\% \text{ Reversal} = 100 \times \frac{\text{Log}_{10}(\text{Postdose mechanical sensitivity in nerve ligated side}) - \text{Log}_{10}(\text{Predose mechanical sensitivity in nerve ligated side})}{\text{Log}_{10}(\text{Predose mechanical sensitivity in sham operated side}) - \text{Log}_{10}(\text{Predose mechanical sensitivity in nerve ligated side})}$$

Evaluation (2)

Mechanical hyperalgesia is evaluated using an analgesy meter (Randall Selitto). Two weeks after nerve ligation, the paw pressure test is performed using an analgesy meter (stimulus pressure increased 16 g per second) to obtain paw withdrawal thresholds (PWT). Measurements are made on both sides of the hind paw and to obtain pre-dose PWT. The rats showing the threshold change from 60 to 90 g (in nerve ligated side) and 100 to 175 g (in sham operated side) are used in the experiments. On the day before the experiment, the rats have their hind paws set on the apparatus to familiarize them with the test procedure. The adopted animal is administrated with the compound of the present invention. The compound of the present invention are homogenized with mortar and pestle and suspended or diluted in 0.5% Methyl Cellulose to prepare 0.03-100 mg/2 mL/kg suspension and orally administered to rat using a syringe attached with a sonde. Post-dose PWT of the right and left hind paws are measured at approximately 1 to 5 hours after drug administration. Percent reversal of mechanical hyperalgesia for each rat is calculated using the following formula. The analgesic effects of the compounds are compared.

$$\% \text{ Reversal} = 100 \times \frac{\text{Postdose } PWT \text{ in nerve ligated side} - \text{Predose } PWT \text{ in nerve ligated side}}{\text{Predose } PWT \text{ in sham operated side} - \text{Predose } PWT \text{ in nerve ligated side}}$$

The antagonistic activity for the P2X7 receptor of the compounds of the present invention can be also evaluated by using the method described in British Journal of Pharmacology (2013) 170 624-640.

Test Example 4: CYP Inhibition Test

Using commercially available pooled human hepatic microsome, and employing, as markers, 7-ethoxyresorufin O-deethylation (CYP1A2), tolbutamide methyl-hydroxylation (CYP2C9), mephenytoin 4'-hydroxylation (CYP2C19), dextromethorphan O-demethylation (CYP2DG), and terfenedine hydroxylation as typical substrate metabolism reactions of human main five CYP enzyme forms (CYP1A2, 2C9, 2C19, 2D6, 3A4), an inhibitory degree of each metabolite production amount by the compound of the present invention is assessed.

The reaction conditions are as follows: substrate, 0.5 mol/L ethoxyresorufin (CYP1A2), 100 μmol/L tolbutamide (CYP2C9), 50 μmol/L S-mephenitoin (CYP2C19), 5 μmol/L dextromethorphan (CYP2D6), 1 μmol/L terfenedine (CYP3A4); reaction time, 15 minutes; reaction temperature, 37° C.; enzyme, pooled human hepatic microsome 0.2 mg protein/mL; concentration of the compound of the present invention, 1.0, 5.0, 10, 20 μmol/L (four points).

Each five kinds of substrates, human hepatic microsome, or the compound of the present invention in 50 mmol/l Hepes buffer as a reaction solution is added to a 96-well plate at the composition as described above. NADPH, as a cofactor is added to initiate metabolism reactions as markers and, after the incubation at 37'C for 15 minutes, a methanol/acetonitrile=1/1 (V/V) solution is added to stop the reaction. After the centrifugation at 3000 rpm for 15 minutes, resorufin (CYP1A2 metabolite) in the supernatant is quantified by a fluorescent multilabel counter or LC/MS/MS and tributamide hydroxide (CYP2CP metabolite), mephenytoin 4' hydroxide (CYP2C19 metabolite), dextromethorphan (CYP2D6 metabolite), and terfenadine alcohol (CYP3A4 metabolite) are quantified by LC/MS/MS.

Addition of only DMSO being a solvent dissolving a drug to a reaction system is adopted as a control (100%), remaining activity (%) is calculated and $IC_{50}$ is calculated by reverse presumption by a logistic model using a concentration and an inhibition rate.

Test Example 5-1: CYP3A4 Fluorescent MBI Test

The CYP3A4 fluorescent MBI test is a test of investigating enhancement of CYP3A4 inhibition of the compound of the present invention by a metabolism reaction. The test is performed using, as an index, a reaction in which 7-benzyloxytrifluoromethylcoumarin (7-BFC) is debenzylated by CYP3A4 enzyme expressed in *Escherichia coli* and employing to produce a metabolite, 7-hydroxy trifluoromethylcoumarin (HFC) emitting fluorescent light.

The reaction conditions are as follows: substrate, 5.6 µmol/L 7-BFC; pre-reaction time, 0 or 30 minutes; reaction time, 15 minutes; reaction temperature, 25° C. (room temperature); CYP3A4 content (expressed in *Escherichia coli*), at pre-reaction 62.5 pmol/mL, at reaction 6.25 pmol/mL (at 10-fold dilution); concentration of the compound of the present invention, 0.625, 1.25, 2.5, 5, 10, 20 µmol/L (six points).

An enzyme in K-Pi buffer (pH 7.4) and a solution of the compound of the present invention as a pre-reaction solution as a pre-reaction solution are added to a 96-well plate at the above composition of the pre-reaction. A part of pre-reaction solution is transferred to another 96-well plate so that it is 1/10 diluted with a substrate and K-Pi buffer. NADPH as a co-factor is added in order to initiate a reaction as an index (without preincubation). After a predetermined time of a reaction, acetonitrile/0.5 mol/L Tris (trishydroxyaminomethane)=4/1 (V/V) is added to stop the reaction. On the other hand, NADPH is also added to a remaining preincubation solution in order to initiate a preincubation (with preincubation). After a predetermined time of a preincubation, a part is transferred to another plate so that it is 1/10 diluted with a substrate and K-Pi buffer to initiate a reaction as an index. After a predetermined time of a reaction, acetonitrile/0.5 mol/L Tris (trishydroxyaminomethane)=4/1 (V/V) is added in order to stop the reaction. For the plate on which each index reaction had been performed, a fluorescent value of 7-HFC which is a metabolite is measured with a fluorescent plate reader. (Ex=420 nm, Em=535 nm).

Addition of only DMSO which is a solvent dissolving the compound of the present invention to a reaction system is adopted as a control (100%), remaining activity (%) is calculated at each concentration of the compound of the present invention added as the solution. $IC_{50}$ is calculated by reverse-presumption by a logistic model using a concentration and an inhibition rate. When a difference between $IC_{50}$ values is 5 µmol/L or more, this is defined as (+). When the difference is 3 µmol/L or less, this is defined as (−).

Test Example 5-2: CYP3A4(MDZ) MBI Test

CYP3A4(MDZ) MBI test is a test of investigating mechanism based inhibition (MBI) ability on CYP3A4 inhibition of a compound by enhancement of a metabolism reaction. CYP3A4 inhibition is evaluated using 1-hydroxylation reaction of midazolam (MDZ) by pooled human liver microsomes as an index.

The reaction conditions are as follows: substrate, 10 µmol/L MDZ; pre-reaction time, 0 or 30 minutes; substrate reaction time, 2 minutes; reaction temperature, 37° C.; protein content of pooled human liver microsomes, at pre-reaction time 0.5 mg/mL, at reaction time 0.05 pmg/mL (at 10-fold dilution); concentrations of the compound of the present invention, 1, 5, 10, 20 µmol/L (four points).

Pooled human liver microsomes in K-Pi buffer (pH 7.4) and a solution of the compound of the present invention as a pre-reaction solution are added to a 96-well plate at the composition of the pre-reaction. A part of pre-reaction solution is transferred to another 96-well plate, and 1/10 diluted by a substrate in K-Pi buffer. NADPH as a co-factor is added in order to initiate a reaction as an index (without preincubation). After a predetermined time of a reaction, methanol/acetonitrile=1/1 (V/V) solution is added in order to stop the reaction. On the other hand, NADPH is also added to a remaining pre-reaction solution in order to initiate a preincubation (with preincubation). After a predetermined time of a preincubation, a part is transferred to another 96-well plate, and 1/10 diluted by a substrate in K-Pi buffer in order to initiate a reaction as an index. After a predetermined time of a reaction, methanol/acetonitrile=1/1 (V/V) solution is added in order to stop the reaction. After centrifuged at 3000 rpm for 15 minutes, 1-hydroxymidazolam in the supernatant is quantified by LC/MS/MS.

The sample adding DMSO to a reaction system instead of a solution of the compound of the present invention is adopted as a control (100%) because DMSO is used as a solvent to dissolve the compound of the present invention. Remaining activity (%) is calculated at each concentration of the compound of the present invention added as the solution, and IC value is calculated by reverse-presumption by a logistic model using a concentration and an inhibition rate. Shifted IC value is calculated as "IC of preincubation at 0 min/IC of preincubation at 30 min". When a shifted IC is 1.5 or more, this is defined as positive. When a shifted IC is 1.0 or less, this is defined as negative.

Test Example 6: BA Test

Materials and Methods for Experiments to Evaluate Oral Absorption
(1) Animals: The mice or rats are used
(2) Breeding conditions: The mice or rats are allowed to freely take solid food and sterilized tap water.
(3) Dose and grouping: orally or intravenously administered at a predetermined dose; grouping is as follows (Dose depends on the compound)
   Oral administration: 1~30 mg/kg (n=2 3)
   Intravenous administration: 0.5~10 mg/kg (n=2~3)
(4) Preparation of dosing solution: for oral administration, in a solution or a suspension state; for intravenous administration, in a solubilized state
(5) Administration method: in oral administration, forcedly administer into ventriculus with oral probe; in intravenous administration, administer from caudal vein with a needle-equipped syringe
(6) Evaluation items: blood is collected over time, and the plasma concentration of drug is measured by LC/MS/MS
(7) Statistical analysis: regarding the transition of the plasma concentration of the compound of the present invention, the area under the plasma concentration-time curve (AUC) is calculated by non-linear least squares program WinNonlin (Registered trade name), and the bioavailability (BA) is calculated from the AUCs of the oral administration group and intravenous administration group.

Test Example 7: Fluctuation Ames Test

Mutagenicity of the compound of the present invention is evaluated.

20 µL of freezing-stored rat typhoid bacillus (*Salmonella typhimurium* TA98 strain, TA100 strain) is inoculated on 10 mL of a liquid nutrient medium (2.5% Oxoid nutrient broth No. 2), and this is cultured before shaking at 37'C for 10 hours. 7.70 mL of a bacterial solution of the TA98 strain is centrifuged (2000×g, 10 minutes) to remove a culturing solution. The bacteria is suspended in 7.70 mL of a Micro F buffer ($K_2HPO_4$: 3.5 g/L, $KH_2PO_4$: 1 g/L, $(NH_4)_2SO_4$: 1 g/L, trisodium citrate dehydrate: 0.25 g/L, $MgSO_4.7H_2O$: 0.1 g/L), the suspension is added to 120 mL of an Exposure medium (Micro F buffer containing Biotin: 8 g/mL, histidine: 0.2 µg/mL, glucose: 8 mg/mL). The TA100 strain is added to 130 mL of the Exposure medium relative to 3.42 mL of the bacterial solution to prepare a test bacterial solution. Each 12 µL of DMSO solution of the compound of the present invention (several stage dilution from maximum dose 50 mg/mL at 2 to 3 fold ratio), DMSO as a negative control, and 50 µg/mL of 4-nitroquinoline-1-oxide DMSO solution for the TA98 strain, 0.25 µg/m, of 2-(2-furyl)-3-(5-nitro-2-furyl)acrylamide DMSO solution for the TA100 strain under the non-metabolism activating condition. 40 µg/mL of 2-aminoanthracene DMSO solution for the TA98 strain, 20 µg/mL of 2-aminoanthracene DMSO solution for the TA100 strain under the metabolism activating condition as a positive control, and 588 µL of the test bacterial solution (a mixed solution of 498 µl of the test bacterial solution and 90 µL of S9 mix under the metabolism activating condition) are mixed, and this is shaking-cultured at 37° C. for 90 minutes. 460 µL of the bacterial solution exposed to the compound of the present invention is mixed with 2300 µL of an Indicator medium (Micro F buffer containing biotin: 8 µg/mL, histidine: 0.2 µg/mL, glucose: 8 mg/mL, Bromo Cresol Purple: 37.5 µg/mL), each 50 µL is dispensed into microplate 48 wells/dose, and this is subjected to stationary culturing at 37° C. for 3 days. Since a well containing a bacterium which has obtained the proliferation ability by mutation of an amino acid (histidine) synthesizing enzyme gene turns from purple to yellow due to a pH change, the bacterium proliferation well which has turned to yellow in 48 wells per dose is counted, and is assessed by comparing with a negative control group. (−) means that mutagenicity is negative and (+) is positive.

Test Example 8: hERG Test

For the purpose of assessing risk of an electrocardiogram QT interval prolongation of the compound of the present invention, effects of the compound of the present invention on delayed rectifier K+ current ($I_{Kr}$), which plays an important role in the ventricular repolarization process, is studied using CHO cells expressing human ether-a-go-go related gene (hERG) channel.

After a cell is retained at a membrane potential of −80 mV by whole cell patch clamp method using an automated patch clamp system (QPatch; Sophion Bioscience A/S) and gave a leak potential of −50 mV, $I_{Kr}$ induced by depolarization pulse stimulation at +20 mV for 2 seconds and, further, repolarization pulse stimulation at −50 mV for 2 seconds, is recorded. After the generated current is stabilized, extracellular solution (NaCl: 145 mmol/L, KCl: 4 mmol/L, $CaCl_2$: 2 mmol/L, $MgCl_2$: 1 mmol/L, glucose: 10 mmol/L, HEPES (4-(2-hydroxyethyl)-1-piperazineethanesulfonic acid): 10 mmol/L, pH=7.4), in which the compound of the present invention had been dissolved at an objective concentration, is applied to the cell at room temperature for 10 minutes. From the recording $I_{Kr}$, an absolute value of the tail peak current is measured based on the current value at the resting membrane potential using analysis software (Falster Patch; Sophion Bioscience A/S). Further, the % inhibition relative to the tail peak current before application of the compound of the present invention is calculated, and compared with the vehicle-applied group (0.1% dimethyl sulfoxide solution) to assess influence of the compound of the present invention on Test Example 9: Solubility Test The solubility of the compound of the present invention is determined under 1% DMSO addition conditions. 10 mmol/L solution of the compound is prepared with DMSO, and 2 µL of the solution of the compound of the present invention is respectively added to 198 µL of JP-1 solution (water is added to 2.0 g of sodium chloride and 7.0 mL of hydrochloric acid to reach 1000 mL) and 198 µL of JP-2 solution (1 volume of water is added to 1 volume of the solution which 3.40 g of potassium dihydrogen phosphate and 3.55 g of anhydrous disodium hydrogen phosphate dissolve in water to reach 1000 mL). The mixture is left standing for 16 hours at 25° C., or shaking at room temperature for 1 hour, and the mixture is vacuum-filtered. The filtrate is two-fold diluted with methanol/water=1/1 (v/v), and the compound concentration in the filtrate is measured with LC/MS or Solid-Phase Extraction (SPE)/MS by the absolute calibration method.

Test Example 10: Metabolism Stability Test

Using commercially available pooled human hepatic microsomes, the compound of the present invention is reacted for a constant time, a remaining rate is calculated by comparing a reacted sample and an unreacted sample, thereby, a degree of metabolism in liver is assessed.

A reaction is performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction. 50 µL of the reaction solution is added to 100 µL of a methanol/acetonitrile=1/1 (v/v), mixed and centrifuged at 3000 rpm for 15 minutes. The compound of the present invention in the supernatant is quantified by LC/MS/MS or Solid-Phase Extraction (SPE)/MS, and a remaining amount of the compound of the present invention after the reaction is calculated, letting a compound amount at 0 minute reaction time to be 100%.

Test Example 11: Powder Solubility Test

Appropriate quantity of the compound of the present invention is put in suitable containers. 200 µL of JP-I solution (water is added to 2.0 g of sodium chloride and 7.0 mL of hydrochloric acid to reach 1000 mL), 200 µL of JP-2 solution (1 volume of water is added to 1 volume of the solution which 3.40 g of potassium dihydrogen phosphate and 3.55 g of anhydrous disodium hydrogen phosphate dissolve in water to reach 1000 mL) or 20 mmol/L sodium taurocholate (TCA)/JP-2 solution (JP-2 solution is added to 1.08 g of TCA to reach 100 mL) is independently added to each container. When total amount is dissolved after adding the test reagent, the compound of the present invention is added appropriately. After sealing and shaking at 37° C. for 1 hour, solution is filtrated and 100 µL of methanol is added to 100 µL of each filtrate to dilute two-fold. The dilution rate is changed as necessary. After checking that there is no bubble and deposit, the container is sealed and shaken. The compound of the present invention is measured using HPLC by absolute calibration curve method.

Formulation Example

The following Formulation Example a are only exemplified and not intended to limit the scope of the invention.

Formulation Example

Formulation Example 1: Tablets

The compounds of the present invention, lactose and calcium stearate are mixed. The mixture is crushed, granulated and dried to give a suitable size of granules. Next, calcium stearate is added to the granules, and the mixture is compressed and molded to give tablets.

Formulation Example 2: Capsules

The compounds of the present invention, lactose and calcium stearate are mixed uniformly to obtain powder medicines in the form of powders or fine granules. The powder medicines are filled into capsule containers to give capsules.

Formulation Example 3: Granules

The compounds of the present invention, lactose and calcium stearate are mixed uniformly and the mixture is compressed and molded. Then, it is crushed, granulated and sieved to give suitable sizes of granules.

Formulation Example 4: Orally Dispersing Tablets

The compounds of the present invention and crystalline cellulose are mixed, granulated and tablets are made to give orally dispersing tablets.

Formulation Example 5: Dry Syrups

The compounds of the present invention and lactose are mixed, crushed, granulated and sieved to give suitable sizes of dry syrups.

Formulation Example 6: Injections

The compounds of the present invention and phosphate buffer are mixed to give injections.

Formulation Example 7: Infusions

The compounds of the present invention and phosphate buffer are mixed to give injections.

Formulation Example 8: Inhalations

The compound of the present invention and lactose are mixed and crushed finely to give inhalations.

Formulation Example 9: Ointments

The compounds of the present invention and petrolatum are mixed to give ointments.

Formulation Example 10: Patches

The compounds of the present invention and base such as adhesive plaster or the like are mixed to give patches.

INDUSTRIAL APPLICABILITY

The compounds of the present invention have an antagonistic activity for the P2X7 receptor and are considered to be useful as a therapeutic and/or preventive agent for diseases or conditions associated with the P2X7 receptor.

The invention claimed is:
1. A compound represented by formula (I):

wherein
$Z_1$ is $C(R^2)$ or N;
$Z_3$ is CH or N;
$Z_2$ is $C(R^3)$ or N;
provided that $Z_1$ is $C(R^2)$ and $Z_3$ is CH when $Z_2$ is N;
$R^1$ is substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;
$R^2$ is a hydrogen atom, halogen, amino, carbamoyl, sulfamoyl, cyano, ureido, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted monoalkylamino, substituted or unsubstituted dialkylamino, substituted or unsubstituted alkylsulfonyl, substituted or unsubstituted monoalkylcarbonylamino, substituted or unsubstituted monoalkylsulfonylamino, substituted or unsubstituted alkylsulfonyl, substituted or unsubstituted monoalkylcarbamoyl, substituted or unsubstituted dialkylcarbamoyl, substituted or unsubstituted monoalkylsulfamoyl, substituted or unsubstituted dialkylsulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfanyl, substituted or unsubstituted non-aromatic carbocyclylsulfanyl, substituted or unsubstituted aromatic heterocyclylsulfanyl, or substituted or unsubstituted non-aromatic heterocyclylsulfanyl;

provided that $R^2$ is a hydrogen atom when $Z_2$ is $C(R^3)$ and $Z_3$ is CH;

$R^3$ is a hydrogen atom, halogen, amino, carbamoyl, sulfamoyl, cyano, ureido, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted monoalkylamino, substituted or unsubstituted dialkylamino, substituted or unsubstituted monoalkylcarbonylamino, substituted or unsubstituted monoalkylsulfonylamino, substituted or unsubstituted alkylsulfanyl, substituted or unsubstituted alkenylsulfanyl, substituted or unsubstituted alkynylsulfanyl, substituted or unsubstituted monoalkylcarbamoyl, substituted or unsubstituted dialkylcarbamoyl, substituted or unsubstituted monoalkylsulfamoyl, substituted or unsubstituted dialkylsulfamoyl, substituted or unsubstituted alkyloxycarbonylamino, substituted or unsubstituted alkenyloxycarbonylamino, substituted or unsubstituted alkynyloxycarbonylamino, substituted or unsubstituted alkylureido, substituted or unsubstituted alkenylureido, substituted or unsubstituted alkynylureido, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylcarbonylamino, substituted or unsubstituted non-aromatic carbocyclylcarbonylamino, substituted or unsubstituted aromatic heterocyclylcarbonylamino, substituted or unsubstituted non-aromatic heterocyclylcarbonylamino, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylureido, substituted or unsubstituted non-aromatic carbocyclylureido, substituted or unsubstituted aromatic heterocyclylureido, substituted or unsubstituted non-aromatic heterocyclylureido, substituted or unsubstituted aromatic carbocyclyloxycarbonylamino, substituted or unsubstituted non-aromatic carbocyclyloxycarbonylamino, substituted or unsubstituted aromatic heterocyclyloxycarbonylamino, or substituted or unsubstituted non-aromatic heterocyclyloxycarbonylamino;

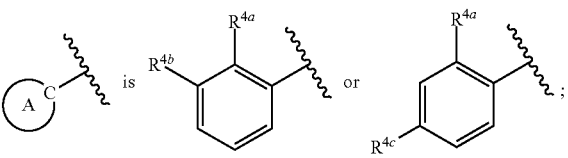

$R^{4a}$, $R^{4b}$ and $R^{4c}$ are each independently halogen, amino, carbamoyl, sulfamoyl, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkenylcarbonyl, substituted or unsubstituted monoalkylamino, substituted or unsubstituted dialkylamino, substituted or unsubstituted monoalkylcarbonylamino, substituted or unsubstituted monoalkylsulfonylamino, substituted or unsubstituted alkylsulfanyl, substituted or unsubstituted alkenylsulfanyl, substituted or unsubstituted alkynylsulfanyl, substituted or unsubstituted monoalkylcarbamoyl, substituted or unsubstituted dialkylcarbamoyl, substituted or unsubstituted monoalkylsulfamoyl, substituted or unsubstituted dialkylsulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylcarbonylamino, substituted or unsubstituted non-aromatic carbocyclylcarbonylamino, substituted or unsubstituted aromatic heterocyclylcarbonylamino, substituted or unsubstituted non-aromatic heterocyclylcarbonylamino, substituted or unsubstituted aromatic carbocyclylcarbamoyl, substituted or unsubstituted non-aromatic carbocyclylcarbamoyl, substituted or unsubstituted aromatic heterocyclylcarbamoyl, or substituted or unsubstituted non-aromatic heterocyclylcarbamoyl; or $R^{4a}$ and $R^{4b}$ are taken together with the adjacent carbon atoms to form a substituted or unsubstituted aromatic carbocycle, a substituted or unsubstituted non-aromatic carbocycle, a substituted or unsubstituted aromatic heterocycle, or a substituted or unsubstituted non-aromatic heterocycle, provided that
$R^1$ is not unsubstituted methyl, unsubstituted n-pentyl, substituted or unsubstituted phenyl, or tetrahydrofuranyl substituted with two hydroxy groups and optionally substituted with one or more and same or different substituent(s), or a pharmaceutically acceptable salt thereof.

2. The compound according to claim 1, wherein

[Chemical Formula 3]

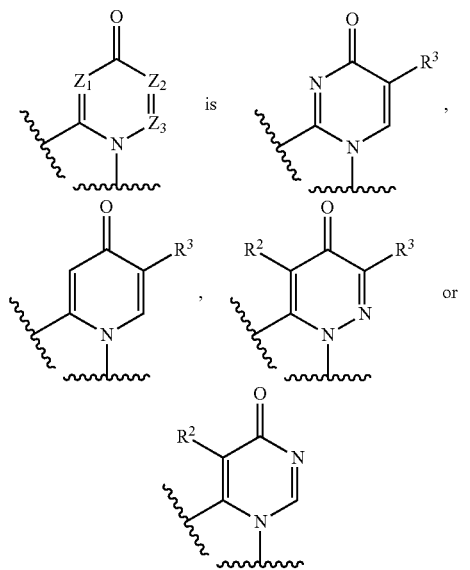

or a pharmaceutically acceptable salt thereof.

3. The compound according to claim 1 or 2,
wherein $R^{4a}$, $R^{4b}$ and $R^{4c}$ are each independently halogen, substituted or unsubstituted alkyl, substituted or unsubstituted alkenyl, substituted or unsubstituted alkynyl, substituted or unsubstituted alkyloxy, substituted or unsubstituted alkenyloxy, or substituted or unsubstituted alkynyloxy,
or a pharmaceutically acceptable salt thereof.

4. The compound according to claim 1 or 2,
wherein $R^1$ is substituted or unsubstituted alkyl, substituted or unsubstituted alkenyl, or substituted or unsubstituted alkynyl,
or a pharmaceutically acceptable salt thereof.

5. The compound according to claim 1,
wherein $R^1$ is substituted alkyl,
or a pharmaceutically acceptable salt thereof.

6. The compound according to claim 1,
wherein $R^1$ is a group represented by the formula: —(C($R^{5a}$)($R^{5b}$))m-$R^{1a}$;

$R^{1a}$ is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

$R^{5a}$ is each independently a hydrogen atom, halogen, or substituted or unsubstituted alkyl;

$R^{5b}$ is each independently a hydrogen atom, halogen, or substituted or unsubstituted alkyl;

$R^{5a}$ and $R^{5b}$ which are attached to the same carbon atom may be taken together with the carbon atom to which they are attached to form a substituted or unsubstituted non-aromatic carbocycle, or a substituted or unsubstituted non-aromatic heterocycle; and m is an integer from 0 to 4,
or a pharmaceutically acceptable salt hereof.

7. The compound according to claim 6,
wherein $R^{1a}$ is substituted or unsubstituted aromatic carbocyclyl, or substituted or unsubstituted aromatic heterocyclyl,
or a pharmaceutically acceptable salt thereof.

8. The compound according to claim 6,
wherein m is an integer from 1 to 4,
or a pharmaceutically acceptable salt thereof.

9. The compound according to claim,
wherein m is 1,
or a pharmaceutically acceptable salt thereof.

10. The compound according to claim 6,
wherein $R^{5a}$ and $R^{5b}$ are each independently a hydrogen atom, halogen, or substituted or unsubstituted alkyl,
or a pharmaceutically acceptable salt thereof.

11. The compound according to claim 1 or 2,
wherein $R^3$ is a hydrogen atom, halogen, amino, carbamoyl, sulfamoyl, cyano, ureido, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted monoalkylamino, substituted or unsubstituted dialkylamino, substituted or unsubstituted monoalkylcarbonylamino, substituted or unsubstituted monoalkylsulfonylamino, substituted or unsubstituted alkylsulfanyl, substituted or unsubstituted alkenylsulfanyl, substituted or unsubstituted alkynylsulfanyl, substituted or unsubstituted alkyloxycarbonylamino, substituted or unsubstituted alkenyloxycarbonylamino, substituted or unsubstituted alkynyloxycarbonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, or substituted or unsubstituted non-aromatic heterocyclylamino, or a pharmaceutically acceptable salt thereof.

12. The compound according to claim 1 or 2,
wherein $R^2$ is a hydrogen atom,
or a pharmaceutically acceptable salt thereof.

13. A pharmaceutical composition comprising the compound according to claim 1, or a pharmaceutically acceptable salt thereof.

14. The pharmaceutical composition according to claim 13 having an antagonistic activity for the P2X7 receptor.

15. The compound according to claim 1, or a pharmaceutically acceptable salt thereof for use in treating pain, central nervous system diseases, immune diseases or inflammatory disease.

16. A method for treating pain, central nervous system diseases, immune diseases or inflammatory disease characterized by administering the compound according to claim 1, or a pharmaceutically acceptable salt thereof.

* * * * *

UNITED STATES PATENT AND TRADEMARK OFFICE
CERTIFICATE OF CORRECTION

PATENT NO. : 9,988,373 B2  
APPLICATION NO. : 15/108089  
DATED : June 5, 2018  
INVENTOR(S) : Satoru Tanaka et al.

Page 1 of 1

It is certified that error appears in the above-identified patent and that said Letters Patent is hereby corrected as shown below:

Claim 9, Column 158, Line 25, "The compound according to claim," should read --The compound according to claim 1,"

Claim 9, Column 158, Line 26, "wherein m is 1," should read --wherein $R^1$ is substituted alkyl,--

Signed and Sealed this
Twenty-first Day of August, 2018

Andrei Iancu
*Director of the United States Patent and Trademark Office*